US008883791B2

(12) United States Patent
Berger et al.

(10) Patent No.: US 8,883,791 B2
(45) Date of Patent: Nov. 11, 2014

(54) N-HETEROARYL COMPOUNDS WITH CYCLIC BRIDGING UNIT FOR THE TREATMENT OF PARASITIC DISEASES

(75) Inventors: Michael Berger, Schwabenheim (DE); Christopher Kern, Schwabenheim (DE); Marko Eck, Schwabenheim (DE); Jörg Schröder, Schwabenheim (DE)

(73) Assignee: Intervet Inc., Summit, NJ (US)

( * ) Notice: Subject to any disclaimer, the term of this patent is extended or adjusted under 35 U.S.C. 154(b) by 0 days.

(21) Appl. No.: 13/876,716

(22) PCT Filed: Sep. 28, 2011

(86) PCT No.: PCT/EP2011/066805
§ 371 (c)(1),
(2), (4) Date: Mar. 28, 2013

(87) PCT Pub. No.: WO2012/041872
PCT Pub. Date: Apr. 5, 2012

(65) Prior Publication Data
US 2013/0203768 A1 Aug. 8, 2013

Related U.S. Application Data

(60) Provisional application No. 61/388,463, filed on Sep. 30, 2010.

(30) Foreign Application Priority Data

Sep. 29, 2010 (EP) ..................... 10181551

(51) Int. Cl.
*A61K 31/497* (2006.01)
*C07D 401/00* (2006.01)
(52) U.S. Cl.
USPC ....... 514/252.16; 514/314; 544/363; 544/360
(58) Field of Classification Search
USPC ..................... 514/252.16, 314; 544/363, 360; 546/175, 159
See application file for complete search history.

(56) References Cited

U.S. PATENT DOCUMENTS 6,861,432 B2 * 3/2005 Cleve et al. ............... 514/252.11
7,019,007 B2 * 3/2006 Du Bois et al. .......... 514/252.13

FOREIGN PATENT DOCUMENTS

| GB | 2407089 A | 4/2005 |
| JP | 59029667 A | 2/1984 |
| WO | 00/59510 A1 | 10/2000 |
| WO | 2006/100591 A1 | 9/2006 |
| WO | 2008/028689 A1 | 3/2008 |
| WO | 2008/028691 A1 | 3/2008 |

OTHER PUBLICATIONS

Saadeh et al. CAS: 151: 425693, 2009.*
European Search Report for EP Application No. EP 10 18 1551, dated Oct. 24, 2011.
Jabbar et al., "Anthelmintic resistance: The sate of play revisited", Life Sciences, 2006, pp. 2413-2431, vol. 79.
McKellar et al., "Veterinary anthelmintics: old and new", Trends in Parasitology, 2004, pp. 456-461, vol. 20(10).
Saadeh et al., "Synthesis of Novel Hybrid Molecules from Precursors With Known Antiparasitic Activity", Molecules, 2009, pp. 1483-1494, vol. 14.
International Search Report for corresponding PCT/EP2011/066805, mailed on Nov. 29, 2011.

* cited by examiner

*Primary Examiner* — Rei-tsang Shiao

(57) ABSTRACT

This invention relates to certain N-heteroaryl compounds that are generally useful as medicaments, more specifically as medicaments for animals. The medicament can preferably be used for the treatment of helminth infections and the treatment of parasitosis, such as caused by helminth infections. This invention also relates to uses of the compounds to make medicaments and treatments comprising the administration of the compounds to animals in need of the treatments. This invention also relates to the preparation of the N-heteroaryl compounds. Moreover this invention relates to pharmaceutical compositions and kits comprising the compounds.

16 Claims, No Drawings

N-HETEROARYL COMPOUNDS WITH CYCLIC BRIDGING UNIT FOR THE TREATMENT OF PARASITIC DISEASES

CROSS-REFERENCE TO RELATED APPLICATIONS

This application is a national stage entry under 35 U.S.C. §371 of PCT/EP2011/066805, filed on Sep. 28, 2011, which claims priority to U.S. Provisional Application No. 61/388,463, filed on Sep. 30, 2010, and EP Application No. 10181551.2, filed on Sep. 29, 2010. The content of PCT/EP2011/066805 is hereby incorporated by reference in its entirety.

FIELD OF THE INVENTION

This invention relates to novel N-heteroaryl compounds that are useful as medicaments, the preparation of such compounds and the use of such compounds. The medicament can preferably be used for the treatment of parasitic infections such as helminth infections and especially for the treatment of parasitoses, such as caused by helminth infections. This invention also relates to uses of the compounds to make medicaments and treatments comprising the administration of the compounds to animals in need of the treatments. Moreover this invention relates to pharmaceutical compositions and kits comprising the compounds.

BACKGROUND OF THE INVENTION

Parasitic diseases in animals cause substantial suffering and economic losses throughout the world. Thus, treatment of parasitic infections remains an important global endeavor. The causative organisms include helminths, such as nematodes, cestodes, and trematodes. These organisms can infect, for example, the stomach, intestinal tract, lymphatic system, muscle tissues, kidney, liver, lungs, heart, and brain of animals.

There are many known drugs (or "anthelmintic agents") available to treat various helminth parasite infections, see, e.g., McKellar, Q. A., et al., "Veterinary anthelmintics: old and new," *Review: Trends in Parasitology,* 20(10), 456-61 (October 2004). These anthelmintic agents treat specifically either nematode, cestode or trematode infections or have a broader anthelmintic spectrum. An example of an anthelmintic agent with sole effect on cestodes (tapeworms) is praziquantel. Some primary nematicidal compounds like fenbendazole, mebendazole, oxfendazole, albendazole have a broader spectrum than nematodes and treat cestode infections as well. Closantel, rafoxanide and triclabendazole are examples of specific compounds for the treatment of trematode infections (flukes).

While many parasitic infections can be treated with known drugs, evolutionary development of resistance by the parasites can render such drugs obsolete over time, see, e.g., Jabbar, A., et al., "Anthelmintic resistance: the state of play revisited," *Life Sciences,* 79, 2413-31 (2006). In addition, known drugs may have other deficiencies, such as limited spectrum of activity and the need for repeated treatments.

In WO 2008/028689 A1 certain N-(1-phthalazin-1-ylpiperidin-4-yl)-amides are described as EP2 receptor modulators. WO 2008/028691 A1 discloses as EP2 receptors certain N-(1-hetaryl-piperidin-4-yl)(het)arylamides.

There still exists a need for new medicaments, such as antiparasitic agents to ensure safe, effective, and convenient treatment of a wide range of parasitic helminth infections over a long period of time.

SUMMARY OF THE INVENTION

Briefly, this invention relates to compounds that can generally be used as a medicament for animals. The compounds correspond in structure to formula (I) or its pharmaceutically acceptable salts, solvates, N-oxides or prodrugs

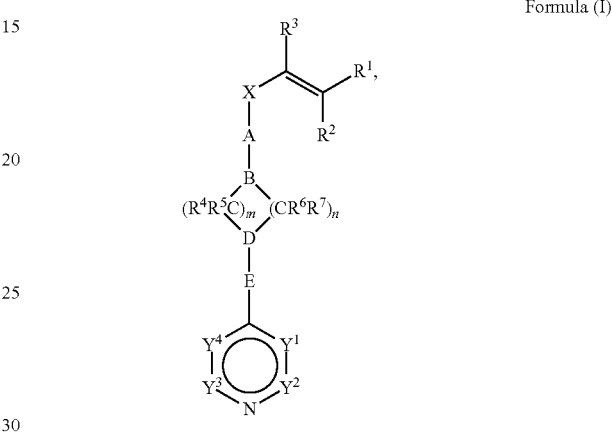

Formula (I)

wherein $R^1$ is halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_1$-$C_6$-alkyloxy carbonyl, $C_2$-$C_6$-alkenyl carbonyl, $SF_5$, $C_1$-$C_6$-alkyl sulfonyl, wherein each of the carbon-containing radicals optionally is substituted by one or more halogen atoms, preferably fluorine atoms, $R^2$ is hydrogen, halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals optionally is substituted by one or more halogen atoms, preferably fluorine atoms, preferably $R^2$ is hydrogen, $R^3$ is hydrogen, $C_1$-$C_6$-alkyl or cycloalkyl, preferably hydrogen, $R^4$ is hydrogen, $C_1$-$C_6$-alkyl or cycloalkyl, preferably hydrogen, $R^5$ is hydrogen, $C_1$-$C_6$-alkyl or cycloalkyl, $R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy, cycloalkyloxy or $C_1$-$C_6$-alkyloxy, $R^7$ is hydrogen, $C_1$-$C_6$-alkyl or cycloalkyl,
or $R^6$ and $R^7$ together represent an oxo-group or a thioxo-group or $R^6$ or $R^7$ is joined together with $R^4$ or $R^5$ to form a $C_1$-$C_3$-alkylene group which is optionally substituted by one or more radicals selected from the group of $C_1$-$C_6$-alkyl, cycloalkyl, m is an integer from 1 to 3, n is an integer from 1 to 3, X is a carbonyl, thiocarbonyl or sulfonyl group, preferably a carbonyl group, A is a bond or $NR^8$, wherein $R^8$ is hydrogen or $C_1$-$C_6$-alkyl, preferably hydrogen, E is a bond or $NR^9$, wherein $R^9$ is hydrogen or $C_1$-$C_6$-alkyl, preferably hydrogen, B is N or $CR^{10}$, wherein $R^{10}$ is hydrogen or $C_1$-$C_6$-alkyl, preferably hydrogen, D is N or $CR^{11}$, wherein $R^{11}$ is hydrogen or $C_1$-$C_6$-alkyl, preferably hydrogen, $Y^1$ is $CR^{12}$ or N, wherein C is substituted by $R^{12}$ which is hydrogen, halogen, $C_1$-$C_6$-alkyl, $C_1$-$C_6$-alkenyl, Cycloalkyl, $C_1$-$C_6$-haloalkyl, $C_1$-$C_6$-alkoxy, Cycloalkyloxy, $C_1$-$C_6$-haloalkoxy, nitrilo, nitro, amino, $C_1$-$C_6$-alkylamino, Cycloalkylamino, ($C_1$-$C_6$-alkyl)-(Cycloalkyl)amino, di($C_1$-$C_6$-alkyl)amino, N-pyrrolidinyl, N-piperidinyl, N-morpholinyl, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^2$ is $CR^{13}$ or N, wherein C is substituted by $R^{13}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, ($C_1$-$C_6$-alkyl)-(Cycloalkyl)amino, di($C_1$-$C_6$-alkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^3$ is $CR^{14}$ or N, wherein C is substituted by $R^{14}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, ($C_1$-$C_6$-alkyl)-(Cycloalkyl)amino, di($C_1$-$C_6$-alkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^4$ is $CR^{15}$ or N, wherein C is substituted by $R^{15}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, ($C_1$-$C_6$-alkyl)-(Cycloalkyl)amino, di($C_1$-$C_6$-alkyl)amino, N-pyrrolidinyl, N-piperidinyl, N-morpholinyl, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl, or $Y^1$ and $Y^2$ and/or $Y^3$ and $Y^4$ are joined together to form a ring system, and wherein at least one of B and D is a nitrogen atom, and wherein $R^1$ and $R^2$ are both different from a perfluorinated methyl group if the group of the formula (A)

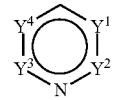

Formula (A)

represents a thienopyrimidine group substituted by $C_1$-$C_6$-alkyl.

This invention also relates to compounds according to formula (I a) or its pharmaceutically acceptable salts, solvates or N-oxides,

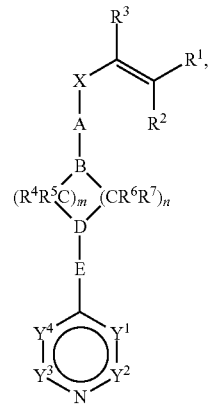

Formula (Ia)

wherein $R^1$ is hydrogen, halogen, amino, $C_1$-$C_6$-alkylamino, cycloalkylamino, di-($C_1$-$C_6$-alkyl)amino, di-(cycloalkyl)amino, $C_1$-$C_6$-alkylamino-$C_1$-$C_6$-alkyl, $C_1$-$C_6$-alkylamino-cycloalkyl, cycloalkylamino-$C_1$-$C_6$-alkyl, cycloalkylamino-cycloalkyl, di-($C_1$-$C_6$-alkyl)amino-$C_1$-$C_6$-alkyl, di-(cycloalkyl)amino-$C_1$-$C_6$-alkyl, di-($C_1$-$C_6$-alkyl)amino-cycloalkyl, di-(cycloalkyl)amino-cycloalkyl, $C_1$-$C_6$-alkyl, cycloalkyl, hydroxy-$C_1$-$C_6$-alkyl, hydroxy-cycloalkyl, $C_1$-$C_6$-alkyloxy, cycloalkyloxy, $C_1$-$C_6$-alkylthio, cycloalkylthio, $C_2$-$C_6$-alkenyl, $C_2$-$C_6$-alkynyl, $C_1$-$C_6$-alkyloxy $C_1$-$C_6$-alkyl, cycloalkyloxy $C_1$-$C_6$-alkyl, $C_1$-$C_6$-alkyloxy cycloalkyl, cycloalkyloxy cycloalkyl, $C_1$-$C_6$-alkylthio $C_1$-$C_6$-alkyl, $C_1$-$C_6$-alkylthio cycloalkyl, cycloalkylthio $C_1$-$C_6$-alkyl, cycloalkylthio cycloalkyl, $C_1$-$C_6$-alkyl carbonyl, cycloalkyl carbonyl, $C_1$-$C_6$-alkyloxy carbonyl, cycloalkyloxy carbonyl, $C_2$-$C_6$-alkenyl carbonyl, phenyl, furanyl, or thiophenyl, wherein each of the carbon-containing radicals optionally is substituted by one or more halogen atoms, preferably fluorine atoms, or $R^1$ is phenyl, furanyl, imidazolyl or thiophenyl, wherein each of the rings is optionally substituted by one or more radicals from the group of halogen, cycloalkyl and $C_1$-$C_6$-alkyl, $R^2$ is hydrogen, halogen, amino, $C_1$-$C_6$-alkylamino, cycloalkylamino, di-($C_1$-$C_6$-alkyl)amino, di-(cycloalkyl)amino, $C_1$-$C_6$-alkylamino-$C_1$-$C_6$-alkyl, $C_1$-$C_6$-alkylamino-cycloalkyl, cycloalkylamino-$C_1$-$C_6$-alkyl, cycloalkylamino-cycloalkyl, di-($C_1$-$C_6$-alkyl)amino-$C_1$-$C_6$-alkyl, di-(cycloalkyl)amino-$C_1$-$C_6$-alkyl, di-($C_1$-$C_6$-alkyl)amino-cycloalkyl, di-(cycloalkyl)amino-cycloalkyl, $C_1$-$C_6$-alkyl, cycloalkyl, hydroxy-$C_1$-$C_6$-alkyl, hydroxy-cycloalkyl, $C_1$-$C_6$-alkyloxy, cycloalkyloxy, $C_1$-$C_6$-alkylthio, cycloalkylthio, $C_2$-$C_6$-alkenyl, $C_2$-$C_6$-alkynyl, $C_1$-$C_6$-alkyloxy $C_1$-$C_6$-alkyl, cycloalkyloxy $C_1$-$C_6$-alkyl, $C_1$-$C_6$-alkyloxy cycloalkyl, cycloalkyloxy cycloalkyl, $C_1$-$C_6$-alkylthio $C_1$-$C_6$-alkyl, $C_1$-$C_6$-alkylthio cycloalkyl, cycloalkylthio $C_1$-$C_6$-alkyl, cycloalkylthio cycloalkyl, $C_1$-$C_6$-alkyl carbonyl, cycloalkyl carbonyl, $C_1$-$C_6$-alkyloxy carbonyl, cycloalkyloxy carbonyl, $C_2$-$C_6$-alkenyl carbonyl, phenyl, furanyl, or thiophenyl, wherein each of the carbon-containing radicals optionally is substituted by one or more halogen atoms, preferably fluorine atoms, or $R^2$ is phenyl, furanyl, imidazolyl or thiophenyl, wherein each of the rings is optionally substituted by one or more radicals from the group of halogen, cycloalkyl and $C_1$-$C_6$-alkyl, preferably $R^2$ is hydrogen, $R^3$ is hydrogen, cycloalkyl or $C_1$-$C_6$-alkyl, preferably hydrogen, $R^4$ is hydrogen, cycloalkyl or $C_1$-$C_6$-alkyl, preferably hydrogen, $R^5$ is hydrogen, cycloalkyl or $C_1$-$C_6$-alkyl, $R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy, cycloalkyloxy or $C_1$-$C_6$-alkyloxy, $R^7$ is hydrogen, cycloalkyl or $C_1$-$C_6$-alkyl, or $R^6$ and $R^7$ together represent an oxo-group or a thioxo-group or $R^6$ or $R^7$ is joined together with $R^4$ or $R^5$ to form a $C_1$-$C_3$-alkylene group which is optionally substituted by one or more radicals selected from the group of cycloalkyl, $C_1$-$C_6$-alkyl, m is an integer from 1 to 3, n is an integer from 1 to 3, X is a carbonyl or sulfonyl group, preferably a carbonyl group, A is a bond or $NR^8$, wherein $R^8$ is hydrogen or $C_1$-$C_6$-alkyl, preferably hydrogen, E is a bond or $NR^9$, wherein $R^9$ is hydrogen or $C_1$-$C_6$-alkyl, preferably hydrogen, B is N or $CR^{10}$, wherein $R^{10}$ is hydrogen or $C_1$-$C_6$-alkyl, preferably hydrogen, D is N or $CR^{11}$, wherein $R^{11}$ is hydrogen or $C_1$-$C_6$-alkyl, preferably hydrogen, $Y^1$ is $CR^{12}$ or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, $Y^2$ is $CR^{13}$ or N, wherein C is substituted by $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, $Y^3$ is $CR^{14}$ or N, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl) amino, cycloalkylthio, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, $Y^4$ is $CR^{15}$ or N, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, or $Y^1$ and $Y^2$ and/or $Y^3$ and $Y^4$ are joined together to form a ring system, and wherein at least one of B and D is a nitrogen atom for treating a helminth infection.

The compounds of the formula (I) and pharmaceutically acceptable solvates, N-oxides, salts and prodrugs thereof are hereinafter together referred to as "compound(s) according to this invention".

The use of the compounds according to formula (I a) and pharmaceutically acceptable solvates, N-oxides and salts thereof is hereinafter referred to as "use according to the invention". The compounds according to formula (I a) are hereinafter referred to as "compound(s) corresponding to the use according to the invention".

This invention is directed, in part, to a novel compound of the formula (I) and pharmaceutically acceptable solvates, N-oxides, salts and prodrugs thereof, and its use as a medicament, preferably a medicament for animals, e.g. for treating parasitic infections such as helminth infections in animals. This invention also is directed, in part, to using at least one compound of the formula (I) and pharmaceutically acceptable solvates, N-oxides, salts and prodrugs thereof to prepare a medicament for treating an infection including diseases caused by such infections (e.g., parasitoses caused by a helminth infection) in animals.

This invention also is directed, in part, to methods of making the novel N-heteroaryl compounds, and novel intermediates thereof. The preferred embodiments specified in this description for the compounds of the formula (I) likewise represent preferred embodiments for the intermediates, including the novel intermediates.

This invention also is directed, in part, to pharmaceutical compositions. The pharmaceutical compositions comprise a) at least one N-heteroaryl compound according to this invention, and b) at least one excipient, and/or at least one active compound (preferably anthelmintic compound) which differs in structure from the component a).

This invention also is directed, in part, to methods for treating a parasitic infection in animals, particularly a treatment of parasitoses caused by a helminth infection. The methods comprise administering at least one compound according to this invention to the animal.

This invention also is directed, in part, to a kit. The kit comprises at least one N-heteroaryl compound according to this invention. In addition, the kit comprises at least one other component, such as another ingredient (e.g., an excipient or active ingredient), and/or an apparatus for combining the compound with another ingredient, and/or an apparatus for administering the compound, and/or a diagnostic tool.

Further benefits of Applicants' invention will be apparent to one skilled in the art from reading this specification.

DETAILED DESCRIPTION OF PREFERRED EMBODIMENTS

Compounds According to this Invention

The present invention also relates to compounds according to formula (I b) and pharmaceutically acceptable solvates, N-oxides, salts and prodrugs thereof and their use as a medicament.

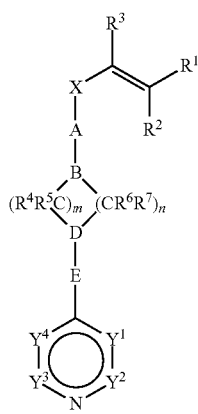

Formula (Ib)

In the compounds of the formula (I b) the radicals, indices and groups have the following meanings $R^1$ is halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals optionally is substituted by one or more halogen atoms, preferably fluorine atoms, $R^2$ is hydrogen, halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals optionally is substituted by one or more halogen atoms, preferably fluorine atoms, preferably $R^2$ is hydrogen, $R^3$ is hydrogen, $C_1$-$C_6$-alkyl or cycloalkyl, preferably hydrogen, $R^4$ is hydrogen, $C_1$-$C_6$-alkyl or cycloalkyl, preferably hydrogen, $R^5$ is hydrogen, $C_1$-$C_6$-alkyl or cycloalkyl, $R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy, cycloalkyloxy, $C_1$-$C_6$-alkyloxy, $R^7$ is hydrogen, $C_1$-$C_6$-alkyl or cycloalkyl, or $R^6$ and $R^7$ together represent an oxo-group or a thioxo-group or $R^6$ or $R^7$ is joined together with $R^4$ or $R^5$ to form a $C_1$-$C_3$-alkylene group which is optionally substituted by one or more radicals selected from the group of $C_1$-$C_6$-alkyl, cycloalkyl m is an integer from 1 to 3, n is an integer from 1 to 3, X is a carbonyl, or sulfonyl group, preferably a carbonyl group, A is a bond or $NR^8$, wherein $R^8$ is hydrogen or $C_1$-$C_6$-alkyl, preferably hydrogen, E is a bond or $NR^9$, wherein $R^9$ is hydrogen or $C_1$-$C_6$-alkyl, preferably hydrogen, B is N or $CR^{10}$, wherein $R^{10}$ is hydrogen or $C_1$-$C_6$-alkyl, preferably hydrogen, D is N or $CR^{11}$, wherein $R^{11}$ is hydrogen or $C_1$-$C_6$-alkyl, preferably hydrogen, $Y^1$ is $CR^{12}$ or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3- dioxolane, dioxane such as 1,3-dioxane, or dioxepane such as 1,3-dioxepane, each said ring being unsubstituted or substituted by $C_1$-$C_6$-alkyl or cycloalkyl, $Y^2$ is $CR^{13}$ or N, wherein C is substituted by $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, $Y^3$ is $CR^{14}$ or N, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, $Y^4$ is $CR^{15}$ or N, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, or $Y^1$ and $Y^2$ and/or $Y^3$ and $Y^4$ are joined together to form a ring system, and wherein at least one of B and D is a nitrogen atom, and wherein $R^1$ and $R^2$ are both different from a perfluorinated methyl group if the group of the formula (A)

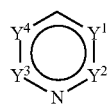

Formula (A)

represents a thienopyrimidine group substituted by $C_1$-$C_6$-alkyl or cycloalkyl For a compound of formula (Ib), the radicals, indices and groups may have the following additional meaning (leading to compounds referred to here-beneath as "additional compound(s)"):

A first additional compound wherein $R^1$ is $SF_5$, a second additional compound wherein X is thiocarbonyl and a third additional compound wherein $R^1$ is $SF_5$ and X is thiocarbonyl.

For a next additional compound of any of the additional compounds mentioned here-above or beneath, $R^1$ may be a $C_1$-$C_6$-alkyl sulfonyl For next additional compounds of any of the additional compounds mentioned here-above or beneath, $Y^1$ is C wherein C is substituted by $R^{12}$ which is $C_1$-$C_6$-alkenyl, or Cycloalkyl, or Cycloalkyloxy, or Cycloalkylamino, or ($C_1$-$C_6$-alkyl)-(Cycloalkyl)amino, or Cycloalkylthio or $C_1$-$C_6$-haloalkylthio.

For next additional compounds of any of the additional compounds mentioned here-above or beneath, $Y^2$ is C wherein C is substituted by $R^{13}$ which is $C_1$-$C_6$-alkenyl, or Cycloalkyl, or Cycloalkyloxy, or Cycloalkylamino, or ($C_1$-$C_6$-alkyl)-(Cycloalkyl)amino, or Cycloalkylthio or $C_1$-$C_6$-haloalkylthio.

For next additional compounds of any of the additional compounds mentioned here-above or beneath, $Y^3$ is C wherein C is substituted by $R^{14}$ which is $C_1$-$C_6$-alkenyl, or Cycloalkyl, or Cycloalkyloxy, or Cycloalkylamino, or ($C_1$-$C_6$-alkyl)-(Cycloalkyl)amino, or Cycloalkylthio or $C_1$-$C_6$-haloalkylthio.

For next additional compounds of any of the compounds mentioned here-above, $Y^4$ is C wherein C is substituted by $R^{15}$ which is $C_1$-$C_6$-alkenyl, or Cycloalkyl, or Cycloalkyloxy, or Cycloalkylamino, or ($C_1$-$C_6$-alkyl)-(Cycloalkyl)amino, or Cycloalkylthio or $C_1$-$C_6$-haloalkylthio.

The compounds according to formula (Ib) and the additional compounds are also included in the terms "compounds according to this invention".

The present invention also relates to compounds of formula (I) and pharmaceutically acceptable solvates, N-oxides, prodrugs and salts thereof and their use as a medicament. In the compounds of the formula (I) the radicals, indices and groups have the following meanings:

$R^1$ is halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl carbonyl, $C_1$-$C_6$-alkyloxy carbonyl, $C_2$-$C_6$-alkenyl carbonyl, $SF_5$, $C_1$-$C_6$-alkyl sulfonyl, wherein each of the carbon-containing radicals optionally is substituted by one or more halogen atoms, preferably fluorine atoms $R^2$ is hydrogen, halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals optionally is substituted by one or more halogen atoms, preferably fluorine atoms, preferably $R^2$ is hydrogen.

$R^3$ is hydrogen, $C_1$-$C_6$-alkyl or cycloalkyl, preferably hydrogen.

$R^4$ is hydrogen, $C_1$-$C_6$-alkyl or cycloalkyl, preferably hydrogen.

$R^5$ is hydrogen, $C_1$-$C_6$-alkyl or cycloalkyl, preferably hydrogen.

$R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy, $C_1$-$C_6$-alkyloxy or cycloalkyloxy. Preferably $R^6$ is hydrogen, $C_1$-$C_6$-alkyl, cycloalkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$- alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl) aminocarbonyl ($C_1$-$C_6$-alkyl), phenyl, phenyl $C_1$-$C_6$-alkyl, more preferably $R^6$ is hydrogen or $C_1$-$C_6$-alkyl.

$R^7$ is hydrogen, $C_1$-$C_6$-alkyl or cycloalkyl, preferably hydrogen.

Alternatively $R^6$ and $R^7$ together represent an oxo-group or a thioxo-group, or $R^6$ or $R^7$ is joined together with $R^4$ or $R^5$ to form a $C_1$-$C_3$-alkylene group which is optionally substituted by one or more radicals selected from the group of $C_1$-$C_6$-alkyl and cycloalkyl.

X is a carbonyl, thiocarbonyl or sulfonyl group, preferably a carbonyl group.

The group $(CR^4R^5)_m$ represents a $C_1$-$C_3$-alkylene group, preferably an ethylene group, which is unsubstituted or substituted by $R^4$ and/or $R^5$ being a $C_1$-$C_6$-alkyl group.

The group $(CR^6R^7)_n$ represents a $C_1$-$C_3$-alkylene group, preferably an ethylene group, which is unsubstituted or is substituted by $R^7=C_1$-$C_6$-alkyl and/or by $R^6=C_1$-$C_6$-alkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl) aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, or phenyl, phenyl $C_1$-$C_6$-alkyl, wherein each phenyl group is optionally substituted by hydroxy or $C_1$-$C_6$-alkyloxy, preferably the group $(CR^6R^7)_n$ represents a $C_1$-$C_3$-alkylene group, preferably an ethylene group, which is unsubstituted or substituted by $C_1$-$C_6$-alkyl.

In a preferred embodiment the substructure D-$(CR^4R^5)_m$—B—$(CR^6R^7)_n$ represents a ring of 4 to 8 ring atoms, preferably of 4 to 7 ring atoms, more preferably of 4 to 6 ring atoms, e.g. an azetidine, pyrrolidine, piperidine, piperazine or homopiperazine ring, wherein the ring is unsubstituted or substituted as defined above. In another preferred embodiment D-$(CR^4R^5)_m$—B—$(CR^6R^7)_n$ represents a ring of 5 or 6 ring atoms, wherein the ring is unsubstituted or substituted as defined above. In another preferred embodiment both groups $(CR^4R^5)_m$ and $(CR^6R^7)_n$ represent an ethylene group to form together with B and D a 6-ring, which is unsubstituted or substituted as defined above.

If $R^6$ or $R^7$ are joined together with $R^4$ or $R^5$ to form a $C_1$-$C_3$-alkylene group, they form for example a bridged ring, preferably of 5 to 8 ring atoms, more preferably of 5 to 7 ring atoms, even more preferably 5 to 6 ring atoms, e.g. a bridged pyrrolidine, piperidine, piperazine or homopiperazine ring, wherein the ring is unsubstituted or substituted as defined above.

The integer m is from 1 to 3, and is preferably 2. If m is larger than 1 the $CR^4R^5$-groups can be identical or different.

The integer n is from 1 to 3, and is preferably 2. If n is larger than 1 the $CR^6R^7$-groups can be identical or different.

The group of the formula (A) in formula (I) and formula (II)

Formula (A)

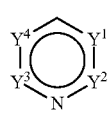

represents a mono- or polycyclic heterocyclic ring system. A monocyclic ring system is obtained if the carbon/nitrogen atoms $Y^1$, $Y^2$, $Y^3$ and $Y^4$ are unsubstituted or substituted but not joined together. A polycyclic ring system is obtained if either $Y^1$ and $Y^2$ are joined together or $Y^3$ and $Y^4$ are joined together or both $Y^1$ and $Y^2$ as well as $Y^3$ and $Y^4$ are joined together.

A ring system formed by joining together $Y^1$ and $Y^2$ is a saturated or non-saturated ring system (e.g. an aromatic ring system). The ring system itself is a monocyclic or polycyclic ring system, preferably a monocyclic, bicyclic or tricyclic, preferably a monocyclic or bicyclic ring system. The ring system contains from 4 to 10 ring atoms, preferably from 5 to 8 ring atoms, more preferably from 5 to 6 ring atoms, wherein the number of ring atoms includes $Y^1$ and $Y^2$. The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of $C_1$-$C_6$-alkyl, $C_1$-$C_6$-alkyloxy, $C_1$-$C_6$-alkoxycarbonyl and $C_1$-$C_6$-alkylthio.

A ring system formed by joining together $Y^3$ and $Y^4$ is a saturated or non-saturated ring system (e.g. an aromatic ring system). The ring system itself is a monocyclic or polycyclic ring system, preferably a monocyclic, bicyclic or tricyclic, preferably a monocyclic or bicyclic ring system. The ring system contains from 4 to 10 ring atoms, preferably from 5 to 8 ring atoms, more preferably from 5 to 6 ring atoms, wherein the number of ring atoms includes $Y^3$ and $Y^4$. The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of $C_1$-$C_6$-alkyl, $C_1$-$C_6$-alkyloxy, $C_1$-$C_6$-alkoxycarbonyl and $C_1$-$C_6$-alkylthio.

The mentioning of the preferred embodiments of the ring system formed by joining together $Y^1$ and $Y^2$ and/or $Y^3$ and $Y^4$ is intended to disclose all combinations of the preferred embodiments, including but not limited to a saturated, monocyclic, bicyclic or tricyclic ring system with 4 to 10 ring atoms, one, two or three ring heteroatoms from the group of nitrogen, sulphur and oxygen, which is unsubstituted or substituted by one or two radicals from the group of $C_1$-$C_6$-alkyl, $C_1$-$C_6$-alkyloxy and $C_1$-$C_6$-alkylthio, or an unsaturated, monocyclic or bicyclic ring system with 5 to 6 ring atoms, one or two ring heteroatoms, which is unsubstituted, etc.

The group of the formula (A) preferably represents a pyridine ($Y^1$, $Y^2$, $Y^3$ and $Y^4$ are C), pyrimidine, quinoline, quinazoline, thienopyrimidine, thienopyridine, triazolopyrimidine, pyridopyridine, pyrrolopyridine, pyrazolopyrimidine, pyrazolopyridine, furopyridine, 2,3-dihydrofuropyridine, 2,3-dihydro-1,4-dioxinopyridine, furopyrimidine, pyridazine or cinnoline group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, Cycloalkyl, Cycloalkyloxy, $C_1$-$C_6$-alkenyl halogen, nitrilo, nitro, amino, $C_1$-$C_6$-alkylamino, di($C_1$-$C_6$-alkyl)amino, Cycloalkylamino, ($C_1$-$C_6$-alkyl)-cycloalkylamino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, Cycloalkyl, Cycloalkyloxy, $C_1$-$C_6$-alkenyl, halogen, nitrilo, nitro, amino, $C_1$-$C_6$-alkylamino, di($C_1$-$C_6$-alkyl)amino, Cycloalkylamino, ($C_1$-$C_6$-alkyl)-cycloalkylamino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group (preferably a pyridine, pyrimidine or quinoline group), wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkoxycarbonyl, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyridine, pyrimidine or quinoline group, preferably a pyridine or pyrimidine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine or quinoline group, preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyrimidine group, which is optionally substituted by one or more radicals, preferably by one or two radicals, selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio In another preferred embodiment of any of the embodiments disclosed herein, the group of the formula (A) is different from a thienopyrimidine group such as a thienopyrimidine group substituted by $C_1$-$C_6$-alkyl.

In another preferred embodiment of any of the embodiments disclosed herein, the group of the formula (A) is different from a pyrazolopyrimidine group such as a pyrazolopyrimidine group substituted by amino, hydroxy, thiol, halogen, cyano, aryl, heteroaryl, $C_1$-$C_4$-alkyl, $C_2$-$C_6$-alkenyl, $C_2$-$C_6$-alkynyl, wherein the aryl, heteroaryl, alkyl, alkenyl and alkynyl are optionally substituted with one or two groups independently selected from hydroxycarbonyl, $C_1$-$C_6$-alkoxycarbonyl, aminocarbonyl, $C_1$-$C_6$-alkylaminocarbonyl, di($C_1$-$C_6$-alkyl)aminocarbonyl, $C_1$-$C_6$-alkoxy, amino, $C_1$-$C_6$-alkylamino, di($C_1$-$C_6$-alkyl)amino, wherein the alkyl are optionally substituted with aryl or heteroaryl.

Preferably at least two of A, B, D and E contain a nitrogen atom. More preferably at least one of A and B and at least one of D and E contains a nitrogen atom, even more preferred one of A and B and one of D and E contains a nitrogen atom.

In some embodiments each of A, B, D and E contains a nitrogen atom. In other embodiments each of A, B and D, or each of A, B and E, or each of A, D and E, or each of B, D and E contains a nitrogen atom. In still other embodiments each of A and D, or each of B and E, or each of B and D contains a nitrogen atom.

In some embodiments B is N, D is N and each of A and E is a bond. In other embodiments A is $NR^8$, B is $CR^{10}$, D is N, and E is a bond, or A is $NR^8$, B is N, D is N and E is a bond, or A is a bond, B is N, D is N and E is $NR^9$, or A is a bond, B is N, D is $CR^{11}$ and E is $NR^9$, wherein $R^8$ to $R^{11}$ are as defined above.

In a preferred compound of formula (I)

$R^1$ is halogen, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals optionally is substituted by one or more halogen atoms, preferably fluorine atoms, $R^2$ is hydrogen, halogen, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals is optionally substituted by one or more halogen atoms, preferably fluorine atoms, preferably $R^2$ is hydrogen, $R^3$ is hydrogen, $(CR^4R^5)_m$ is a $C_1$-$C_3$-alkylene group, preferably an ethylene group, which is optionally substituted by one or more $C_1$-$C_6$-alkyl radicals, $(CR^6R^7)_n$ is a $C_1$-$C_3$-alkylene group, preferably an ethylene group, which is optionally substituted by one or more $C_1$-$C_6$-alkyl radicals, A is a bond or $NR^8$, wherein $R^8$ is H or $C_1$-$C_6$-alkyl, E is a bond or $NR^9$, wherein $R^9$ is H or $C_1$-$C_6$-alkyl, B is N or $CR^{10}$, wherein $R^{10}$ is H or $C_1$-$C_6$-alkyl, D is N or $CR^{11}$, wherein $R^{11}$ is H or $C_1$-$C_6$-alkyl, $Y^1$ is C or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^2$ is C or N, wherein C is substituted $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-

$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^3$ is C or N, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^4$ is C or N, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl, or $Y^1$ and $Y^2$ and/or $Y^3$ and $Y^4$ are joined together to form a ring system, and wherein two of A, B, D and E contain a nitrogen atom and at least one of B and D is a nitrogen atom, preferably B and D represent a nitrogen atom and A and E are a bond.

A more preferred compound has the formula (II),

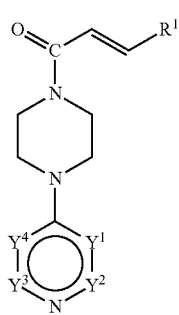

Formula (II)

$R^1$ is $C_1$-$C_6$-alkyl, $C_1$-$C_6$-alkyloxy $C_1$-$C_6$-alkyl, $C_1$-$C_6$-alkylamino-$C_1$-$C_6$-alkyl, di-($C_1$-$C_6$-alkyl)amino-$C_1$-$C_6$-alkyl, or $C_1$-$C_6$-alkylthio $C_1$-$C_6$-alkyl, wherein each of the radicals is unsubstituted or substituted by one or more halogen atoms, preferably by one or more fluorine atoms, e.g. by 1 to 10, preferably by 1 to 5, fluorine atoms, $Y^1$ is C or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, cycloalkyl, cycloalkyloxy, cycloalkylamino, ($C_1$-$C_6$-alkyl)-(cycloalkyl)amino, cycloalkylthio, phenyl, $Y^2$ is C or N, preferably C, wherein C is substituted by $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, cycloalkyl, cycloalkyloxy, cycloalkylamino, ($C_1$-$C_6$-alkyl)-(cycloalkyl)amino, cycloalkylthio, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^3$ is C or N, preferably C, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, cycloalkyl, cycloalkyloxy, cycloalkylamino, ($C_1$-$C_6$-alkyl)-(cycloalkyl)amino, cycloalkylthio, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^4$ is C or N, preferably C, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, cycloalkyl, cycloalkyloxy, cycloalkylamino, ($C_1$-$C_6$-alkyl)-(cycloalkyl)amino, cycloalkylthio, phenyl, or $Y^1$ and $Y^2$ and/or $Y^3$ and $Y^4$ are joined together to form a 5- or 6-membered ring system.

In a preferred compound of the formula (II)

$R^1$ is $C_1$-$C_6$-alkyl, $C_1$-$C_6$-alkyloxy $C_1$-$C_6$-alkyl, $C_1$-$C_6$-alkylamino-$C_1$-$C_6$-alkyl, di-($C_1$-$C_6$-alkyl)amino-$C_1$-$C_6$-alkyl or $C_1$-$C_6$-alkylthio $C_1$-$C_6$-alkyl, wherein each of the radicals unsubstituted or substituted by one or more halogen atoms, preferably by one or more fluorine atoms, e.g. by 1 to 10, preferably by 1 to 5, fluorine atoms, $Y^1$ is C or N, wherein C is substituted by $R^{12}$ which is hydrogen, $C_1$-$C_6$-alkyl, or $C_1$-$C_6$-alkoxy, $Y^2$ is C, wherein C is substituted by $R^{13}$ which is hydrogen, $C_1$-$C_6$-alkyl, $C_1$-$C_6$-alkoxy, $C_1$-$C_6$-alkyl carbonyl, $Y^3$ is C, wherein C is substituted by $R^{14}$ which is hydrogen, $C_1$-$C_6$-alkyl, $C_1$-$C_6$-alkoxy, $C_1$-$C_6$-alkyl carbonyl, $Y^4$ is C, wherein C is substituted by $R^{15}$ which is hydrogen, $C_1$-$C_6$-alkyl, $C_1$-$C_6$-alkoxy, or $Y^1$ and $Y^2$ or $Y^3$ and $Y^4$ are joined together to form a 5- or 6-membered ring system.

In a preferred compound of the formula (I) or (II)

$R^2$ is hydrogen, $R^3$ is hydrogen, $R^4$ is hydrogen, $R^5$ is hydrogen, $R^6$ is hydrogen or $C_1$-$C_6$-alkyl, $R^7$ is hydrogen, X is a carbonyl group, m is 2 n is 2, the group of formula (A) represents a pyridine, pyrimidine or quinoline group, preferably a pyridine or pyrimidine group, more preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3- dioxane, or dioxepane such as 1,3-dioxepane, wherein each ring is unsubstituted or substituted by $C_1$-$C_6$-alkyl, and one of A and B and one of D and E contains a nitrogen atom.

In another preferred compound of the formula (II) $R^1$ is $C_1$-$C_6$-alkyl which is unsubstituted or substituted by one or more halogen atoms, preferably by one or more fluorine atoms, e.g. by 1 to 10, preferably by 1 to 5, fluorine atoms.

In another preferred compound of the formula (II) the group of the formula (A)

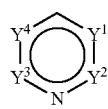

Formula (A)

represents a pyridine, pyrimidine, quinoline, quinazoline, thienopyrimidine, thienopyridine, triazolopyrimidine, pyridopyridine, pyrrolopyridine, pyrazolopyrimidine, pyrazolopyridine, furopyridine, 2,3-dihydrofuropyridine, 2,3-dihydro-1,4-dioxinopyridine, furopyrimidine, pyridazine or cinnoline group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, halogen, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, halogen, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group (preferably a pyridine, pyrimidine or quinoline group), wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyridine, pyrimidine or quinoline group, preferably a pyridine or pyrimidine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl, more preferably each group is optionally substituted by one or more radicals, preferably by one or two radicals selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio.

In another preferred embodiment the group of formula (A) is a pyridine or quinoline group, preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyrimidine group, which is optionally substituted by one or more radicals, preferably by one or two radicals, selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio.

In another preferred embodiment in the group of formula (A) both $R^{13}$ and $R^{14}$ are different from amino, $C_1$-$C_6$-alkylamino, di($C_1$-$C_6$-alkyl)amino, N-pyrrolidinyl, N-piperidinyl.

In another preferred embodiment in the group of formula (A) both $R^{13}$ and $R^{14}$ are different from $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl.

In another preferred embodiment if the group of formula (A) represents a triazine group, both $R^{13}$ and $R^{14}$ are different from $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl.

In another preferred embodiment in the group of formula (A) all of $R^{12}$, $R^{13}$ $R^{14}$, $R^{15}$ are different from $C_1$-$C_6$-alkoxy and $C_1$-$C_6$-haloalkoxy if X is a sulfonyl group.

Use According to this Invention

The present invention also relates to compounds of formula (I a) and pharmaceutically acceptable solvates, N-oxides and salts thereof and their use for treating a helminth infection In the compounds of the formula (I a) the radicals, indices and groups have the following meanings:

$R^1$ is hydrogen, halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals optionally is substituted by one or more halogen atoms, preferably fluorine atoms, or $R^1$ is phenyl, furanyl, imidazolyl or thiophenyl, wherein each of the rings is optionally substituted by one or more radicals from the group of halogen and $C_1$-$C_6$-alkyl.

$R^2$ is hydrogen, halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals is optionally substituted by one or more halogen atoms, preferably fluorine atoms, or $R^2$ is phenyl, furanyl, imidazolyl or thiophenyl, wherein each of the rings is optionally substituted by one or more radicals from the group of halogen and $C_1$-$C_6$-alkyl. preferably $R^2$ is hydrogen.

$R^3$ is hydrogen or $C_1$-$C_6$-alkyl, preferably hydrogen.
$R^4$ is hydrogen or $C_1$-$C_6$-alkyl, preferably hydrogen.
$R^5$ is hydrogen or $C_1$-$C_6$-alkyl, preferably hydrogen.
$R^6$ is hydrogen, $C_1$-$C_6$-alkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy or $C_1$-$C_6$-alkyloxy. Preferably $R^6$ is hydrogen, $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), phenyl, phenyl $C_1$-$C_6$-alkyl, more preferably $R^6$ is hydrogen or $C_1$-$C_6$-alkyl.

$R^7$ is hydrogen or $C_1$-$C_6$-alkyl, preferably hydrogen.

Alternatively $R^6$ and $R^7$ together represent an oxo-group or a thioxo-group, or $R^6$ or $R^7$ is joined together with $R^4$ or $R^5$ to form a $C_1$-$C_3$-alkylene group which is optionally substituted by one or more radicals selected from the group of $C_1$-$C_6$-alkyl.

X is a carbonyl or sulfonyl group, preferably a carbonyl group.

The group $(CR^4R^5)_m$ represents a $C_1$-$C_3$-alkylene group, preferably an ethylene group, which is unsubstituted or substituted by $R^4$ and/or $R^5$ being a $C_1$-$C_6$-alkyl group.

The group $(CR^6R^7)_n$ represents a $C_1$-$C_3$-alkylene group, preferably an ethylene group, which is unsubstituted or substituted by $R^7$=$C_1$-$C_6$-alkyl and/or by $R^6$=$C_1$-$C_6$-alkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl) aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, or phenyl, phenyl $C_1$-$C_6$-alkyl, wherein each phenyl group is optionally substituted by hydroxy or $C_1$-$C_6$-alkyloxy, preferably the group $(CR^6R^7)_n$ represents a $C_1$-$C_3$-alkylene group, preferably an ethylene group, which is unsubstituted or substituted by $C_1$-$C_6$-alkyl.

In a preferred embodiment the substructure D-$(CR^4R^5)_m$—B—$(CR^6R^7)_n$ represents a ring of 4 to 8 ring atoms, preferably of 4 to 7 ring atoms, more preferably of 4 to 6 ring atoms, e.g. an azetidine, pyrrolidine, piperidine, piperazine or homopiperazine ring, wherein the ring is unsubstituted or substituted as defined above. In another preferred embodiment D-$(CR^4R^5)_m$—B—$(CR^6R^7)_n$ represents a ring of 5 or 6 ring atoms, wherein the ring is unsubstituted or substituted as defined above. In another preferred embodiment both groups $(CR^4R^5)_m$ and $(CR^6R^7)_n$ represent an ethylene group to form together with B and D a 6-ring, which is unsubstituted or substituted as defined above.

If $R^6$ or $R^7$ are joined together with $R^4$ or $R^5$ to form a $C_1$-$C_3$-alkylene group, they form for example a bridged ring, preferably of 5 to 8 ring atoms, more preferably of 5 to 7 ring atoms, even more preferably 5 to 6 ring atoms, e.g. a bridged pyrrolidine, piperidine, piperazine or homopiperazine ring, wherein the ring is unsubstituted or substituted as defined above.

The integer m is from 1 to 3, and is preferably 2. If m is larger than 1 the $CR^4R^5$-groups can be identical or different.

The integer n is from 1 to 3, and is preferably 2. If n is larger than 1 the $CR^6R^7$-groups can be identical or different.

The group of the formula (A) in formula (Ia)

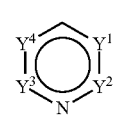

Formula (A)

represents a mono- or polycyclic heterocyclic ring system. A monocyclic ring system is obtained if the carbon/nitrogen atoms $Y^1$, $Y^2$, $Y^3$ and $Y^4$ are unsubstituted or substituted but not joined together. A polycyclic ring system is obtained if either $Y^1$ and $Y^2$ are joined together or $Y^3$ and $Y^4$ are joined together or both $Y^1$ and $Y^2$ as well as $Y^3$ and $Y^4$ are joined together.

A ring system formed by joining together $Y^1$ and $Y^2$ is a saturated or non-saturated ring system (e.g. an aromatic ring system). The ring system itself is a monocyclic or polycyclic ring system, preferably a monocyclic, bicyclic or tricyclic, preferably a monocyclic or bicyclic ring system. The ring system contains from 4 to 10 ring atoms, preferably from 5 to 8 ring atoms, more preferably from 5 to 6 ring atoms, wherein the number of ring atoms includes $Y^1$ and $Y^2$. The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of $C_1$-$C_6$-alkyl, $C_1$-$C_6$-alkyloxy, $C_1$-$C_6$-alkoxycarbonyl and $C_1$-$C_6$-alkylthio.

A ring system formed by joining together $Y^3$ and $Y^4$ is a saturated or non-saturated ring system (e.g. an aromatic ring system). The ring system itself is a monocyclic or polycyclic ring system, preferably a monocyclic, bicyclic or tricyclic, preferably a monocyclic or bicyclic ring system. The ring system contains from 4 to 10 ring atoms, preferably from 5 to 8 ring atoms, more preferably from 5 to 6 ring atoms, wherein the number of ring atoms includes $Y^3$ and $Y^4$. The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of $C_1$-$C_6$-alkyl, $C_1$-$C_6$-alkyloxy, $C_1$-$C_6$-alkoxycarbonyl and $C_1$-$C_6$-alkylthio.

The mentioning of the preferred embodiments of the ring system formed by joining together $Y^1$ and $Y^2$ and/or $Y^3$ and $Y^4$ is intended to disclose all combinations of the preferred embodiments, including but not limited to a saturated, monocyclic, bicyclic or tricyclic ring system with 4 to 10 ring atoms, one, two or three ring heteroatoms from the group of nitrogen, sulphur and oxygen, which is unsubstituted or substituted by one or two radicals from the group of $C_1$-$C_6$-alkyl, $C_1$-$C_6$-alkyloxy and $C_1$-$C_6$-alkylthio, or an unsaturated, monocyclic or bicyclic ring system with 5 to 6 ring atoms, one or two ring heteroatoms, which is unsubstituted, etc.

The group of the formula (A) preferably represents a pyridine ($Y^1$, $Y^2$, $Y^3$ and $Y^4$ are C), pyrimidine, quinoline, quinazoline, thienopyrimidine, thienopyridine, triazolopyrimidine, pyridopyridine, pyrrolopyridine, pyrazolopyrimidine, pyrazolopyridine, furopyridine, 2,3-dihydrofuropyridine, 2,3-dihydro-1,4-dioxinopyridine, furopyrimidine, pyridazine or cinnoline group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, halogen, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, halogen, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group (preferably a pyridine, pyrimidine or quinoline group), wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkoxycarbonyl, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyridine, pyrimidine or quinoline group, preferably a pyridine or pyrimidine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine or quinoline group, preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyrimidine group, which is optionally substituted by one or more radicals, preferably by one or two radicals, selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio.

In another preferred embodiment of any of the embodiments as described herein, the group of the formula (A) is different from a thienopyrimidine group such as a thienopyrimidine group substituted by $C_1$-$C_6$-alkyl.

In another preferred embodiment of any of the embodiments as described herein, the group of the formula (A) is different from a pyrazolopyrimidine group such as a pyrazolopyrimidine group substituted by amino, hydroxy, thiol, halogen, cyano, aryl, heteroaryl, $C_1$-$C_4$-alkyl, $C_2$-$C_6$-alkenyl, $C_2$-$C_6$-alkynyl, wherein the aryl, heteroaryl, alkyl, alkenyl and alkynyl are optionally substituted with one or two groups independently selected from hydroxycarbonyl, $C_1$-$C_6$-alkoxycarbonyl, aminocarbonyl, $C_1$-$C_6$-alkylaminocarbonyl, di($C_1$-$C_6$-alkyl)aminocarbonyl, $C_1$-$C_6$-alkoxy, amino, $C_1$-$C_6$-alkylamino, di($C_1$-$C_6$-alkyl)amino, wherein the alkyl are optionally substituted with aryl or heteroaryl.

Preferably at least two of A, B, D and E contain a nitrogen atom. More preferably at least one of A and B and at least one of D and E contains a nitrogen atom, even more preferred one of A and B and one of D and E contains a nitrogen atom.

In some embodiments each of A, B, D and E contains a nitrogen atom. In other embodiments each of A, B and D, or each of A, B and E, or each of A, D and E, or each of B, D and E contains a nitrogen atom. In still other embodiments each of A and D, or each of B and E, or each of B and D contains a nitrogen atom.

In some embodiments B is N, D is N and each of A and E is a bond. In other embodiments A is $NR^8$, B is $CR^{10}$, D is N, and E is a bond, or A is $NR^8$, B is N, D is N and E is a bond, or A is a bond, B is N, D is N and E is $NR^9$, or A is a bond, B is N, D is $CR^{11}$ and E is $NR^9$, wherein $R^8$ to $R^{11}$ are as defined above.

In a preferred use according to the invention, in the compound of formula (I) the radicals, indices and groups have the following meanings:

$R^1$ is hydrogen, halogen, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl carbonyl, $C_1$-$C_6$-alkyloxy carbonyl, $C_2$-$C_6$-alkenyl carbonyl, phenyl, furanyl, imidozolyl or thiophenyl, wherein each of the carbon-containing radicals optionally is substituted by one or more halogen atoms, preferably fluorine atoms, $R^2$ is hydrogen, halogen, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl carbonyl, $C_1$-$C_6$-alkyloxy carbonyl, $C_2$-$C_6$-alkenyl carbonyl, phenyl, furanyl, imidozolyl or thiophenyl, wherein each of the carbon-containing radicals is optionally substituted by one or more halogen atoms, preferably fluorine atoms, preferably $R^2$ is hydrogen, $R^3$ is hydrogen, $(CR^4R^5)_m$ is a $C_1$-$C_3$-alkylene group, preferably an ethylene group, which is optionally substituted by one or more $C_1$-$C_6$-alkyl radicals, $(CR^6R^7)_n$ is a $C_1$-$C_3$-alkylene group, preferably an ethylene group, which is optionally substituted by one or more $C_1$-$C_6$-alkyl radicals, A is a bond or $NR^8$, wherein $R^8$ is H or $C_1$-$C_6$-alkyl,
E is a bond or $NR^9$, wherein $R^9$ is H or $C_1$-$C_6$-alkyl,
B is N or $CR^{10}$, wherein $R^{10}$ is H or $C_1$-$C_6$-alkyl,
D is N or $CR^{11}$, wherein $R^{11}$ is H or $C_1$-$C_6$-alkyl,
$Y^1$ is C or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl,
$Y^2$ is C or N, wherein C is substituted $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl,
$Y^3$ is C or N, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl,
$Y^4$ is C or N, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl,
or $Y^1$ and $Y^2$ and/or $Y^3$ and $Y^4$ are joined together to form a ring system,
and wherein two of A, B, D and E contain a nitrogen atom and at least one of B and D is a nitrogen atom, preferably B and D represent a nitrogen atom and A and E are a bond.

A more preferred compound has the formula (II) as depicted immediately here-beneath,

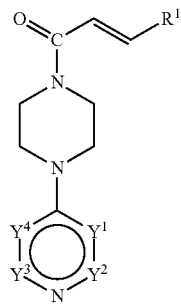

Formula (II)

wherein
$R^1$ is $C_1$-$C_6$-alkyl, $C_1$-$C_6$-alkyloxy $C_1$-$C_6$-alkyl, $C_1$-$C_6$-alkylamino-$C_1$-$C_6$-alkyl, di-($C_1$-$C_6$-alkyl)amino-$C_1$-$C_6$-alkyl, or $C_1$-$C_6$-alkylthio $C_1$-$C_6$-alkyl, wherein each of the radicals is unsubstituted or substituted by one or more halogen atoms, preferably by one or more fluorine atoms, e.g. by 1 to 10, preferably by 1 to 5, fluorine atoms, $Y^1$ is C or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, phenyl, $Y^2$ is C or N, preferably C, wherein C is substituted by $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^3$ is C or N, preferably C, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^4$ is C or N, preferably C, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, phenyl, or $Y^1$ and $Y^2$ and/or $Y^3$ and $Y^4$ are joined together to form a 5- or 6-membered ring system.

In a preferred use according to the invention, in compound of the formula (IIa) the radicals, indices and groups have the following meanings:

$R^1$ is $C_1$-$C_6$-alkyl, $C_1$-$C_6$-alkyloxy $C_1$-$C_6$-alkyl, $C_1$-$C_6$-alkylamino-$C_1$-$C_6$-alkyl, di-($C_1$-$C_6$-alkyl)amino-$C_1$-$C_6$-alkyl or $C_1$-$C_6$-alkylthio $C_1$-$C_6$-alkyl, wherein each of the radicals unsubstituted or substituted by one or more halogen atoms, preferably by one or more fluorine atoms, e.g. by 1 to 10, preferably by 1 to 5, fluorine atoms, $Y^1$ is C or N, wherein C is substituted by $R^{12}$ which is hydrogen, $C_1$-$C_6$-alkyl, or $C_1$-$C_6$-alkoxy, $Y^2$ is C, wherein C is substituted by $R^{13}$ which is hydrogen, $C_1$-$C_6$-alkyl, $C_1$-$C_6$-alkoxy, $C_1$-$C_6$-alkyl carbonyl, $Y^3$ is C, wherein C is substituted by $R^{14}$ which is hydrogen, $C_1$-$C_6$-alkyl, $C_1$-$C_6$-alkoxy, $C_1$-$C_6$-alkyl carbonyl, $Y^4$ is C, wherein C is substituted by $R^{15}$ which is hydrogen, $C_1$-$C_6$-alkyl, $C_1$-$C_6$-alkoxy, or $Y^1$ and $Y^2$ or $Y^3$ and $Y^4$ are joined together to form a 5- or 6-membered ring system.

In a preferred compound for use in the invention of the formula (Ia) or (IIa)
$R^2$ is hydrogen,
$R^3$ is hydrogen,
$R^4$ is hydrogen,
$R^5$ is hydrogen,
$R^6$ is hydrogen or $C_1$-$C_6$-alkyl,
$R^7$ is hydrogen,
X is a carbonyl group,
m is 2
n is 2, the group of formula (A) represents a pyridine, pyrimidine or quinoline group, preferably a pyridine or pyrimidine group, more preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl, and one of A and B and one of D and E contains a nitrogen atom.

In another preferred compound of the formula (IIa)
$R^1$ is $C_1$-$C_6$-alkyl which is unsubstituted or substituted by one or more halogen atoms, preferably by one or more fluorine atoms, e.g. by 1 to 10, preferably by 1 to 5, fluorine atoms.

In another preferred use according to the invention, in the compound of the formula (IIa) the group of the formula (A)

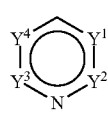

Formula (A)

represents a pyridine, pyrimidine, quinoline, quinazoline, thienopyrimidine, thienopyridine, triazolopyrimidine, pyridopyridine, pyrrolopyridine, pyrazolopyrimidine, pyrazolopyridine, furopyridine, 2,3-dihydrofuropyridine, 2,3-dihydro-1,4-dioxinopyridine, furopyrimidine, pyridazine or cinnoline group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, halogen, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, halogen, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group (preferably a pyridine, pyrimidine or quinoline group), wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyridine, pyrimidine or quinoline group, preferably a pyridine or pyrimidine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl, more preferably each group is optionally substituted by one or more radicals, preferably by one or two radicals selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio.

In another preferred embodiment the group of formula (A) is a pyridine or quinoline group, preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyrimidine group, which is optionally substituted by one or more radicals, preferably by one or two radicals, selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio.

In another preferred embodiment of any of the embodiments as described herein, in the group of formula (A) both $R^{13}$ and $R^{14}$ are different from amino, $C_1$-$C_6$-alkylamino, di($C_1$-$C_6$-alkyl)amino, N-pyrrolidinyl, N-piperidinyl.

In another preferred embodiment of any of the embodiments as described herein, in the group of formula (A) both $R^{13}$ and $R^{14}$ are different from $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl.

In another preferred embodiment of any of the embodiments as described herein, if the group of formula (A) represents a triazine group, both $R^{13}$ and $R^{14}$ are different from $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl.

In another preferred embodiment of any of the embodiments as described herein, in the group of formula (A) all of $R^{12}$, $R^{13}$ $R^{14}$, $R^{15}$ are different from $C_1$-$C_6$-alkoxy and $C_1$-$C_6$-haloalkoxy if X is a sulfonyl group.

Salts, Solvates, N-Oxides and Prodrugs

A salt of the compounds of the formula (I), (Ia) or (Ib), or another compound may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e. to an animal) for a therapeutic benefit, the salt is pharmaceutically acceptable.

Salts may also be of advantage in the synthesis of the compounds according to this invention. For instance certain intermediates may advantageously be used in form of their salts in the preparation process of the compounds according to this invention.

In general, an acid addition salt can be prepared by reacting a free base compound with an approximately stoichiometric amount of an inorganic or organic acid. Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

A solvate of a compound of the formula (I), (Ia) or (Ib), or another compound may be formed by aggregation of said compound of the formula (I) with solvent molecules such as water, alcohols, for example ethanol, aromatic solvents such as toluene, ethers, halogenated organic solvents such as dichloromethane, preferably in a definite proportion by weight.

An N-oxide of a compound of the formula (I), (Ia) or (Ib), or another compound may be formed by oxidation of an N-atom in an amine or N-heterocycle such as pyridine by oxidation agents such as hydrogen peroxide, peracids or inorganic oxidation agents such as potassium peroxymonosulfate (oxone). In preferred N-oxides a nitrogen atom in the group of formula (A) is oxidized, more preferred are N-oxides wherein the nitrogen atom in the para-position is oxidized:

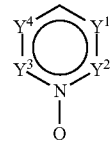

This invention also encompasses prodrug derivatives of the compounds of formula (I) and (Ib). The term prodrug refers to compounds that are transformed in vivo to yield the parent compound of formula (I) or (Ib). In vivo means that in the case of, for example, treatment of a parasitic infection this transformation can occur in the host organism and/or the parasite. Various forms of prodrugs are well known in the art. For example, if the group of formula (A) represents a pyridine, it is possible to form pyridinium salts such as, for example, acyloxyalkylpyridinium salts, which can offer advantages in terms of higher solubility for parenteral dosage forms, which are described in S. K. Davidsen et al., *J. of Med. Chem.* 37 4423-4429 (1994). Other examples of possible prodrugs are compounds that form the double bond present in formula (I) and (Ib) by elimination from a saturated precursor compound:

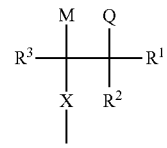

Elimination of MQ will generate compounds of formula (I) or (Ib). If M is hydrogen, this type of elimination is also known in the art as retro-Michael reaction or retro-Michael addition. Examples of such retro-Michael reactions that occur in vivo to generate unsaturated compounds are described in, for example, S. C. Alley, *Bioconjugate Chem.* 19, 759-765 (2008); D. Lopez, *Abstracts of Papers*, 231$^{st}$ National Meeting, Atlanta, Ga., United States, Mar. 26-30, 2006, MEDI-292.

Isomers

The compounds according to this invention, their intermediates and compounds corresponding to the use according to the invention, may exist in various isomeric forms. A reference to a compound according to this invention, an intermediate thereof and a compound corresponding to the use according to the invention always includes all possible isomeric forms of such compound.

In some embodiments, such compounds may have two or more isomers, such as optical isomers or conformational isomers. For example, the compounds can have a (E) or (Z) configuration at the —$CXR^3$=$CR^1R^2$ double bond. In some preferred embodiments, such compound has the (E) configuration, in other embodiments, the compound has the (Z) configuration. In a preferred embodiment the compounds have (E) configuration. For instance the compounds of formula (II) and the compounds of tables A, C and D below exhibit (E) configuration.

Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound.

Treatment Methods Using Compounds According to this Invention

This section pertains to compounds according to the invention and compounds corresponding to the use according to the invention. The compounds and were applicable pharmaceutically acceptable solvates, N-oxides, salts and prodrugs thereof may generally be used as a medicament for animals. In some embodiments of this invention, one or more, preferably one compound according to this invention is administered to treat infections such as parasitic infections (e.g. helminth infections) of an animal (or make a medicament to treat infections such as parasitic infections of an animal). In one embodiment one or more, preferably one compound according to this invention is administered to treat parasitoses of an animal (or make a medicament to treat parasitoses of an animal). The use according to the invention is directed to treat helminth infections.

The term "(parasitic) infection" includes conditions associated with or caused by one or more (parasitic) pathogens; said conditions include clinical conditions (parasitoses) and sub-clinical conditions. The term "treatment of parasitic infection" thus includes both the treatment of parasitoses and the treatment of sub-clinical conditions. The treatment of a parasite infection generally implies the suppression of parasite (e.g. helminth) burdens in the animal below that level at which economic loss occurs.

Sub-clinical conditions are typically conditions not directly leading to clinical symptoms in the parasite infected animal but leading to economic losses. Such economic losses can be e.g. by depression of growth in young animals, lower feed efficiency, lower weight gain in meat producing animals, lower milk production in ruminants, lower egg production in laying hens, or lower wool-production in sheep.

The term "parasitoses" relates to clinically manifest pathologic conditions and diseases associated with or caused by an infection by one or more parasites, such as, for example parasitic gastroenteritis or anemia in ruminants e.g. sheep and goats or colic in horses.

In general, the prevention or treatment of parasitic infection including parasitoses is achieved by administering one or more, preferably one compound according to this invention to treat a parasitic infection such as a helminth infection, the latter treatment being the sole treatment of the use according to the invention.

Thus the invention provides a method of treating a (parasitic) infection such as a helminth infection, including parasitoses, which comprises administering to the animal an antiparasitically, preferably an anthelmintically, effective amount of one or more compounds according to this invention, or where applicable, a compound corresponding to the use according to the invention. Preferably nematode, cestode or trematode infections are treated, more preferably nematode infections.

"Treating (parasitic) infections" includes treating parasitoses and means to partially or completely inhibit the development of (parasitic) infections of an animal susceptible to (parasitic) infection, reduce or completely eliminate the symptoms of infections of an animal having infections, and/or partially or completely cure infections of an animal having infections. This can be achieved by alleviating or reducing pathogen numbers such as parasite numbers in an animal.

The effect of the compounds according to this invention or the use according to the invention can be e.g. ovicidal, larvicidal, and/or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate. Alternatively the parasite is not killed but paralyzed and is then dislodged and excreted by the host animal.

In another aspect the present invention thus provides a pharmaceutical composition comprising an anthelmintically effective amount of one or more, preferably one compound according to this invention or a compound corresponding to the use according to the invention and one or more pharmaceutically acceptable excipients.

The compounds and pharmaceutical compositions according to this invention are useful in treating parasitic infections such as helminth infections of animals. An "effective amount," is the amount or quantity of a compound that is required to alleviate or reduce parasite numbers in an animal, and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound e.g. the parasite count is reduced, after a first administration, by an amount ranging from 5% to about 100%.

This can be evaluated by counting parasites (especially helminthes) directly after necroscopy of the host animal.

The reduction of parasite numbers, especially gastrointestinal helminth parasites can be alternatively measured indirectly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount.

A single administration of a compound according to this invention or a compound corresponding to the use according to the invention is typically sufficient to treat a parasitic infection such as a helminth infection, preferably a nematode, cestode or trematode infection, more preferably a nematode infection. Although such a single dose is typically preferred, it is contemplated that multiple doses can be used. When the compound according to this invention is orally administered, the total dose to treat a disease such as a helminth infection is generally greater than about 0.01 mg/kg (i.e., milligram of compound according to this invention per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 0.5 to about 15 mg/kg, from about 1 to about 10 mg/kg. The same dose range may be suitable for other dosage routes. For example, in some embodiments, the same dose range is used for subcutaneous administration. The desired dose, however, may be less in some instances where the compound according to this invention is administered intravenously.

If the compound according to this invention or a compound corresponding to the use according to the invention is administered parenterally via an injection, the concentration of the compound according to this invention in the dosage form preferably is sufficient to provide the desired therapeutically effective amount of the compound according to this invention in a volume that is acceptable for parenteral administration.

Factors affecting the preferred dosage may include, for example, the parasite species infection to be treated and the development stages of the parasites, the type (e.g., species and breed), age, size, sex, diet, activity, and condition of the of the infected animal; the dosage route; pharmacological considerations, such as the activity, efficacy, pharmacokinetic, and toxicology profiles of the particular composition administered; and whether the compound according to this invention being administered as part of a combination of active ingredients. Thus, the preferred amount of the compound according to this invention can vary, and, therefore, can deviate from the typical dosages set forth above. Determining such dosage adjustments is generally within the skill of those in the art.

In a preferred embodiment the compounds according to this invention are used to treat a helminth infection, such as an infection caused by one or more helminths selected from the group consisting of a) cestodes: e.g. *Anaplocephala* spp.; *Dipylidium* spp.; *Diphyllobothrium* spp.; *Echinococcus* spp.; *Moniezia* spp.; *Taenia* spp.; b) trematodes e.g. *Dicrocoelium* spp.; *Fasciola* spp.; *Paramphistomum* spp.; *Schistosoma* spp.; or c) nematodes, e.g.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., and/or *Wuchereria* spp.;

It is contemplated that the compounds according to this invention and compounds corresponding to the use according to the invention may be used to treat animals, including humans and non-human animals, especially non-human mammals. Such non-human mammals include, for example, livestock mammals (e.g., swine, livestock ruminats like bovines, sheep, goats, etc.), laboratory mammals (e.g., mice, rats, jirds, etc.), companion mammals (e.g., dogs, cats, equines, etc.), and wild and zoo mammals (e.g., buffalo, deer, etc.). It is contemplated that the compounds according to this invention also are suitable to treat non-mammals, such as poultry (e.g., turkeys, chickens, ducks, etc.) and fish (e.g., salmon, trout, koi, etc.).

In some embodiments, one or more, preferably one compound according to this invention or a compound corresponding to the use according to the invention is used to treat an infection by a helminth, such as a nematode, cestode or trematode, preferably a nematode (such as *Haemonchus contortus*), that is resistant to one or more other anthelmintic agents. In some embodiments, the compound according to this invention is active against a helminth, such as a nematode, cestode or trematode, preferably a nematode such as *Haemonchus contortus*, that is resistant to one or more of the following anthelmintics: an avermectin (e.g., ivermectin, selamectin, doramectin, abamectin, and eprinomectin); a milbemycin (moxidectin and milbemycin oxime); a pro-benzimidazole (e.g., febantel, netobimin, and thiophanate); a benzimidazole derivative, such as triclabendazole or a thiazole benzimidazole derivative (e.g., thiabendazole and cambendazole) or a carbamate benzimidazole derivative (e.g., fenbendazole, albendazole (oxide), mebendazole, oxfendazole, parbendazole, oxibendazole, flubendazole); an imidazothiazole (e.g., levamisole and tetramisole); a tetrahydropyrimidine (morantel and pyrantel), an organophosphate (e.g., trichlorphon, haloxon, dichlorvos, and naphthalophos); a salicylanilide (e.g., closantel, oxyclozanide, rafoxanide, and niclosamide); a nitrophenolic compound (e.g., nitroxynil and nitroscanate); benzoenedisulphonamide (e.g., clorsulon); a pyrazinaisoquinoline (e.g., praziquantel and epsiprantel); a heterocyclic compound (e.g., piperazine, diethylcarbamazine, dichlorophen, and phenothiazine); an arsenical (e.g., thiacetarsamide, melorsamine, and arsenamide); cyclooctadepsipeptide (e.g., emodepside); and a paraherquamide.

In some such embodiments, for example, the compound according to this invention or a compound corresponding to the use according to the invention is active against a helminth (for example, *Haemonchus contortus*) resistant to an avermectin, such as ivermectin. In other embodiments, the compound according to this invention is alternatively or additionally active against a helminth (for example, *Haemonchus contortus*) resistant to a benzimidazole derivative, such as fenbendazole. In other embodiments, the compound according to this invention is alternatively or additionally active against a helminth (for example, *Haemonchus contortus*) resistant to levamisole. And, in other embodiments, the compound according to this invention is alternatively or additionally active against a helminth (for example, *Haemonchus contortus*) resistant to pyrantel.

The compounds according to this invention or the compounds corresponding to the use according to the invention may be administered in various dosage forms. The term "dosage form" means that the compounds according to this invention are formulated into a product suitable for administering to the animal via the envisaged dosage route. Such dosage forms are sometimes referred to herein as formulations or pharmaceutical composition.

The formulation type chosen for a dosage form in any instance will depend upon the particular purpose envisaged and the physical, chemical and biological properties of the compound according to this invention.

Dosage forms useful in the current invention can be liquid, semi-solid or solid dosage forms.

Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability. A dry powder (or granule) for reconstitution is reconstituted as a solution or as a suspension immediately prior to injection. The principal advantage of this dosage form is that it overcomes the problem of instability in solution or suspension.

One possible dosage route is the oral dosage route, wherein the compound according to this invention is administered via the mouth. Oral dosage forms suitable for oral administration comprise liquids (e.g. drench or drinking water formulations), semi-solids (e.g. pastes, gels), and solids (e.g. tablets, capsules, powders, granules, chewable treats, premixes and medicated blocks).

A drench is a liquid oral formulation that is administered directly into the mouth/throat of an animal, especially a livestock animal, by means of a "drench gun" or syringe or another suitable device. When the composition is administered in the animal recipient's drinking water or as a drench, it may be convenient to use a solution or suspension formulation. This formulation can be, for example, a concentrated suspension that is mixed with water or a dry preparation that is mixed and suspended in the water.

Semi-solid oral formulations (pastes or gels) are generally administered via an applicator directly into the mouth of an animal or mixed with the feed.

Solid oral formulations are either administered directly to an animal (tablet, capsule) or mixed with the feed or via medicated feed blocks.

When the oral formulation is administered via a non-human animal's feed, it may, for example, be fed as a discrete feed or as a chewable treat. Alternatively (or additionally), it may, for example, be intimately dispersed in the animal recipient's regular feed, used as a top dressing, or in the form of solid pellets, paste or liquid that is added to the finished feed. When the oral formulation is administered as a feed additive, it may be convenient to prepare a "premix" in which the oral formulation is dispersed in a liquid or solid carrier. This "premix" is, in turn, dispersed in the animal's feed using, for example, a conventional mixer.

Several modified-release delivery systems have been developed, that take advantage of the unique anatomy of the ruminant forestomach, i.e. for intra-ruminal administration. An intraruminal bolus is a specific formulation for ruminants (cattle, sheep, goats, buffalos, camelids, deer etc). It is a veterinary delayed release delivery system which remains in the rumeno-reticular sac of a ruminant animal over an extended period of time and in which the therapeutically active substance has a predictable and delayed release pattern. Such intraruminal boluses are usually administered using a balling gun or another suitable device.

It is contemplated that the compounds according to this invention or compounds corresponding to the use according to the invention may alternatively be administered via non-oral dosage routes, such as topically (e.g., via a spot-on, pour-on or transdermal patch), or parenterally (e.g., subcutaneous injection, intravenous injection, intramuscular injection, etc.).

For instance the compounds according to this invention may be administered topically using a transdermal formulation (i.e. a formulation that passes through the skin). Alternatively the compounds according to this invention may be administered topically via the mucosa.

Topical dosage forms suitable for topical administration comprise liquids (e.g. bath, spray, spot-on), semi-solids (e.g. creams, gels), and solids (e.g. patches, powders, collars). Typical topical formulations for animals are liquid or semi-liquid dosage forms. Typical formulations for transdermal and mucosal administration include, for example, pour-ons, spot-ons, dips, sprays, mousses, shampoos, powders, gels, hydrogels, lotions, solutions, creams, ointments, dusting powders, dressings, foams, films, skin patches, limb bands, collars, ear tags, wafers, sponges, fibers, bandages, and microemulsions. When a liquid formulation is used topically on skin, it can be administered by, for example, pouring on (pour-on or spot-on), spreading, rubbing, atomizing, spraying, dipping, bathing, or washing.

The pour-on or spot-on methods, for example, comprise applying the formulation to a specific location of the skin or coat, such as on the neck or backbone of the animal. This may be achieved by, for example, applying a swab or drop of the pour-on or spot-on formulation to a relatively small area of the recipient animal's skin or coat (i.e., generally no greater than about 10% of the animal recipient's skin or coat). In some embodiments, the compound according to this invention is dispersed from the application site to wide areas of the fur due to the spreading nature of the components in the formulation and the animal's movements while, in parallel, being absorbed through the skin and distributed via the animal recipient's fluids and/or tissues.

Parenteral formulations and delivery systems for non-oral routes comprise liquids (e.g. solutions, suspensions, emulsions, and dry powders for reconstitution), semi-solids and solids (e.g. implants). The majority of implants that are used in veterinary medicine are compressed tablets or dispersed matrix systems in which the drug is uniformly dispersed within a nondegradable polymer or alternatively extrusion products.

Pharmaceutical Compositions

This invention also is directed to pharmaceutical compositions (or medicaments) comprising one or more, preferably one compound according to this invention. The compositions also may (and preferably will) comprise one or more pharmaceutically acceptable excipients. The following subject matter about pharmaceutical compositions is also applicable to pharmaceutical compositions comprising compounds corresponding to the use according to this invention.

Pharmaceutical compositions of the present invention may be manufactured by, for example, processes known in the art. These processes include, for example, a variety of known mixing, dissolving, granulating, emulsifying, encapsulating, entrapping, and lyophilizing processes. Optimal formulation depends on, for example, the dosage route (e.g. oral, injection, topical).

Solid dosage forms, for example, may be prepared by, for example, intimately and uniformly mixing the compounds with fillers, binders, lubricants, glidants, disintegrants, flavoring agents (e.g., sweeteners), buffers, preservatives, pharmaceutical-grade dyes or pigments, and controlled release agents.

Oral dosage forms other than solids may be prepared by mixing the compounds with, for example, one or more solvents, viscosity-enhancing agents, surfactants, preservatives, stabilizers, resins, fillers, binders, lubricants, glidants, disintegrants, co-solvents, sweeteners, flavorings, perfuming agents, buffers, suspending agents, and pharmaceutical-grade dyes or pigments.

Contemplated binders include, for example, gelatin, acacia, and carboxymethyl cellulose.

Contemplated lubricants include, for example, magnesium stearate, stearic acid, and talc.

Contemplated disintegrants include, for example, corn starch, alginic acid, sodium carboxymethylcellulose, and sodium croscarmellose.

Contemplated buffers include, for example, sodium citrate, and magnesium and calcium carbonate and bicarbonate.

Contemplated solvents include, for example, water, petroleum, animal oils, vegetable oils, mineral oil, and synthetic oil. Physiological saline solution or glycols (e.g., ethylene glycol, propylene glycol, or polyethylene glycol) also may be included. The solvent preferably has sufficient chemical properties and quantity to keep the compounds solubilized at temperatures in which the composition is stored and used.

Contemplated viscosity-enhancing agents include, for example, polyethylene, methylcellulose, sodium carboxymethylcellulose, hydroxypropyl-methylcellulose, hydroxypropylcellulose, sodium alginate, carbomer, povidone, acacia, guar gum, xanthan gum, tragacanth, methylcellulose, carbomer, xanthan gum, guar gum, povidone, sodium carboxymethylcellulose, magnesium aluminum silicate, carboxyvinyl polymers, carrageenan, hydroxyethyl cellulose, laponite, water-soluble salts of cellulose ethers, natural gums, colloidal magnesium aluminum silicateor finely divided silica, homopolymers of acrylic acid crosslinked with an alkyl ether of pentaerythritol or an alkyl ether of sucrose, and carbomers.

Contemplated surfactants include, for example, polyoxyethylene sorbitan fatty acid esters; polyoxyethylene monoalkyl ethers; sucrose monoesters; lanolin esters and ethers; alkyl sulfate salts; and sodium, potassium, and ammonium salts of fatty acids.

Contemplated preservatives include, for example, phenol, alkyl esters of parahydroxybenzoic acid (e.g., methyl p-hydroxybenzoate (or "methylparaben") and propyl p-hydroxybenzoate (or "propylparaben")), sorbic acid, o-phenylphenol benzoic acid and the salts thereof, chlorobutanol, benzyl alcohol, thimerosal, phenylmercuric acetate and nitrate, nitromersol, benzalkonium chloride, and cetylpyridinium chloride.

Contemplated stabilizers include, for example, chelating agents and antioxidants.

Solid dosage forms also may comprise, for example, one or more excipients to control the release of the compounds. For example, it is contemplated that the compounds may be dispersed in, for example, hydroxypropylmethyl cellulose. Some oral dosage forms (e.g., tablets and pills) also may be prepared with enteric coatings.

Topical dosage route uses, for example, a concentrated liquid or semi-liquid solution, suspension (aqueous or non-aqueous), emulsion (water-in-oil or oil-in-water), or microemulsion comprising a compounds dissolved, suspended, or emulgated in a pharmaceutically-acceptable liquid vehicle. In such embodiments, a crystallization inhibitor optionally may generally be present.

Such a pour-on or spot-on formulation can be prepared by dissolving, suspending, or emulsifying the compounds in a suitable skin-fitted solvent or solvent mixture. Other excipients may be included as well, such as, for example, a surfactant, colorant, antioxidant, stabilizer, adhesive, etc. Contemplated solvents include, for example, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oil, DMF, liquid paraffin, silicone, dimethylacetamide, N-methylpyrrolidone, or 2,2-dimethyl-4-oxy-methylene-1,3-dioxolane.

In some embodiments, a topical formulation (particularly a pour-on or spot-on formulation) comprises a carrier that promotes the absorption or penetration of the compounds through the skin into the blood stream, other bodily fluids (lymph), and/or body tissue (fat tissue). Contemplated examples of dermal penetration enhancers include, for example, dimethylsulfoxide, isopropyl myristate, dipropylene glycol pelargonate, silicone oil, aliphatic esters, triglycerides, and fatty alcohols.

Topical formulations also (or alternatively) may comprise, for example, one or more spreading agents. These substances act as carriers that assist in distributing an active ingredient over the animal recipient's coat or skin. They may include, for example, isopropyl myristate, dipropylene glycol pelargonate, silicone oils, fatty acid esters, triglycerides, and/or fatty alcohols. Various spreading oil/solvent combinations also may be suitable, such as, for example, oily solutions, alcoholic and isopropanolic solutions (e.g., solutions of 2-octyl dodecanol or oleyl alcohol), solutions of esters of monocarboxylic acids (e.g., isopropyl myristate, isopropyl palmitate, lauric acid oxalic ester, oleic acid oleyl ester, oleic acid decyl ester, hexyl laurate, oleyl oleate, decyl oleate, and caproic acid esters of saturated fatty alcohols having a carbon chain of 12 to 18 carbons), solutions of esters of dicarboxylic acids (e.g., dibutyl phthalate, diisopropyl isophthalate, adipic acid diisopropyl ester, and di-n-butyl adipate), or solutions of esters of aliphatic acids (e.g., glycols). When the formulation comprises a spreading agent, it also may be advantageous to include a dispersant, such as, for example, pyrrolidin-2-one, N-alkylpyrrolidin-2-one, acetone, polyethylene glycol or ether or ester thereof, propylene glycol, or synthetic triglycerides.

When formulated in, for example, an ointment, it is contemplated that the compounds may be mixed with, for example, either a paraffinic or a water-miscible ointment base. When formulated in a cream, it is contemplated that the compounds may be formulated with, for example, an oil-in-water cream base. In some instances, the aqueous phase of the cream base includes, for example at least about 30% (w/w) of a polyhydric alcohol, such as propylene glycol, butane-1,3-diol, mannitol, sorbitol, glycerol, polyethylene glycol, or a mixture thereof.

Injectable formulations may be prepared according to, for example, the known art using suitable solvents, solubilizing agents, protecting agents, dispersing agents, wetting agents, and/or suspending agents. Contemplated carrier materials include, for example, water, ethanol, butanol, benzyl alcohol, glycerin, 1,3-butanediol, Ringer's solution, isotonic sodium chloride solution, bland fixed oils (e.g., synthetic mono- or diglycerides), vegetable oil (e.g., corn oil), dextrose, mannitol, fatty acids (e.g., oleic acid), dimethyl acetamide, surfactants (e.g., ionic and non-ionic detergents), N-methylpyrrolidone, propylene glycol, and/or polyethylene glycols (e.g., PEG 400). Contemplated solubilizing agents include, for example, polyvinyl pyrrolidone, polyoxyethylated castor oil, polyoxyethylated sorbitan ester, and the like. Contemplated protecting agents include, for example, benzyl alcohol, trichlorobutanol, p-hydroxybenzoic acid ester, n-butanol, and the like.

In some embodiments, a parenteral formulation is, for example, prepared from sterile powders or granules having one or more of the carriers materials discussed above for other formulations. The compound is, for example, dissolved or suspended in a liquid comprising water, polyethylene glycol, propylene glycol, ethanol, corn oil, cottonseed oil, peanut oil, sesame oil, benzyl alcohol, sodium chloride, and/or various buffers. The pH generally may be adjusted, if necessary, with a suitable acid, base, or buffer.

Other inert ingredients may generally be added to the composition as desired. To illustrate, it is contemplated that these may include, for example, lactose, mannitol, sorbitol, calcium carbonate, sodium carbonate, tribasic calcium phosphate, dibasic calcium phosphate, sodium phosphate, kaolin, compressible sugar, starch, calcium sulfate, dextro or microcrystalline cellulose, colloidal silicon dioxide, starch, sodium starch glycolate, crospovidone, microcrystalline cellulose, tragacanth, hydroxypropylcellulose, pregelatinized starch, povidone, ethylcellulose, hydroxypropylcellulose, hydroxypropylmethylcellulose, and methylcellulose.

Further aspects regarding formulation of drugs and various excipients are found in, for example, Gennaro, A. R., et al., eds., *Remington: The Science and Practice of Pharmacy* (Lippincott Williams & Wilkins, 20th Ed., 2000). Another source regarding formulation of drugs and various excipients is found in, for example, Liberman, H. A., et al., eds., *Pharmaceutical Dosage Forms* (Marcel Decker, New York, N.Y., 1980).

The concentration of the compounds according to this invention in the applied dosage form may vary widely depending on, for example, the dosage route. In general, the concentration is from about 1 to about 70% (by weight). In some such embodiments, for example, the concentration is from about 1 to about 50% (by weight), or from about 10 to about 50% (by weight). In other embodiments, the concentration is from about 35 to about 65% (by weight), from about 40 to about 60% (by weight), from about 45 to about 55% (by weight), or about 50% (by weight).

In another aspect the present invention thus provides a pharmaceutical composition comprising an anthelmintically effective amount of one or more, preferably one compound according to this invention and one or more pharmaceutically acceptable excipients.

The formulation type chosen for a dosage form in any instance will depend upon the particular purpose envisaged and the physical, chemical and biological properties of the compound according to this invention.

The compounds and pharmaceutical compositions according to this invention are useful in treating parasitic infections such as helminth infections of animals. An "effective amount," is the amount or quantity of a compound that is required to alleviate or reduce parasite numbers in an animal, and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound.

This can be evaluated by counting parasites (especially helminthes) directly after necroscopy of the host animal.

The reduction of parasite numbers, especially gastrointestinal helminth parasites can be alternatively measured indirectly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount".

Examples of Contemplated Combination Therapies

The methods and pharmaceutical compositions of this invention encompass methods wherein a compound according to this invention or a compound corresponding to the use according to the invention is the sole active ingredient administered to the recipient animal. It is contemplated, however, that the methods and pharmaceutical compositions also encompass combination therapies wherein a compound is administered in combination with one or more other pharmaceutically acceptable active ingredients. The other active ingredient(s) may be, for example, one or more other compounds according to this invention or one or more other compounds corresponding to the use according to the invention. Alternatively (or additionally), the other active ingredient(s) may be one or more pharmaceutically acceptable compounds that are not compounds according to this invention or compounds corresponding to the use according to the invention. The other active ingredient(s) may target the same and/or different parasites and conditions.

Contemplated active ingredient(s) that may be administered in combination with the compounds include, for example, pharmaceutically acceptable anthelmintics, insecticides and acaricides, insect growth regulators, anti-inflammatories, anti-infectives, anti-protozoals, hormones, dermatological preparations (e.g., antiseptics and disinfectants), and immunobiologicals (e.g., vaccines and antisera) for disease prevention.

Therefore this invention is also directed to the use as a medicament of combinations comprising a) one or more compounds according to this invention or one or more compounds corresponding to the use according to this invention with b) one or more pharmaceutically acceptable active compounds which differ in structure from component a). The active compounds b) are preferably anthelmintic compounds, more preferably selected from the group consisting of avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); benzimidazole derivatives, such as triclabendazole or a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole, flubendazole); an imidazothiazoles (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazineisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); and amino-acetonitrile compounds (e.g. monepantel, AAD 1566); tribendimidine (amidine compound); amidine compounds (e.g., amidantel and tribendimidin), including all pharmaceutically acceptable forms, such as salts, solvates or N-oxides.

Preferred combinations are comprising a) one compound selected from the group of compounds A-1 to A-1162, Aa-1, Aa-2, Aa-3, B-1 to B-19, C-1 to C-331 and D-1 to D-95 of the tables A, B, C and D below and variants as mentioned at the bottom of these tables (or salts, solvates, N-oxides or pro-drugs thereof) and b) one compound selected from the group consisting of anthelmintic avermectins (e.g., ivermectin, selamectin, doramectin, abamectin, emamectin and eprinomectin); milbemycins (moxidectin and milbemycin oxime); pro-benzimidazoles (e.g., febantel, netobimin, and thiophanate); benzimidazole derivatives, such as thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidines (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazineisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); amino-acetonitrile compounds (e.g. monepantel, AAD 1566); tribendimidine (amidine compound); and amidantel (amidine compound); including all pharmaceutically acceptable forms, such as salts.

Preferred combinations comprise at least one compound selected from the group of compounds A-1 to A-1162, Aa-1, Aa-2, Aa-3, B-1 to B-19, C-1 to C-331 and D-1 to D-95 of the tables A, B, C and D below and variants as mentioned at the bottom of these tables (or salts, solvates, N-oxides or prodrugs thereof) and abamectin, ivermectin, emamectin, eprinomectin, doramectin, moxidectin, milbemycin oxime; or
closantel, oxyclozanide, rafoxanide, niclosamide; or
nitroxynil, nitroscanate, clorsulon; or
praziquantel, epsiprantel; or
emodepside, derquantel, monepantel.

Examples of such combinations are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with abamectin.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with ivermectin.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with emamectin.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with eprinomectin.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with doramectin.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with moxidectin.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with milbemycin oxime.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with closantel.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with oxyclozanide.

Other examples are combinations of one of the compounds A-1 to A-1162, Aa-1, Aa-2, Aa-3, B-1 to B-19, C-1 to C-331 and D-1 to D-95 of tables A, B, C and D below and variants as mentioned at the bottom of these tables with rafoxanide.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with niclosamide.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with nitroxynil.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with nitroscanate.

Other examples are combinations of one of the compounds A-1 to A-1162, Aa-1, Aa-2, Aa-3, B-1 to B-19, C-1 to C-331 and D-1 to D-95 of tables A, B, C and D below and variants as mentioned at the bottom of these tables with clorsulon.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with praziquantel.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with epsiprantel.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with emodepside.

Other examples are combinations of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with derquantel.

Other examples are combinations of one of the compounds A-1 to A-1162, Aa-1, Aa-2, Aa-3, B-1 to B-19, C-1 to C-331 and D-1 to D-95 of the Tables A, B, C and D below and variants as mentioned at the bottom of these tables with monepantel.

Examples of such combinations are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with abamectin.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with ivermectin.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with emamectin.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with eprinomectin.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables and D with doramectin.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with moxidectin.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with milbemycin oxime.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with closantel.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with oxyclozanide.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with rafoxanide.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with niclosamide.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with nitroxynil.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with nitroscanate.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with clorsulon.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with praziquantel.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with epsiprantel.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with emodepside.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with derquantel.

Other examples are combinations of a salt of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with monepantel.

Examples of such combinations are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with abamectin.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with ivermectin.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with emamectin.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with eprinomectin.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with doramectin.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with moxidectin.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with milbemycin oxime.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with closantel.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with oxyclozanide.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with rafoxanide.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with niclosamide.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with nitroxynil.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with nitroscanate.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with clorsulon.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with praziquantel.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with epsiprantel.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with emodepside.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with derquantel.

Other examples are combinations of a solvate of one of the compounds A-1 to A-1162, Aa-1, Aa-2, Aa-3, B-1 to B-19, C-1 to C-331 and D-1 to D-95 of the tables A, B, C and D below and variants as mentioned at the bottom of these tables with monepantel.

Examples of such combinations are combinations of a N-oxide of one of the compounds A-1 to A-1162, B-1 to B-19, C-1 to C-331 and D-1 to D-95 of the tables A, B, C and D below and variants as mentioned at the bottom of these tables with abamectin.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with ivermectin.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with emamectin.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with eprinomectin.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with doramectin.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with moxidectin.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with milbemycin oxime.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with closantel.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with oxyclozanide.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with rafoxanide.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with niclosamide.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with nitroxynil.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with nitroscanate.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with clorsulon.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with praziquantel.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with epsiprantel.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with emodepside.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with derquantel.

Other examples are combinations of a N-oxide of one of the compounds A-1 to A-1162, B-1 to B-19, C-1 to C-331 and D-1 to D-95 of the tables A, B, C and D below and variants as mentioned at the bottom of these tables with monepantel.

The compounds as described herein can be combined with pharmaceutically acceptable insecticides or acaricides. Such pharmaceutically acceptable insecticides and acaricides include, for example, acetamiprid, acetoprole, amitraz, amidoflumet, avermectin, azadirachtin, bifenthrin, bifenazate, buprofezin, bistrifluoron, chlorfenapyr, chlorfluazuron, chlorantraniliprole, chlorpyrifos, chromafenozide, clothianidin, cyantraniliprole, cyflumetofen, β-cyfluthrin, cyhalothrin, λ-cyhalothrin, cymiazole cypermethrin, cyromazine, deltamethrin, demiditraz, diafenthiuron, diazinon, diflubenzuron, dimefluthrin, dinotefuran, emamectin, esfenvalerate, ethiprole, fenoxycarb, fenpropathrin, fenvalerate, fipronil, flonicamid, flubendiamide, flucythrinate, tau-fluvalinate, flufenoxuron, halofenozide, hexaflumuron, imidacloprid, indoxacarb, lufenuron, metaflumizone, methoprene, metofluthrin, methoxyfenozide, nitenpyram, novaluron, noviflumuron, permethrin, phosmet, profluthrin, protrifenbute, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen, spirotetramat, sulfoxaflor, tebufenozide, tebufenpyrad, teflubenzuron, tefluthrin, tetrachlorvinphos, tetramethylfluthrin, thiacloprid, thiamethoxam, tolfenpyrad, tralomethrin, and triflumuron. General references discussing antiparasitic agents, such as insecticides and acaricides, include, for example, *The Pesticide Manual*, 13th Edition, C. D. S. Tomlin, Ed., British Crop Protection Council, Farnham, Surrey, U.K. (2003).

The compounds as described herein can be combined with pharmaceutically acceptable insect growth regulators. Such pharmaceutically acceptable insect growth regulators include, for example, methoprene, pyriproxyfen, tetrahydroazadirachtin, chlorfluazuron, cyromazine, diflubenzuron, fluazuron, flucycloxuron, flufenoxuron, hexaflumuron, lufenuron, ifenuron, tebufenozide, and triflumuron. These compounds tend to provide both initial and sustained treatment of parasite infections at all stages of insect development, including eggs, on the animal subject, as well as within the environment of the animal subject.

The compounds as described herein can be combined with pharmaceutically acceptable anti-protozoals. Such pharmaceutically acceptable anti-protozoals include, for example, triazintriones like toltrazuril and ponazuril and triazindiones such as clazuril, diclazuril and letrazuril.

In some contemplated embodiments, the compounds are administered with pyridylmethylamine derivatives, such as, for example, pyridylmethylamine derivatives discussed in European Patent Appl. EP0539588 or Int'l Patent Appl. Publ. WO2007/115643.

In some contemplated embodiments, the compounds is administered with nodulisporic acids and derivatives thereof, such as, for example, compounds discussed in U.S. Pat. Nos. 5,399,582; 5,945,317; 5,962,499; 5,834,260; 6,221,894; or 5,595,991; or Int'l Patent Appl. Publ. 1996/29073.

In some contemplated embodiments, the compounds are administered with dihydroazole compounds, such as, for example, compounds discussed in WO 2010/75591.

In some contemplated embodiments, the compounds are administered with anthelminic proteins, such as, for example *Bacillus thuringensis* crystal proteins e.g. described in WO 2010/053517.

Other antiparasitic compounds contemplated to be useful in combination therapies with the compounds include, for example, imidazo[1,2-b]pyridazine compounds discussed in US Patent Appl. Publ. No. 2005-0182059; 1-(4-Mono and di-halomethylsulphonylphenyl)-2-acylamino-3-fluoropropanol compounds discussed U.S. Pat. No. 7,361,689; trifluoromethanesulfonanilide oxime ether compounds discussed in U.S. Pat. No. 7,312,248; n-[(phenyloxy)phenyl]-1,1,1-trifluoromethanesulfonamide and n-[(phenylsulfanyl)phenyl]-1,1,1-trifluoromethanesulfonamide compounds discussed in US Patent Appl. Publ. 2006-0281695; and 2-phenyl-3-(1H-pyrrol-2-yl)acrylonitrile compounds discussed in US Appl. Publ. 2006/0128779; isoxazoline compounds discussed in WO Patent Appl, Publ. 2005-085216, WO 2007-026965, WO 2007-070606, WO 2007-075459, WO 2007-079162, WO 2007-105814, WO 2007-125984, WO 2008-019760, WO 2008-122375, WO 2008-150393, WO 2009-002809, WO 2009-003075, WO 2009-022746, WO 2009-035004, WO 2009-045999, WO 2009-051956, WO 2009-035004.

In the contemplated combination therapies, the compounds according to this invention may be administered before, simultaneously, and/or after the other active ingredient(s). In addition, the compounds according to this invention may be administered in the same composition as the other active ingredient(s) and/or in separate compositions from the other active ingredient(s). Further, the compounds according to this invention and other active ingredient(s) may be administered via the same and/or different dosage route.

When the compounds according to this invention are administered in a combination therapy, the weight ratio of the active ingredients may vary widely. Factors influencing this ratio include, for example, the particular compounds; the identity of the other active ingredient(s) be administered in the combination therapy; the dosage route of the compounds and other active ingredient(s); the target condition and pathogen; the type (e.g., species and breed), age, size, sex, diet, activity, and condition of the animal; and pharmacological considerations, such as the activity, efficacy, pharmacokinetic, and toxicology profiles of the compounds and other active ingredient(s). In some contemplated embodiments, for example, the weight ratio of the compounds to the other active ingredient(s) is, for example, is from about 1:3000 to about 3000:1. In some such instances, the weight ratio is from about 1:300 to about 300:1. In other such instances, the weight ratio is from about 1:30 and about 30:1.

In addition to other active ingredients, it is contemplated that the compounds may be administered with one or more other compounds that beneficially affects (e.g. enhances or prolongs) the activity (or other characteristic, such as safety) of the compounds. For example, it is contemplated that the compounds may be administered with one or more synergists, such as, for example, piperonyl butoxide (PBO) and triphenyl phosphate (TPP). Other synergists include, for example, N-(2-ethylhexyl)-8,9,10-trinorborn-5-ene-2,3-dicarboxamide (also known as "ENT 8184" or "MGK 264") and Verbutin (also known as "MB-599").

This invention also is directed to kits that are, for example, suitable for use in performing the methods of treatment described above. The kit comprises a therapeutically effective amount of one or more compounds of this invention, and an additional component. The additional component(s) may be, for example, one or more of the following: another ingredient (e.g., an excipient or active ingredient), an apparatus for combining the compound of this invention with another ingredient and/or for administering the compound of this invention, or a diagnostic tool.

The compounds used according to this invention show an excellent activity in treating parasite infections and in addition are acceptable for the animals treated.

EXAMPLES

The following examples are merely illustrative, and not limiting to the remainder of the disclosure in any way.

A: General Description of Synthesis of Compounds as Described in this Specification The compounds as described in this specification can be obtained by various synthesis routes. A person skilled in the art will choose the synthetic route to obtain a compound as described in this specification depending on the nature of its radicals as defined in Formula (I). This is illustrated in the following schemes, which are merely illustrative but not limiting the disclosure in any way.

Scheme 1:
route 1a

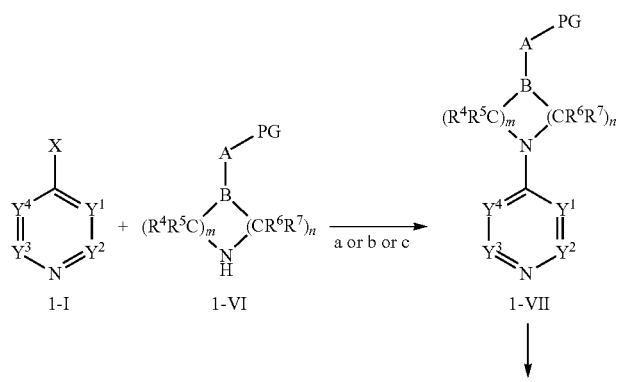

-continued
route 1
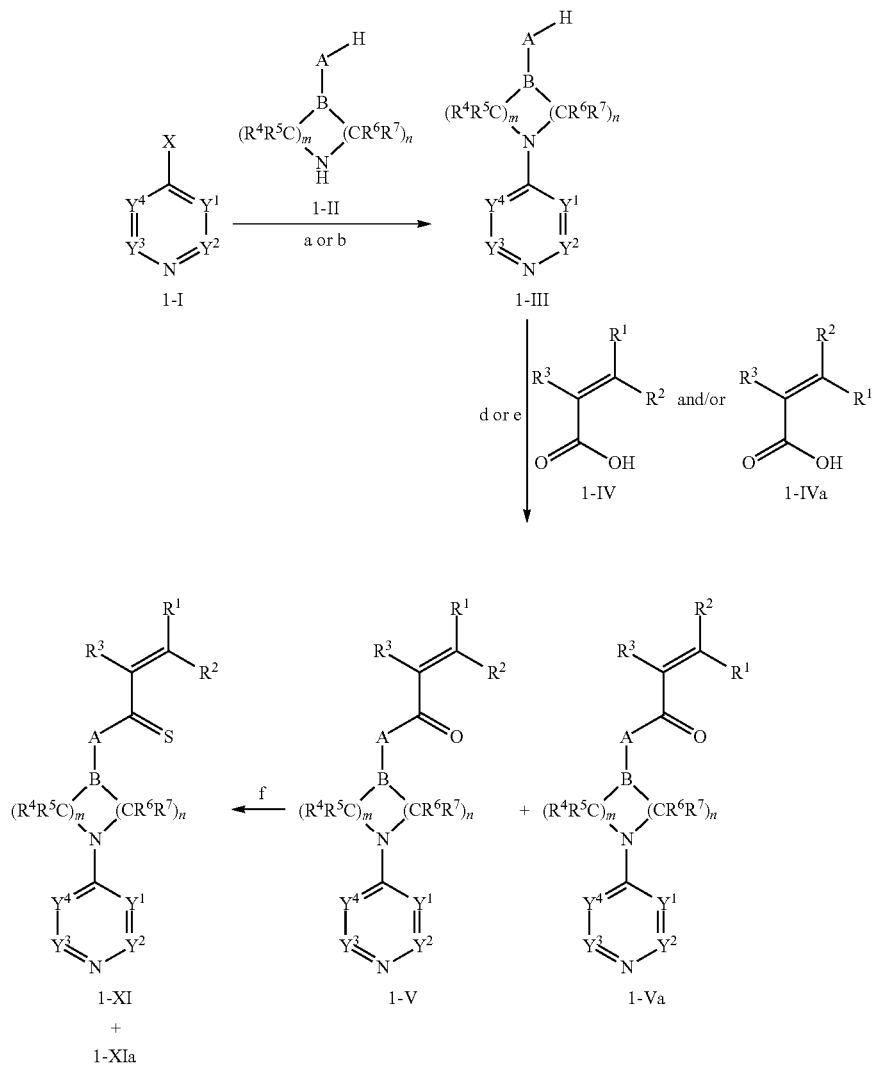
route 2
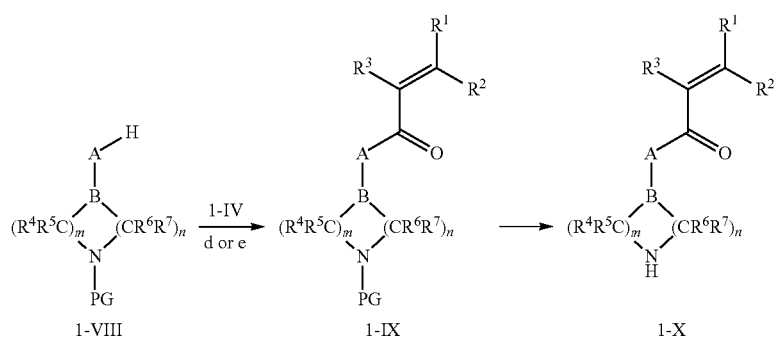

Exemplary conditions: a: propyleneglycolmonomethylether, 115° C.; b: pyridine, reflux; c: palladium acetate, 2,2'-Bis(diphenylphosphino)-1,1'-binaphthyl (BINAP), caesium carbonate, dioxane; d: oxalyl chloride, dichloromethane (DCM), dimethylformamide (DMF) then DCM, triethylamine; e: 1-[bis(dimethylamino)methylene]-1H-1,2,3-Triazolo[4,5-b]pyridinium-3-oxide hexafluorophosphate (HATU), diisopropylethylamine, DMF, room temperature; f: Lawesson's reagent, tetrahydrofuran (THF), 130° C.

A compound of general formula 1-V can be synthesized as shown in scheme 1: in route 1 a heteroarylcompound 1-I is reacted with a cyclic diamine 1-II to give 1-III. 1-I contains a suitable leaving group X, which is preferably a halogen like chloro or bromo or a nitro group. The reaction with 1-II takes place in an inert solvent like DMF or dimethylacetamide, preferably in a diol-derived solvent like ethyleneglycolmonomethylether or propyleneglycolmonomethylether and preferably at elevated temperatures. 1-II is employed preferably in excess. An additional base might be added. Alternatively, the reaction can be done in pyridine as solvent. The diamine can be protected with a suitable protecting group as in 1-VI of route 1a. Suitable protecting groups (PG) for the nitrogen in 1-VI include, but are not limited to, preferably tert-butyl carbamate (Boc), benzyl carbamate (Cbz) and the like. A protected diamine 1-VI can be reacted under the same conditions as 1-II, alternatively Pd-catalysis can be used employing a Pd-containing molecule like palladium acetate, a phosphorus-containing ligand like BINAP, a base like caesium carbonate or sodium tert-butoxide in a solvent like an ether-containing solvent like diethylether, dioxane or tetrahydrofuran, preferably dioxane or an inert solvent like toluene. The protecting group in the intermediate 1-VII can be removed by suitable methods known to a person skilled in the art; if PG is a Boc-group, for example, the protecting group can be removed by an acid like trifluoroacetic acid or hydrochloric acid to give the amine 1-III. Other suitable methods for protection and deprotection are described in, for example, Green and Wuts, *Protective Groups in Organic Synthesis*, 3$^{rd}$ edition, John Wiley & Sons, New York, 1999. 1-III is acylated with an unsaturated acid derivative 1-IV to give the final product 1-V. 1-IV can be accompanied by the isomeric 1-IVa, so that a mixture of 1-IV and 1-IVa is used in the acylation step. In this case a mixture of 1-V and 1-Va is formed that can be separated by methods known to a person skilled in the art, e.g. by chromatography. Or 1-IVa can be used in a pure form in the acylation step to give 1-Va. Thus, if in the following descriptions and schemes the acid 1-IV is mentioned, the same applies for the isomeric acid 1-IVa, either in its pure form or in form of a mixture of 1-IV and 1-IVa. The same applies for reaction products derived from 1-IV: these can be obtained in pure form if the isomerically pure 1-IV or 1-IVa are used in the acylation step, or they can be obtained as a mixture if a mixture of 1-IV and 1-IVa is used and might be separated then by methods known to a person skilled in the art, e.g. by chromatography. There are many acylation methods known to a person skilled in the art: 1-IV can be converted to an acid chloride with oxalyl chloride, thionyl chloride or the like which can be isolated or used directly to react with 1-III in the presence of a base like triethylamine or diisopropylethylamine to give 1-V. The base might also be polymer-supported to ease work-up. The base might be used in excess, the excess might be removed using aqueous work-up or polymer-supported reagents like polymer-supported acid chloride. The acid 1-IV can also be reacted directly with the amine 1-III using coupling reagents like N,N,N',N'-tetramethyl-O-(7-azabenzotriazol-1-yl)-uronium hexafluorophosphate (HATU), N,N,N',N'-tetramethyl-O-(1H-benzotriazol-1-yl)-uronium hexafluorophosphate (HBTU), 1-hydroxy-7-azabenzotriazole (HOAt), N,N'-dicyclohexylcarbodiimide (DCC) or the like. Other suitable amide coupling procedures are described in Goodman, M.; Felix, A.; Moroder, L.; Toniolo, C. in volume E22a of *Methods of Organic Chemistry (Houben-Weyl), Synthesis of Peptides and Peptidomimetics, 4$^{th}$ edition*, Georg Thieme Verlag, Stuttgart—New York, 2002. In an alternative synthetic route (route 2) the diamine can also be used as 1-VIII where the other nitrogen is protected. Coupling with 1-IV can be done as described for 1-III followed by deprotection as described for 1-VII yielding 1-X which is reacted with 1-I as described for the reaction of 1-I with 1-VI. 1-V and 1-Va can be converted into their thiocarbonyl analogue 1-XI and 1-XIa by treatment with, for example, Lawesson's reagent under microwave heating. A compound of general formula 1-V can be substituted at $Y^1$-$Y^4$. This substituent can already be present in the heteroaryl compound 1-I. A person skilled in the art will appreciate that it can also be introduced in a compound 1-VII, 1-III or 1-V. For example, $Y^1$-$Y^4$ in 1-I might be substituted by a potential leaving group like, for example, halogen, which can be replaced by another group, for example a nucleophilic group in, for example, a nucleophilic substitution reaction. Or, for example, $Y^1$-$Y^4$ in 1-III might be substituted by a potential leaving group like, for example, halogen, which can be replaced by another group, for example a nucleophilic group in, for example, a nucleophilic substitution reaction. Or, for example, $Y^1$-$Y^4$ in 1-VII might be substituted by a potential leaving group like, for example, halogen, which can be replaced by another group, for example a nucleophilic group in, for example, a nucleophilic substitution reaction. 1-I might also be substituted at $Y^1$-$Y^4$ with a group that can react with a group present in the reaction partner 1-VI or 1-II like, for example, the amino group in 1-II or 1-VI. In this case the reacting group in 1-I can be protected by a protecting group by methods known to a person skilled in the art. For example, 1-I can be substituted by an acyl group. This acyl group can be protected as, for example, an oxolan prior to the reaction with 1-II or 1-VI and deprotected by, for example, aqueous acid after the reaction with 1-II or 1-VII as described in, for example, Green and Wuts, *Protective Groups in Organic Synthesis*, 3$^{rd}$ edition, John Wiley & Sons, New York, 1999. The same applies for the following schemes in an analogous way. The heteroaryl compound 1-I can be substituted at the N-Atom with oxygen, thus being a heteroaryl-N-oxide, for example a quinoline-N-oxide or a pyridine-N-oxide. Methods for the synthesis of such heteroaryl-N-oxides are described in, for example, R. Kreher (editor), volume E7a of *Methods of Organic Chemistry (Houben-Weyl), Hetarenes II, part 1, 4$^{th}$ edition*, Georg Thieme Verlag, Stuttgart—New York, 1991. A person skilled in the art will appreciate that the synthetic transformations described in scheme 1 result in this case in the corresponding heteroaryl-N-oxides of heteroaryl compounds of general formula 1-V and 1-Va, for example.

Intermediates of formula 1-III in which $Y^1$-$Y^4$ is C, substituted by $R^{12}$ and $R^{15}$=H, $R^{13}$=$C_1$-$C_6$-alkoxy or $C_1$-$C_6$-haloalkoxy, and $R^{14}$=$C_1$-$C_6$-alkyl or $C_1$-$C_6$-haloalkyl, B is N, A is N or a bond, n is 2 or 3, m is 2 or 3, and $R^6$, $R^7$, $R^8$ and $R^9$ are defined as in formula (I) above, are new and a subject of this invention.

Intermediates of formula 1-III in which $Y^1$-$Y^4$ is C, substituted by $R^{12}$ and $R^{15}$=H, $R^{13}$=$C_1$-$C_6$-alkoxy or $C_1$-$C_6$-haloalkoxy, and $R^{14}$=$C_1$-$C_6$-alkyl or $C_1$-$C_6$-haloalkyl, B is C, A is N, n is 1, 2 or 3, m is 1, 2 or 3, and $R^6$, $R^7$, $R^8$ and $R^9$ are defined as in formula (I) above, are new and a subject of this invention.

Intermediates of formula 1-III in which $Y^1$-$Y^4$ is C, substituted by $R^{12}$ and $R^{15}$=H, $R^{13}$=$C_1$-$C_6$-alkylcarbonyl or $C_1$-$C_6$-haloalkylcarbonyl, $R^{14}$=$C_1$-$C_6$-alkyl or $C_1$-$C_6$-haloalkyl, B is N, A is N or a bond, n is 2 or 3, m is 2 or 3, and $R^6$, $R^7$, $R^8$ and $R^9$ are defined as in formula (I) above, are new and a subject of this invention.

Intermediates of formula 1-III in which $Y^1$-$Y^4$ is C, substituted by $R^{12}$ and $R^{15}$=H, $R^{13}$=$C_1$-$C_6$-alkylcarbonyl or $C_1$-$C_6$-haloalkylcarbonyl, $R^{14}$=$C_1$-$C_6$-alkyl or $C_1$-$C_6$-haloalkyl, B is C, A is N, n is 1, 2 or 3, m is 1, 2 or 3, and $R^6$, $R^7$, $R^8$ and $R^9$ are defined as in formula (I) above, are new and a subject of this invention.

Intermediates of formula 1-III in which $Y^1$-$Y^4$ is C, substituted by $R^{15}$=H, $R^{13}$=$C_1$-$C_6$-alkoxy or $C_1$-$C_6$-haloalkoxy, $R^{12}$=$C_1$-$C_6$-alkyl or $C_1$-$C_6$-haloalkyl, and $R^{14}$ as defined as in formula (I) above, B is N, A is N or a bond, n is 2 or 3, m is 2 or 3, and $R^6$, $R^7$, $R^8$ and $R^9$ are defined as in formula (I) above, are new and a subject of this invention.

Intermediates of formula 1-III in which $Y^1$-$Y^4$ is C, substituted by $R^{15}$=H, $R^{13}$=$C_1$-$C_6$-alkoxy or $C_1$-$C_6$-haloalkoxy, $R^{12}$=$C_1$-$C_6$-alkyl or $C_1$-$C_6$-haloalkyl, and $R^{14}$ as defined as in formula (I) above, B is C, A is N, n is 1, 2 or 3, m is 1, 2 or 3, and $R^6$, $R^7$, $R^8$ and $R^9$ are defined as in formula (I) above, are new and a subject of this invention.

Scheme 2:

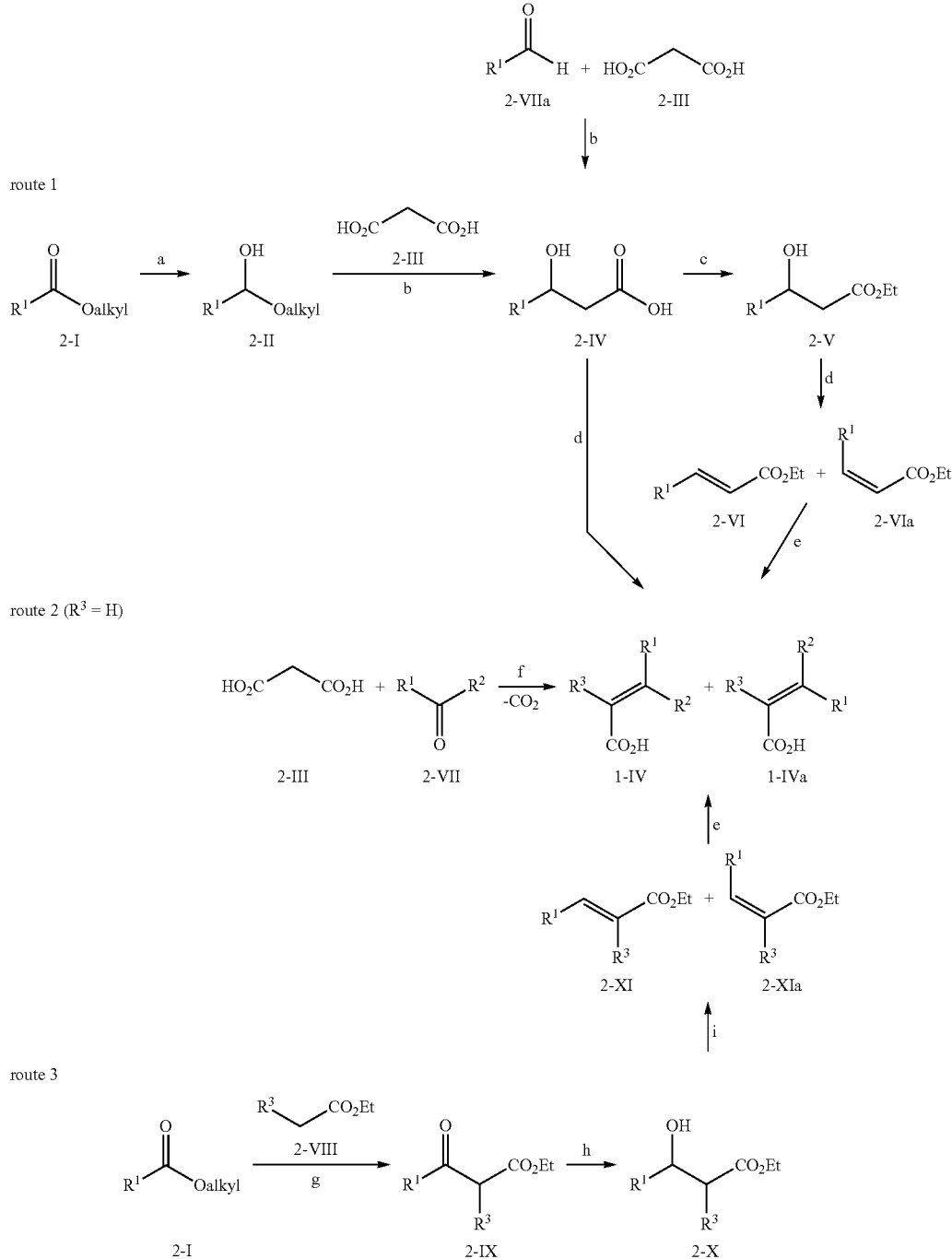

Exemplary conditions: a: sodium borohydride, methanol; b: pyridine, piperidine; c: ethanol, HCl; d: phosphorpentoxide; e: NaOH; f: pyridine, piperidine, reflux; g: LiN(Si(CH$_3$)$_3$)$_2$, THF; h: sodium borohydride, toluene; i: phosphorpentoxide The unsaturated acids used for acylation (1-IV in scheme 1) can be synthesized in several ways, many of which are described in: J. Falbe in volume E5 of *Methods of Organic Chemistry* (*Houben-Weyl*), *Carboxylic acids, part* 1, 4$^{th}$ *edition*, Georg Thieme Verlag, Stuttgart—New York, 1985. The preferred route will be chosen by a person skilled in the art according to the nature of the radicals R$^1$, R$^2$ and R$^3$. For example, in scheme 2, if R$^2$ is H and R$^1$ is alkyl preferably route 2 will be chosen. If R$^2$ is H and R$^1$ is alkyl substituted by halogen like F and/or Cl, route 1 or 3 will preferably be chosen. According to route 2 in scheme 2 malonic acid is condensed with an aldehyde or ketone 2-VII to yield directly the crotonic acid 1-IV, which can be accompanied by the isomeric 1-IVa. Suitable reaction conditions include heating the reactants in a solvent, preferably pyridine with the addition of piperidine. According to route 1, an ester is reduced to the hemiacetal 2-II, which is condensed with malonic acid in a manner analogous to route 1. Alternatively, the aldehyde 2-VIIa can be condensed with malonic acid to give the hydroxyacid 2-IV. The hydroxyacid 2-IV might be isolated or used directly in a dehydration step to yield 1-IV. Preferably, the hydroxyacid will be esterified to 2-V which is dehydrated to 2-VI and hydrolysed to the acid 1-IV. Methods for the dehydration of 2-IV and 2-V are described in, for example, M. Jagodzinska et al.; *Tetrahedron* 63 (2007), 2042-2046; P. F. Bevilaqua, *J. Org. Chem.* 94 (1984), 1430-1434 and include treatment of a hydroxyacid or hydroxyester like 2-IV or 2-V with P$_2$O$_5$ at preferably elevated temperatures or treatment with diethylazodicarboxylate and triphenylphosphine. According to route 3 an ester 2-I is condensed with a CH-acidic ester 2-VIII to give a beta-keto ester 2-IX which is reduced to the hydroxyester 2-X. Methods for the condensation of an ester with another CH-acidic ester are known to a person skilled in the art, as well as methods for the reduction of a keto group to a hydroxygroup and are described in, for example, M. Jagodzinska et al.; *Tetrahedron* 63 (2007), 2042-2046; T. Kitazume; *J. Fluorine Chemistry* 42 (1989), 17-29. 2-X is then converted to the crotonic acid 1-IV in a manner analogous to the one described above for 2-V. In all of the described routes, 1-IV might be accompanied by the isomeric 1-IVa. Depending on the nature of the radicals R$^1$ and R$^2$ the isomers I-IV and I-IVa can be formed in varying proportions. For example if R$^2$ is H, the E-isomer I-IV is predominantly formed. The isomeric 1-IV and 1-IVa can be separated by methods known to a person skilled in the art, e.g. by chromatography and can be used as pure isomers in subsequent reactions. Or 1-IV and 1-IVa can be used as a mixture in subsequent reactions and the resulting isomeric products can be separated in a later step. Unsaturated acids with R$^1$=alkyl substituted by alkylamino or dialkylamino and R$^2$=H and R$^3$=H can also be obtained as described in, for example, WO2006/127203 or US2003/50222, respectively. Unsaturated acids with R$^1$=SF$_5$ and R$^2$=H and R$^3$=H can also be obtained as described in, for example, V. K. Brel, *Synthesis* 2006, 339-343. Unsaturated acids with R$^1$=alkylthio and alkylsulfonyl and R$^2$=H and R$^3$=H can also be obtained as described in, for example, J. T. Moon, *Bioorg. Med. Chem. Letters* 20 (2010) 52-55. Many unsaturated acids 1-IV used as starting materials are also commercially available by a large number of vendors as listed in, for example, the Symyx Available Chemicals Directory (ACD).

Intermediates according to formula 1-IV in which R$^1$ is CF$_2$CF$_2$H, R$^2$ is H and R$^3$ is H and intermediates according to formula 1-IV in which R$^1$ is CF$_2$CH$_3$, R$^2$ is H and R$^3$ is H are new and also a subject of this invention.

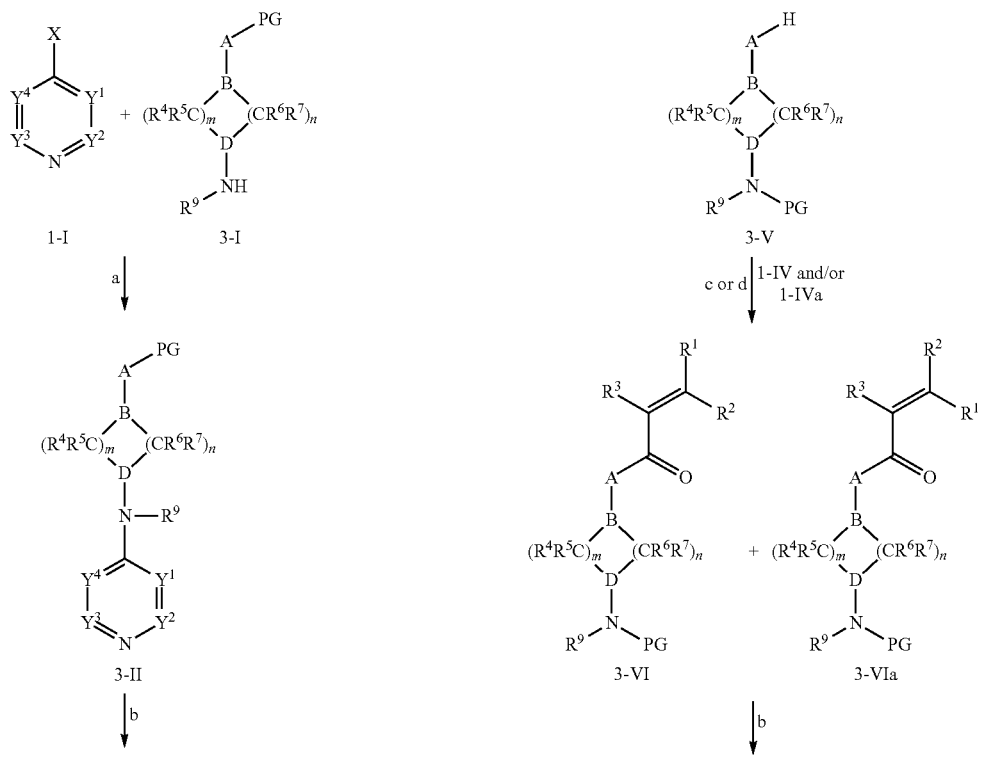

Scheme 3: route 1

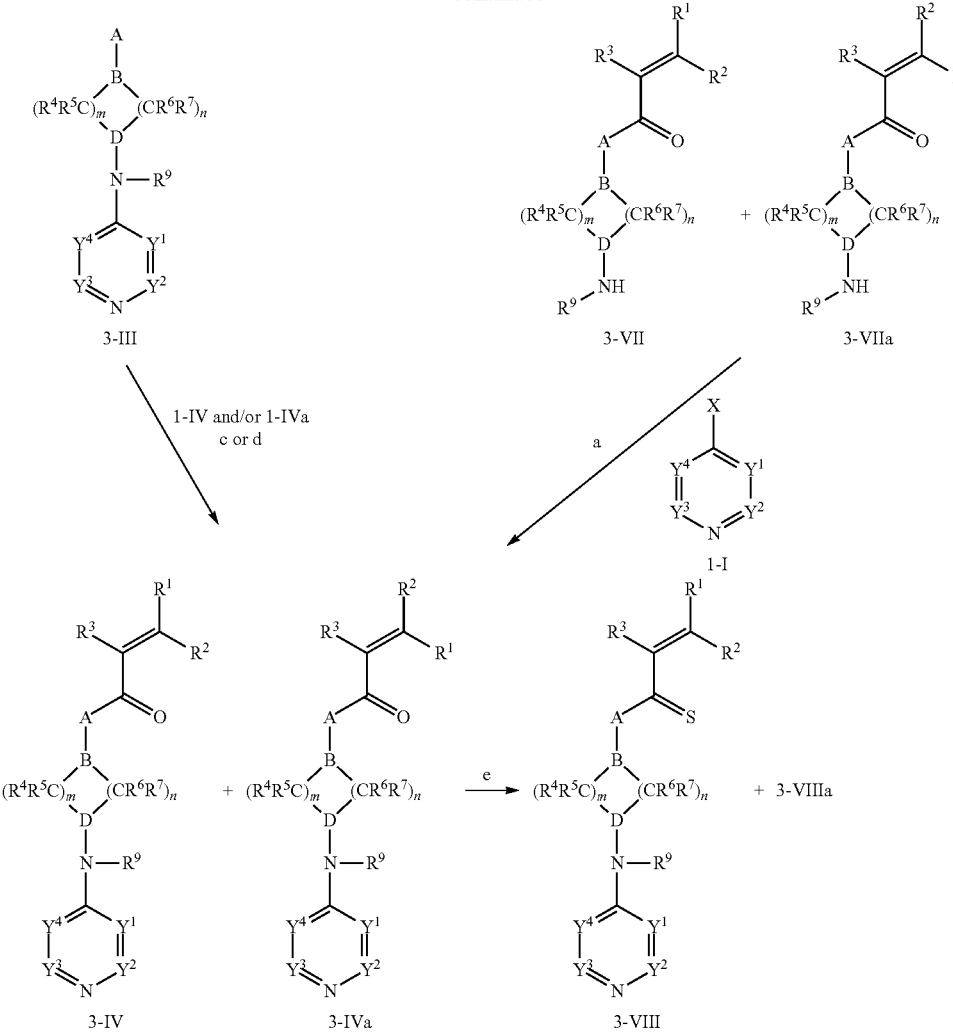

Exemplary conditions: a: Pd(OAc)$_2$, BINAP, CsCO$_3$, dioxane; b: HCl, dioxane; c: (COCl)$_2$, DCM, DMF then DCM, triethylamine; d: HATU, N-ethyldiisopropylamine (EDIPA), DMF, room temperature; e: Lawesson's reagent, THF, 130° C.

Compounds of general formula 3-IV can be synthesized as shown in scheme 3: a monoprotected diaminocompound 3-I is reacted with a heteroarylcompound 1-I containing a suitable leaving group X as described in scheme 1. Suitable protecting groups are the ones which have already been described in scheme 1. Possible reaction conditions include steps a, b, or c from route 1a of scheme 1, preferably Pd-catalysis is employed using, for example, palladium acetate, a phosphorus-containing ligand like BINAP, a base like caesium carbonate or sodium tert-butoxide in a solvent like an ether-containing solvent like diethylether, dioxane or tetrahydrofuran, preferably dioxane. The protecting group is removed and 3-III is acylated with 1-IV as already described in scheme 1. 1-IV can be accompanied by the isomeric 1-IVa, so that a mixture of 1-IV and 1-IVa is used in the acylation step. In this case a mixture of 3-IV and 3-IVa is formed that can be separated by methods known to a person skilled in the art, e.g. by chromatography. Or 1-IVa can be used in a pure form in the acylation step to give 3-IVa. The sequence might be altered as shown in route 2: the monoprotected diamine 3-V is acylated first, deprotection as described above and coupling with 1-I follow to give 3-IV. Also here 1-IV can be accompanied by the isomeric 1-IVa, so that a mixture of 1-IV and 1-IVa is used in the acylation step. In this case a mixture of 3-VI and 3-VIa is formed after acylation that can be separated by methods known to a person skilled in the art, e.g. by chromatography, or separation can be done after deprotection to 3-VII and 3-VIIa or after reaction to the final product 3-IV and 3-IVa. Or 1-IVa can be used in a pure form in the acylation step to give 3-VIa. The heteroaryl compound 1-I can be substituted at $Y^1$-$Y^4$ with a group that might react with an amine like 3-I, 3-VII or 3-VIIa. In this case the reacting group can be protected by a protecting group by methods known to a person skilled in the art. For example, 1-I can be substituted by an acyl group. This acyl group can be protected as, for example, an oxolan prior to the reaction with 3-I, 3-VII or 3-VIIa and deprotected by, for example, aqueous acid after the reaction with 3-I, 3-VII or 3-VIIa as described in, for example, Green and Wuts, *Protective Groups in Organic Synthesis*, 3$^{rd}$ edition, John Wiley & Sons, New York, 1999. 3-IV and 3-IVa can be converted into their thiocarbonyl analogue 3-VIII and 3-VIIIa by treatment with, for example, Lawesson's reagent under microwave heating.

Intermediates of formula 3-III in which $Y^1$-$Y^4$ is C, substituted by $R^{13}$=$C_1$-$C_6$-alkoxy or $C_1$-$C_6$-haloalkoxy, $R^{14}$=$C_1$-$C_6$-alkyl or $C_1$-$C_6$-haloalkyl, and $R^{12}$ and $R^{15}$ as defined in formula (I) above, $R^9$ is H or $C_1$-$C_6$-alkyl, B is N, A is N or a bond, D is C, n is 1, 2 or 3, m is 1, 2 or 3, and $R^6$, $R^7$, $R^8$ and $R^9$ are defined as in formula (I) above, are new and subject of this invention.

Intermediates of formula 3-III in which $Y^1$-$Y^4$ is C, substituted by $R^{12}$=$C_1$-$C_6$-alkyl or $C_1$-$C_6$-haloalkyl, $R^{13}$=$C_1$-$C_6$-alkoxy or $C_1$-$C_6$-haloalkoxy, and $R^{14}$ and $R^{15}$ as defined in formula (I) above, $R^9$ is H or $C_1$-$C_6$-alkyl, B is N, A is N or a bond, D is C, n is 1, 2 or 3, m is 1, 2 or 3, and $R^6$, $R^7$, $R^8$ and $R^9$ are defined as in formula (I) above, are new and subject of this invention.

Intermediates of formula 3-III in which $Y^1$-$Y^4$ is C, substituted by $R^{13}$=$C_1$-$C_6$-alkylcarbonyl, and $R^{12}$, $R^{14}$ and $R^{15}$ as defined in formula (I) above, $R^9$ is H or $C_1$-$C_6$-alkyl, B is N, A is N or a bond, D is C, n is 1, 2 or 3, m is 1, 2 or 3, and $R^6$, $R^7$, $R^8$ and $R^9$ are defined as in formula (I) above, are new and subject of this invention.

Scheme 4:

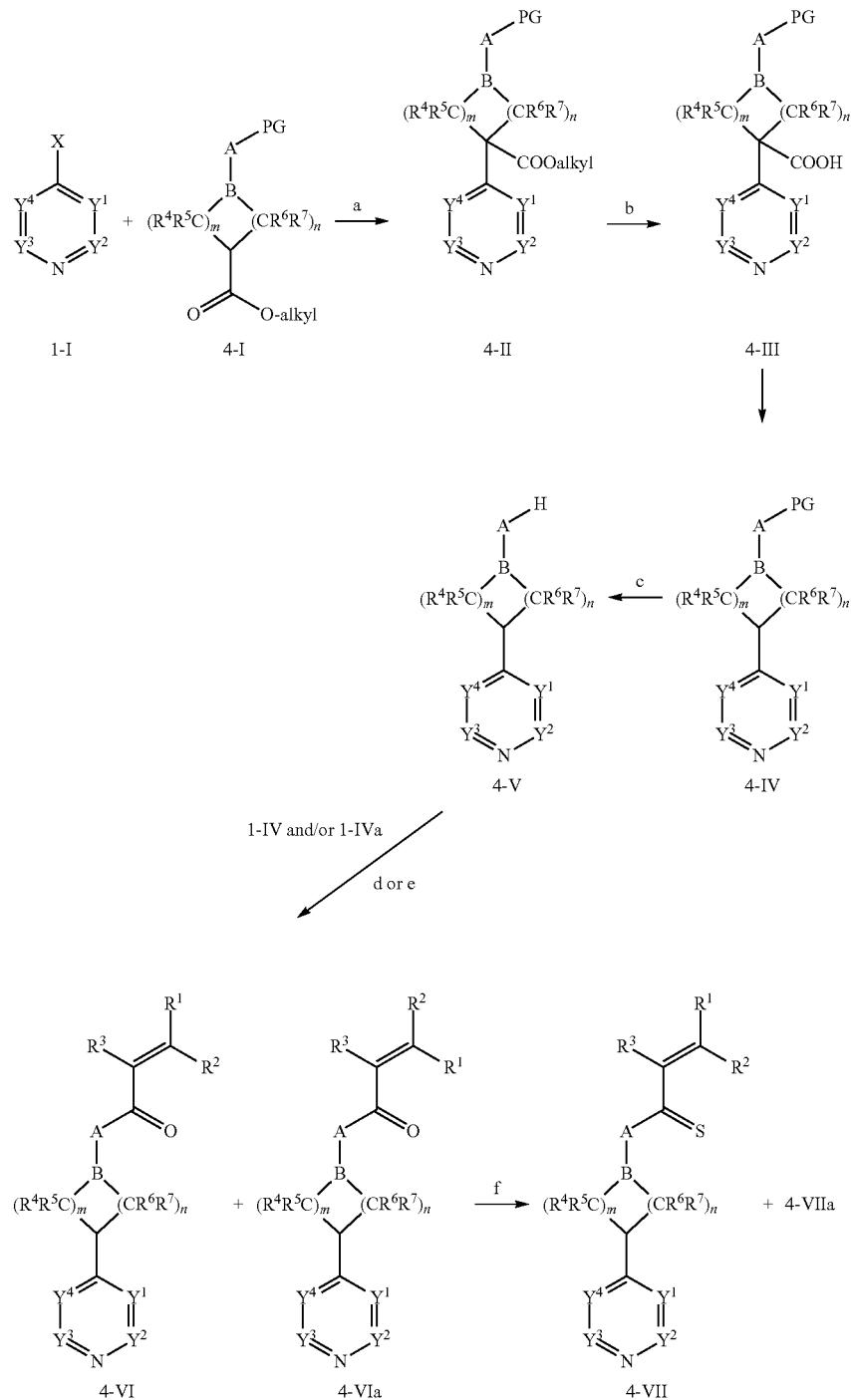

Exemplary conditions: a: LiN(Si(CH$_3$)$_3$)$_2$, THF, 0° C.; b: KOH, DMSO, H$_2$O, 100° C.; c: 6N HCl, H$_2$O, 100° C.; d: (COCl)$_2$, DCM, DMF then DCM, triethylamine; e: HATU, EDIPA, DMF, room temperature; f: Lawesson's reagent, THF, 130° C.

A compound of general formula 4-VI can be synthesized as shown in scheme 4: a cyclic carboxylic ester 4-I containing a protected amino function is deprotonated with a suitable strong base such as lithium hexamethyldisilazide or N''''-(1,1-dimethylethyl)-N,N',N'''-tris[tris(dimethylamino)phosphoranylidene]-phosphorimidic triamide (Phosphazene P$_4$-base) in a solvent like THF at a temperature ranging from −78° C. to 0° C. and reacted with a heteroarylcompound 1-I containing a suitable leaving group X as described in scheme 1. Similar reaction conditions are described in, for example, US2006/0281772. The ester group in 4-II is hydrolysed under conditions known to those skilled in the art and the intermediate free carboxylic acid 4-III decarboxylates to 4-IV which occurs either under the reaction conditions b or which is induced by elevated temperatures. The protecting group in 4-IV is removed as described in scheme 1 and 4-V is acylated with the unsaturated acid 1-IV as described in scheme 1 to give the final product 4-VI. 1-IV in the acylation step can be accompanied by the isomeric 1-IVa, so that a mixture of 1-IV and 1-IVa is used in the acylation step. In this case a mixture of 4-VI and 4-VIa is formed that can be separated by methods known to a person skilled in the art, e.g. by chromatography. Or 1-IVa can be used in a pure form in the acylation step to give 4-VIa. 4-VI and 4-VIa can be converted into their thiocarbonyl analogue 4-VII and 4-VIIa by treatment with, for example, Lawesson's reagent under microwave heating.

Intermediates of formula 4-V in which Y$^1$-Y$^4$ is C, substituted by R$^{12}$ and R$^{15}$=H, R$^{13}$=C$_1$-C$_6$-alkoxy or C$_1$-C$_6$-haloalkoxy, and R$^{14}$=C$_1$-C$_6$-alkyl or C$_1$-C$_6$-haloalkyl, B is N, A is N or a bond, n is 1, 2 or 3, m is 1, 2 or 3, and R$^6$, R$^7$, R$^8$ and R$^9$ are defined as in formula (I) above, are new and subject of this invention.

Scheme 5:

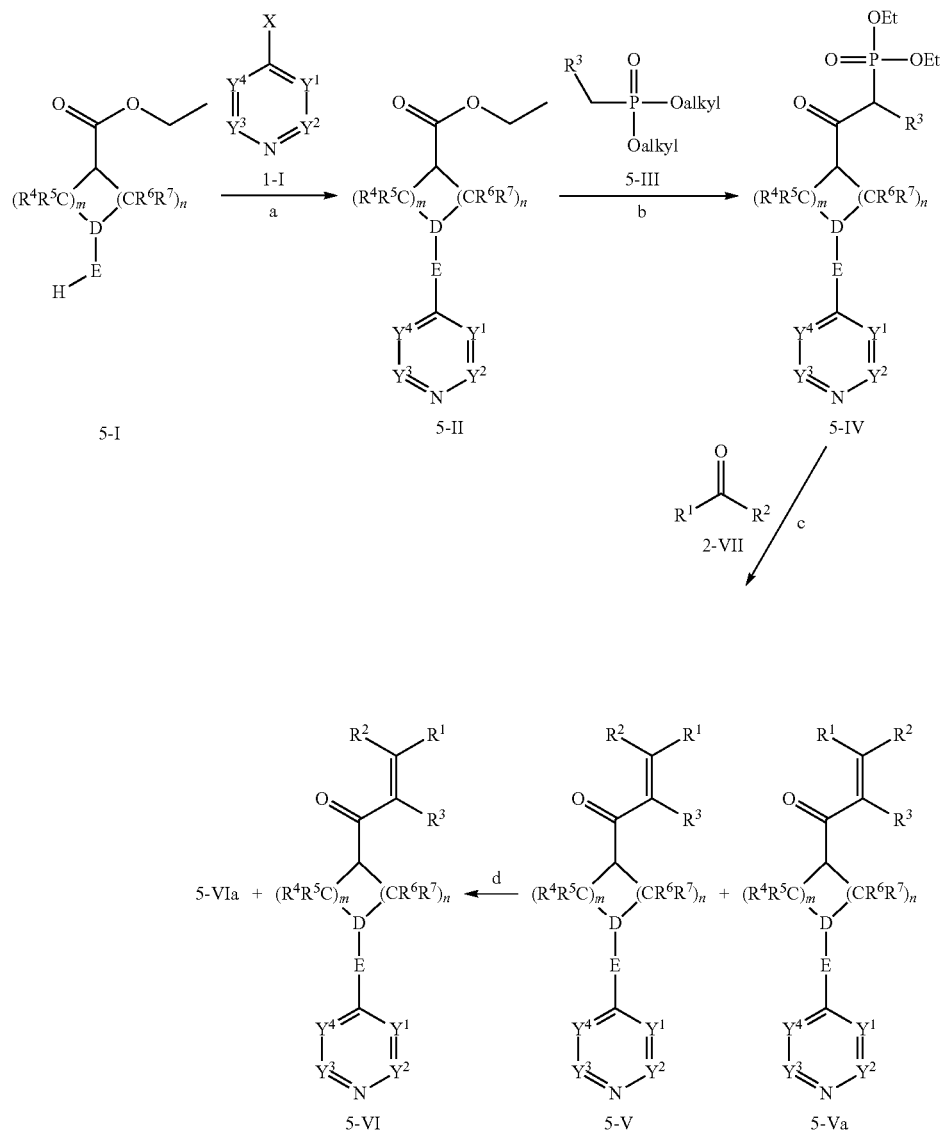

Exemplary conditions: a: propylenglycolmonomethylether, 150° C.; b: n-butyllithium, THF, −78° C.; c: LiCl, acetonitrile, N-ethyl-diisopropylamine; d: Lawesson's reagent, THF, 130° C.

A compound of general formula 5-V can be synthesized as shown in scheme 5: a cyclic carboxylic ester 5-I containing an amino function is reacted with a heteroarylcompound 1-I containing a suitable leaving group as already described in scheme 1 to give 5-II. The reaction is carried out in a solvent like propyleneglycolmonomethylether at elevated temperatures like at 150° C. 5-II is reacted with a dialkyl phosphonate in the presence of a base like lithium diisopropylamide in a solvent like THF at a temperature like −78° C. Similar reactions are described in, for example, U.S. Pat. No. 4,024,179. The ketophosphonate 5-IV can be reacted with the carbonyl compound 2-VII in a Wittig-Horner reaction under conditions such as, for example, described in S. V. Ley, *J. Chem. Soc., Perkin Trans.* 1., 1997, 3299-3313 using a base like diisopropylethylamine in the presence of lithium chloride in a solvent like acetonitrile. Depending on the nature of the radicals $R^1$ and $R^2$ the isomeric final products 5-V and 5-Va can be formed in differing proportions. For example, if $R^2$ is H and $R^3$ is H, then the E-isomer 5-VI is formed predominantly. If a mixture of 5-V and 5-Va is formed, this can be separated by methods known to a person skilled in the art, e.g. by chromatography. 5-V and 5-Va can be converted into their thiocarbonyl analogue 5-VI and 5-VIa by treatment with, for example, Lawesson's reagent under microwave heating.

Scheme 6:

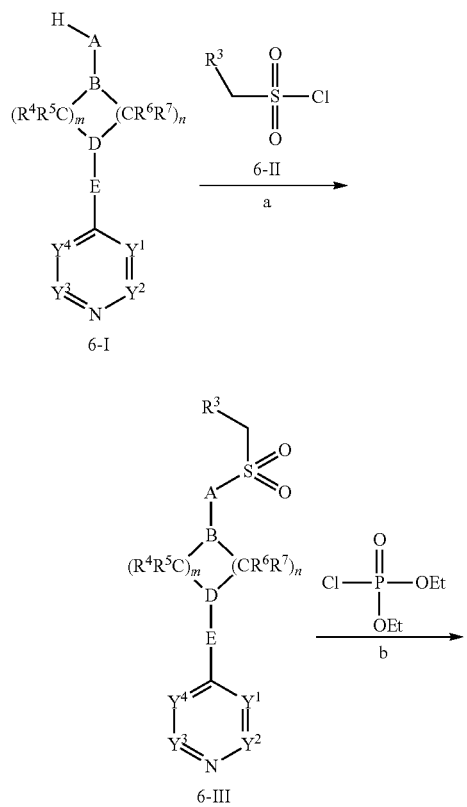

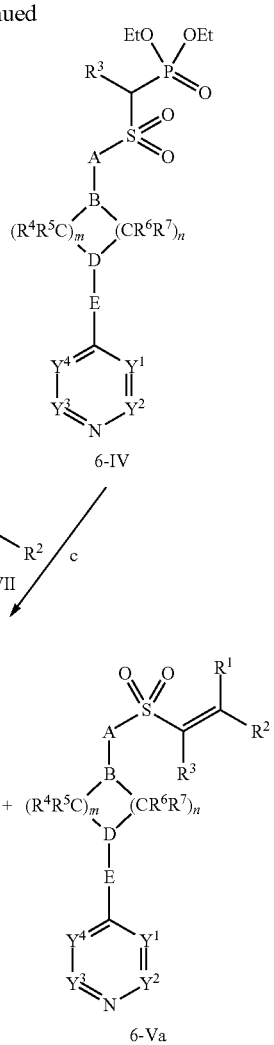

Exemplary conditions: a: dichloromethane, triethylamine, 0° C.; b: LiN(Si(CH$_3$)$_3$)$_2$, THF, −78° C.; c: LiBr, DBU, THF, −10° C. to room temperature A compound of the general formula 6-V can be synthesized as shown in scheme 6: A compound 6-I which contains an NH-group is reacted with an alkylsulfonic acid chloride 6-II in the presence of a suitable base like triethylamine in a solvent like dichloromethane. 6-I can be synthesized, for example, according to schemes 1, 3 or 4. The sulfonamide 6-III is deprotonated with a strong base like lithium diisopropylamide, lithium hexamethyldisilazide or n-butyllithium at low temperature like −78° C. and reacted with diethylchlorophosphate to give 6-IV. 6-IV is then reacted with a carbonyl-compound 2-VII to give the final product 6-V. The last step is carried out in the presence of lithium bromide and a strong base like 1,8-diaza-bicyclo[5.4.0]undec-7-en (DBU). Similar reactions are described in, for example, Z. Wróbel, *Tetrahedron* 57 (2001), 7899-7907. Depending on the nature of the radicals $R^1$, $R^2$ and $R^3$ the isomeric final products 6-V and 6-Va can be formed in differing proportions. For example, if $R^2$ is H and $R^3$ is H, then the E-isomer 6-V is formed predominantly. If a mixture of 6-V and 6-Va is formed, this can be separated by methods known to a person skilled in the art, e.g. by chromatography.

Scheme 7:
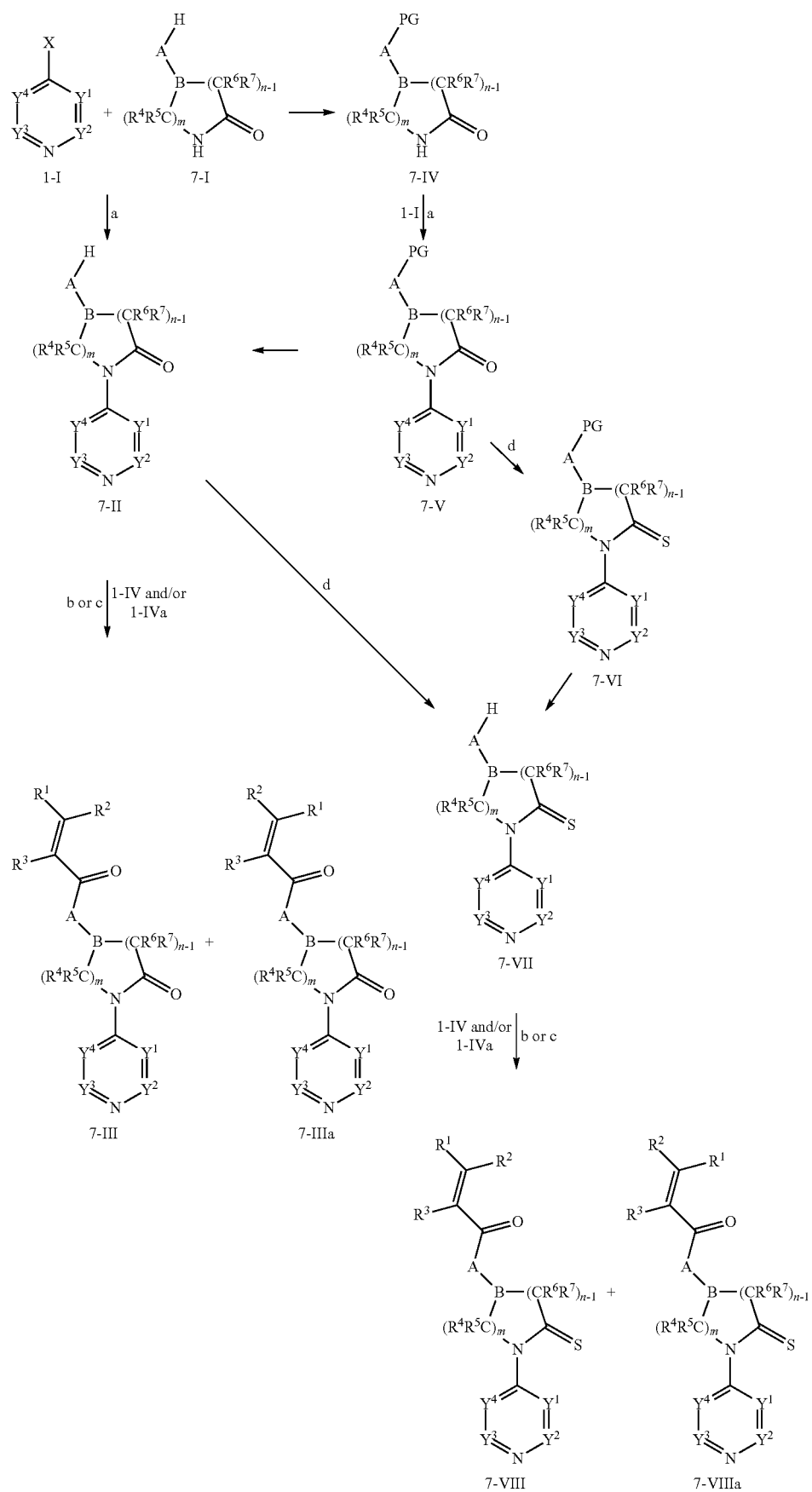

Exemplary conditions: a: CuI, K$_3$PO$_4$, trans-1,2-di(methylamino)cyclohexane, dioxane, 110° C.; b: (COCl)$_2$, DCM, DMF then DCM, triethylamine, room temperature; c: HATU, EDIPA, DMF, room temperature; d: Lawesson's reagent A compound of the general formula 7-III can be synthesized as shown in scheme 7: a heteroaryl compound 1-I is reacted with an amino-amide 7-I in the presence of a suitable catalytic system composed of, for example, copper(I)iodide, a ligand like trans-1,2-di(methylamino)cyclohexane in a solvent like dioxane at preferably elevated temperatures to give the heteroarylamide 7-II. Other catalytic systems are described in, for example, A. Klapars, *J. Am. Chem. Soc.* 124 (2002), 7421-7428. 7-II is then acylated to give the final product 7-III under conditions that have been described in scheme 1. 1-IV in the acylation step can be accompanied by the isomeric 1-IVa, so that a mixture of 1-IV and 1-IVa is used in the acylation step. In this case a mixture of 7-III and 7-IIIa is formed that can be separated by methods known to a person skilled in the art, e.g. by chromatography. Or 1-IVa can be used in a pure form in the acylation step to give 7-IIIa. The radical A might be protected by a suitable protecting group as in 7-IV by methods known to a person skilled in the art, for example as described in scheme 1. After coupling of 7-IV to the heteroarylcompound 1-I as described for 7-I to give 7-V, the protecting group is removed by methods known to those skilled in the art, for example as described in scheme 1, to give 7-II which is acylated as described above. The oxo-group in 7-V can be transformed into a thioxogroup in 7-VI. There are several methods known to a person skilled in the art for this reaction, some of which are described in, for example, *March's Advanced Organic Chemistry*, 6$^{th}$ edition 2007, Wiley, pages 1277-1280. 7-VI is then deprotected to give 7-VII analogously to the deprotection of 7-V. Alternatively, the oxo group in 7-II can be transformed into a thioxo group to give 7-VII. 7-VII is then acylated to give the final product 7-VIII under conditions that have been described in scheme 1. 1-IV in the acylation step can be accompanied by the isomeric 1-IVa, so that a mixture of 1-IV and 1-IVa can be used in the acylation step. In this case a mixture of 7-VIII and 7-VIIIa is formed that can be separated by methods known to a person skilled in the art, e.g. by chromatography. Or 1-IVa can be used in a pure form in the acylation step to give 7-VIIIa.

Heteroaryl compounds 1-I used as starting materials can be synthesized by several methods known to those skilled in the art. Quinoline derivatives are described in, for example, R. Kreher (editor), volume E7a of *Methods of Organic Chemistry (Houben-Weyl), Hetarenes II, part 1*, 4$^{th}$ edition, Georg Thieme Verlag, Stuttgart—New York, 1991; pyridine derivatives are described in, for example, R. Kreher (editor), volume E7b of *Methods of Organic Chemistry (Houben-Weyl), Hetarenes II, part 2*, 4$^{th}$ edition, Georg Thieme Verlag, Stuttgart—New York, 1992; pyrimidines are described in, for example, E. Schaumann (editor), volume E9b of *Methods of Organic Chemistry (Houben-Weyl), Hetarenes IV, part 2a*, 4$^{th}$ edition, Georg Thieme Verlag, Stuttgart—New York, 1998; quinazoline derivatives are described in E. Schaumann (editor), in volume E9b of *Methods of Organic Chemistry (Houben-Weyl), Hetarenes IV, part 2b*, 4$^{th}$ edition, Georg Thieme Verlag, Stuttgart—New York, 1997; pyridazines and cinnolines in, for example, E. Schaumann (editor), volume E9a of *Methods of Organic Chemistry (Houben-Weyl), Hetarenes IV, part I*, 4$^{th}$ edition, Georg Thieme Verlag, Stuttgart—New York, 1997; pyridopyridines in *The Chemistry of Heterocyclic Compounds*, Volume 63, The Naphthyridines, D. J. Brown, P. Wipf, E. C. Taylor (Eds), John Wiley & Sons, New York, 2007; thienopyridines, furopyridines, thienopyrimidines, furopyrimidines, pyrrolopyridines, pyrazolopyrimidines, pyrazolopyridines, pyridopyridines and triazolopyrimidines are described in, for example, A. R. Katritzky, C. W. Rees, E. F. V. Scriven (Editors), volume 7 of *Comprehensive Heterocyclic Chemistry II*, Elsevier Science Ltd., Oxford—New York, 1996. The synthesis of furopyridines is also described in, for example, S. Shiotani, K. Tanaguchi, *J. Heterocyclic Chem.*, 33, (1996), 1051-1056; S. Shiotani, K. Tanaguchi, *J. Heterocyclic Chem.*, 34, (1997), 925-929. 2-3-Dihydrofuropyridines are described in, for example, F. Suzenet, M. Khouili, S. Lazar, G. Guillaument, *Synlett*, 92-96, (2009). 2,3-Dihydro-1,4-dioxinopyridines are described in, for example, B. Joseph, A. Benarab, G. Guillaument, *Heterocycles* 38, (1994), 1355-1360. Many heteroaryl compounds 1-I used as starting materials are also commercially available by a large number of vendors as listed in, for example, the Symyx Available Chemicals Directory (ACD).

Cyclic diamines 1-II, 1-VI, 1-VIII, 3-I, 3-V and amines 4-I, 5-I and 7-I used as starting materials are commercially available by a large number of vendors as well as carboxylic esters 2-I and 2-VIII, aldehydes 2-VIIa and carbonyl compounds 2-VII as listed in, for example, the Symyx Available Chemicals Directory (ACD). In addition, carboxylic esters can be obtained by methods known to a person skilled in the art and described in, for example, J. Falbe (editor), volume E5 of *Methods of Organic Chemistry (Houben-Weyl), Carboxylic acids and Derivatives, part I*, 4$^{th}$ edition, Georg Thieme Verlag, Stuttgart—New York, 1985. Likewise, aldehydes can be obtained by methods described in, for example, J. Falbe (editor), volume E3 of *Methods of Organic Chemistry (Houben-Weyl), Aldehydes*, 4$^{th}$ edition, Georg Thieme Verlag, Stuttgart—New York, 1983 and ketones as described in, for example, volume VII, part 2 a-c of *Methods of Organic Chemistry (Houben-Weyl), Ketones I-III*, 4$^{th}$ edition, Georg Thieme Verlag, Stuttgart—New York, 1973-1977. Alkyl phosphonates 5-III are commercially available or can be obtained by methods known to a person skilled in the art described in, for example, in M. Regitz (editor), in volume E2 of *Methods of Organic Chemistry (Houben-Weyl), Organic Phosphorus Compounds II*, 4$^{th}$ edition, Georg Thieme Verlag, Stuttgart—New York, 1982. Alkyl sulfonic acid chlorides 6-II are commercially available or can be obtained by methods known to a person skilled in the art described in, for example, in D. Klamann (editor), in volume E11, part 2 of *Methods of Organic Chemistry (Houben-Weyl), Organic Sulfur Compounds II*, 4$^{th}$ edition, Georg Thieme Verlag, Stuttgart—New York, 1987.

B. Synthesis Examples

The following examples are for illustrative purposes only and are not intended to limit the scope of the invention. The compounds were named using Symyx®draw version 3.1.Net software (Symyx Technologies, Inc.).

The methods described in the examples can be easily adapted by a person skilled in the art to make other compounds as described in this specification and intermediates thereof. For instance, a person skilled in the art could replace in the examples the exemplified starting compounds by other compounds of the formulae 1-I, 1-II, 1-VI, 2-I, 2-VII, 2-VIIa, 2-VIII, 3-I, 3-V, 4-I, 5-I, 5-III, 6-I, 6-II, 7-I (e.g. commercially available compounds), perform routine adaptions of the reaction conditions, if any, and use them for the synthesis of further compounds according to this invention.

Example 1

Synthesis of (E)-1-[4-(2-methoxy-4-quinolyl)piperazin-1-yl]-4-methyl-hept-2-en-1-one (Table A-265)

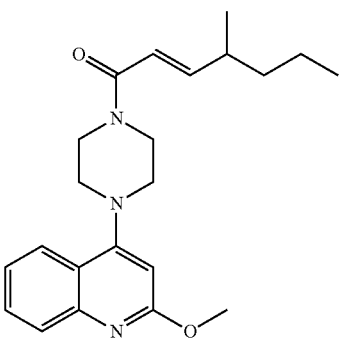 [SMILES: CCCC(C)/C=C/C(=O)N1CCN(c2cc(OC)nc3ccccc23)CC1]

Step A: 4-Chloro-6-methoxyquinoline 2,4-Dichloroquinoline (2.5 g, 12.6 mmol) was dissolved in anhydrous toluene (20 ml), a suspension of sodium methoxide (2.5 g, 46.3 mmol) in anhydrous toluene (20 ml) was added and the mixture was heated under reflux for 16 hours. After cooling to room temperature the suspension was filtered, the filter cake washed once with toluene (50 ml), the combined filtrates were evaporated under reduced pressure to dryness to yield 2.1 g (10.8 mmol, 86%) of a red solid. MS (ES) m/z=193.1 [M+H]$^+$.

Step B: 2-Methoxy-4-piperazin-1-yl-quinoline

A mixture of 4-chloro-6-methoxyquinoline (0.97 g, 5 mmol), piperazine (4.3 g, 50 mmol) and glacial acetic acid (0.3 ml) was heated under reflux with stirring in dipropyleneglycolmonomethylether for 48 hours. The mixture was filtered, the filtrate was evaporated to dryness under reduced pressure and the raw product was purified by column chromatography on a silica column using ethyl acetate and methanol with the addition of 0.1% NH$_3$ to yield 0.85 g of a brown solid (3.3 mmol, 66%). MS (ES) m/z=243.8 [M+H]$^+$.

Step C: (E)-4-Methylhept-2-enoic acid

Malonic acid (44 g, 0.42 mol), 2-methylpentan-1-al (14 g, 0.14 mol) and piperidine (1.7 ml) were suspended in 85 ml pyridine and heated under reflux. Gas formation was observed which ceased after two hours. Heating was continued for 1 hour. The cooled reaction mixture was poured into 2M hydrochloric acid (200 ml) after which two phases were obtained which were separated in a separating funnel. The aqueous phase was extracted once with dichloromethane (60 ml). The organic phases were combined and the solvent removed under reduced pressure. The residue was purified by column chromatography (pre-packed silica column, gradient of pentane/ethyl acetate). 9.3 g (0.065 mol, 47% yield) of (E)-4-methyl-hept-2-enoic acid were obtained as a solid. NMR ($^1$H, CDCl$_3$, 300 MHz): 11.86 (s, 1H), 7.00 (dd, 1H), 5.79 (d, 1H), 2.35 (m, 1H), 1.35 (m, 4H), 1.06 (d, 3H), 0.89 (m, 3H).

Step D: (E)-1-[4-(2-Methoxy-4-quinolyl)piperazin-1-yl]-4-methyl-hept-2-en-1-one (E)-4-Methyl-hept-2-enoic acid (21.3 mg, 0.15 mmol) was dissolved in DMF (350 µl), diisopropylethylamine was added (26 µl, 0.15 mmol) followed by HATU (57 mg, 0.15 mmol dissolved in 0.25 ml DMF). The mixture was stirred at room temperature for 15 minutes, then 2-methoxy-4-piperazin-1-yl-quinoline (36.4 mg, 0.15 mmol, dissolved in 1 ml DMF) was added and stirring was continued overnight. The mixture was evaporated under reduced pressure, the residue was dissolved in dichloromethane and the resulting solution was washed with 5% sodium bicarbonate solution, water, evaporated to dryness under reduced pressure. The residue was purified by preparative HPLC (gradient of water containing 0.1% NH$_3$ and acetonitrile) to yield 21.1 mg (0.06 mmol, 39.8%) of a solid.

Example 2

Synthesis of (E)-4-methyl-1-[4-(4-quinolyl)-1-piperidyl]pent-2-en-1-one (C-40)

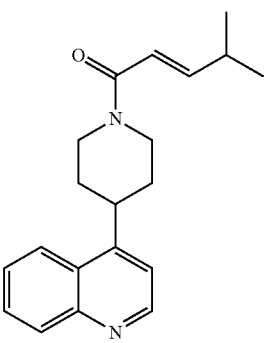 [SMILES: CC(C)/C=C/C(=O)N1CCC(c2ccnc3ccccc23)CC1]

Step A: Ethyl O1-tert-butyl O4-ethyl 4-(4-quinolyl)piperidine-1,4-dicarboxylate 4-Chloroquinoline (163 mg, 1 mmol) and O1-tert-butyl O4-ethyl piperidine-1,4-dicarboxylate (283 mg, 1.1 mmol) were dissolved under argon in 0.5 ml anhydrous THF and cooled to −70° C. Phosphazenebase P4-tBu (2M in THF) was added dropwise (0.5 ml, 1.5 mmol) with stirring. Stirring was continued for two hours, the temperature was raised to −20° C. and afterwards to room temperature overnight. Stirring was continued at room temperature for 48 hours. The mixture was filtered and the filtrate concentrated under reduced pressure. The residue was dissolved in acetonitrile and purified by preparative HPLC. 200 mg were obtained. (0.52 mmol, 52%) MS (APCI): m/z=384.9 [M+1]$^+$.

Step B: 4-(4-Piperidyl)quinoline

Ethyl O1-tert-Butyl O4-ethyl 4-(4-quinolyl)piperidine-1,4-dicarboxylate (200 mg, 0.52 mmol) was dissolved in a solution of potassium hydroxide (2.4 g) in methanol (10 ml). The mixture was heated briefly to reflux and cooled to room temperature. Hydrochloric acid (6M, 10 ml) and water (10 ml) were added and the mixture refluxed for one hour. The mixture was basified with 20% KOH and extracted with dichloromethane. The organic phase was evaporated under reduced pressure. 113 mg of a yellow, viscous oil were obtained and used directly in the next step. MS (APCI): m/z=212.9 [M+1]$^+$.

Step C: (E)-4-Methyl-1-[4-(4-quinolyl)-1-piperidyl]pent-2-en-1-one 4-(4-Piperidyl)quinoline (0.1 mmol, 21 mg) was dissolved in dichloromethane (1 ml). Triethylamine (1 ml of a 0.12M solution in dichloromethane) was added, the solution was shaken for 30 seconds and (E)-4-methylpent-2-enoyl chloride was added (1 ml of a 0.12 M solution in dichloromethane. The mixture was shaken for one hour at room temperature and evaporated to dryness under reduced pressure. The residue was purified by preparative HPLC. 5.1 mg were obtained (0.017 mmol, 17%).

Example 3

Synthesis of 2-methyl-4-[4-[(E)-pent-1-enyl]sulfonylpiperazin-1-yl]quinoline (A-669)

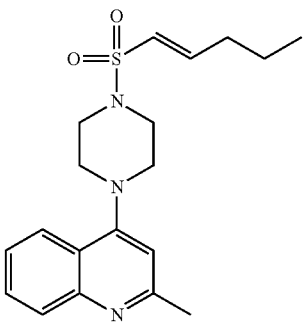 [SMILES: CCC/C=C/S(=O)(=O)N1CCN(c2cc(C)nc3ccccc23)CC1]

Step A: tert-Butyl 4-(2-methyl-4-quinolyl)piperazine-1-carboxylate

4-Chloro-2-methylquinoline (5 g, 28 mmol) was mixed with 1-methoxy-2-propanol, tert-butyl piperazine-1-carboxylate was added (5.74 g, 30.8 mmol) and the mixture was refluxed for 4.5 hours after which the product started to precipitate. The mixture was concentrated under reduced pressure and left at room temperature for 48 hours. The product was separated by filtration, washed with ethylacetate and dried at 50° C. 4.382 g of a solid were obtained (13.38 mmol, 48%). MS (APCI): m/z=327.9 [M+1]+.

Step B: 2-Methyl-4-piperazin-1-yl-quinoline

To tert-butyl 4-(2-methyl-4-quinolyl)piperazine-1-carboxylate (4.382 g, 13.38 mmol) was added 40 ml of a 1:1 mixture of dichloromethane and trifluoroacetic acid. The mixture was stirred at room temperature for 15 minutes. The mixture was evaporated to dryness under reduced pressure and the residue dissolved in dichloromethane. The solution was washed with 5% sodium bicarbonate solution and 3M NaOH was added until the aqueous phase remained basic. The phases were separated, the aqueous phase was extracted twice with dichloromethane, the combined organic phases were washed with saturated sodium carbonate solution, water, dried over magnesium sulfate and evaporated to dryness. 2.1 g of a solid were obtained (9.25 mmol, 69%). MS (APCI): m/z=227.8 [M+1]+.

Step C: 2-Methyl-4-(4-methylsulfonylpiperazin-1-yl)quinoline

2-Methyl-4-piperazin-1-yl-quinoline (227.3 mg, 1 mmol) was dissolved in anhydrous dichloromethane (7 ml), triethylamine was added (209 µl, 1.5 mmol), followed by methanesulfonyl chloride (85 µl, 1.1 mmol) which was added dropwise with ice-cooling. The mixture was diluted with dichloromethane and washed with 5% sodium bicarbonate solution. The wash solution was extracted with dichloromethane, the organic phases were combined and washed with 5% sodium bicarbonate solution, water and dried over magnesium sulfate. After evaporation of the solvent under reduced pressure 265 mg of a white foam were obtained (0.87 mmol, 87%) which was used directly in the next step.

Step D: 4-[4-(Diethoxyphosphorylmethylsulfonyl)piperazin-1-yl]-2-methyl-quinoline 2-Methyl-4-(4-methylsulfonylpiperazin-1-yl)quinoline (70 mg, 0.23 mmol) was placed in a Schlenk tube under an argon atmosphere, anhydrous THF (1.5 ml) was added and the solution cooled to −78° C. Lithium hexamethyldisilazid (50.6 mmol, 50.6 µl of a 1M solution in anhydrous THF) was added dropwise and the mixture stirred for one hour at −78° C. Diethylchlorophosphate (33.3 µl, 0.23 mmol) was added dropwise and stirring was continued for one hour. Acetic acid (100 µl) and water (1.5 ml) were added, the temperature raised slowly to room temperature and the mixture was extracted with diethylether (3×). The combined organic phases were washed with water and brine and evaporated to dryness under reduced pressure. 99 mg of an oily residue were obtained (0.22 mmol, 98%). MS (APCI) m/z=441.7 [M+1]+.

Step E: 2-Methyl-4-[4-[(E)-pent-1-enyl]sulfonylpiperazin-1-yl]quinoline

4-[4-(Diethoxyphosphorylmethylsulfonyl)piperazin-1-yl]-2-methyl-quinoline (47 mg, 0.106 mmol) was dissolved in anhydrous THF (1 ml), lithium bromide (11.1 mg, 0.128 mmol) and propionaldehyde (9.2 µl, 0.128 mmol) were added with stirring and the mixture was cooled to −10° C. DBU (15.2 µl, 0.102 mmol) was added, and the temperature was raised to room temperature. Stirring was continued for 30 minutes, the reaction mixture was diluted with dichloromethane, washed with 5% sodium bicarbonate solution (2×), water and evaporated to dryness. The residue was purified with preparative HPLC (gradient of water containing 0.1% ammonia and acetonitrile). 5 mg of a solid were obtained (0.014 mmol, 14%).

Example 4

Synthesis of 4-[(E)-4-methylpent-2-enoyl]-1-(4-quinolyl)piperazin-2-one (D-53)

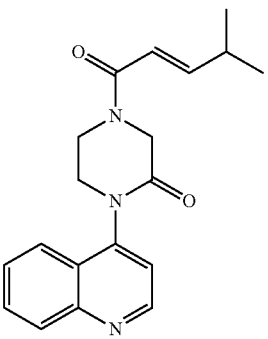 [SMILES: CC(C)/C=C/C(=O)N1CCN(c2ccnc3ccccc23)C(=O)C1]

Step A: 1-(4-Quinolyl)piperazin-2-one

CuI (80 mg, 0.42 mmol) and $K_3PO_4$ (1.7 g, 8 mmol) were placed in a 5 ml V-bottom vial and dried overnight at 50° C. 4-Bromoquinoline (416 mg, 2 mmol), piperazinone (200 mg, 2 mmol) were added under argon followed by anhydrous dioxane (3.4 ml), after which the vial was heated at 110° C. for 7 hours. The mixture was filtered and the residue washed with copious amounts of dichloromethane and ethyl acetate. The combined filtrates were evaporated to dryness under reduced pressure. The residue was purified by filtration over a plug of silica (dichloromethane followed by dichloromethane/methanol 9:1). The raw product was dissolved in 1M hydrochloric acid, washed with dichloromethane (2×), the aqueous phase was basified with 4M NaOH and extracted with dichloromethane (7×). The combined organic phases were dried over magnesium sulfate and evaporated to give 170 mg of a solid residue (0.75 mmol, 37%). MS (APCI): m/z=227.7 $[M+1]^+$.

Step B: (E)-4-Methylpent-2-enoyl chloride (E)-4-Methylpent-2-enoic acid (5 g, 45 mmol), was dissolved under argon in anhydrous dichloromethane (150 ml). Oxalyl chloride was slowly added (6.74 g, 53 mmol) with stirring followed by dropwise addition of dimethylformamide (100 μl) which resulted in gas formation. The mixture was stirred at room temperature overnight, the solvent was removed at reduced pressure and the residue was distilled at 32 mbar pressure and 65° C. 3.9 g of a clear liquid was obtained (29 mmol, 66%).

Step C: 4-[(E)-4-Methylpent-2-enoyl]-1-(4-quinolyl)piperazin-2-one 1-(4-Quinolyl)piperazin-2-one (23 mg, 0.1 mmol) was dissolved in dichloromethane (1 ml), triethylamine was added (21 μl, 0.15 mmol) followed by a solution of (E)-4-methylpent-2-enoyl chloride in 0.5 ml dichloromethane. The mixture was shaken briefly, washed with 5% sodium bicarbonate solution (2×), water and evaporated to dryness. The raw product was purified by preparative HPLC (gradient of water containing 0.1% ammonia and acetonitrile). 14.4 mg of a solid residue were obtained (0.044 mmol, 44%).

Example 5

Synthesis of (E)-4-methyl-1-[1-(2-methyl-4-quinolyl)-4-piperidyl]pent-2-en-1-one (C-45)

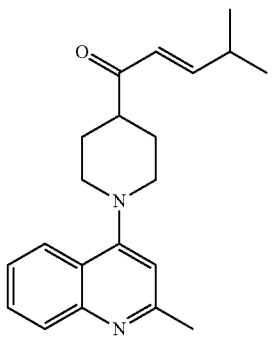 [SMILES: Cc1cc(N2CCC(C(=O)/C=C/C(C)C)CC2)c2ccccc2n1]

Step A: Ethyl 1-(2-methyl-4-quinolyl)piperidine-4-carboxylate

4-Chloroquinaldine (0.888 g, 5 mmol) and ethyl piperidine-4-carboxylate (1.18 g, 7.5 mmol) were mixed together with dipropyleneglycolmonomethylether (5 ml) and stirred at 150° C. for 48 hours. The solvent was removed under reduced pressure and the residue purified by column chromatography (pre-packed silica column, gradient of dichloromethane/ethyl acetate) to give 2.43 g of a brown oil that was used directly in the next step. MS (APCI): m/z=298.9 $[M+1]^+$.

Step B: 2-Diethoxyphosphoryl-1-[1-(2-methyl-4-quinolyl)-4-piperidyl]ethanone 1-(Ethoxy(methyl)phosphoryl)oxyethane (2.43 g, product of step A) was dissolved under argon in anhydrous THF (20 ml). The mixture was cooled to −78° C. and n-butyllithium (2M in cyclohexane, 8.5 ml, 17 mmol) was added dropwise at such a rate that the temperature remained below −65° C. Stirring was continued for 30 minutes and ethyl 1-(2-methyl-4-quinolyl)piperidine-4-carboxylate from step A (2.3 g, 7.7 mmol), dissolved in THF (2.5 ml) was added dropwise at such a rate that the temperature remained below −70° C. The reaction mixture was allowed to reach room temperature overnight, neutralized with acetic acid and the solvent evaporated under reduced pressure. Water (20 ml) was added to the residue, the mixture was extracted 3 times with dichloromethane. The combined organic phases were washed with water, dried over sodium sulfate and the solvent evaporated under reduced pressure. 3.94 g of a brown oil were obtained and used directly in the next step MS (APCI): m/z=404.8 $[M+1]^+$.

Step C: (E)-4-Methyl-1-[1-(2-methyl-4-quinolyl)-4-piperidyl]pent-2-en-1-one

Lithiumchloride (4.2 mg, 0.1 mmol) which had been dried before in vacuum at 125° C. was placed in anhydrous acetonitrile (4 ml), the mixture was cooled to −78° C. and diethoxyphosphoryl-1-[1-(2-methyl-4-quinolyl)-4-piperidyl]ethanone from step B (40 mg, 0.1 mmol) dissolved in 1 ml anhydrous acetonitrile was added dropwise with stirring. The mixture was allowed to reach room temperature, stirring was continued for 10 minutes and diisopropylethylamine (10.1 mg, 0.1 mmol) and isobutyraldehyde (7.2 mg, 0.1 mmol) were added. Stirring was continued overnight. Water and dichloromethane (10 ml each) were added and the mixture poured into saturated ammoniumchloride solution (20 ml). The phases were separated, the aqueous phase extracted with dichloromethane (3×) and the combined organic phases washed with brine, dried over sodium sulfate and the solvent removed under reduced pressure. The raw product was purified with preparative HPLC (gradient of water containing 0.1% ammonia and acetonitrile). 9.5 mg of an amber-coloured solid were obtained (0.029 mmol, 29%).

Example 6

Synthesis of (E)-4-methyl-1-[(3S)-3-(4-quinoly-lamino)pyrrolidin-1-yl]pent-2-en-1-one (C-76)

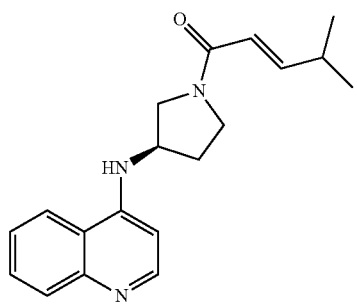 [SMILES: CC(C)/C=C/C(=O)N1CC[C@@H](Nc2ccnc3ccccc23)C1]

Step A: tert-Butyl (3S)-3-(4-quinolylamino)pyrrolidine-1-carboxylate

A 5 ml vial was charged with $Cs_2CO_3$ (654 mg, 3.3 mmol) and was dried in vacuo at 60° C. for two hours. Palladium acetate (31.5 mg, 0.14 mmol), BI NAP (43 mg, 0.07 mmol) were added followed by anhydrous dioxane (2 ml). The mixture was sonicated for one hour after which tert-butyl (3R)-3-aminopyrrolidine-1-carboxylate (186.3 mg, 1.0 mmol) and 4-chloroquinoline (163 mg, 1 mmol) dissolved in 2 ml anhydrous dioxane were added. The mixture was stirred at 100° C. overnight. The reaction mixture was purified directly by column chromatography (prepacked silica column, gradient heptan/ethyl acetate). 231 mg (0.68 mmol, 68%) of a solid were obtained. MS (APCI): m/z=314.0 [M+1]$^+$.

Step B: N-[(3S)-Pyrrolidin-3-yl]quinolin-4-amine tert-Butyl (3S)-3-(4-quinolylamino)pyrrolidine-1-carboxylate (231 mg, 0.68 mmol) was dissolved in a 1:1 mixture of dichloromethane and trifluoroacetic acid (2 ml) and stirred at room temperature for 15 minutes. The mixture was evaporated to dryness under reduced pressure and the residue obtained was used directly in the next step.

Step C: (E)-4-Methyl-1-[(3S)-3-(4-quinolylamino)pyrrolidin-1-yl]pent-2-en-1-one To N-[(3S)-Pyrrolidin-3-yl]quinolin-4-amine (32 mg, 0.15 mmol) dissolved in 1.5 ml anhydrous dichloromethane triethylamine (0.9 mmol, 91 mg) was added with stirring followed by (E)-4-methylpent-2-enoyl chloride dissolved in anhydrous dichloromethane (29.8 mg, 0.23 mmol). The mixture was stirred at room temperature for 5 minutes after which polymer-supported toluenesulfonyl chloride (600 mg, 1-2 mmol/g) was added and the mixture was shaken for 15 minutes, filtered and the filtrate evaporated to dryness under reduced pressure. The raw product was purified by preparative HPLC (gradient of water containing 0.1% ammonia and acetonitrile) to yield 18 mg of a solid (0.58 mmol, 39%).

Example 7

Synthesis of (E)-1-[(1S,4S)-5-(4-quinolyl)-2,5-diazabicyclo[2.2.1]heptan-2-yl]hex-2-en-1-one (D-41)

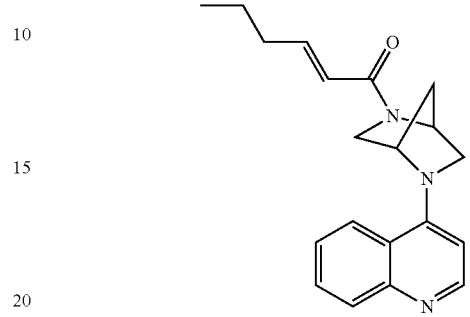

Step A: tert-Butyl (1S,4S)-5-(4-quinolyl)-2,5-diazabicyclo[2.2.1]heptane-2-carboxylate 4-Chloroquinoline (163.6 mg, 1 mmol) dissolved in 1-methoxy-2-propanol (4 ml) was added to tert-butyl (1S,4S)-2,5-diazabicyclo[2.2.1]heptane-2-carboxylate (237 mg, 1.2 mmol) and stirred at 115° C. for 72 hours. The solvent was removed under reduced pressure and the residue obtained (325 mg) was used directly in the next step. MS (APCI) m/z=326.0 [M+H]$^+$.

Step B: 4-[(1S,4S)-2,5-Diazabicyclo[2.2.1]heptan-5-yl]quinoline hydrochloride tert-Butyl (1S,4S)-5-(4-quinolyl)-2,5-diazabicyclo[2.2.1]heptane-2-carboxylate (325 mg from step A) was dissolved in a 4M solution of HCl in anhydrous dioxane (4 ml) and stirred for one hour at room temperature. The volatiles were evaporated under reduced pressure, the residue was triturated two times with diethylether and the supernatant removed. The residue was dried in vacuo to obtain 317 mg of a solid. MS (APCI) m/z=225.9 [M+H]$^+$.

Step C: (E)-1-[(1S,4S)-5-(4-Quinolyl)-2,5-diazabicyclo[2.2.1]heptan-2-yl]hex-2-en-1-one To 4-[(1S,4S)-2,5-diazabicyclo[2.2.1]heptan-5-yl]quinoline hydrochloride (26.2 mg, 0.1 mmol), dissolved in 0.5 ml anhydrous dichloromethane, polymer-supported diisopropylethylamine (80 mg, 3-4 mmol/g) was added followed by (E)-hex-2-enoyl chloride (19.9 mg, 0.15 mmol) dissolved in anhydrous dichloromethane (1 ml). The mixture was shaken at room temperature for 20 minutes, filtered and the filtrate evaporated to dryness under reduced pressure. The raw product was purified by preparative HPLC (gradient of water containing 0.1% ammonia and acetonitrile) to yield 9 mg of a solid (0.028 mmol, 28%).

Example 8

Synthesis of (E)-4-chloro-4,4-difluoro-1-[4-(4-quinolyl)piperazin-1-yl]but-2-en-1-one (A-256) and (Z)-4-chloro-4,4-difluoro-1-[4-(4-quinolyl)piperazin-1-yl]but-2-en-1-one (B-5)

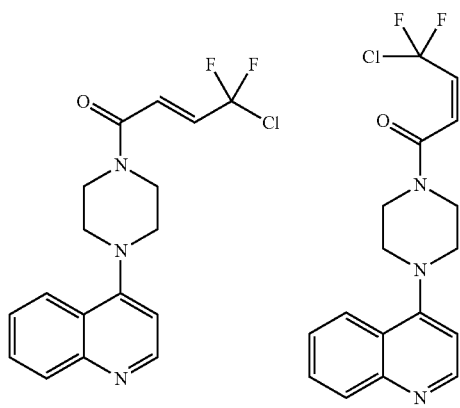 [SMILES: O=C(/C=C/C(F)(F)Cl)N1CCN(c2ccnc3ccccc23)CC1 ; O=C(/C=C\C(F)(F)Cl)N1CCN(c2ccnc3ccccc23)CC1]

Step A: 4-piperazin-1-ylquinoline

4-Chloroquinoline (25 g, 0.153 mol) and anhydrous piperazine (59.2 g, 0.69 mol) were dissolved in dimethylacetamide (400 ml) and stirred at 130° C. for 4 hours. The mixture was allowed to reach room temperature, water (600 ml) and 2M NaOH (150 ml) were added and the mixture was extracted with dichloromethane (600 ml). The organic phase was dried over magnesium sulfate, the solvent was removed at reduced pressure and the residue crystallized with diisopropylether. The raw product was mixed with a mixture of dichloromethane, diisopropylether and ethyl acetate (1:1:1), and stirred overnight at room temperature. The mixture was filtered, the filtrate evaporated under reduced pressure and the residue crystallized with diisopropylether to yield 10.0 g of off-white crystals (0.047 mol, 31%). NMR ($^1$H, CDCl$_3$, 300 MHz): 8.74 (s, 1H), 8.04 (m, 2H), 7.65 (m, 1H), 7.48 (m, 1H), 6.85 (d, 1H), 3.19 (m, 8H).

Step B: Ethyl 4-(4-quinolyl)piperazine-1-carboxylate 4-piperazin-1-ylquinoline (213 mg, 1 mmol) was dissolved in anhydrous dichloromethane (5 ml), triethylamine was added (140 µl, 1 mmol) followed by dropwise addition of ethylchloroformiate (95 µl, 1 mmol) with stirring. Stirring was continued for 5 minutes at room temperature, after which the mixture was diluted with dichloromethane, washed with 5% sodium bicarbonate solution, water, dried over magnesium sulfate and evaporated to dryness under reduced pressure. 284 mg were obtained (1 mmol, 100%). MS (ESI): m/z=286.1 [M+1]$^+$.

Step C: 2-Diethoxyphosphoryl-1-[4-(4-quinolyl)piperazin-1-yl]ethanone

Diethylmethylphosphonate (302.8 mg, 2 mmol) was dissolved in anhydrous THF (2.5 ml), the mixture was cooled to −78° C. under argon, n-butyllithium (2.11 mmol, 846 µl of a 2.5 M solution in hexane) was added dropwise with stirring. After addition was complete, stirring was continued for 20 minutes, after which ethyl 4-(4-quinolyl)piperazine-1-carboxylate (284 mg, 1 mmol) dissolved in 0.5 µl THF was added dropwise. The mixture was allowed to reach room temperature overnight with continued stirring. Glacial acetic acid (0.25 ml) and water (2 ml) was added, after which the mixture was basified with 0.1 NaOH and extracted with diethylether (2×). The organic phases were combined, washed with 5% sodium bicarbonate and water. The aqueous phases were back-extracted with diethylether after basification with 0.1 N NaOH and the combined organic phases dried over magnesium sulfate and the solvent was removed under reduced pressure to yield 271 mg (0.693 mmol, 69%). MS (ESI): m/z=392.1 [M+1]$^+$.

Step D: 2-Chloro-2,2-difluoro-acetaldehyde

Ethyl 2-chloro-2,2-difluoro-acetate (43.4 mg, 0.3 mmol) was dissolved in anhydrous THF (650 µl) and cooled under argon to −78° C. Diisobutylaluminium hydride (0.3 ml of a 1M solution in dichloromethane) was added dropwise with stirring. Stirring was continued for 30 minutes. The mixture was allowed to reach room temperature and was used directly in the next step.

Step E

2-Diethoxyphosphoryl-1-[4-(4-quinolyl)piperazin-1-yl]ethanone (78.3 mg, 0.2 mmol) was dissolved in anhydrous THF (1 ml), NaH was added (12 mg of a 60% dispersion in mineral oil, 0.3 mmol) and the mixture was stirred for 30 minutes at room temperature. 2-Chloro-2,2-difluoro-acetaldehyde (0.3 mmol, the solution of step D) was added, the temperature was raised to 45° C. and stirring was continued for 3 hours. The mixture was diluted with water, basified with 0.1 NaOH and extracted with diethylether (2×). The combined organic phases were washed with 5% sodium bicarbonate solution, water, dried over magnesium sulfate and the solvent was removed under reduced pressure. The raw product was purified by preparative HPLC (gradient of water containing 0.1% ammonia and acetonitrile) to yield (E)-4-chloro-4,4-difluoro-1-[4-(4-quinolyl)piperazin-1-yl]but-2-en-1-one (5 mg, 0.014 mmol, 7%) and (Z)-4-chloro-4,4-difluoro-1-[4-(4-quinolyl)piperazin-1-yl]but-2-en-1-one (7 mg, 0.02 mmol, 10%).

Example 9

Synthesis of (E)-4-fluoro-1-[4-(2-methyl-4-quinolyl)piperazin-1-yl]pent-2-en-1-one (A-179)

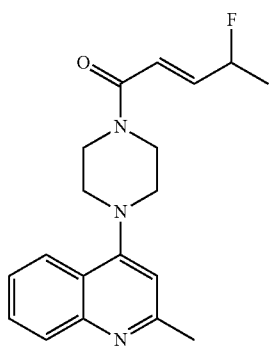 [SMILES: Cc1cc(N2CCN(C(=O)/C=C/C(C)F)CC2)c2ccccc2n1]

Step A: (E)-4-Hydroxypent-2-enoic acid

3-Acetylacrylic acid (114.1 mg, 1 mmol) was dissolved in methanol (3 ml), cooled to 0° C., sodium borohydride (113 mg, 3 mmol) was added portionwise, the mixture was stirred for 20 minutes at 0° C., neutralized with 1M HCl and concentrated at reduced pressure. The remaining aqueous mixture was extracted with ethyl acetate (2×), the combined organic phases were washed with water, dried over magnesium sulfate and the solvent removed under reduced pressure to yield 67 mg of a residue which was used directly in the next step.

Step B: 2-Methyl-4-piperazin-1-yl-quinoline

4-Chloro-2-methylquinoline (1.8 g, 10 mmol) and anhydrous piperazine (5.25 g, 60 mmol) were dissolved in ethyleneglycol monoethylether (15 ml) and stirred at 140° C. overnight. The mixture was concentrated under reduced pressure, toluene was added (2×100 ml) and the solvent removed under reduced pressure. To the residue was added 0.5 M NaOH (100 ml) and the mixture was extracted with a mixture of dichloromethane/diethylether/ethyl acetate (1:1:1, 3×100 ml). The combined organic phases were washed with brine, dried over sodium sulfate and the solvent was removed under reduced pressure. 2.78 g of an off-white solid (8.5 mmol, 85%) were obtained that were used directly in the next step.

Step C: (E)-4-Hydroxy-1-[4-(2-methyl-4-quinolyl)piperazin-1-yl]pent-2-en-1-one (A-178)

(E)-4-Hydroxypent-2-enoic acid (67 mg, 0.52 mmol) was dissolved in anhydrous DMF (2.5 ml), DCC (107.5, 0.52 mmol) and HOAt (106.7 mg, 0.79 mmol) were added and the mixture was stirred at room temperature for 15 minutes. 2-Methyl-4-piperazin-1-yl-quinoline (118.2 mg, 0.52 mmol) was added and stirring was continued for 90 minutes. The mixture was evaporated to dryness, taken up in a mixture of acetonitrile and methanol and filtered. The filtrate was evaporated to dryness again and purified by preparative HPLC (gradient of water containing 0.1% TFA and acetonitrile). 110 mg were obtained (0.33 mmol, 65%). MS (ES): m/z=326.1 [M+1]+.

Step D: (E)-4-Fluoro-1-[4-(2-methyl-4-quinolyl)piperazin-1-yl]pent-2-en-1-one (E)-4-Hydroxy-1-[4-(2-methyl-4-quinolyl)piperazin-1-yl]pent-2-en-1-one (32.5 mg, 0.1 mmol) was dissolved in anhydrous dichloromethane (200 μl) and added to a solution of (diethylamino)sulphur trifluoride (DAST; 19 μl, 0.12 mmol) in 200 μl dichloromethane. The mixture was stirred for 30 minutes at room temperature, additional DAST was added (10 μl, 0.063 mmol) and stirring was continued for additional 30 minutes. Solid sodium carbonate (25 mg) was added, the mixture was filtered, the filtrate evaporated to dryness and the residue purified by preparative HPLC (gradient of water containing 0.1% NH3 and acetonitrile) to yield 4 mg (0.012 mmol, 12%).

Example 10

Synthesis of (E)-4-chloro-1-[4-(4-quinolyl)piperazin-1-yl]but-2-en-1-one (A-251) and (Z)-4-chloro-1-[4-(4-quinolyl)piperazin-1-yl]but-2-en-1-one (B-14)

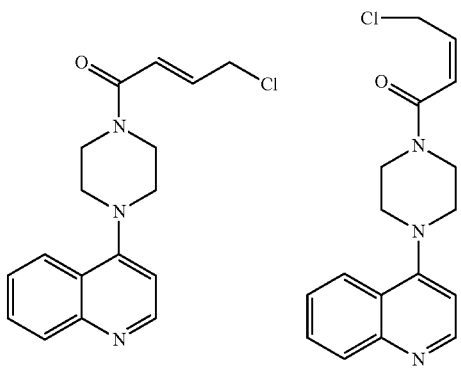 [SMILES: O=C(/C=C/CCl)N1CCN(c2ccnc3ccccc23)CC1 ; O=C(/C=C\CCl)N1CCN(c2ccnc3ccccc23)CC1]

Step A: (E)-4-Chlorobut-2-enoic acid and (Z)-4-chlorobut-2-enoic acid (E)-4-Bromobut-2-enoic acid (41.3 mg, 0.25 mmol) was dissolved in anhydrous DMF (1 ml), anhydrous lithium chloride (53 mg, 1.25 mmol) was added and the mixture was stirred at room temperature overnight and used directly for the next step.

Step B: (E)-4-Chloro-1-[4-(4-quinolyl)piperazin-1-yl]but-2-en-1-one and (Z)-4-chloro-1-[4-(4-quinolyl)piperazin-1-yl]but-2-en-1-one The mixture of (E)- and (Z)-4-chlorobut-2-enoic acid (750 μl of the solution from step A, 0.19 mmol) together with HATU (72 mg, 0.19 mmol) and diisopropylethylamine (21.6 μl, 0.375 mmol) was stirred at room temperature for 15 minutes. 4-piperazin-1-ylquinoline (39.9 mg, 0.19 mmol) and diisopropylethylamine (10.8 μl) were added and stirring was continued for one hour. The mixture was diluted with dichloromethane, washed with 5% sodium bicarbonate solution, water, evaporated to dryness under reduced pressure and purified by preparative HPLC (gradient of water containing 0.1% NH3 and acetonitrile) to yield 20 mg (E)-4-chloro-1-[4-(4-quinolyl)piperazin-1-yl]but-2-en-1-one (0.063 mmol, 33%) and 9 mg (Z)-4-chloro-1-[4-(4-quinolyl)piperazin-1-yl]but-2-en-1-one (0.029 mmol, 15%).

Example 11

Synthesis of (E)-4-bromo-1-[4-(4-quinolyl)piperazin-1-yl]pent-2-en-1-one (A-250)

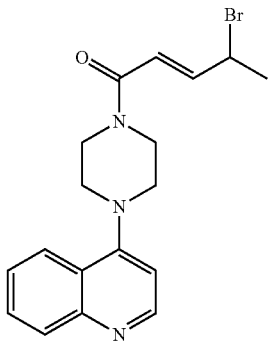 [SMILES: CC(Br)/C=C/C(=O)N1CCN(c2ccnc3ccccc23)CC1]

Step A: (E)-4-Bromopent-2-enoyl chloride (E)-Pent-2-enoyl chloride (118.6 mg, 1 mmol) was dissolved in $CCl_4$ (5 ml), and the solution was heated to reflux. N-bromosuccinimide (187 mg, 1.05 mmol) and 2,2'-azo[bisisobutyronitrile] (AIBN; 2.5 mg) were added portionwise with stirring. Stirring was continued at reflux for one hour, every 20 minutes additional 2.5 mg AIBN were added. The mixture was left at room temperature overnight, filtered, the filtrate evaporated to dryness to yield 157 mg of a white solid (0.79 mmol, 79%) that were used directly in the next step.

Step B: (E)-4-Bromo-1-[4-(4-quinolyl)piperazin-1-yl]pent-2-en-1-one 4-piperazin-1-ylquinoline (21.3 mg, 0.1 mmol) was dissolved in anhydrous dichloromethane (0.5 ml), TEA (20.9 µl, 1.5 mmol) followed by (E)-4-bromopent-2-enoyl chloride (29.6 mg, 0.15 mmol) were added, the mixture was shaken for 10 minutes, diluted with dichloromethane, washed with 5% sodium bicarbonate solution, water and the organic phase was evaporated to dryness under reduced pressure. The residue was purified by preparative HPLC (gradient of water containing 0.1% $NH_3$ and acetonitrile) to yield 7 mg of a solid (0.019 mmol, 19%).

Example 12

Synthesis of (E)-1-[4-(2,6-Dimethoxy-4-pyridyl)piperazin-1-yl]-4,4,5,5,5-pentafluoro-pent-2-en-1-one (A-435)

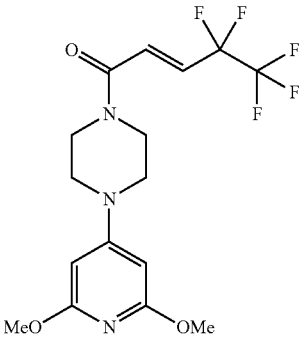 [SMILES: COc1cc(N2CCN(C(=O)/C=C/C(F)(F)C(F)(F)F)CC2)cc(OC)n1]

Step A: 1-Ethoxy-2,2,3,3,3-pentafluoro-propan-1-ol

Ethyl 2,2,3,3,3-pentafluoropropionate (10.99 grams, 57.2 mmol) was dissolved in anhydrous methanol (57 ml) and cooled in an argon atmosphere to −60° C. Sodium borohydride (2.16 g, 57.2 mmol) was added in four portions. After the addition was complete, stirring was continued for one hour and the temperature was held below −45° C. The mixture was cooled to −60° C. and 1M hydrochloric acid (172 ml) was added dropwise so that the temperature remained below −45° C. The mixture was slowly warmed to room temperature and extracted with diethylether (3×100 ml). The combined organic phases were washed with water (two times), dried over magnesium sulfate, the solvent was removed under reduced pressure. 9.76 g (50.3 mmol, 88%) were obtained and used directly in the next step.

Step B: 6,6,7,7,7-Pentafluoro-3-hydroxypentanoic acid

1-Ethoxy-2,2,3,3,3-pentafluoro-propan-1-ol (9.76 g, 50.3 mmol) was mixed with malonic acid (15.73 g, 0.15 mol), piperidine (0.611 ml) and pyridine (30 ml) and heated at 120° C. until gas evolution ceased (4 hours). The solvent was removed under reduced pressure, the residue treated with 1M hydrochloric acid and extracted with diethylether (3×). The combined organic phases were washed with water (2×), dried over magnesium sulfate, the solvent was removed under reduced pressure. 9.81 g (47.2 mmol, 94%) were obtained and used directly in the next step.

Step C: Ethyl 4,4,5,5,5-pentafluoro-3-hydroxy-pentanoate 6,6,7,7,7-Pentafluoro-3-hydroxypentanoic acid (9.81 g, 47.2 mmol) was dissolved in anhydrous ethanol (47 ml), concentrated sulfuric acid was added (0.534 ml) and the mixture was heated to reflux. A solution of hydrochloric acid in anhydrous methanol was added (1M, 8 ml) and heating was continued for 3 hours. The solvent was removed under reduced pressure and 11.9 g were obtained which were used directly in the next step.

Step D: Ethyl (E)-4,4,5,5,5-pentafluoropent-2-enoate

Ethyl 4,4,5,5,5-pentafluoro-3-hydroxy-pentanoate (11.9 g from step C) was placed in a 25 ml round-bottom flask and phosphorpentoxid was added in small portions until the educt was almost completely absorbed. The temperature was raised slowly to 140° C. until a brown syrup was obtained. The flask was connected to a distilling apparatus and the product isolated by distillation at reduced pressure (50 mbar, 50° C.). 5.5 g (25.2 mmol, 50% over 2 steps) were obtained which were used directly in the next step.

Step E: (E)-4,4,5,5,5-Pentafluoropent-2-enoic acid

Ethyl (E)-4,4,5,5,5-pentafluoropent-2-enoate (5.5 g, 25.2 mmol) was suspended in 10% NaOH (14.5 ml) and heated at reflux until a homogenous solution was obtained (40 min). After cooling the mixture was washed with diethylether (2×) and acidified under ice-cooling with concentrated sulfuric acid. The mixture was extracted with diethylether (3×), the combined organic phases were washed with water, dried over magnesium sulfate and the solvent removed under reduced pressure. 2.64 g (13.9 mmol, 55%) were obtained. MS (ES) M/z=189.0 [M−H]⁻.

Step F: 2,6-Dimethoxy-4-chloro-pyridine 2,4,6-Trichloropyridine (3.0 g, 19 mmol) was suspended in anhydrous toluene (35 ml) and solid sodium methoxide (3.6 g, 76 mmol) was added. The suspension was heated under reflux with stirring for 3 hours. The mixture was filtered and the filtrate evaporated to dryness under reduced pressure to yield 2.5 g of a colourless oil. (0.014 mmol, 76%) MS (APCI) M/z=173.9 [M+H]⁻.

Step G: 1-(2,6-Dimethoxy-4-pyridyl)piperazine 2.5 g (13 mmol) 2,6-dimethoxy-4-chloro-pyridine and 6.21 g (65 mmol) piperazine were heated at reflux in 22 ml anhydrous pyridine for 20 hours. After cooling (precipitation was detected) 50 ml of toluene was added and the suspension was filtered. The filtrate was concentrated under reduced pressure, piperazine and pyridine were azeotropically removed by repeated evaporation with toluene (five times). The residue was triturated with diethylether/petrolether (1:1) and dried in vacuo. The product was obtained as yellow solid and used directly in the next step.

Step H: (E)-1-[4-(2,6-Dimethoxy-4-pyridyl)piperazin-1-yl]-4,4,5,5,5-pentafluoro-pent-2-en-1-one 1-(2,6-Dimethoxy-4-pyridyl)piperazine (30 mg, 0.13 mmol) was dissolved in anhydrous dichloromethane (2 ml) together with (E)-4,4,5,5,5-pentafluoropent-2-enoic acid (35 mg, 0.18 mmol), triethylamine (31 mg, 44 µl, 0.32 mmol), HBTU (74 mg, 0.15 mmol) and stirred at room temperature for two hours. The mixture was evaporated to dryness under reduced pressure and the residue was purified by preparative HPLC (gradient of water containing 0.1% NH₃ and acetonitrile) to yield 9 mg of a solid (0.023 mmol, 15%).

Example 13

Synthesis of (E)-4-ethyl-1-[4-[2-methyl-7-(trifluoromethyl)-4-quinolyl]piperazin-1-yl]hex-2-en-1-one (A-274)

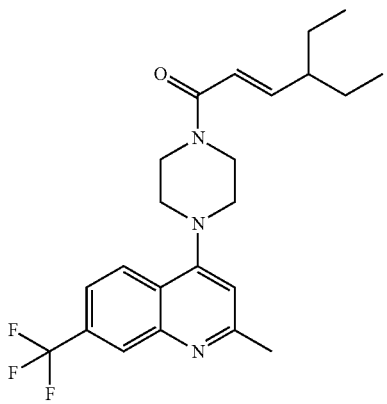 [SMILES: CCC(/C=C/C(=O)N1CCN(c2cc(C)nc3cc(C(F)(F)F)ccc23)CC1)CC]

Step A:
2-Methyl-4-chloro-7-(trifluoromethyl)quinoline

2-Methyl-7-(trifluoromethyl)quinolin-4-ol (1 g, 4.4 mmol) was heated in phosphoroxychloride (3 ml) for under reflux for one hour. The mixture was poured on ice and left at 4° C. overnight. The mixture was extracted with ethylacetate, the organic phase was washed with water, dried over sodium sulfate and evaporated to dryness under reduced pressure to yield 1.1 g (4.4 mmol, quantitative) which were used directly in the next step.

Step B: 2-Methyl-4-piperazin-1-yl-7-(trifluoromethyl)quinoline

2-Methyl-4-chloro-7-(trifluoromethyl)quinoline (1.1 g, 4.4 mmol) was dissolved in dipropyleneglycolmonomethylether, piperazine was added (12 g, 14 mmol) and the mixture was stirred at 140° C. overnight. The solvent was removed under reduced pressure and the residue purified by column chromatography (prepacked silica column, gradient ethyl acetate/methanol with the addition of 1% ammonia) to yield 1.07 g of a solid. (3.6 mmol, 82%) MS (APCI): m/z=295.8 [M+1]⁺.

Step C: (E)-4-Ethyl-1-[4-[2-methyl-7-(trifluoromethyl)-4-quinolyl]piperazin-1-yl]hex-2-en-1-one (E)-4-Ethyl-hex-2-enoic acid (21.3 mg, 0.15 mmol) was dissolved in DMF (350 µl), diisopropylethylamine was added (26 µl, 0.15 mmol) followed by HATU (57 mg, 0.15 mmol dissolved in 0.25 ml DMF). The mixture was stirred at room temperature for 15 minutes, then 2-methyl-4-piperazin-1-yl-7-(trifluoromethyl)quinoline (44 mg, 0.15 mmol, dissolved in 1 ml DMF) was added and stirring was continued overnight. The mixture was evaporated under reduced pressure, the residue was dissolved in dichloromethane, the solution was washed with 5% sodium bicarbonate solution and water, evaporated to dryness under reduced pressure. The residue was purified by preparative HPLC (gradient of water containing 0.1% NH₃ and acetonitrile) to yield 20.3 mg (0.48 mmol, 32.3%) of a solid.

Example 14

Synthesis of (E)-1-[4-(8-methyl-4-quinolinyl)piperazin-1-yl]pent-2-en-1-one (A-209)

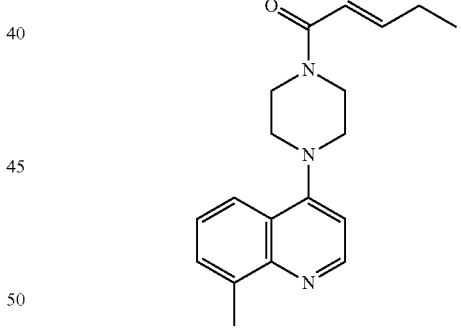

Step A: 8-Methyl-4-piperazin-1-yl-quinoline

8-Methyl-4-chloroquinoline (355 mg, 2 mmol) was suspended in dipropyleneglycolmonomethylether (4 ml), a solution of tert-butyl piperazine-1-carboxylate (440 mg, 2.4 mmol) in dipropyleneglycolmonomethylether (4 ml) was added and the mixture was stirred at 140° C. overnight and the solvent was evaporated under reduced pressure. The residue was dissolved in a mixture of dichloromethane and trifluoroacetic acid (1:1, 4 ml) and stirred at room temperature for 90 minutes. The mixture was evaporated to dryness under reduced pressure and the residue was dissolved in dichloromethane. The solution was washed with 5% sodium bicarbonate solution and water, dried over sodium sulfate and evaporated to dryness under reduced pressure. The residue was purified by column chromatography (prepacked silica column, gradient ethyl acetate/methanol with the addition of 1% ammonia) to yield 364 mg of a solid (1.6 mmol, 80%). MS (APCI): m/z=227.9 [M+1]⁺.

Step B: (E)-1-[4-(8-Methyl-4-quinolinyl)piperazin-1-yl]pent-2-en-1-one

8-Methyl-4-piperazin-1-yl-quinoline (22.7 mg, 0.1 mmol) was dissolved in dichloromethane (1 ml), triethylamine was added (1 ml of a 0.12 M solution in dichloromethane) followed by a solution of (E)-pent-2-enoyl chloride (1 ml, 0.12 M in dichloromethane). The mixture was shaken briefly, washed with 5% sodium bicarbonate solution (2×), water and evaporated to dryness. The raw product was purified by preparative HPLC (gradient of water containing 0.1% ammonia and acetonitrile) to yield 2.8 mg of a solid (0.009 mmol, 9%).

Example 15

Synthesis of (E)-1-[4-(3-methoxy-2-methyl-4-pyridyl)piperazin-1-yl]-4-methyl-pent-2-en-1-one (A-376)

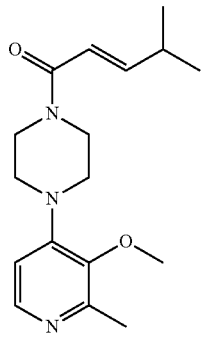 [SMILES: COc1c(N2CCN(C(=O)/C=C/C(C)C)CC2)ccnc1C]

Step A: 1-(3-Methoxy-2-methyl-4-pyridyl)piperazine

4-Chloro-3-methoxy-2-methyl-pyridine (0.47 g, 3 mmol) was mixed with dipropyleneglycolmonomethylether (3 ml), piperazine (1.1 g, 7.2 mmol) and N,N-dimethylaniline (0.36 g, 3 mmol) and stirred at 140° C. for 72 hours. The solvent was removed under reduced pressure and the residue was purified by column chromatography (prepacked silica column, gradient ethyl acetate/methanol with the addition of 1% ammonia). The raw product was dissolved in 1M NaOH and extracted with a mixture of diethylether, dichloromethane and ethylacetate (1:1:1) several times. The combined organic phases were washed with water, dried over sodium sulfate, and the solvent was removed under reduced pressure to yield 585 mg of a yellow solid (2.8 g, 94%). MS (APCI): m/z=208.0 [M+1]⁺.

Step B: (E)-1-[4-(3-Methoxy-2-methyl-4-pyridyl)piperazin-1-yl]-4-methyl-pent-2-en-1-one 1-(3-Methoxy-2-methyl-4-pyridyl)piperazine (20.7 mg, 0.1 mmol) was dissolved in dichloromethane (1 ml), triethylamine was added (1 ml of a 0.12 M solution in dichloromethane) followed by a solution of (E)-4-methylpent-2-enoyl chloride (1 ml, 0.12 M in dichloromethane). The mixture was shaken briefly, washed with 5% sodium bicarbonate solution (2×), water and evaporated to dryness. The raw product was purified by preparative HPLC (gradient of water containing 0.1% ammonia and acetonitrile) to yield 2.2 mg of a solid (0.007 mmol, 7%).

Example 16

Synthesis of N,2,6-trimethyl-4-[4-[(E)-4,4,4-trifluorobut-2-enoyl]piperazin-1-yl]pyridine-3-carboxamide (A-471)

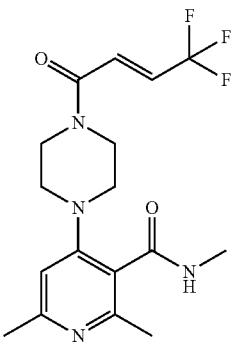

Step A:
4-Chloro-N,2,6-trimethyl-pyridine-3-carboxamide

4-Chloro-2,6-dimethyl-pyridine-3-carboxylic acid (925 mg, 5 mmol) was suspended in anhydrous dichloromethane (15 ml), the mixture was cooled to 0° C. and oxalyl chloride (560 µl, 6.5 mmol) was added dropwise with stirring followed by two drops of DMF. The mixture was stirred at room temperature for 90 minutes, the solvent was removed under reduced pressure, the residue was dissolved in anhydrous dichloromethane (15 ml), the solution was evaporated to dryness again, and the residue was dissolved in anhydrous dichloromethane (15 ml) and cooled to 0° C. TEA (2.1 ml, 15 mmol) was added dropwise followed by dropwise addition of a 2M solution of methylamine in THF (5 ml, 10 mmol). The mixture was stirred at 0° C. for 30 minutes, the solvent was removed under reduced pressure and the residue taken up in saturated sodium bicarbonate solution (40 ml). The mixture was extracted with dichloromethane (3×), the combined extracts were dried over sodium sulfate, the solvent was evaporated under reduced pressure and the residue was triturated with diethylether to yield 610 mg of a crystalline solid (3.1 mmol, 62%). MS (APCI): m/z=198.8 [M+1]⁺.

Step B: N,2,6-Trimethyl-4-piperazin-1-yl-pyridine-3-carboxamide

4-Chloro-N,2,6-trimethyl-pyridine-3-carboxamide (300 mg, 1.5 mmol) was mixed with piperazine (645 mg, 7.5 mmol) and pyridine (3 ml) and heated under microwave irridation at 180° C. for 15 minutes. The solvent was removed under reduced pressure, the residue was taken up in 0.5 M NaOH saturated with sodium chloride and extracted with dichloromethane (2×). The combined extracts were dried over sodium sulfate, the solvent was evaporated under reduced pressure to yield 280 mg of a yellow solid (1.1 mmol, 75%). NMR (¹H, 300 MHz, CD₃CN): 6.73 (s, 1H), 6.70 (s, 1H), 2.99-3.02 (m, 4H), 2.82-2.86 (m, 7H), 2.37 (s, 3H), 2.35 (s, 3H).

Step C: N,2,6-Trimethyl-4-[4-[(E)-4,4,4-trifluorobut-2-enoyl]piperazin-1-yl]pyridine-3-carboxamide (E)-4,4,4-Trifluorobut-2-enoic acid (21 mg, 0.15 mmol) was dissolved in anhydrous DMF (1 ml), diisopropylethylamine (52 µl, 0.3 mmol) was added followed by HBTU (60 mg, 0.15 mmol) and the mixture was stirred at room temperature for 15 minutes. N,2,6-trimethyl-4-piperazin-1-yl-pyridine-3-carboxamide (37.2 mg, 0.15 mmol) was dissolved in a mixture of DMF (0.5 ml) and diisopropylethylamine (26 µl, 0.15 mmol) and the resulting solution was added to the solution of the activated carboxylic acid. The resulting mixture was stirred at room temperature for three hours, the solvent was removed under reduced pressure and the raw product was purified by preparative HPLC (gradient of water containing 0.1% ammonia and acetonitrile) to yield 21.4 mg of a solid (0.058 mmol, 38%).

Example 17

Synthesis of (E)-1-[4-(2-methyl-4-quinolyl)piperazin-1-yl]oct-2-en-1-one (A-14)

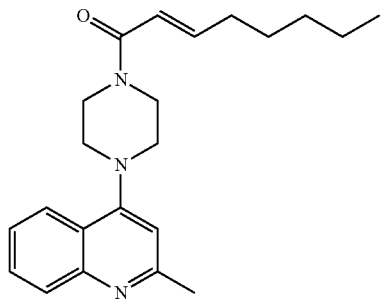 [SMILES: CCCCC/C=C/C(=O)N1CCN(c2cc(C)nc3ccccc23)CC1]

(E)-Oct-2-enoic acid (71.1 mg, 0.5 mmol) was dissolved in dichloromethane (1 ml) and a 2M solution of oxalyl chloride in dichloromethane was added (0.3 ml, 0.6 mmol). The solution was stirred at room temperature for one hour after which a drop of DMF was added. Stirring was continued for another hour, the mixture was evaporated to dryness under reduced pressure. The residue was dissolved in dichloromethane (1 ml), the resulting solution was added to a solution of 2-methyl-4-piperazin-1-yl-quinoline (103 mg, 0.45 mmol) and triethylamine (90 µl, 0.64 mmol) in dichloromethane (1 ml). The resulting mixture was stirred at room temperature overnight, diluted with dichloromethane (1 ml), washed with water and 2M NaOH (2 ml each) and evaporated to dryness under reduced pressure. The residue was purified by preparative HPLC (gradient of water containing 0.1% ammonia and acetonitrile) to yield 121.3 mg of a solid (0.34 mmol, 77%).

Example 18

Synthesis of (E)-1-[4-(5-methoxypyrazolo[1,5-a]pyrimidin-7-yl)piperazin-1-yl]pent-2-en-1-one (A-289)

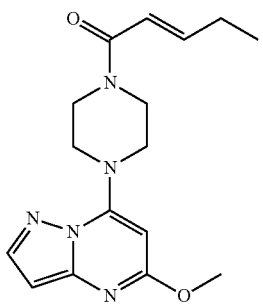 [SMILES: CC/C=C/C(=O)N1CCN(c2cc(OC)nc3ccnn23)CC1]

Step A: tert-Butyl 4-(5-chloro-pyrazolo[1,5-a]pyrimidin-7-yl)piperazine-1-carboxylate 5,7-Dichloro-pyrazolo[1,5-a]pyrimidine (980 mg, 5.2 mmol) and tert-butyl piperazine-1-carboxylate (2.3 g, 12.6 mmol) were dissolved in 1-methoxy-2-propanol (40 ml) and heated under microwave irridation at 110° C. for one hour. The solvent was removed under reduced pressure and the residue purified by column chromatography (silica, pentane/ethylacetate). The raw product was crystallized from ethanol to yield 1.23 g of a crystalline solid (3.65 mmol, 70%). MS (APCI): m/z=338.2 [M+1]$^+$.

Step B: tert-Butyl 4-(5-methoxy-pyrazolo[1,5-a]pyrimidin-7-yl)piperazine-1-carboxylate tert-Butyl 4-(5-chloro-pyrazolo[1,5-a]pyrimidin-7-yl)piperazine-1-carboxylate (1.23 g, 3.65 mmol) was dissolved under an argon atmosphere in anhydrous methanol (6 ml). Sodium methanolat (3.65 ml of a 1M solution in methanol) was added and the mixture was heated under reflux for 9 hours. The solvent was removed under reduced pressure, the residue taken up in dichloromethane, the resulting solution was washed with water, dried over magnesium sulfate, the solvent removed under reduced pressure to yield 1.186 g of a solid (3.56 mmol, 98%). MS (APCI): m/z=334.3 [M+1]$^+$.

Step C: 5-Methoxy-7-piperazin-1-yl-pyrazolo[1,5-a]pyrimidine tert-Butyl 4-(5-methoxy-pyrazolo[1,5-a]pyrimidin-7-yl)piperazine-1-carboxylate (1.186 g, 3.56 mmol) was stirred for 10 minutes at room temperature in a 1:1 mixture of dichloromethane and trifluoroacetic acid. The mixture was evaporated to dryness under reduced pressure, the residue was dissolved in water, the resulting solution was washed with dichloromethane, basified with 4M NaOH and extracted with dichloromethane (3×). The combined organic phases were washed with water, dried over magnesium sulfate and the solvent was removed under reduced pressure to yield 624 mg of a solid (2.68 mmol, 75%). MS (APCI): m/z=234.1 [M+1]$^+$.

Step D: (E)-1-[4-(5-methoxypyrazolo[1,5-a]pyrimidin-7-yl)piperazin-1-yl]pent-2-en-1-one 5-Methoxy-7-piperazin-1-yl-pyrazolo[1,5-a]pyrimidine (23.3 mg, 0.1 mmol) was dissolved in anhydrous dichloromethane (1 ml), TEA (17.4 µl, 1.25 mmol) followed by (E)-pent-2-enoyl chloride (14.8 mg, 0.125 mmol) were added, the mixture was shaken for 10 minutes, diluted with dichloromethane, washed with 10% sodium bicarbonate solution, water and the organic phase was evaporated to dryness under reduced pressure. The residue was purified by preparative HPLC (gradient of water containing 0.1% NH$_3$ and acetonitrile) to yield 16.1 mg of a solid (0.05 mmol, 51%).

Example 19

Synthesis of (E)-1-[4-(2-methyl-1-oxido-quinolin-1-ium-4-yl)piperazin-1-yl]pent-2-en-1-one (Aa-3)

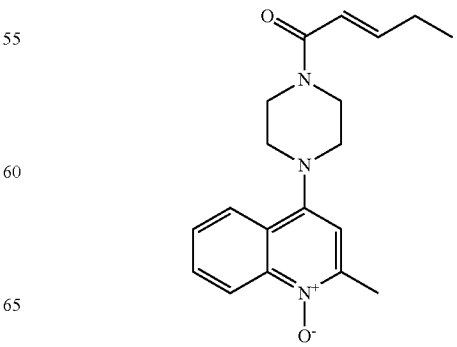

Step A: (E)-1-[4-(2-Methyl-4-quinolyl)piperazin-1-yl]pent-2-en-1-one

2-Methyl-4-piperazin-1-yl-quinoline (113.7 mg, 0.5 mmol) was dissolved in anhydrous dichloromethane (1 ml), TEA (77 μl, 0.5 mmol) followed by (E)-pent-2-enoyl chloride (65 mg, 0.55 mmol dissolved in 1 ml anhydrous dichloromethane) were added and the mixture was shaken for 15 minutes. The mixture was diluted with dichloromethane, washed with 5% sodium bicarbonate solution and water and the organic phase was evaporated to dryness under reduced pressure. The residue was purified by preparative HPLC (gradient of water containing 0.1% $NH_3$ and acetonitrile) to yield 143 mg of a solid (0.44 mmol, 88%). MS (ES): m/z=354.2 $[M+1]^+$.

Step B

(E)-1-[4-(2-Methyl-1-oxido-quinolin-1-ium-4-yl)piperazin-1-yl]pent-2-en-1-one (E)-1-[4-(2-Methyl-4-quinolyl)piperazin-1-yl]pent-2-en-1-one (30.9 mg, 0.1 mmol) was dissolved in anhydrous dichloromethane, meta-chloroperbenzoic acid (mCPBA) was added (44.6 mg, 0.2 mmol) and the mixture was stirred at room temperature for 15 minutes. The mixture was evaporated to dryness under reduced pressure and the residue was purified by preparative HPLC (gradient of water containing 0.1% $NH_3$ and acetonitrile) to yield 6 mg of a solid (0.0185 mmol, 18.5%). MS (APCI): m/z=325.8 $[M+1]^+$.

Example 20

Synthesis of N-methyl-4-[4-[(E)-4,4,5,5-tetrafluoropent-2-enoyl]piperazin-1-yl]pyridine-2-carboxamide (A-618)

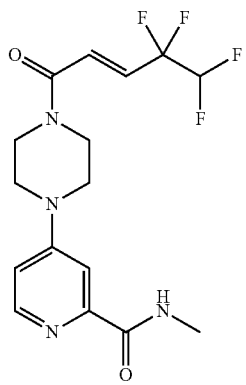 [SMILES: CNC(=O)c1cc(N2CCN(C(=O)/C=C/C(F)(F)C(F)F)CC2)ccn1]

Step A: Ethyl 4,4,5,5-tetrafluoro-3-oxo-pentanoate

Lithium hexamethyldisilazide (250 ml of a 1M solution in THF, 0.25 mol) was cooled in an argon atmosphere to −78° C. and ethyl acetate (23 ml, 0.26 mol) was added dropwise with stirring. Stirring was continued for one hour at −78° C., then methyl 2,2,3,3-tetrafluoropropionate (22 g, 0.137 mol) was added dropwise with stirring. Stirring was continued for three hours at −78° C., then a saturated solution of ammonium chloride (175 ml) was added dropwise. The mixture was allowed to reach room temperature overnight. The mixture was acidified with 1M HCl, the phases were separated. The aqueous phase was extracted with ethyl acetate, the combined organic phases were washed two times with 1M HCl, brine, dried over sodium sulfate. The solvent was removed under reduced pressure and the residue was purified by vacuum distillation to yield 25.7 g (0.119 mmol, 87%) of a colourless liquid that was used directly in the next step.

Step B: Ethyl 4,4,5,5-tetrafluoro-3-hydroxy-pentanoate

Ethyl 4,4,5,5-tetrafluoro-3-oxo-pentanoate (25.7 g, 0.119 mmol) was dissolved in toluene (260 ml) and cooled to 0° C. Sodium borohydride (5.4 g, 0.143 g) was added portionwise, and the mixture was allowed to reach room temperature overnight with stirring. The mixture was then cooled to 0° C. and acidified with 1 m HCl. The phases were separated, the aqueous phase was extracted two times with ethyl acetate, the combined organic phases were dried over magnesium sulfate and the solvent was removed under reduced pressure. The residue was dissolved in a minimum amount of methanol, the resulting solution was evaporated to dryness under reduced pressure to yield 22.9 g of a residue (0.105 mol, 88%) that were used directly in the next step.

Step C: Ethyl (E)-4,4,5,5-tetrafluoropent-2-enoate

Ethyl 4,4,5,5-tetrafluoro-3-hydroxy-pentanoate (22.9 g, 0.105 mol) was mixed with phosphorus pentoxide (7.5 g, 0.053 mol) and the resulting mixture was stirred at 80° C. for two hours. The product was isolated by vacuum distillation (53 mbar, 92° C.) to yield 15.9 g of a liquid (0.08 mol, 76%) that was used directly in the next step.

Step D: (E)-4,4,5,5-Tetrafluoropent-2-enoic acid

Ethyl (E)-4,4,5,5-tetrafluoropent-2-enoate (15.9 g, 0.08 mol) was dissolved in ethanol (30 ml), 4M NaOH was added (15 ml) and the mixture was stirred at room temperature overnight. The mixture was diluted with water, washed with ethylacetate, acidified with 1M HCl and extracted with ethyl acetate. The organic extract was dried over magnesium sulfate, the solvent was removed under reduced pressure. 12.8 g of a colourless oil were obtained (0.074 mmol, 93%). MS (ESI) m/z=170.9 $[M-1]^-$.

Step E: 4-Chloropyridine-2-carbonyl chloride

A mixture of 2-picolinic acid (5 g, 40.6 mmol) and sodium bromide (0.418 g, 4.06 mmol) in thionyl chloride (25 ml, 343 mmol) was heated under reflux for 24 hours. The reaction mixture was cooled to room temperature. The black mixture was concentrated under reduced pressure and coevaporated with toluene (3×) to give a black oil that was used directly in the next step.

Step F: 4-Chloro-N-methyl-pyridine-2-carboxamide

To a solution of methylamine hydrochloride (2.057 g, 30.5 mmol) and triethylamine (14.16 ml, 102 mmol) in DCM (30 ml) at 0° C., was added 4-chloropyridine-2-carbonyl chloride (3.575 g, 20.31 mmol) in DCM (20 ml). The resulting black suspension was allowed to reach room temperature and stirred overnight. The mixture was concentrated under reduced pressure and dissolved in ethyl acetate. Water was added and the layers were separated. The aqueous layer was extracted with ethyl acetate (3×), the combined organic layers were washed with water (3×) and brine, dried with Na2SO4 and concentrated under reduced pressure. The residue was purified with column chromatography (20-50% ethyl acetate in n-heptane) to give 2.04 gram of a yellow oil (10.64 mmol, 52%). MS (ESI) m/z=170.0 [M+1]$^+$.

Step G:
N-Methyl-4-piperazin-1-yl-pyridine-2-carboxamide hydrochloride

A mixture of 4-Chloro-N-methyl-pyridine-2-carboxamide (400 mg, 2.345 mmol), piperazine (808 mg, 9.38 mmol) and sodium bicarbonate (591 mg, 7.03 mmol) in 1-butanol (4 ml) was heated under reflux for 18 hours. The mixture was filtered, the filtrate was concentrated under reduced pressure and the residue was purified by column chromatography (silica, 1-5% MeOH—basified with ammonia—in DCM) to give a colourless oil. The oil was dissolved in 2 ml ethanol and 4N HCl in dioxane (1.11 ml, 4.4 mmol) was added. The mixture was stirred for 1 hour at room temperature and filtered. The filter residue was rinsed with DCM and ethanol, dried under reduced pressure to give 200 mg of a white solid (0.779 mmol, 33%). MS (ESI) m/z=221.2 [M+1]$^+$.

Step H: N-Methyl-4-[4-[(E)-4,4,5,5-tetrafluoropent-2-enoyl]piperazin-1-yl]pyridine-2-carboxamide (E)-4,4,5,5-tetrafluoropent-2-enoic acid (19 mg, 0.11 mmol) was dissolved in DCM (1 ml), oxalyl chloride was added (9 µl, 0.11 mmol) followed by a drop of DMF. The mixture was stirred for 10 minutes at room temperature. N-methyl-4-piperazin-1-yl-pyridine-2-carboxamide hydrochloride (25.6 mg, 0.1 mmol) was dissolved in DMF (0.5 ml), the mixtures were combined, diisopropylethylamine (75 µl, 0.4 mmol) was added and the resulting mixture was stirred at room temperature for 1 hour. The mixture was evaporated to dryness under reduced pressure, the residue was purified by preparative HPLC (gradient of water containing 0.1% NH$_3$ and acetonitrile) to yield 20.2 mg (0.054 mmol, 54%).

Example 21

Synthesis of methyl 2-[1-(2-methyl-4-quinolyl)-4-[(E)-4,4,4-trifluorobut-2-enoyl]piperazin-2-yl]acetate (D-57)

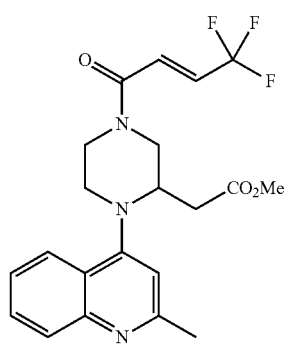 [SMILES: COC(=O)CC1CN(C(=O)/C=C/C(F)(F)F)CCN1c1cc(C)nc2ccccc12]

Step A: tert-Butyl 3-(2-methoxy-2-oxo-ethyl)-4-(2-methyl-4-quinolyl)piperazine-1-carboxylate 4-Chloroquinaldine (263 mg, 1.481 mmol), tert-butyl 3-(2-methoxy-2-oxo-ethyl)piperazine-1-carboxylate (318 mg, 1.231 mmol) and caesium carbonate (885 mg, 2.72 mmol) were mixed with anhydrous toluene (4 ml) in an argon atmosphere. 9,9-dimethyl-4,5-bis(diphenylphosphino)xanthene (128 mg, 0.221 mmol) and tris(dibenzylideneacetone)dipalladium(0) (67 mg, 0.073 mmol) were added and the resulting mixture was stirred at 110° C. for six hours. Additional 9,9-dimethyl-4,5-bis(diphenylphosphino)xanthene (128 mg, 0.221 mmol) and tris(dibenzylideneacetone)dipalladium(0) (67 mg, 0.073 mmol) were added and the mixture was stirred at 110° C. overnight. After reaching room temperature the mixture was filtered, the filtrate was evaporated to dryness to give a red oil that was purified by column chromatography (silica, gradient from DCM to DCM/methanol 1:20) to yield 136 mg of a yellow foam (0.214 mmol, 17%). MS (ESI) m/z=400.2 [M+1]$^+$.

Step B: Methyl 2-[1-(2-methyl-4-quinolyl)piperazin-2-yl]acetate tert-Butyl 3-(2-methoxy-2-oxo-ethyl)-4-(2-methyl-4-quinolyl)piperazine-1-carboxylate (239 mg, 0.28 mmol) was dissolved in dioxane (1 ml), combined with a solution of HCl in dioxane (4N, 4 ml, 16 mmol) and stirred overnight. The mixture was diluted with diethylether, the precipitate was collected by filtration and dissolved in DCM. The solution was washed with a saturated solution of sodium bicarbonate and dried over sodium sulfate. The solvent was removed under reduced pressure, the residue was triturated with diethylether to yield 85 mg of a yellow solid (0.253 mmol, 72%).

Step C: Methyl 2-[1-(2-methyl-4-quinolyl)-4-[(E)-4,4,4-trifluorobut-2-enoyl]piperazin-2-yl]acetate (E)-4,4,4-Trifluorobut-2-enoic acid (15.4 mg, 0.08 mmol) was dissolved in DCM (1 ml), oxalyl chloride was added (9.4 µl, 0.11 mmol) followed by a drop of DMF. The mixture was stirred for 10 minutes at room temperature. Methyl 2-[1-(2-methyl-4-quinolyl)piperazin-2-yl]acetate (33.6 mg, 0.1 mmol) was dissolved in DMF (1 ml) together with diisopropylethylamine (44 µl, 0.25 mmol), the solutions were combined and the resulting mixture was stirred at room temperature overnight. The volatiles were removed under reduced pressure and the residue was purified by preparative HPLC (gradient of water containing 0.1% NH$_3$ and acetonitrile) to yield 3.9 mg (0.0093 mmol, 9%).

Example 22

Synthesis of (E)-4-methyl-1-[4-[7-(trifluoromethyl)-4-quinolyl]piperazin-1-yl]hex-2-ene-1-thione (A-673)

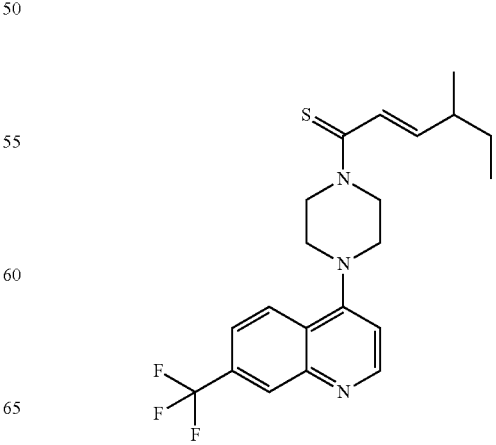

Step A:
4-piperazin-1-yl-7-(trifluoromethyl)quinoline

4-Chloro-7-(trifluoromethyl)quinoline (2.3 g, 10 mmol) was dissolved in dipropyleneglycolmonomethyl ether (10 ml) together with piperazine (6.8 g, 0.1 mol) and glacial acetic acid (0.3 ml) and heated at reflux for 2 days. The mixture was concentrated under reduced pressure and the residue was purified by column chromatography (silica, gradient from ethylacetate to methanol containing 1% ammonia) to yield a yellow crystalline solid (1.2 g, 43%).

Step B: (E)-4-Methyl-1-[4-[7-(trifluoromethyl)-4-quinolyl]piperazin-1-yl]hex-2-en-1-one (E)-4-Methylhex-2-enoic acid (26 mg, 0.2 mmol) was dissolved in DMF (0.5 ml) together with diisopropylethylamine (35 µl), HATU was added (76 mg, 0.2 mmol) and the mixture was stirred at room temperature for 15 minutes. 4-piperazin-1-yl-7-(trifluoromethyl)quinoline (56 mg, 0.2 mmol) was dissolved in DMF (0.5 ml) together with diisopropylethylamine (35 µl), the two solutions were combined and stirred at room temperature overnight. The mixture was evaporated to dryness under reduced pressure and the residue was purified by preparative HPLC (gradient of water containing 0.1% $NH_3$ and acetonitrile) to yield 62.6 mg (0.16 mmol, 80%). MS (APCI) m/z=391.9 $[M+1]^+$.

Step C: (E)-4-Methyl-1-[4-[7-(trifluoromethyl)-4-quinolyl]piperazin-1-yl]hex-2-ene-1-thione (E)-4-methyl-1-[4-[7-(trifluoromethyl)-4-quinolyl]piperazin-1-yl]hex-2-en-1-one (20 mg, 0.049 mmol) was dissolved in THF (1 ml), Lawesson's reagent (20 mg, 0.051 mmol) was added in one portion and the resulting mixture was stirred overnight at room temperature. The volatiles were removed under reduced pressure and the residue was purified by preparative HPLC (gradient of water containing 0.1% $NH_3$ and acetonitrile) to yield 5.4 mg (0.013 mmol, 25%).

C. Analytics: HPLC Methods

Method 1
HPLC-MS System:
   Agilent HPLC/MSD 1100 series composed of:
   Binary pump G 1312A included degasser G1379A, well plate sampler G1367A, column oven G1316A, diode array detector G1315B, mass detector G1946D SL with ESI-source and evaporative light scattering detector Sedex 75.
Chromatographic System:
Column: Zorbax SB-C18 from Agilent, 4.6*30 mm, 3.5 µ
Oven: 30° C.
Injection: 5.0 µl
Eluents:
Solvent A: water/formic acid: 99.9/0.1 vol./vol.
Solvent B: acetonitrile/formic acid: 99.9/0.1 vol./vol.
Flow: 1.0 ml/min
Gradient:

| Time [min] | Solvent A [%] | Solvent B [%] |
|---|---|---|
| 0.0 | 90 | 10 |
| 0.2 | 90 | 10 |
| 4.0 | 2 | 98 |
| 5.3 | 2 | 98 |

Run time: 8 min (equilibration included)
Detection Methods:
   UV at 210 nm and 254 nm
   ESI/MS (100-1000 m/z), positive ions
   ELSD (Sedex 75)
Comment: Samples diluted in a 1 to 1 mixture of solvents A and B prior to analysis
Method 2
HPLC-MS System:
   Agilent LC/MSD Trap 1100 series composed of:
   Binary pump G 1312A included degasser G1379A, well plate sampler G1367A, column oven G1316A, diode array detector G1315B, and mass detector G2445D with APCI-source.
Chromatographic System:
Column: Zorbax-SB-18 von Agilent, 4.6*30 mm, 3.5 µ
Oven: 30° C.
Injection: 2.0 µl
Eluents:
Solvent A: water/formic acid: 99.9/0.1 vol./vol.
Solvent B: acetonitrile/formic acid: 99.9/0.1 vol./vol.
Flow: 1.0 ml/min
Gradient:

| Time [min] | Solvent A [%] | Solvent B [%] |
|---|---|---|
| 0.0 | 90 | 10 |
| 0.2 | 90 | 10 |
| 4.2 | 2 | 98 |
| 5.5 | 2 | 98 |

Run time: 8 min (equilibration included)
Detection Methods:
   UV at 254 nm, 210 nm
   APCI/MS (100-1500 m/z), positive ions
Comment: Samples diluted in a 1 to 1 mixture of solvents A and B prior to analysis
Method 3
HPLC-MS System:
   Agilent LC/MSD Trap 1100 series composed of:
   Binary pump G 1312A included degasser G1379A, well plate sampler G1367A, column oven G1316A, diode array detector G1315B, and mass detector G2445D with APCI-source.
Chromatographic System:
Column: Waters Xbridge C-18, 4.6*50 mm, 2.5 µ
Oven: 40° C.
Injection: 2.0 µl
Eluents:
Solvent A: water/ammonia: 99.9/0.1 vol./vol.
Solvent B: acetonitrile/ammonia: 99.9/0.1 vol./vol.
Flow: 1.0 ml/min
Gradient:

| Time [min] | Solvent A [%] | Solvent B [%] |
|---|---|---|
| 0.0 | 95 | 5 |
| 5 | 0 | 100 |
| 7 | 0 | 100 |

Run time: 10 min (equilibration included)
Detection Methods:
 UV at 254 nm, 210 nm
 APCI/MS (100-1500 m/z), positive ions
Comment: Samples diluted in a 1 to 1 mixture of solvents A and B prior to analysis Method 4
HPLC-MS System:
 Agilent LC/MSD Trap 1100 series composed of:
 Binary pump G 1312A included degasser G1379A, well plate sampler G1367A, column oven G1316A, diode array detector G1315B, and mass detector G2445D with APCI-source.
Chromatographic System:
Column: Waters Xbridge C-18, 4.6*50 mm, 2.5 µ
Oven: 40° C.
Injection: 2.0 µl
Eluents:
Solvent A: water/ammonia: 99.9/0.1 vol./vol.
Solvent B: acetonitrile/ammonia: 99.9/0.1 vol./vol.
Flow: 1.0 ml/min
Gradient:

| Time [min] | Solvent A [%] | Solvent B [%] |
|---|---|---|
| 0.0 | 95 | 5 |
| 4 | 0 | 100 |
| 5 | 0 | 100 |

Run time: 7 min (equilibration included)
Detection Methods:
 UV at 254 nm, 210 nm
 APCI/MS (80-1000 m/z), positive ions
Comment: Samples diluted in a 1 to 1 mixture of solvents A and B prior to analysis Method 5
HPLC-MS System:
 Agilent LC/MSD Trap 1100 series composed of:
 Binary pump G 1312A included degasser G1379A, well plate sampler G1367A, column oven G1316A, diode array detector G1315B, and mass detector G2445D with APCI-source.
Chromatographic System:
Column: Waters Xbridge C-18, 4.6*50 mm, 2.5 µ
Oven: 40° C.
Injection: 2.0 µl
Eluents:
Solvent A: water/ammonia: 99.9/0.1 vol./vol.
Solvent B: acetonitrile/ammonia: 99.9/0.1 vol./vol.
Flow: 1.0 ml/min
Gradient:

| Time [min] | Solvent A [%] | Solvent B [%] |
|---|---|---|
| 0.0 | 90 | 10 |
| 4 | 0 | 100 |
| 5 | 0 | 100 |

Run time: 7 min (equilibration included)
Detection Methods:
 UV at 254 nm, 210 nm
 APCI/MS (80-1000 m/z), positive ions
Comment: Samples diluted in a 1 to 1 mixture of solvents A and B prior to analysis Method 6
HPLC-MS System:
 Agilent LC/MSD Trap 1100 series composed of:
 Binary pump G 1312A included degasser G1379A, well plate sampler G1367A, column oven G1316A, diode array detector G1315B, and mass detector G2445D with APCI-source.
Chromatographic System:
Column: Waters Xbridge C-18, 4.6*50 mm, 2.5 µ
Oven: 40° C.
Injection: 2.0 µl
Eluents:
Solvent A: water/ammonia: 99.9/0.1 vol./vol.
Solvent B: acetonitrile/ammonia: 99.9/0.1 vol./vol.
Flow: 1.0 ml/min
Gradient:

| Time [min] | Solvent A [%] | Solvent B [%] |
|---|---|---|
| 0.0 | 95 | 5 |
| 4 | 0 | 100 |
| 5 | 0 | 100 |

Run time: 7 min (equilibration included)
Detection Methods:
 UV at 280 nm, 254 nm, 210 nm
 APCI/MS (80-1000 m/z), positive ions
Comment: Samples diluted in a 1 to 1 mixture of solvents A and B prior to analysis Method 7
HPLC-MS System:
 Agilent HPLC/MSD 1100 series composed of:
 Binary pump G 1312A included degasser G1379A, well plate sampler G1367A, column oven G1316A, diode array detector G1315B, mass detector G1946D SL with ESI-source and evaporative light scattering detector Sedex 75.
Chromatographic System:
Column: Atlantis dC18 from Waters, 4.6*50 mm, 3 µ
Oven: 30° C.
Injection: 5.0 µl
Eluents:
Solvent A: water/formic acid: 99.9/0.1 vol./vol.
Solvent B: acetonitrile/formic acid: 99.9/0.1 vol./vol.
Flow: 1.0 ml/min
Gradient:

| Time [min] | Solvent A [%] | Solvent B [%] |
|---|---|---|
| 0.0 | 95 | 5 |
| 1.0 | 95 | 5 |
| 5.0 | 2 | 98 |
| 7.0 | 2 | 98 |

Run time: 10 min (equilibration included)
Detection Methods:
  UV at 210 nm and 254 nm
  ESI/MS (85-1000 m/z), positive ions
  ELSD (Sedex 75)
Comment: Samples diluted in a 1 to 1 mixture of solvents A and B prior to analysis
Method 8
HPLC-MS System:
  Agilent HPLC/MSD 1100 series composed of:
  Binary pump G 1312A included degasser G1379A, well plate sampler G1367A, column oven G1316A, diode array detector G1315B, mass detector G1946D SL with ESI-source and evaporative light scattering detector Sedex 75.
Chromatographic System:
Column: Chromolith FastGradient RP-18e from Merck, 2*50 mm
Oven: 30° C.
Injection: 1.0 μl
Eluents:
Solvent A: water/formic acid: 99.9/0.1 vol./vol.
Solvent B: acetonitrile/formic acid: 99.9/0.1 vol./vol.
Flow: 1.2 ml/min
Gradient:

| Time [min] | Solvent A [%] | Solvent B [%] |
|---|---|---|
| 0.0 | 98 | 2 |
| 0.2 | 98 | 2 |
| 2.2 | 2 | 98 |
| 2.7 | 2 | 98 |

Run time: 3.5 min (equilibration included)
Detection Methods:
  UV at 210 nm and 254 nm
  ESI/MS (100-1000 m/z), positive ions
  ELSD (Sedex 75)
Comment: Samples diluted in a 1 to 1 mixture of solvents A and B prior to analysis
Method 9
HPLC-MS System:
  Agilent HPLC/MSD 1100 series composed of:
  Binary pump G 1312A included degasser G1379A, well plate sampler G1367A, column oven G1316A, diode array detector G1315B, mass detector G1946D SL with ESI-source and evaporative light scattering detector Sedex 75.
Chromatographic System:
Column: Chromolith FastGradient RP-18e from Merck, 2*50 mm
Oven: 30° C.
Injection: 1.0 μl
Eluents:
Solvent A: water/formic acid: 99.9/0.1 vol./vol.
Solvent B: acetonitrile/formic acid: 99.9/0.1 vol./vol.
Flow: 1.2 ml/min
Gradient:

| Time [min] | Solvent A [%] | Solvent B [%] |
|---|---|---|
| 0.0 | 90 | 10 |
| 2 | 0 | 100 |
| 2.7 | 0 | 100 |

Run time: 3.5 min (equilibration included)
Detection Methods:
  UV at 210 nm and 254 nm
  ESI/MS (105-1000 m/z), positive ions
  ELSD (Sedex 75)
Comment: Samples diluted in a 1 to 1 mixture of solvents A and B prior to analysis
Method 10
HPLC-MS System:
  Agilent LC/MSD Trap 1100 series composed of:
  Binary pump G 1312A included degasser G1379A, well plate sampler G1367A, column oven G1316A, diode array detector G1315B, and mass detector G2445D with APCI-source.
Chromatographic System:
Column: Waters Xbridge C-18, 4.6*50 mm, 2.5 μ
Oven: 40° C.
Injection: 2.0 μl
Eluents:
Solvent A: water/ammonia: 99.9/0.1 vol./vol.
Solvent B: acetonitrile/ammonia: 99.9/0.1 vol./vol.
Flow: 1.0 ml/min
Gradient:

| Time [min] | Solvent A [%] | Solvent B [%] |
|---|---|---|
| 0.0 | 75 | 25 |
| 5 | 0 | 100 |
| 7 | 0 | 100 |

Run time: 10 min (equilibration included)
Detection Methods:
  UV at 254 nm, 210 nm
  APCI/MS (100-1500 m/z), positive ions
Comment: Samples diluted in a 1 to 1 mixture of solvents A and B prior to analysis
Method 11
HPLC-MS System:
  Agilent LC/MSD Trap 1100 series composed of:
  Binary pump G 1312A included degasser G1379A, well plate sampler G1367A, column oven G1316A, diode array detector G1315B, and mass detector G2445D with APCI-source.
Chromatographic System:
Column: Waters Sunfire C-18, 4.6*50 mm, 3.5 μ
Oven: 40° C.
Injection: 2.0 μl
Eluents:
Solvent A: water/formic acid: 99.9/0.1 vol./vol.
Solvent B: acetonitrile/formic acid: 99.9/0.1 vol./vol.
Flow: 1.0 ml/min
Gradient:

| Time [min] | Solvent A [%] | Solvent B [%] |
|---|---|---|
| 0.0 | 90 | 10 |
| 4 | 0 | 100 |
| 5 | 0 | 100 |

Run time: 7.5 min (equilibration included)

Detection Methods:
UV at 254 nm, 210 nm
APCI/MS (80-1000 m/z), positive ions

Comment: Samples diluted in a 1 to 1 mixture of solvents A and B prior to analysis

D. Specific Compounds

Table A below provides for each of the exemplified compounds of the formula (A') the structure, the calculated molecular weight (MW) (gram/mol), the observed MS signal (m/z), the HPLC retention time (Rt) in minutes, and the number of the HPLC-method as described in paragraph C above ("Analytics: HPLC-Methods") used for analysis. From compound A-674 until to the end of the table the methods by which the compounds are synthesized are identified by referring to the synthesis steps described in the synthesis examples of paragraph B above ("Synthesis Examples"). If a compound contains a chiral center, the mentioning of such compound is indicating the racemate.

In Table A—in case of a) a ring formation between $Y^1$ and $Y^2$ by the substituents $R^{12}$ and $R^{13}$ or b) a ring formation between $Y^3$ and $Y^4$ by the substituents $R^{14}$ and $R^{15}$—in the columns for $R^{12}$ and $R^{13}$ or in the columns for $R^{14}$ and $R^{15}$, as the case may be, the symbols Y1, Y2, Y3 and Y4 indicate the ring atoms $Y^1$, $Y^2$, $Y^3$ and $Y^4$ in formula (A') to which the respective substituents are bound.

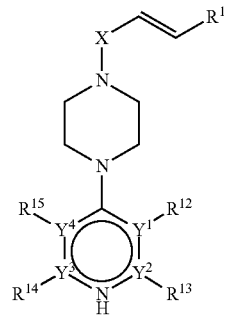

Formula (A')

TABLE A

| No | R¹ | X | Y¹ | Y² | Y³ | Y⁴ | R¹² | R¹³ | R¹⁴ | R¹⁵ | HPLC | Rt | m/z | MW |
|---|---|---|---|---|---|---|---|---|---|---|---|---|---|---|
| A-1 | CH₃ | CO | C | C | C | C | H | H | Y3—CH=CCl—CH=CH— | CH—Y4 | 1 | 2.16 | 316.1 | 315.8 |
| A-2 | CH₃ | CO | C | C | C | C | H | H | Y3—CH=CH—CH=CH— | CH—Y4 | 2 | 2.22 | 282.0 | 281.4 |
| A-3 | CH₃ | CO | C | C | C | C | H | H | Y3—CH=C(CF₃)—CH=CH— | CH—Y4 | 2 | 2.69 | 350.0 | 349.4 |
| A-4 | CH₃ | CO | C | C | C | C | H | CH₃ | Y3—CH=CCl—CH=CH— | CH—Y4 | 2 | 2.35 | 296.0 | 295.4 |
| A-5 | H | CO | C | C | C | C | H | H | Y3—CH=CCl—CH=CH— | CH—Y4 | 2 | 2.27 | 301.9 | 301.8 |
| A-6 | Phenyl | CO | C | C | C | C | H | H | Y3—CH=CH—CH=CH— | CH—Y4 | 2 | 3.03 | 377.9 | 377.9 |
| A-7 | CH₂CH₃ | CO | C | C | C | C | H | H | Y3—CH=CCl—CH=CH— | CH—Y4 | 2 | 2.49 | 330.0 | 329.8 |
| A-8 | CH₂CH₃ | CO | C | C | C | C | H | H | Y3—CH=CH—CH=CH— | CH—Y4 | 1 | 2.71 | 344.1 | 343.9 |
| A-9 | CH₂CH₃ | CO | C | C | C | C | H | CH₃ | Y3—CH=CH—CH=CH— | CH—Y4 | 3 | 3.20 | 310.0 | 309.4 |
| A-10 | CH₂CH₃ | CO | C | C | C | C | H | CH₃ | Y3—CH=CH—C(OCF₃)=CH— | CH—Y4 | 1 | 2.61 | 324.2 | 323.4 |
| A-11 | CH₂CH₃ | CO | C | C | C | C | H | CF₃ | Y3—CH=CCl—CH=CH— | CH—Y4 | 1 | 4.29 | 434.1 | 433.4 |
| A-12 | CH₃ | CO | C | C | C | C | H | CF₃ | Y3—CH=CH—CH=CH— | CH—Y4 | 1 | 3.72 | 350.1 | 349.4 |
| A-13 | CH₃ | CO | C | C | C | C | H | CF₃ | Y3—C(CF₃)=CH—CH=CH— | CH—Y4 | 1 | 4.24 | 418.1 | 417.4 |
| A-14 | (CH₂)₄CH₃ | CO | C | C | C | C | H | H | Y3—CH=CH—CH=CH— | CH—Y4 | 1 | 2.79 | 352.2 | 351.5 |
| A-15 | (E)-CHCHCH₃ | CO | C | C | C | C | H | H | Y3—CH=CCl—CH=CH— | CH—Y4 | 3 | 4.18 | 322.1 | 321.4 |
| A-16 | CH(CH₃)₂ | CO | C | C | C | C | H | CH₃ | Y3—CH=CH—CH=CH— | CH—Y4 | 1 | 2.60 | 324.2 | 323.4 |
| A-17 | (CH₂)₅CH₃ | CO | C | C | C | C | H | CH₃ | Y3—CH=CH—CH=CH— | CH—Y4 | 1 | 3.35 | 366.2 | 365.5 |
| A-18 | CH₂CH₂CH₃ | CO | C | C | C | C | H | CF₃ | Y3—CH=CH—CH=CH— | CH—Y4 | 1 | 4.19 | 378.2 | 377.4 |
| A-19 | CH₂CH₂CH₃ | CO | N | C | C | C | H | H | Y3—S—C(CH₃)=C(CH₃)— | CH—Y4 | 1 | 3.86 | 359.2 | 358.5 |
| A-20 | CH₂CH₂CH₃ | CO | C | C | C | C | Y1—CH₂—CH₂—CH₂—Y2 | H | Y3—CH=CH—C(OCF₃)=CH— | CH—Y4 | 1 | 2.70 | 354.2 | 353.5 |
| A-21 | CH₂CH₂CH₃ | CO | N | C | C | C | H | H | Y3—CH=CH—CH=CH— | CH—Y4 | 1 | 2.84 | 364.2 | 363.5 |
| A-22 | CH₂CH₂CH₃ | CO | C | C | C | C | H | H | Y3—S—CH=CH— | CH—Y4 | 1 | 3.14 | 317.1 | 316.4 |
| A-23 | CH₃ | CO | C | C | C | C | H | H | Y3—CH=CH—CH=CH— | CH—Y4 | 1 | 2.50 | 310.2 | 309.4 |
| A-24 | CH₃ | CO | C | C | C | C | C(O)OCH₂CH₃ | H | Y3—CF=CF—CH=CH— | CH—Y4 | 5 | 3.55 | 372.2 | 371.4 |
| A-25 | CH₃ | CO | C | C | C | C | C(O)OCH₂CH₃ | H | Y3—C(OCF₃)=CH—CH=CH— | CH—Y4 | 5 | 4.04 | 438.2 | 437.4 |
| A-26 | CH₃ | CO | C | C | C | C | C(O)OCH₂CH₃ | H | Y3—CF=CF—CF=CH— | CH—Y4 | 5 | 3.91 | 408.2 | 407.4 |
| A-27 | CH₃ | CO | C | C | C | C | H | C(O)OCH₂CH₃ | Y3—CH=C(CF₃)—CH=CH— | CH—Y4 | 5 | 4.11 | 422.2 | 421.4 |
| A-28 | CH₂CH₂CH₃ | CO | C | C | C | C | H | CF₃ | Y3—C(CH₃)=CH—CH=CH— | CH—Y4 | 5 | 3.47 | 354.2 | 353.4 |
| A-29 | CH₂CH₂CH₃ | CO | C | C | C | C | H | CF₃ | Y3—CCl=CH—CH=CH— | CH—Y4 | 5 | 4.49 | 364.2 | 363.4 |
| A-30 | CH₂CH₂CH₃ | CO | C | C | C | C | H | CF₃ | Y3—CH=CH—C(CF₃)=CH— | CH—Y4 | 5 | 4.23 | 384.2 | 383.8 |
| A-31 | CH₃ | CO | C | C | C | C | H | CF₃ | Y3—CH=CCl—CH=CH— | CH—Y4 | 5 | 4.33 | 418.2 | 417.4 |
| A-32 | CH₃ | CO | C | C | C | C | H | CF₃ | Y3—CF=CH—CH=CH— | CH—Y4 | 5 | 3.94 | 368.2 | 367.3 |
| A-33 | CH₃ | CO | C | C | C | C | H | CF₃ | Y3—CH=CH—C(OCF₃)=CH— | CH—Y4 | 5 | 4.11 | 438.2 | 437.4 |
| A-34 | CH₃ | CO | C | C | C | C | C(O)OCH₂CH₃ | H | Y3—CH=CCl—CH=CCl— | CH—Y4 | 5 | 4.60 | 418.2 | 418.2 |
| A-35 | CH₃ | CO | C | C | C | C | H | H | Y3—CH=CCl—CH=CH— | CH—Y4 | 3 | 4.29 | 384.2 | 383.8 |
| A-36 | (CO)OCH₂CH₃ | CO | C | C | C | C | H | H | Y3—CH=CH—CH=CH— | CH—Y4 | 3 | 3.84 | 340.2 | 339.4 |
| A-37 | (CH₂)₃CH₃ | CO | C | C | C | C | H | H | Y3—CH=CH—CH=CH— | CH—Y4 | 3 | 4.52 | 324.2 | 323.4 |
| A-38 | CH(CH₃)CH₂CH₃ | CO | C | C | C | C | H | H | Y3—CH=CH—CH=CH— | CH—Y4 | 3 | 4.45 | 324.2 | 323.4 |
| A-39 | CH(CH₂CH₃)CH₂CH₃ | CO | C | C | C | C | H | H | Y3—CH=CH—CH=CH— | CH—Y4 | 3 | 4.72 | 338.2 | 337.5 |
| A-40 | cyclopentyl | CO | C | C | C | C | H | H | Y3—CH=CH—CH=CH— | CH—Y4 | 3 | 4.55 | 336.2 | 335.4 |
| A-41 | cyclopropyl | CO | C | C | C | C | H | H | Y3—CH=CH—CH=CH— | CH—Y4 | 3 | 3.89 | 308.1 | 307.4 |
| A-42 | (CH₂)₄CH₃ | CO | C | C | C | C | H | H | Y3—CH=CH—C(CF₃)=CH— | CH—Y4 | 3 | 4.82 | 338.2 | 337.5 |
| A-43 | (CH₂)₅CH₃ | CO | C | C | C | C | H | H | Y3—CH=CH—CH=CH— | CH—Y4 | 3 | 5.11 | 352.2 | 351.5 |
| A-44 | (E)-CHCHCH₃ | CO | C | C | C | C | H | H | Y3—CH=CH—CH=CH— | CH—Y4 | 3 | 4.06 | 308.1 | 307.4 |
| A-45 | cyclohexyl | CO | C | C | C | C | H | H | Y3—CH=CH—CH=CH— | CH—Y4 | 3 | 4.82 | 350.2 | 349.5 |
| A-46 | furan-2-yl | CO | C | C | C | C | H | H | Y3—CH=CH—CH=CH— | CH—Y4 | 3 | 4.01 | 334.1 | 333.4 |
| A-47 | thiophen-2-yl | CO | C | C | C | C | H | H | Y3—CH=CH—CH=CH— | CH—Y4 | 3 | 4.19 | 350.1 | 349.5 |
| A-48 | imidazol-4-yl | CO | C | C | C | C | H | H | Y3—CH=CH—CH=CH— | CH—Y4 | 3 | 3.07 | 334.2 | 333.4 |
| A-49 | furan-3-yl | CO | C | C | C | C | H | H | Y3—CH=CH—CH=CH— | CH—Y4 | 3 | 3.94 | 334.1 | 333.4 |

TABLE A-continued

| | | | | | | | | | |
|---|---|---|---|---|---|---|---|---|---|
| A-50 | C(CH₃)₃ | CO | C | C | H | H | Y3—CH=CH—CH=CH—Y4 | 3 | 4.41 | 324.2 | 323.4 |
| A-51 | CH(CH₃)CH₂CH₂CH₃ | CO | C | C | H | H | Y3—CH=CH—CH=CH—Y4 | 3 | 4.76 | 338.2 | 337.5 |
| A-52 | (CO)OCH₂CH₃ | CO | C | C | H | CH₃ | Y3—CH=CH—CH=CH—Y4 | 3 | 3.95 | 354.0 | 353.4 |
| A-53 | (CH₂)₃CH₃ | CO | C | C | H | CH₃ | Y3—CH=CH—CH=CH—Y4 | 3 | 4.64 | 338.2 | 337.5 |
| A-54 | CH(CH₃)CH₂CH₃ | CO | C | C | H | CH₃ | Y3—CH=CH—CH=CH—Y4 | 3 | 4.58 | 338.2 | 337.5 |
| A-55 | CH(CH₃)CH₂CH₂CH₃ | CO | C | C | H | CH₃ | Y3—CH=CH—CH=CH—Y4 | 3 | 4.85 | 352.2 | 351.5 |
| A-56 | cyclopentyl | CO | C | C | H | CH₃ | Y3—CH=CH—CH=CH—Y4 | 3 | 4.68 | 350.2 | 349.5 |
| A-57 | cyclopropyl | CO | C | C | H | CH₃ | Y3—CH=CH—CH=CH—Y4 | 3 | 4.02 | 322.2 | 321.4 |
| A-58 | cyclohexyl | CO | C | C | H | CH₃ | Y3—CH=CH—CH=CH—Y4 | 3 | 4.95 | 364.2 | 363.5 |
| A-59 | thiophen-2-yl | CO | C | C | H | CH₃ | Y3—CH=CH—CH=CH—Y4 | 3 | 4.30 | 363.9 | 363.5 |
| A-60 | imidazol-4-yl | CO | C | C | H | CH₃ | Y3—CH=CH—CH=CH—Y4 | 3 | 3.16 | 348.2 | 347.4 |
| A-61 | furan-3-yl | CO | C | C | H | CH₃ | Y3—CH=CH—CH=CH—Y4 | 3 | 4.04 | 347.9 | 347.4 |
| A-62 | C(CH₃)₄ | CO | C | C | H | CH₃ | Y3—CH=CH—CH=CH—Y4 | 3 | 4.53 | 338.3 | 337.5 |
| A-63 | CH(CH₃)CH₂CH₂CH₃ | CO | C | C | H | CH₃ | Y3—CH=CH—CH=CH—Y4 | 3 | 4.87 | 352.2 | 351.5 |
| A-64 | phenyl | CO | C | C | H | H | Y3—CH=CH—CH=CH—Y4 | 3 | 3.58 | 344.0 | 343.4 |
| A-65 | CH(CH₃)₂ | CO | C | C | H | CH₃ | Y3—CH=CH—CH=CH—Y4 | 3 | 3.35 | 310.0 | 309.4 |
| A-66 | CH₂CH₃ | CO | C | C | H | CH₃ | Y3—CH=CH—CH=CH—Y4 | 3 | 3.07 | 296.0 | 295.4 |
| A-67 | CH₂CH(CH₃)₂ | CO | C | C | H | CH₃ | Y3—CH=CH—CH=CH—Y4 | 3 | 3.69 | 324.0 | 323.4 |
| A-68 | CH₂CH₂SCH₃ | CO | C | C | H | CH₃ | Y3—CH=CH—CH=CH—Y4 | 3 | 3.20 | 342.0 | 341.5 |
| A-69 | phenyl | CO | C | C | H | CH₃ | Y3—CH=CH—CH=CH—Y4 | 3 | 3.72 | 358.0 | 357.5 |
| A-70 | furan-2-yl | CO | C | C | H | CH₃ | Y3—CH=CH—CH=CH—Y4 | 3 | 3.36 | 348.0 | 347.4 |
| A-71 | CH(CH₃)₂ | CO | C | C | H | CH₃ | Y3—CH=CH—CH=CH—Y4 | 3 | 3.81 | 338.0 | 337.5 |
| A-72 | CH₂CH(CH₃)₂ | CO | C | C | H | CH₃ | Y3—CH=CH—CH=CH—Y4 | 3 | 3.31 | 355.9 | 355.5 |
| A-73 | CH₂CF₃ | CO | C | C | H | CH₃ | Y3—CH=CH—CH=CH—Y4 | 3 | 3.41 | 363.9 | 363.4 |
| A-74 | CH₂CF₃ | CO | C | C | H | H | Y3—CH=CH—CH=CH—Y4 | 3 | 3.20 | 349.9 | 349.4 |
| A-75 | CH(CH₃)₂ | CO | N | C | — | H | Y3—S—CH=CH—Y4 | 3 | 3.94 | 316.9 | 316.4 |
| A-76 | CH(CH₃)₂ | CO | C | C | H | H | Y4=N—CH=N—Y4 | 3 | 3.28 | 301.0 | 300.4 |
| A-77 | CH₂CH₂CH₃ | CO | N | C | — | H | Y3=N—CH=N—Y4 | 3 | 3.32 | 301.0 | 300.4 |
| A-78 | CH₂CH₃ | CO | N | C | — | H | Y3—S—CH=CH—Y4 | 3 | 3.64 | 302.9 | 302.4 |
| A-79 | CH₂CH₃ | CO | C | C | H | H | Y3—N=CH=N—Y4 | 3 | 3.00 | 286.9 | 286.3 |
| A-80 | CH₂CH₃ | CO | C | C | C(O)OCH₂CH₃ | C(O)OCH₂CH₄ | Y3—CH=CH—CH=CH—Y4 | 4 | 3.80 | 367.8 | 367.4 |
| A-81 | CH₂CH₃ | CO | C | C | H | CH₂CH₂CH₃ | Y3—CH=CH—CH=CH—Y4 | 4 | 4.08 | 362.9 | 362.5 |
| A-82 | CH₂CH₃ | CO | C | C | H | CH₃ | Y3—CH=CH—C(CN)=CH—Y4 | 4 | 3.98 | 343.8 | 343.9 |
| A-83 | CH₂CH₃ | CO | C | C | H | CH₃ | Y3—CH=C(CH₃)=CH—CH=CH—Y4 | 4 | 4.25 | 323.9 | 323.4 |
| A-84 | CH₂CH₃ | CO | C | C | H | CH₂CH₃ | Y3—CH=CH—C(OCF₃)=CH—Y4 | 4 | 4.41 | 451.7 | 451.4 |
| A-85 | CH₂CH₃ | CO | C | C | H | SCH₃ | Y3—CH=CH—CH=CH—Y4 | 4 | 3.86 | 323.9 | 323.4 |
| A-86 | CH₂CH₂CH₃ | CO | C | C | C(O)OCH₂CH₃ | CF₃ | Y3—CH=CH—CCl=CH—Y4 | 4 | 5.11 | 461.7 | 462.0 |
| A-87 | CH₂CH₂CH₃ | CO | C | C | H | C(O)OCH₂CH₃ | Y3—CH=CH—C(OCF₃)=CH—Y4 | 4 | 4.82 | 461.7 | 461.4 |
| A-88 | CH₂CH₂CH₃ | CO | C | C | H | CH₂CH₂CH₃ | Y3—CH=CH—C(CN)=CH—Y4 | 4 | 4.04 | 381.8 | 381.5 |
| A-89 | CH₂CH₂CH₃ | CO | C | C | H | CH₃ | Y3—CH=CH—C(CN)=CH—Y4 | 4 | 4.30 | 376.8 | 376.5 |
| A-90 | CH₂CH₂CH₃ | CO | C | C | H | CH₂CH₃ | Y3—CH=CH—CCl=CH—Y4 | 4 | 4.22 | 357.8 | 357.9 |
| A-91 | CH₂CH₂CH₃ | CO | C | C | H | CH₃ | Y3—CH=C(CH₃)=CH—CH=CH—Y4 | 4 | 4.49 | 337.9 | 337.5 |
| A-92 | CH₂CH₂CH₃ | CO | C | C | H | CH₃ | Y3—CH=CH—C(OCF₃)=CH—Y4 | 4 | 4.60 | 465.7 | 465.5 |
| A-93 | CH₂CH₂CH₃ | CO | C | C | H | CH₃ | Y3—CH=CH—CCl=CH—Y4 | 4 | 4.10 | 337.8 | 337.5 |
| A-94 | CH(CH₃)₂ | CO | C | C | C(O)OCH₂CH₃ | C(O)OCH₂CH₆ | Y3—CH=CH—CCl=CH—Y4 | 4 | 5.10 | 461.7 | 462.0 |
| A-95 | CH(CH₃)₂ | CO | C | C | H | CH₂CH₂CH₃ | Y3—CH=CH—CH=CH—Y4 | 4 | 4.81 | 461.7 | 461.4 |
| A-96 | CH(CH₃)₂ | CO | C | C | H | CH₂CH₂CH₃ | Y3—CH=CH—C(CN)=CH—Y4 | 4 | 4.02 | 381.8 | 381.5 |
| A-97 | CH(CH₃)₂ | CO | C | C | H | CH₃ | Y3—CH=CH—CCl=CH—Y4 | 4 | 4.28 | 376.8 | 376.5 |
| A-98 | CH(CH₃)₂ | CO | C | C | H | CH₃ | Y3—CH=CH—CH=CH—Y4 | 4 | 4.20 | 357.8 | 357.9 |
| A-99 | CH(CH₃)₂ | CO | C | C | H | CH₃ | Y3—C(CH₃)=CH—CH=CH—Y4 | 4 | 4.47 | 337.8 | 337.5 |

TABLE A-continued

| ID | C1 | C2 | C3 | C4 | C5 | C6 | C7 | C8 | C9 | C10 |
|---|---|---|---|---|---|---|---|---|---|---|
| A-100 | CH(CH₃)₂ | CO | C | C | C(O)OCH₂CH₃ | H | Y3—CH=CH—C(OCF₃)=CH—Y4 | 4 | 4.59 | 465.7 | 465.5 |
| A-101 | CH(CH₃)₂ | CO | C | C | H | CH₂CH₃ | Y3—CH=CH—CH=CH—Y4 | 4 | 4.08 | 337.8 | 337.5 |
| A-102 | CH₂CH₃ | CO | C | C | C(O)OCH₂CH₃ | SCH₃ | Y3—CH=CH—CCl=CH—Y4 | 4 | 4.97 | 447.6 | 448.0 |
| A-103 | CH(CH₃)₂ | CO | C | C | H | CF₃ | Y3—CH=CH—C(OCF₃)=CH—Y4 | 4 | 4.66 | 447.6 | 447.4 |
| A-104 | CH₂CH₂CH₃ | CO | C | C | H | N(CH₃)₂ | Y3—CH=CH—CH=CH—Y4 | 4 | 4.30 | 353.0 | 352.5 |
| A-105 | CH₂CH₂CH₃ | CO | C | C | H | N(CH₃)₂ | Y3—CH=CH—CH=CH—Y4 | 4 | 4.33 | 352.9 | 352.5 |
| A-106 | CH₂CH₃ | CO | C | C | H | N(CH₃)₂ | Y3—CH=CH—CH=CH—Y4 | 4 | 4.09 | 338.9 | 338.5 |
| A-107 | CH(CH₃)₂ | CO | C | C | H | NH₂ | Y3—CH=CH—CH=CH—Y4 | 4 | 3.66 | 324.7 | 324.4 |
| A-108 | CH₂CH₂CH₃ | CO | C | C | H | NH₂ | Y3—CH=CH—CH=CH—Y4 | 4 | 3.69 | 324.7 | 324.4 |
| A-109 | CH₂CH₃ | CO | C | C | H | NH₂ | Y3—CH=CH—CH=CH—Y4 | 4 | 3.44 | 310.6 | 310.4 |
| A-110 | CH₂CH₃ | CO | C | C | H | H | Y3—CCl=CH—CH=CH—Y4 | 4 | 3.72 | 329.5 | 329.8 |
| A-111 | CH₂CH₃ | CO | C | C | H | CH₃ | Y3—CH=CH—C(N(CH₃)₂)=CH—Y4 | 4 | 3.77 | 352.6 | 352.5 |
| A-112 | CH₂CH₃ | CO | C | C | H | CH₃ | Y3—CH=CH—C(CH₃)=CH—Y4 | 4 | 3.80 | 323.6 | 323.4 |
| A-113 | CH₂CH₃ | CO | C | C | H | OCH₃ | Y3—CH=CH—CH=CH—Y4 | 4 | 4.12 | 325.6 | 325.4 |
| A-114 | CH₂CH₃ | CO | C | C | H | CH₃ | Y3—C(CF₃)=CH—CH=CH—Y4 | 4 | 4.07 | 363.5 | 363.4 |
| A-115 | CH₂CH₃ | CO | C | C | H | CH₃ | Y3—C(CF₃)=CH—CH=CH—Y4 | 4 | 4.43 | 377.5 | 377.4 |
| A-116 | CH₂CH₂CH₃ | CO | C | C | H | CH₃ | Y3—CH=CH—CF=CH—Y4 | 4 | 3.75 | 327.6 | 327.4 |
| A-117 | CH(CH₃)₂ | CO | C | C | H | H | Y3—CCl=CH—CH=CH—Y4 | 4 | 3.97 | 343.5 | 343.9 |
| A-118 | CH₂CH₂CH₃ | CO | C | C | H | CH₃ | Y3—CH=CH—C(N(CH₃)₂)=CH—Y4 | 4 | 4.01 | 366.6 | 366.5 |
| A-119 | CH₂CH₂CH₃ | CO | C | C | H | CH₃ | Y3—CH=CH—C(CH₃)=CH—Y4 | 4 | 4.03 | 337.6 | 337.5 |
| A-120 | CH₂CH₂CH₃ | CO | C | C | H | OCH₃ | Y3—CH=CH—CH=CH—Y4 | 4 | 4.05 | 339.6 | 339.4 |
| A-121 | CH₂CH₃ | CO | C | C | H | CH₃ | Y3—C(CF₃)=CH—CH=CH—Y4 | 4 | 4.34 | 339.6 | 339.4 |
| A-122 | CH₂CH₃ | CO | C | C | H | CH₃ | Y3—C(CF₃)=CH—CH=CH—Y4 | 4 | 4.28 | 377.5 | 377.4 |
| A-123 | CH₂CH₂CH₃ | CO | C | C | H | CH₃ | Y3—C(CF₃)=CH—CH=CH—Y4 | 4 | 4.61 | 391.5 | 391.4 |
| A-124 | CH(CH₃)₂ | CO | C | C | H | CH₃ | Y3—CH=CH—CF=CH—Y4 | 4 | 3.99 | 341.6 | 341.4 |
| A-125 | CH(CH₃)₂ | CO | C | C | H | H | Y3—CCl=CH—CH=CH—Y4 | 4 | 3.95 | 343.5 | 343.9 |
| A-126 | CH(CH₃)₂ | CO | C | C | H | CH₃ | Y3—CH=CH—C(N(CH₃)₂)=CH—Y4 | 4 | 3.99 | 366.6 | 366.5 |
| A-127 | CH(CH₃)₂ | CO | C | C | H | CH₃ | Y3—CH=CH—C(CH₃)=CH—Y4 | 4 | 4.03 | 337.6 | 337.5 |
| A-128 | CH(CH₃)₂ | CO | C | C | H | OCH₃ | Y3—CH=CH—CH=CH—Y4 | 4 | 4.32 | 339.6 | 339.4 |
| A-129 | CH(CH₃)₂ | CO | C | C | H | CH₃ | Y3—C(CF₃)=CH—CH=CH—Y4 | 4 | 4.26 | 377.6 | 377.4 |
| A-130 | CH(CH₃)₂ | CO | C | C | H | CH₃ | Y3—C(CF₃)=CH—CH=CH—Y4 | 4 | 4.59 | 391.7 | 391.4 |
| A-131 | CH₂CH₃ | CO | C | C | H | CH₃ | Y3—CCl=CH—CF=CH—Y4 | 4 | 3.97 | 341.6 | 341.4 |
| A-132 | CH(CH₃)₂ | CO | C | C | H | CH₃ | Y3—CH=CH—C(OCH₃)=CH—Y4 | 4 | 3.67 | 339.9 | 339.4 |
| A-133 | CH(CH₃)₂ | CO | C | C | C(O)OCH₂CH₃ | CH₃ | Y3—CH=CH—C(OCH₃)=CH—Y4 | 4 | 3.89 | 353.9 | 353.5 |
| A-134 | CH(CH₃)₂ | CO | C | C | H | H | Y3—CH=CH—CH=CH—Y4 | 4 | 3.86 | 367.7 | 367.4 |
| A-135 | CH₂CH₃ | CO | C | C | C(O)OCH₂CH₃ | CF₃ | Y3—CH=CH—CCl=CH—Y4 | 4 | 4.85 | 431.5 | 432.3 |
| A-136 | CH₂CH₃ | CO | C | C | C(O)OCH₂CH₃ | CH₃ | Y3—CH=CH—CCl=CH—Y4 | 4 | 3.97 | 381.7 | 381.5 |
| A-137 | CH₂CH₂CH₃ | CO | C | C | H | CH₃ | Y3—CH=CH—CCl=CH—Y4 | 4 | 4.09 | 381.7 | 381.5 |
| A-138 | CH₂CH₂CH₃ | CO | C | C | H | CF₃ | Y3—CH=CH—CCl=CH—Y4 | 4 | 5.00 | 445.5 | 446.3 |
| A-139 | CH₂CH₂CH₃ | CO | C | C | H | CH₃ | Y3—CH=CH—C(COOCH₂CH₃)=CH—Y4 | 4 | 4.20 | 395.7 | 395.5 |
| A-140 | CH(CH₃)₂ | CO | C | C | H | CH₃ | Y3—CH=CH—C(COOCH₂CH₃)=CH—Y4 | 4 | 4.14 | 395.7 | 395.5 |
| A-141 | CH(CH₃)₂ | CO | C | C | C(O)OCH₂CH₃ | CH₃ | Y3—CH=CH—CCl=CH—Y4 | 4 | 4.07 | 381.7 | 381.5 |
| A-142 | CH(CH₃)₂ | CO | C | N | H | CF₃ | Y3—CH=CH—CCl=CH—Y4 | 4 | 4.99 | 445.5 | 446.3 |
| A-143 | CH(CH₃)₂ | CO | C | N | C(O)OCH₂CH₃ | CH₃ | Y3—CH=CH—S—Y4 | 4 | 3.47 | 316.7 | 316.4 |
| A-144 | CH(CH₃)₂ | CO | N | C | H | CH₃ | Y3—CH=CH—CH=CH—Y4 | 4 | 4.18 | 395.7 | 395.5 |
| A-145 | CH₂CH₃ | CO | C | C | H | CH₃ | Y3—CH=CH—S—Y4 | 4 | 4.12 | 395.7 | 395.5 |
| A-146 | CH₂CH₃ | CO | C | C | — | H | Y3—CH=CH—CH=CH—Y4 | 4 | 3.39 | 301.7 | 301.4 |
| A-147 | CH₂CH₃ | CO | C | C | H | H | Y3—CH=CH—C(OCH₃)=C(OCH₃)—CH=CH—Y4 | 4 | 3.26 | 296.8 | 296.4 |
| A-148 | CH₂CH₃ | CO | C | C | — | H | Y3—CH=C(OCH₃)—CH=CH—Y4 | 4 | 3.24 | 356.8 | 356.4 |
| A-149 | CH₂CH₃ | CO | C | C | H | CH₃ | Y3—CCl=CH—CH=CH—Y4 | 4 | 3.57 | 325.8 | 325.4 |
| | | | | | | | Y3—CCl=CH—CH=CH—Y4 | 4 | 4.00 | 343.7 | 343.9 |

TABLE A-continued

| | | | | | | | | | |
|---|---|---|---|---|---|---|---|---|---|
| A-150 | CH₂CH₃ | CO | C | C | C | H | CH₃ | Y3—CH═CCl—CH═CH—Y4 | 4 | 4.01 | 343.7 | 343.9 |
| A-151 | CH₂CH₃ | CO | C | C | C | H | CH₃ | Y3—CH═C(CF₃)—CH═CH—Y4 | 4 | 4.17 | 377.7 | 377.4 |
| A-152 | CH₂CH₂CH₃ | CO | C | C | C | H | H | Y3—CH═CH—S—Y4 | 4 | 3.65 | 315.7 | 315.4 |
| A-153 | CH₂CH₂CH₃ | CO | N | C | C | — | H | Y3—CH═CH—CH═CH—Y4 | 4 | 3.55 | 310.8 | 310.4 |
| A-154 | CH₂CH₂CH₃ | CO | C | C | C | H | H | Y3—CH═C(OCH₃)—C(OCH₃)═CH—CH—Y4 | 4 | 3.49 | 370.7 | 370.5 |
| A-155 | CH₂CH₂CH₃ | CO | C | C | C | H | CH₃ | Y3—CH═C(OCH₃)—CH═CH—Y4 | 4 | 3.82 | 339.8 | 339.4 |
| A-156 | CH₂CH₂CH₃ | CO | C | C | C | H | CH₃ | Y3—CCl═CH—CH═CH—Y4 | 4 | 4.24 | 357.7 | 357.9 |
| A-157 | CH₂CH₂CH₃ | CO | C | C | C | H | CH₃ | Y3—CH═C(CF₃)—CH═CH—Y4 | 4 | 4.24 | 357.7 | 357.9 |
| A-158 | CH(CH₃)₂ | CO | C | C | C | H | CH₃ | Y3—CH═C(CF₃)—CH═CH—Y4 | 4 | 4.38 | 391.7 | 391.4 |
| A-159 | CH(CH₃)₂ | CO | C | C | C | H | H | Y3—CH═CH—S—Y4 | 4 | 3.63 | 315.7 | 315.4 |
| A-160 | CH(CH₃)₂ | CO | N | C | C | — | H | Y3—CH═CH—CH═CH—Y4 | 4 | 3.50 | 310.8 | 310.4 |
| A-161 | CH(CH₃)₂ | CO | C | C | C | H | H | Y3—CH═C(OCH₃)—C(OCH₃)═CH—CH—Y4 | 4 | 3.47 | 370.8 | 370.5 |
| A-162 | CH(CH₃)₂ | CO | C | C | C | H | CH₃ | Y3—CH═C(OCH₃)—CH═CH—Y4 | 4 | 3.79 | 339.8 | 339.4 |
| A-163 | CH(CH₃)₂ | CO | C | C | C | H | CH₃ | Y3—CCl═CH—CH═CH—Y4 | 4 | 4.22 | 357.7 | 357.9 |
| A-164 | CH(CH₃)₂ | CO | C | C | C | H | CH₃ | Y3—CH═CCl—CH═CH—Y4 | 4 | 4.22 | 357.8 | 357.9 |
| A-165 | CH(CH₃)₂ | CO | C | C | C | H | CH₃ | Y3—CH═C(CF₃)—CH═CH—Y4 | 4 | 4.36 | 391.7 | 391.4 |
| A-166 | COCH₃ | CO | C | C | C | H | H | Y3—CH═CH—CH═CH—Y4 | 5 | 3.90 | 309.8 | 309.4 |
| A-167 | COCH₃ | CO | C | C | C | H | CH₃ | Y3—CH═CH—CH═CH—Y4 | 5 | 2.99 | 323.4 | 323.4 |
| A-168 | Phenyl | CO | C | C | C | H | H | Y3—CH═CH—S—Y4 | 5 | 3.60 | 371.7 | 371.4 |
| A-169 | COC₆H₅ | CO | C | C | C | H | H | Y3—CH═CH—CH═CH—Y4 | 5 | 3.70 | 385.7 | 385.5 |
| A-170 | CON(CH₃)₂ | CO | C | C | C | H | CH₃ | Y3—CH═CH—CH═CH—Y4 | 5 | 2.80 | 352.7 | 352.4 |
| A-171 | CON(CH₃)₂ | CO | N | C | C | — | CH₃ | Y3—CCl═CH—CH═CH—Y4 | 5 | 2.72 | 338.7 | 338.4 |
| A-172 | CONHCH₃ | CO | N | C | C | — | H | Y3—CH═CH—CH═CH—Y4 | 5 | 2.61 | 325.1 | 324.4 |
| A-173 | CONHCH₃ | CO | C | C | C | H | CH₃ | Y3—CH═CH—CH═CH—Y4 | 5 | 2.69 | 338.7 | 338.4 |
| A-174 | COCH₂CH₃ | CO | C | C | C | H | CH₃ | Y3—CH═CH—CH═CH—Y4 | 5 | 3.27 | 337.7 | 337.4 |
| A-175 | COCH₂CH₃ | CO | C | C | C | H | CH₃ | Y3—CH═CH—CH═CH—Y4 | 5 | 3.16 | 323.8 | 323.4 |
| A-176 | CONCH₂CH₃ | CO | C | C | C | H | CH₃ | Y3—CH═CBr—CH═CH—Y4 | 5 | 2.76 | 338.9 | 338.4 |
| A-177 | CONCH₂CH₃ | CO | C | C | C | H | CH₃ | Y3—CH═CH—CH═CH—Y4 | 5 | 2.84 | 352.9 | 352.4 |
| A-178 | CH(OH)CH₃ | CO | C | C | C | H | CH₃ | Y3—CH═CH—CH═CH—Y4 | 5 | 2.87 | 326.2 | 325.4 |
| A-179 | CHFCH₃ | CO | C | C | C | H | CH₃ | Y3—CH═CH—CH═CH—Y4 | 5 | 3.43 | 328.2 | 327.4 |
| A-180 | CH(CH₃)₂ | CO | N | C | C | — | H | Y3—S—C(CH₃)═C(CH₃)—Y4 | 6 | 4.12 | 344.7 | 344.5 |
| A-181 | CH(CH₃)₂ | CO | N | C | C | — | H | Y3—S—C(CH₃)═C(CH₃)—Y4 | 6 | 4.38 | 358.7 | 358.5 |
| A-182 | CH(CH₃)₂ | CO | C | C | C | H | CH₃ | Y3—CH═CH—CH═CH—Y4 | 6 | 4.10 | 323.7 | 323.4 |
| A-183 | CH(CH₃)₂ | CO | C | C | C | H | CH₃ | Y3—CH═CH—C(CF₃)═CH—Y4 | 6 | 4.33 | 391.6 | 391.4 |
| A-184 | CH(CH₃)₂ | CO | C | C | N | H | CH₂CH₂CH₃ | Y3═N—C(SCH₃)═N—Y4 | 6 | 3.33 | 360.8 | 360.5 |
| A-185 | CH(CH₃)₂ | CO | C | C | C | H | CH₃ | Y3—CH═CF—CH═CH—Y4 | 5 | 4.27 | 351.7 | 351.5 |
| A-186 | CH(CH₃)₂ | CO | C | C | C | H | CH₂CH₃ | Y3—CH═C(CH₃)—CH═CH—Y4 | 6 | 3.98 | 341.7 | 341.4 |
| A-187 | CH(CH₃)₂ | CO | C | C | C | H | H | Y3—CH═CH—C(CH₃)═CH—Y4 | 6 | 3.94 | 323.7 | 323.4 |
| A-188 | CH(CH₃)₂ | CO | C | C | C | H | CH₃ | Y3—CH═C(CH₃)—CH═CH—Y4 | 6 | 3.89 | 353.6 | 353.5 |
| A-189 | CH(CH₃)₂ | CO | C | C | C | H | CH₂CH₃ | Y3—CH═CH—CBr═CH—Y4 | 6 | 4.52 | 415.5 | 416.4 |
| A-190 | CH(CH₃)₂ | CO | C | C | C | H | H | Y3—CH═CBr—CH═CH—Y4 | 6 | 4.16 | 387.5 | 388.3 |
| A-191 | CH(CH₃)₂ | CO | C | C | C | H | CH₃ | Y3—C(CF₃)═CH—C(CH₃)═CH—Y4 | 5 | 3.62 | 339.6 | 339.4 |
| A-192 | CH(CH₃)₂ | CO | C | C | C | H | H | Y3—CH═C(CH₃)—CH═C(CH₃)—Y4 | 6 | 4.13 | 351.9 | 351.5 |
| A-193 | CH(CH₃)₂ | CO | C | C | C | H | H | Y3—CH═C(CH₃)—C(CH₃)═CH—Y4 | 5 | 3.96 | 337.9 | 337.5 |
| A-194 | CH₂CH₂CH₃ | CO | C | C | C | H | CH₃ | Y3—S—C(CH₃)═C(CH₃)—Y4 | 6 | 4.15 | 344.7 | 344.5 |
| A-195 | CH₂CH₂CH₃ | CO | C | C | C | H | CH₃ | Y3—CH═CH—CH═CH—Y4 | 6 | 4.13 | 323.7 | 323.4 |
| A-196 | CH₂CH₂CH₃ | CO | C | C | C | H | CH₃ | Y3—CH═CH—C(CF₃)═CH—Y4 | 6 | 4.35 | 391.6 | 391.4 |
| A-197 | CH₂CH₂CH₃ | CO | C | C | N | H | CH₂CH₂CH₃ | Y3═N—C(SCH₃)═N—Y4 | 6 | 3.35 | 360.8 | 360.5 |
| A-198 | CH₂CH₂CH₃ | CO | C | C | C | H | CH₃ | Y3—CH═CF—CH═CH—Y4 | 6 | 4.29 | 351.7 | 351.5 |
| A-199 | CH₂CH₂CH₃ | CO | C | C | C | H | CH₃ | Y3—CH═CH—CH═CH—Y4 | 6 | 4.00 | 341.6 | 341.4 |

TABLE A-continued

| | | | | | | | | |
|---|---|---|---|---|---|---|---|---|
| A-200 | CH₂CH₂CH₃ | CO | C | C | H | H | Y3—CH=CH—C(CH₃)=CH—Y4 | 6 | 3.96 | 323.7 | 323.4 |
| A-201 | CH₂CH₂CH₃ | CO | C | C | H | CH₃ | Y3—CH=C(OCH₃)—CH=CH—Y4 | 6 | 3.92 | 353.7 | 353.5 |
| A-202 | CH₂CH₂CH₃ | CO | C | C | H | CH₂CH₃ | Y3—CH=CH—CBr=CH—Y4 | 6 | 4.54 | 415.5 | 416.4 |
| A-203 | CH₂CH₂CH₃ | CO | C | C | H | H | Y3—CH=CH—CBr=CH—Y4 | 5 | 4.06 | 389.7 | 388.3 |
| A-204 | CH₂CH₂CH₃ | CO | C | C | H | CH₃ | Y3—C(OCF₃)=CH—CH=CH—Y4 | 5 | 3.51 | 339.8 | 339.4 |
| A-205 | CH₂CH₂CH₃ | CO | C | C | H | H | Y3—CH=C(CH₃)—CH=C(CH₃)—Y4 | 5 | 4.15 | 351.8 | 351.5 |
| A-206 | CH₂CH₂CH₃ | CO | C | C | H | H | Y3—CH=C(CH₃)—C(CH₃)=CH—Y4 | 5 | 3.98 | 337.9 | 337.5 |
| A-207 | CH₂CH₃ | CO | C | C | H | CH₃ | Y3—S—C(CH₃)=C(CH₃)—Y4 | 6 | 3.98 | 330.7 | 330.5 |
| A-208 | CH₂CH₃ | CO | N | C | — | H | Y3—S—C(CH₃)=C(CH₃)—Y4 | 6 | 4.15 | 344.7 | 344.5 |
| A-209 | CH₂CH₃ | CO | N | C | — | CH₃ | Y3—C(CH₃)=CH—CH=CH—Y4 | 6 | 3.88 | 309.7 | 309.4 |
| A-210 | CH₂CH₃ | CO | C | C | H | CH₃ | Y3—CH=CH—C(CF₃)=CH—Y4 | 6 | 4.14 | 377.6 | 377.4 |
| A-211 | CH₂CH₃ | CO | C | N | H | CH₃ | Y3—N=C(SCH₃)=N—Y4 | 5 | 3.09 | 346.8 | 346.5 |
| A-212 | CH₂CH₃ | CO | C | C | H | CH₂CH₂CH₃ | Y3—CH=CH—CH=CH—Y4 | 6 | 4.07 | 337.7 | 337.5 |
| A-213 | CH₂CH₃ | CO | C | C | H | CH₃ | Y3—CH=CF—CH=CH—Y4 | 6 | 3.76 | 327.6 | 327.4 |
| A-214 | CH₂CH₃ | CO | C | C | H | H | Y3—CH=CH—C(CH₃)=CH—Y4 | 6 | 3.72 | 309.6 | 309.4 |
| A-215 | CH₂CH₃ | CO | C | C | H | CH₃ | Y3—CH=CH—C(OCH₃)—CH=CH—Y4 | 6 | 3.67 | 339.7 | 339.4 |
| A-216 | CH₂CH₃ | CO | C | C | H | H | Y3—CH=CH—CBr=CH—Y4 | 6 | 4.31 | 401.5 | 402.3 |
| A-217 | CH₂CH₃ | CO | C | C | H | CH₃ | Y3—CH=CH—CBr=CH—Y4 | 6 | 3.94 | 373.5 | 374.3 |
| A-218 | CH₂CH₃ | CO | C | C | H | H | Y3—C(OCF₃)=CH—CH=CH—Y4 | 6 | 3.40 | 325.6 | 325.4 |
| A-219 | CH₂CH₃ | CO | C | C | H | CH₃ | Y3—CH=C(CH₃)—CH=CH—Y4 | 6 | 3.91 | 337.7 | 337.5 |
| A-220 | CH₂CH₃ | CO | C | C | H | H | Y3—CH=C(CH₃)—C(CH₃)=CH—Y4 | 5 | 3.74 | 323.8 | 323.4 |
| A-221 | CH(CH₃)₂ | CO | C | C | H | CH₃ | Y3—CH=CC1—CC1=CH—Y4 | 5 | 4.52 | 391.7 | 392.3 |
| A-222 | CH(CH₃)₂ | CO | C | C | H | H | Y3—CH=CH—C(OCH₃)—CH=CH—Y4 | 5 | 3.67 | 339.9 | 339.4 |
| A-223 | CH(CH₃)₂ | CO | C | C | H | CH₃ | Y3—CH=CH—CH=N—Y4 | 5 | 3.11 | 310.9 | 310.4 |
| A-224 | CH(CH₃)₂ | CO | C | C | CH₃ | CH₃ | Y3—CH=CH—CH=CH—Y4 | 5 | 3.98 | 337.9 | 337.5 |
| A-225 | CH(CH₃)₂ | CO | C | C | H | H | Y3—N(CH₃)—CH=CH—Y4 | 5 | 3.45 | 312.9 | 312.4 |
| A-226 | CH(CH₃)₂ | CO | C | C | H | CH₃ | Y3—CH=CH—CBr=CH—Y4 | 5 | 4.25 | 352.0 | 351.5 |
| A-227 | CH₂CH₂CH₃ | CO | C | C | H | CH(CH₃)₂ | Y3—CH=CH—CCl=CH—Y4 | 5 | 4.54 | 391.8 | 392.3 |
| A-228 | CH₂CH₂CH₃ | CO | C | C | H | CH₃ | Y3—CH=CH—C(CH₃)=CH—Y4 | 5 | 3.70 | 339.9 | 339.4 |
| A-229 | CH₂CH₂CH₃ | CO | C | C | H | H | Y3—CH=CH—N=CH—Y4 | 5 | 3.06 | 310.9 | 310.4 |
| A-230 | CH₂CH₂CH₃ | CO | C | C | H | CH₃ | Y3—CH=CH—CH=N—Y4 | 5 | 3.14 | 310.9 | 310.4 |
| A-231 | CH₂CH₂CH₃ | CO | C | C | H | CH₃ | Y3—CH=CH—CH=CH—Y4 | 5 | 3.98 | 337.9 | 337.5 |
| A-232 | CH₂CH₂CH₃ | CO | C | C | CH₃ | CH(CH₃)₂ | Y3—N(CH₃)—CH=CH—Y4 | 5 | 3.49 | 312.9 | 312.4 |
| A-233 | CH₂CH₃ | CO | C | C | H | CH₃ | Y3—CH=CH—CH=CH—Y4 | 5 | 4.26 | 352.0 | 351.5 |
| A-234 | CH₂CH₃ | CO | C | C | H | CF₃ | Y3—CH=CH—CH=CH—Y4 | 5 | 4.11 | 363.9 | 363.4 |
| A-235 | CH₂CH₃ | CO | C | C | H | CH₃ | Y3—CH=CH—CCl=CCl—Y4 | 5 | 4.31 | 377.8 | 378.3 |
| A-236 | CH₂CH₃ | CO | C | C | H | H | Y3—CH=CH—C(OCH₃)—CH=CH—Y4 | 5 | 3.44 | 325.9 | 325.4 |
| A-237 | CH₂CH₃ | CO | C | C | H | H | Y3—CH=CH—N=CH—Y4 | 5 | 2.87 | 296.9 | 296.4 |
| A-238 | CH₂CH₃ | CO | C | C | CH₃ | CH₃ | Y3—CH=CH—CH=N—Y4 | 5 | 3.73 | 323.9 | 323.4 |
| A-239 | CH₂CH₃ | CO | C | C | H | H | Y3—N(CH₃)—CH=CH—Y4 | 5 | 3.21 | 298.9 | 298.4 |
| A-240 | CH₂CH₃ | CO | C | C | H | CH(CH₃)₂ | Y3—CH=CH—CH=CH—Y4 | 5 | 4.04 | 338.0 | 337.5 |
| A-241 | OCH₂CH₃ | CO | C | C | H | H | Y3—CH=CH—N=CH—Y4 | 7 | 3.64 | 312.1 | 311.4 |
| A-242 | 2-methylcyclopropyl | CO | C | C | H | H | Y3—CH=CH—CH=N—Y4 | 7 | 3.87 | 322.1 | 321.4 |
| A-243 | CF₃ | CO | C | C | H | CH₃ | Y3—CH=CH—CH=CH—Y4 | 7 | 3.75 | 336.0 | 335.3 |
| A-244 | Cl | CO | C | C | H | CH₃ | Y3—CH=CH—CH=CH—Y4 | 8 | 1.36 | 316.0 | 315.8 |
| A-245 | CH₂CH₃ | CO | C | C | H | CH₃ | Y3—CH=CH—CH=CH—Y4 | 8 | 1.48 | 336.1 | 335.4 |
| A-246 | 2-methylcyclopropyl | CO | C | C | H | H | Y3—CH=CH—CH=CH—Y4 | 8 | 1.43 | 350.1 | 349.4 |
| A-247 | CF₃ | CO | C | C | H | CH₃ | Y3—CH=CH—CH=CH—Y4 | 8 | 1.86 | 436.0 | 435.3 |
| A-248 | CF₂CF₂CF₃ | CO | C | C | H | CH₃ | Y3—CH=CH—CH=CH—Y4 | 8 | 1.62 | 450.0 | 449.4 |
| A-249 | OCH₂CH₃ | CO | C | C | H | CH₃ | Y3—CH=CH—CH=CH—Y4 | 8 | 1.37 | 326.1 | 325.4 |

TABLE A-continued

| | | | | | | | | |
|---|---|---|---|---|---|---|---|---|
| A-250 | CHBrCH₃ | CO | C | C | C | H | H | Y3—CH=CH—CH=CH—Y4 | 8 | 1.66 | 374.0 | 374.3 |
| A-251 | CH₂Cl | CO | C | C | C | H | H | Y3—CH=CH—CH=CH—Y4 | 5 | 3.29 | 315.7 | 315.8 |
| A-252 | CHBrCH₃ | CO | C | C | C | H | CH₃ | Y3—CH=CH—CH=CH—Y4 | 8 | 1.47 | 388.0 | 388.3 |
| A-253 | CF₂CF₃ | CO | C | C | C | H | H | Y3—CH=CH—CH=CH—Y4 | 8 | 1.52 | 386.1 | 385.3 |
| A-254 | CF₂CF₃ | CO | C | C | C | H | CH₃ | Y3—CH=CH—CH=CH—Y4 | 8 | 1.57 | 400.1 | 399.4 |
| A-255 | CF₂Cl | CO | C | C | C | H | CH₃ | Y3—CH=CH—CH=CH—Y4 | 8 | 1.49 | 366.1 | 365.8 |
| A-256 | CF₂Cl | CO | C | C | C | H | H | Y3—CH=CH—CH=CH—Y4 | 8 | 1.45 | 352.1 | 351.8 |
| A-257 | CF₂CHF₂ | CO | C | C | C | H | CH₃ | Y3—CH=CH—CH=CH—Y4 | 8 | 1.48 | 382.1 | 381.4 |
| A-258 | C₂H₅CH₃ | CO | C | C | C | H | H | Y3—CH=CH—CH=CH—Y4 | 8 | 1.20 | 332.1 | 331.4 |
| A-259 | CF₂CH₃ | CO | C | C | C | H | CH₃ | Y3—CH=CH—CH=CH—Y4 | 8 | 1.66 | 346.2 | 345.4 |
| A-260 | CH(CH₃)CH₂CH₃ | CO | C | C | C | H | OCH₃ | Y3—CH=CH—CH=CH—Y4 | 5 | 4.44 | 354.3 | 353.5 |
| A-261 | CH(CH₃)CH₂CH₃ | CO | C | C | C | H | H | Y3—CH=C(OCH₃)—CH=CH—Y4 | 5 | 3.92 | 354.3 | 353.5 |
| A-262 | CH(CH₃)CH₂CH₃ | CO | C | C | C | H | CH₃ | Y3—CH=C(OCH₃)—CH=CH—Y4 | 5 | 4.36 | 372.3 | 371.9 |
| A-263 | CH(CH₃)CH₂CH₃ | CO | C | C | C | H | CH₃ | Y3—CH=CCl—CH=CH—Y4 | 5 | 4.02 | 368.3 | 367.5 |
| A-264 | CH(CH₃)CH₂CH₃ | CO | C | C | C | H | CH₃ | Y3—CH=C(CF₃)—CH=CH—Y4 | 5 | 4.47 | 406.3 | 405.5 |
| A-265 | CH(CH₃)CH₂CH₃ | CO | C | C | C | H | OCH₃ | Y3—CH=C(OCH₃)—CH=CH—Y4 | 5 | 4.64 | 368.4 | 367.5 |
| A-266 | CH(CH₃)CH₂CH₂CH₃ | CO | C | C | C | H | H | Y3—CH=C(OCH₃)—CH=CH—Y4 | 5 | 4.16 | 368.4 | 367.5 |
| A-267 | CH(CH₃)CH₂CH₂CH₃ | CO | C | C | C | H | CH₃ | Y3—CH=C(OCH₃)—CH=CH—Y4 | 5 | 4.57 | 386.4 | 385.9 |
| A-268 | CH(CH₃)CH₂CH₂CH₃ | CO | C | C | C | H | CH₃ | Y3—CH=CCl—CH=CH—Y4 | 5 | 4.25 | 382.4 | 381.5 |
| A-269 | CH(CH₃)CH₂CH₂CH₃ | CO | C | C | C | H | CH₃ | Y3—CH=C(CF₃)—CH=CH—Y4 | 5 | 4.67 | 420.4 | 419.5 |
| A-270 | CH(CH₃)CH₂CH₂CH₃ | CO | C | C | C | H | OCH₃ | Y3—CH=CH—CH=CH—Y4 | 5 | 4.63 | 368.4 | 367.5 |
| A-271 | CH(CH₃)CH₂CH₂CH₃ | CO | C | C | C | H | OCH₃ | Y3—CH=C(OCH₃)—CH=CH—Y4 | 5 | 4.13 | 368.4 | 367.5 |
| A-272 | CH(CH₃)CH₂CH₂CH₃ | CO | C | C | C | H | CH₃ | Y3—CH=CCl—CH=CH—Y4 | 5 | 4.54 | 386.3 | 385.9 |
| A-273 | CH(CH₃)CH₂CH₂CH₃ | CO | C | C | C | H | CH₃ | Y3—CH=C(CF₃)—CH=CH—Y4 | 5 | 4.23 | 382.3 | 381.5 |
| A-274 | CH(CH₃)CH₂CH₂CH₃ | CO | C | C | C | H | OCH₃ | Y3—CH=C(CF₃)—CH=CH—Y4 | 5 | 4.64 | 420.4 | 419.5 |
| A-275 | cyclopropyl | CO | C | C | C | H | H | Y3—CH=CH—CH=CH—Y4 | 5 | 4.02 | 338.3 | 337.4 |
| A-276 | cyclopropyl | CO | C | C | C | H | CH₃ | Y3—CH=C(OCH₃)—CH=CH—Y4 | 5 | 3.45 | 338.3 | 337.4 |
| A-277 | cyclopropyl | CO | C | C | C | H | CH₃ | Y3—CH=CCl—CH=CH—Y4 | 5 | 3.91 | 356.3 | 355.9 |
| A-278 | cyclopropyl | CO | C | C | C | H | CH₃ | Y3—CH=C(CF₃)—CH=CH—Y4 | 5 | 3.55 | 352.3 | 351.4 |
| A-279 | cyclopropyl | CO | C | C | C | H | OCH₃ | Y3—CH=CH—CH=CH—Y4 | 5 | 4.08 | 390.3 | 389.4 |
| A-280 | 2-methylcyclopropyl | CO | C | C | C | H | CH₃ | Y3—CH=CH—N=N—Y4 | 5 | 3.71 | 352.3 | 351.4 |
| A-281 | 2-methylcyclopropyl | CO | C | N | N | C | H | CH₃ | Y3—CH=CH—N=N—Y4 | 5 | 4.14 | 370.3 | 369.9 |
| A-282 | 2-methylcyclopropyl | CO | C | C | C | H | CH₃ | Y3—CH=CCl—CH=N—Y4 | 5 | 3.80 | 366.4 | 365.5 |
| A-283 | 2-methylcyclopropyl | CO | C | C | C | H | CH₃ | Y3—CH=C(CF₃)—CH=N—Y4 | 5 | 4.28 | 404.3 | 403.4 |
| A-284 | CF₃ | CO | C | C | C | H | OCH₃ | Y3—CH=C(OCH₃)—CH=CH—Y4 | 5 | 4.19 | 366.3 | 365.4 |
| A-285 | CF₃ | CO | C | C | C | H | CH₃ | Y3—CH=C(OCH₃)—CH=CH—Y4 | 8 | 3.63 | 366.3 | 365.4 |
| A-286 | CF₃ | CO | C | C | C | H | CH₃ | Y3—CH=CCl—CH=CH—Y4 | 8 | 3.73 | 380.3 | 379.4 |
| A-287 | CF₃ | CO | C | C | C | H | CH₃ | Y3—CH=C(CF₃)—CH=CH—Y4 | 8 | 4.21 | 418.2 | 417.4 |
| A-288 | CH(CH₃)₂ | CO | C | C | C | H | OCH₃ | Y3—CH=CH—CH=N—Y4 | 8 | 1.90 | 330.2 | 329.4 |
| A-289 | CH₂CH₃ | CO | C | C | C | H | OCH₃ | Y3—CH=CH—CH=N—Y4 | 8 | 1.80 | 316.2 | 315.4 |
| A-290 | CH₂CH₂CH₃ | CO | C | C | C | H | OCH₃ | Y3—CH=CH—CH=N—Y4 | 8 | 1.91 | 330.2 | 329.4 |
| A-291 | CF₃ | CO | C | C | C | H | OCH₃ | Y3—CH=CH—CH=N—Y4 | 8 | 1.88 | 356.1 | 355.3 |
| A-292 | CH(CH₃)₂ | CO | C | C | C | H | H | Y3—N(CH₃)—N=C(CH₃)—Y4 | 8 | 1.57 | 328.1 | 327.4 |
| A-293 | CF₃ | CO | C | C | C | H | H | Y3—N(CH₃)—N=C(CH₃)—Y4 | 8 | 1.54 | 354.2 | 354.2 |
| A-294 | CH(CH₃)₂ | CO | C | C | C | H | OCH₂CH₃ | Y3—CH=CH—CH=CH—Y4 | 5 | 4.59 | 354.0 | 353.5 |
| A-295 | CH₂CH₂CH₃ | CO | C | C | C | H | OCH₂CH₃ | Y3—CH=CH—CH=CH—Y4 | 5 | 4.61 | 354.0 | 353.5 |
| A-296 | CH₂CH₃ | CO | C | C | C | H | OCH₂CH₃ | Y3—CH=CH—CH=CH—Y4 | 5 | 4.40 | 340.0 | 339.4 |
| A-297 | CH(CH₃)₂ | CO | C | C | C | H | H | Y3—CH₂—CH₂—CH₂—Y4 | 5 | 3.55 | 300.0 | 299.4 |
| A-298 | CH₂CH₂CH₃ | CO | C | C | C | H | H | Y3—CH₂—CH₂—CH₂—Y4 | 5 | 3.58 | 300.0 | 299.4 |
| A-299 | CH₂CH₃ | CO | C | C | C | H | H | Y3—CH₂—CH₂—CH₂—Y4 | 5 | 3.30 | 286.0 | 285.4 |

TABLE A-continued

| | | | | | | | | | | |
|---|---|---|---|---|---|---|---|---|---|---|
| A-300 | CH(CH₃)₂ | CO | C | C | C | H | H | Y3—CH₂—CH₂—CH₂—Y4 | 2 | 2.76 | 314.0 | 313.4 |
| A-301 | CH₂CH₂CH₃ | CO | C | C | C | H | H | Y3—CH₂—CH₂—CH₂—Y4 | 2 | 2.77 | 314.0 | 313.4 |
| A-302 | CH₂CH₃ | CO | C | C | C | H | H | Y3—CH₂—CH₂—CH₂—Y4 | 2 | 2.51 | 300.0 | 299.4 |
| A-303 | CF₃ | CO | C | C | C | H | H | Y3—CH₂—CH₂—CH₂—Y4 | 5 | 3.47 | 325.9 | 325.3 |
| A-304 | CF₃ | CO | C | C | C | H | OCH₂CH₃ | Y3—CH₂—CH₂—CH₂—Y4 | 5 | 3.73 | 339.9 | 339.4 |
| A-305 | CF₃ | CO | C | C | C | H | OCH₃ | Y3—CH=C(OCH₃)—CH=CH—Y4 | 5 | 4.50 | 379.8 | 379.4 |
| A-306 | CF₃ | CO | C | C | C | H | OCH₃ | Y3—C(OCF₃)=CH—CH=CH—Y4 | 5 | 4.24 | 395.8 | 395.4 |
| A-307 | CF₃ | CO | C | C | C | H | H | Y3—CH=CF—CH=CH—Y4 | 5 | 3.97 | 395.8 | 395.4 |
| A-308 | CF₃ | CO | C | C | C | H | H | Y3—CH=CCl—CH=CH—Y4 | 5 | 3.70 | 353.8 | 353.3 |
| A-309 | CF₃ | CO | C | C | C | H | H | Y3—CH=C(CF₃)—CH=CH—Y4 | 5 | 3.94 | 369.8 | 369.8 |
| A-310 | CF₃ | CO | C | C | C | H | H | Y3—CH=C(OCH₃)—CH=CH—Y4 | 5 | 4.09 | 403.8 | 403.3 |
| A-311 | CH(CH₃)₂ | CO | C | C | C | H | OCH₃ | Y3—CH=C(OCH₃)—CH=CH—Y4 | 5 | 4.32 | 369.9 | 369.5 |
| A-312 | CH(CH₃)₂ | CO | C | C | C | H | OCH₃ | Y3—(OCF₃)=CH—CH=CH—Y4 | 5 | 4.05 | 369.9 | 369.5 |
| A-313 | CH(CH₃)₂ | CO | C | C | C | H | H | Y3—CH=CF—CH=CH—Y4 | 5 | 3.77 | 327.9 | 327.4 |
| A-314 | CH(CH₃)₂ | CO | C | C | C | H | H | Y3—CH=CCl—CH=CH—Y4 | 5 | 4.03 | 343.9 | 343.9 |
| A-315 | CH(CH₃)₂ | CO | C | C | C | H | H | Y3—CH=C(CF₃)—CH=CH—Y4 | 5 | 4.17 | 377.9 | 377.4 |
| A-316 | CH₂CH₂CH₃ | CO | C | C | C | H | OCH₃ | Y3—CH=C(OCH₃)—CH=CH—Y4 | 5 | 4.34 | 369.9 | 369.5 |
| A-317 | CH₂CH₂CH₃ | CO | C | C | C | H | OCH₃ | Y3—C(OCF₃)=CH—CH=CH—Y4 | 5 | 4.06 | 369.9 | 369.5 |
| A-318 | CH₂CH₂CH₃ | CO | C | C | C | H | H | Y3—CH=CF—CH=CH—Y4 | 5 | 3.80 | 327.9 | 327.4 |
| A-319 | CH₂CH₂CH₃ | CO | C | C | C | H | H | Y3—CH=C(CF₃)—CH=CH—Y4 | 5 | 4.19 | 377.9 | 377.4 |
| A-320 | CH₂CH₃ | CO | C | C | C | H | OCH₃ | Y3—CH₂—CH₂—CH₂—Y4 | 5 | 4.11 | 355.9 | 355.4 |
| A-321 | CH(CH₃)₂CH₂CH₃ | CO | C | C | C | H | H | Y3—CH₂—CH₂—CH₂—Y4 | 5 | 3.82 | 314.0 | 313.4 |
| A-322 | cyclopropyl | CO | C | C | C | H | H | Y3—CH₂—CH₂—CH₂—Y4 | 5 | 3.32 | 297.9 | 297.4 |
| A-323 | 2-methylcyclopropyl | CO | C | C | C | H | H | Y3—CH₂—CH₂—CH₂—Y4 | 5 | 3.60 | 311.9 | 311.4 |
| A-324 | CH(CH₃)₂CH₂CH₃ | CO | C | C | C | H | H | Y3—CH=CF—CH=CH—Y4 | 5 | 4.09 | 328.0 | 327.5 |
| A-325 | cyclopropyl | CO | C | C | C | H | H | Y3—CH=CF—CH=CH—Y4 | 5 | 3.59 | 311.9 | 311.4 |
| A-326 | 2-methylcyclopropyl | CO | C | C | C | H | H | Y3—CH=CF—CH=CH—Y4 | 5 | 3.86 | 326.0 | 325.5 |
| A-327 | CH(CH₃)₂CH₂CH₃ | CO | C | C | C | H | OCH₂CH₃ | Y3—CH=C(OCH₃)—CH=CH—Y4 | 5 | 4.80 | 367.9 | 367.5 |
| A-328 | cyclopropyl | CO | C | C | C | H | OCH₂CH₃ | Y3—CH=C(OCH₃)—CH=CH—Y4 | 5 | 4.38 | 351.9 | 351.4 |
| A-329 | 2-methylcyclopropyl | CO | C | C | C | H | OCH₂CH₃ | Y3—CH=C(OCH₃)—CH=CH—Y4 | 5 | 4.59 | 365.9 | 365.5 |
| A-330 | CH(CH₃)₂CH₂CH₃ | CO | C | C | C | H | OCH₃ | Y3—CH=C(OCH₃)—CH=CH—Y4 | 5 | 4.53 | 383.9 | 383.5 |
| A-331 | cyclopropyl | CO | C | C | C | H | OCH₃ | Y3—CH=C(OCH₃)—CH=CH—Y4 | 5 | 4.10 | 367.9 | 367.4 |
| A-332 | 2-methylcyclopropyl | CO | C | C | C | H | OCH₃ | Y3—CH=C(OCH₃)—CH=CH—Y4 | 5 | 4.33 | 381.9 | 381.5 |
| A-333 | CH(CH₃)₂CH₂CH₃ | CO | C | C | C | H | H | Y3—CH=CF—CH=CH—Y4 | 5 | 4.01 | 341.9 | 341.4 |
| A-334 | cyclopropyl | CO | C | C | C | H | H | Y3—CH=CF—CH=CH—Y4 | 5 | 3.55 | 325.9 | 325.4 |
| A-335 | 2-methylcyclopropyl | CO | C | C | C | H | H | Y3—CH=CF—CH=CH—Y4 | 5 | 3.80 | 339.9 | 339.4 |
| A-336 | CH(CH₃)₂CH₂CH₃ | CO | C | C | C | H | H | Y3—CH=CCl—CH=CH—Y4 | 5 | 4.25 | 357.9 | 357.9 |
| A-337 | cyclopropyl | CO | C | C | C | H | H | Y3—CH=CCl—CH=CH—Y4 | 5 | 3.80 | 341.8 | 341.8 |
| A-338 | 2-methylcyclopropyl | CO | C | C | C | H | H | Y3—CH=CCl—CH=CH—Y4 | 5 | 4.04 | 355.8 | 355.9 |
| A-339 | CH(CH₃)₂CH₂CH₃ | CO | C | C | C | H | H | Y3—CH=C(CF₃)—CH=CH—Y4 | 5 | 4.37 | 391.9 | 391.4 |
| A-340 | cyclopropyl | CO | C | C | C | H | H | Y3—CH=C(CF₃)—CH=CH—Y4 | 5 | 3.95 | 375.8 | 375.4 |
| A-341 | 2-methylcyclopropyl | CO | C | C | C | H | H | Y3—CH=C(CF₃)—CH=CH—Y4 | 5 | 4.18 | 389.8 | 389.4 |
| A-342 | CH(CH₃)₂CH₂CH₃ | CO | C | C | C | H | OCH₃ | Y3—CH=C(OCH₃)—CH=CH—Y4 | 5 | 4.07 | 384.9 | 384.5 |
| A-343 | CH₃ | CO | C | N | C | — | CH₃ | Y3—CH₂—CH₂—CH₂—Y4 | 5 | 2.99 | 286.9 | 286.4 |
| A-344 | CH₂CH₂CH₃ | CO | C | N | C | — | CH₃ | Y3—CH₂—CH₂—CH₂—Y4 | 5 | 3.27 | 300.9 | 300.4 |
| A-345 | CH(CH₃)₂ | CO | C | N | C | — | CH₃ | Y3—CH₂—CH₂—CH₂—Y4 | 5 | 3.57 | 314.9 | 314.4 |
| A-346 | CH(CH₃)₂CH₂CH₃ | CO | C | N | C | — | CH₃ | Y3—CH₂—CH₂—CH₂—Y4 | 5 | 3.80 | 328.9 | 328.5 |
| A-347 | cyclopropyl | CO | C | N | C | — | CH₃ | Y3—CH₂—CH₂—CH₂—Y4 | 5 | 3.29 | 312.9 | 312.4 |
| A-348 | 2-methylcyclopropyl | CO | C | N | C | — | CH₃ | Y3—CH₂—CH₂—CH₂—Y4 | 5 | 3.57 | 326.9 | 326.4 |

TABLE A-continued

| # | R | L | X1 | X2 | R2 | R3 | Chain | n | v1 | v2 | v3 |
|---|---|---|----|----|----|----|-------|---|-----|-----|-----|
| A-350 | CF₃ | CO | N | C | — | CH₃ | Y3—CH₂—CH₂—CH₂—Y4 | 5 | 3.48 | 340.8 | 340.3 |
| A-351 | CF₂CHF₂ | CO | N | C | — | CH₃ | Y3—CH₂—CH₂—CH₂—Y4 | 5 | 3.48 | 372.8 | 372.4 |
| A-352 | cyclopropyl | CO | N | C | — | OCH₃ | Y3—CH=C(OCH₃)—CH=CH—Y4 | 5 | 3.61 | 368.8 | 368.4 |
| A-353 | 2-methylcyclopropyl | CO | N | C | — | OCH₃ | Y3—CH=C(OCH₃)—CH=CH—Y4 | 5 | 3.86 | 382.8 | 382.5 |
| A-354 | CF₃ | CO | N | C | — | OCH₃ | Y3—CH=C(OCH₃)—CH=CH—Y4 | 5 | 3.80 | 396.8 | 396.4 |
| A-355 | CH(CH₃)₂ | CO | N | C | — | OCH₃ | Y3—CH=C(OCH₃)—CH=CH—Y4 | 5 | 3.84 | 370.9 | 370.5 |
| A-356 | CH₂CH₂CH₃ | CO | N | C | — | OCH₃ | Y3—CH=C(OCH₃)—C(OCH₃)=CH—Y4 | 5 | 3.87 | 370.9 | 370.5 |
| A-357 | CH₂CH₃ | CO | N | C | — | OCH₃ | Y3—CH=C(OCH₃)—CH=CH—Y4 | 5 | 3.60 | 356.9 | 356.4 |
| A-358 | CH(CH₃)CH₂CH₃ | CO | C | C | H | Cl | Y3—CH=CH—CH=CH—Y4 | 5 | 4.84 | 357.8 | 357.9 |
| A-359 | cyclopropyl | CO | C | C | H | Cl | Y3—CH=CH—CH=CH—Y4 | 5 | 4.42 | 341.8 | 341.8 |
| A-360 | 2-methylcyclopropyl | CO | C | C | H | Cl | Y3—CH=CH—CH=CH—Y4 | 5 | 4.64 | 355.8 | 355.9 |
| A-361 | CF₃ | CO | C | C | H | Cl | Y3—CH=CH—CH=CH—Y4 | 5 | 4.55 | 369.7 | 369.8 |
| A-362 | CH(CH₃)₂ | CO | C | C | H | Cl | Y3—CH=CH—CH=CH—Y4 | 5 | 4.65 | 343.8 | 343.9 |
| A-363 | CH₂CH₃ | CO | C | C | H | Cl | Y3—CH=CH—CH=CH—Y4 | 5 | 4.45 | 329.8 | 329.8 |
| A-364 | CH(CH₃)CH₂CH₃ | CO | C | C | H | Cl | Y3—CH=CH—CH=CH—Y4 | 5 | 4.68 | 343.8 | 343.9 |
| A-365 | cyclopropyl | CO | C | C | H | OCH₃ | Y3—CH=CH—CH=CH—Y4 | 5 | 4.31 | 359.9 | 359.5 |
| A-366 | CH₂CH₃ | CO | C | C | H | OCH₃ | Y3—CH=CH—S—Y4 | 5 | 3.83 | 343.8 | 343.4 |
| A-367 | 2-methylcyclopropyl | CO | C | C | H | OCH₃ | Y3—CH=CH—S—Y4 | 5 | 4.09 | 357.8 | 357.5 |
| A-368 | CF₃ | CO | C | C | H | OCH₃ | Y3—CH=CH—S—Y4 | 5 | 4.01 | 371.8 | 371.4 |
| A-369 | CH(CH₃)₂ | CO | C | C | H | OCH₃ | Y3—CH=CH—S—Y4 | 5 | 4.11 | 345.8 | 345.5 |
| A-370 | CH₂CH₃ | CO | C | C | H | OCH₃ | Y3—CH=CH—S—Y4 | 5 | 4.08 | 345.8 | 345.5 |
| A-371 | CH₃ | CO | C | C | H | OCH₃ | Y3—CH=CH—S—Y4 | 5 | 3.84 | 331.8 | 331.4 |
| A-372 | CH₂CH₂CH₃ | CO | C | C | H | H | H | 2 | 3.41 | 232.2 | 231.3 |
| A-373 | CH(CH₃)₂ | CO | C | C | H | H | H | 1 | 2.02 | 260.1 | 259.4 |
| A-374 | CH₂CH₃ | CO | C | C | OCH₃ | H | H | 3 | 3.57 | 260.1 | 259.4 |
| A-375 | CH(CH₃)₂ | CO | C | C | CH₃ | CH₃ | H | 5 | 3.27 | 246.0 | 245.3 |
| A-376 | CH₂CH₃ | CO | C | C | H | H | H | 5 | 3.47 | 303.9 | 303.4 |
| A-377 | CH(CH₃)₂ | CO | C | C | OCH₃ | CH₃ | H | 5 | 3.36 | 273.9 | 273.4 |
| A-378 | CH(CH₃)₂ | CO | C | C | CH₃ | CH₃ | H | 5 | 3.25 | 273.9 | 273.4 |
| A-379 | CH₂CH₂CH₃ | CO | C | C | H | H | H | 5 | 3.50 | 303.9 | 303.4 |
| A-380 | CH₂CH₂CH₃ | CO | C | C | OCH₃ | H | H | 5 | 3.39 | 273.9 | 273.4 |
| A-381 | CH₂CH₂CH₃ | CO | C | C | CH₃ | H | H | 5 | 3.28 | 273.9 | 273.4 |
| A-382 | CH₂CH₃ | CO | C | C | OCH₃ | CH₃ | H | 5 | 3.22 | 289.9 | 289.4 |
| A-383 | CH₂CH₃ | CO | C | C | H | CH₃ | H | 5 | 3.05 | 260.0 | 259.4 |
| A-384 | CH(CH₃)₂ | CO | C | C | H | CH₃ | H | 5 | 3.00 | 259.8 | 259.4 |
| A-385 | CH(CH₃)₂ | CO | C | C | H | CH₃ | H | 5 | 3.43 | 287.9 | 287.4 |
| A-386 | CH₂CH₂CH₃ | CO | C | C | H | CH₃ | H | 5 | 3.46 | 287.9 | 287.4 |
| A-387 | CH₂CH₃ | CO | C | C | H | H | H | 5 | 3.17 | 273.9 | 273.4 |
| A-388 | CH(CH₃)CH₂CH₃ | CO | C | C | H | CH₃ | H | 5 | 3.64 | 302.3 | 301.4 |
| A-389 | CH(CH₃)CH₂CH₃ | CO | C | C | H | H | H | 5 | 3.47 | 288.3 | 287.4 |
| A-390 | CH(CH₃)CH₂CH₃ | CO | C | C | H | CH₃ | H | 5 | 3.93 | 316.4 | 315.5 |
| A-391 | CH(CH₃)CH₂CH₃ | CO | C | C | H | CH₃ | H | 5 | 3.75 | 302.3 | 301.4 |
| A-392 | CH(CH₃)CH₂CH₃ | CO | C | C | H | CH₃ | H | 5 | 3.90 | 316.4 | 315.5 |
| A-393 | CH(CH₃)CH₂CH₃ | CO | C | C | H | CH₃ | H | 5 | 3.71 | 302.3 | 301.4 |
| A-394 | cyclopropyl | CO | C | C | H | CH₃ | H | 5 | 3.13 | 286.3 | 285.4 |
| A-395 | cyclopropyl | CO | C | C | H | H | H | 5 | 2.99 | 272.2 | 271.4 |
| A-396 | 2-methylcyclopropyl | CO | C | C | H | CH₃ | H | 5 | 3.43 | 300.3 | 299.4 |
| A-397 | 2-methylcyclopropyl | CO | C | C | H | H | H | 5 | 3.27 | 286.3 | 285.4 |
| A-398 | CF₃ | CO | C | C | H | CH₃ | H | 5 | 3.32 | 314.3 | 313.3 |
| A-399 | CF₃ | CO | C | C | H | H | H | 5 | 3.17 | 300.2 | 299.3 |

| | | | | | | | | | | | | |
|---|---|---|---|---|---|---|---|---|---|---|---|---|
| A-400 | CH(CH₃)₂ | CO | N | C | C | — | OCH₃ | H | 8 | 1.37 | 291.2 | 290.4 |
| A-401 | CH₂CH₃ | CO | N | C | C | — | OCH₃ | H | 5 | 2.96 | 276.9 | 276.3 |
| A-402 | CH₂CH₂CH₃ | CO | N | C | C | — | OCH₃ | H | 8 | 1.35 | 291.2 | 290.4 |
| A-403 | CF₃ | CO | N | C | C | — | OCH₃ | H | 5 | 3.17 | 316.9 | 316.3 |
| A-404 | CH(CH₃)₂ | CO | N | C | C | — | CH₃ | CH₃ | 8 | 1.84 | 321.2 | 320.4 |
| A-405 | CH₂CH₃ | CO | N | C | C | — | OCH₃ | OCH₃ | 8 | 1.72 | 307.2 | 306.4 |
| A-406 | CH₂CH₂CH₃ | CO | N | C | C | — | OCH₃ | OCH₃ | 8 | 1.83 | 321.2 | 320.4 |
| A-407 | CF₃ | CO | N | C | C | — | OCH₃ | OCH₃ | 8 | 1.82 | 347.1 | 346.3 |
| A-408 | CH(CH₃)₂ | CO | N | C | C | — | CH₃ | CH₃ | 8 | 1.39 | 289.2 | 288.4 |
| A-409 | CH₂CH₃ | CO | N | C | C | — | CH₃ | CH₃ | 5 | 2.98 | 274.9 | 274.4 |
| A-410 | CH₂CH₂CH₃ | CO | N | C | C | — | CH₃ | CH₃ | 8 | 1.37 | 289.2 | 288.4 |
| A-411 | CF₃ | CO | N | C | C | — | CH₃ | CH₃ | 5 | 3.19 | 314.9 | 314.3 |
| A-412 | CH(CH₃)₂ | CO | C | C | C | H | OCH₃ | H | 5 | 3.45 | 289.9 | 289.4 |
| A-413 | CH₂CH₃ | CO | C | C | C | H | OCH₃ | H | 5 | 3.19 | 275.9 | 275.3 |
| A-414 | CH₂CH₂CH₃ | CO | C | C | C | H | OCH₃ | H | 5 | 3.48 | 289.9 | 289.4 |
| A-415 | 2-methylcyclopropyl | CO | C | C | C | H | OCH₃ | H | 5 | 3.48 | 301.9 | 301.4 |
| A-416 | CF₃ | CO | C | C | C | H | OCH₃ | H | 5 | 3.40 | 315.9 | 315.3 |
| A-417 | CH(CH₃)₂ | CO | C | C | C | H | OCH₃ | CH₃ | 5 | 3.68 | 304.0 | 303.4 |
| A-418 | CH₂CH₃ | CO | C | C | C | H | OCH₃ | CH₃ | 5 | 3.41 | 289.9 | 289.4 |
| A-419 | CH₂CH₂CH₃ | CO | C | C | C | H | OCH₃ | CH₃ | 5 | 3.70 | 303.9 | 303.4 |
| A-420 | 2-methylcyclopropyl | CO | C | C | C | H | OCH₃ | CH₃ | 5 | 3.70 | 316.0 | 315.4 |
| A-421 | CF₃ | CO | C | C | C | H | OCH₃ | CH₃ | 5 | 3.62 | 329.9 | 329.3 |
| A-422 | CH₃CH₂CH₃ | CO | C | C | C | H | OCH₃ | CH₃ | 5 | 3.71 | 303.9 | 303.4 |
| A-423 | CF₂CHF₂ | CO | C | C | C | H | OCH₃ | CH₃ | 5 | 3.45 | 347.8 | 347.3 |
| A-424 | CF₂CF₃ | CO | C | C | C | H | OCH₃ | CH₃ | 5 | 3.77 | 365.8 | 365.3 |
| A-425 | cyclopropyl | CO | C | C | C | H | OCH₃ | H | 5 | 3.43 | 301.9 | 301.4 |
| A-426 | CF₂CHF₂ | CO | C | C | C | H | OCH₃ | H | 5 | 3.66 | 361.8 | 361.3 |
| A-427 | CF₂CF₃ | CO | C | C | C | H | OCH₃ | H | 5 | 3.98 | 379.8 | 379.3 |
| A-428 | CH₃ | CO | C | C | C | H | OCH₃ | OCH₃ | 5 | 3.47 | 291.8 | 291.3 |
| A-429 | CH₃CH₂CH₃ | CO | C | C | C | H | OCH₃ | OCH₃ | 5 | 4.01 | 319.9 | 319.4 |
| A-430 | CH(CH₃)₂ | CO | C | C | C | H | OCH₃ | OCH₃ | 5 | 3.99 | 319.9 | 319.4 |
| A-431 | CH(CH₃)CH₂CH₃ | CO | C | C | C | H | OCH₃ | OCH₃ | 5 | 4.21 | 333.9 | 333.4 |
| A-432 | 2-methylcyclopropyl | CO | C | C | C | H | OCH₃ | OCH₃ | 5 | 4.00 | 331.9 | 331.4 |
| A-433 | CF₃ | CO | C | C | C | H | OCH₃ | OCH₃ | 5 | 3.93 | 345.8 | 345.3 |
| A-434 | CF₂CHF₂ | CO | C | C | C | H | OCH₃ | OCH₃ | 5 | 3.94 | 377.8 | 377.3 |
| A-435 | CF₂CF₃ | CO | C | C | C | H | OCH₃ | OCH₃ | 5 | 4.23 | 395.8 | 395.3 |
| A-436 | CH₃ | CO | C | C | C | H | CH(CH₃)₂ | H | 5 | 3.31 | 273.9 | 273.4 |
| A-437 | CH₂CH₃ | CO | C | C | C | H | CH(CH₃)₂ | H | 5 | 3.43 | 287.9 | 287.4 |
| A-438 | CH₃CH₂CH₃ | CO | C | C | C | H | CH(CH₃)₂ | H | 5 | 3.80 | 301.9 | 301.4 |
| A-439 | CH(CH₃)₂ | CO | C | C | C | H | CH(CH₃)₂ | H | 5 | 3.69 | 302.3 | 301.4 |
| A-440 | 2-methylcyclopropyl | CO | C | C | C | H | CH(CH₃)₂ | H | 5 | 3.92 | 315.9 | 315.5 |
| A-441 | cyclopropyl | CO | C | C | C | H | CH(CH₃)₂ | H | 5 | 3.58 | 299.9 | 299.4 |
| A-442 | 2-methylcyclopropyl | CO | C | C | C | H | CH(CH₃)₂ | H | 5 | 3.47 | 313.8 | 313.4 |
| A-443 | CF₃ | CO | C | C | C | H | CH(CH₃)₂ | H | 5 | 3.62 | 328.3 | 327.3 |
| A-444 | CF₂CHF₂ | CO | C | C | C | H | CH(CH₃)₂ | H | 5 | 3.64 | 360.3 | 359.4 |
| A-445 | CF₂CF₃ | CO | C | C | C | H | CH(CH₃)₂ | H | 5 | 3.94 | 377.8 | 377.4 |
| A-446 | CH₃CH₂CH₃ | CO | C | C | C | CH₃ | CH₃ | H | 5 | 3.55 | 287.9 | 287.4 |
| A-447 | CH(CH₃)₂ | CO | C | C | C | CH₃ | CH₃ | H | 5 | 3.54 | 287.9 | 287.4 |
| A-448 | CH(CH₃)CH₂CH₃ | CO | C | C | C | CH₃ | CH₃ | H | 5 | 3.79 | 301.9 | 301.4 |
| A-449 | cyclopropyl | CO | C | C | C | CH₃ | CH₃ | H | 5 | 3.30 | 285.9 | 285.4 |

TABLE A-continued

| ID | R1 | | | | R2 | R3 | R4 | n | val1 | val2 |
|---|---|---|---|---|---|---|---|---|---|---|
| A-450 | 2-methylcyclopropyl | CO | C | C | CH3 | CH3 | H | 5 | 3.58 | 299.9 | 299.4 |
| A-451 | CF3 | CO | C | C | CH3 | CH3 | H | 5 | 3.46 | 313.8 | 313.3 |
| A-452 | CF2CF3 | CO | C | C | CH3 | CH3 | H | 5 | 3.80 | 363.8 | 363.3 |
| A-453 | CH3 | CO | C | C | H | CF3 | H | 5 | 3.19 | 299.8 | 299.3 |
| A-454 | CH3CH3 | CO | C | C | H | CF3 | H | 5 | 3.46 | 313.8 | 313.3 |
| A-455 | CH(CH3)2 | CO | C | C | H | CF3 | H | 5 | 3.73 | 327.8 | 327.3 |
| A-456 | CH(CH3)CH2CH3 | CO | C | C | H | CF3 | H | 5 | 3.92 | 341.8 | 341.4 |
| A-457 | cyclopropyl | CO | C | C | H | CF3 | H | 5 | 3.46 | 325.8 | 325.3 |
| A-458 | 2-methylcyclopropyl | CO | C | C | H | CF3 | H | 5 | 3.71 | 339.8 | 339.4 |
| A-459 | CF3 | CO | C | C | H | CF3 | H | 5 | 3.64 | 353.8 | 353.3 |
| A-460 | CF2CHF2 | CO | C | C | H | CF3 | H | 5 | 3.67 | 385.7 | 385.3 |
| A-461 | CF2CF3 | CO | C | C | H | CF3 | H | 5 | 3.96 | 403.7 | 403.3 |
| A-462 | CH3 | CO | C | C | H | COCH3 | H | 5 | 2.80 | 273.9 | 273.3 |
| A-463 | CH3CH3 | CO | C | C | H | COCH3 | H | 5 | 3.05 | 287.9 | 287.4 |
| A-464 | CH(CH3)2 | CO | C | C | H | COCH3 | H | 5 | 3.36 | 301.9 | 301.4 |
| A-465 | CH(CH3)CH2CH3 | CO | C | C | H | COCH3 | H | 5 | 3.34 | 301.9 | 301.4 |
| A-466 | cyclopropyl | CO | C | C | H | COCH3 | H | 5 | 3.59 | 315.9 | 315.4 |
| A-467 | 2-methylcyclopropyl | CO | C | C | H | COCH3 | H | 5 | 3.09 | 299.9 | 299.4 |
| A-468 | CF2CHF2 | CO | C | C | H | COCH3 | H | 5 | 3.38 | 313.9 | 313.4 |
| A-469 | CF2CF3 | CO | C | C | H | COCH3 | H | 5 | 3.35 | 359.8 | 359.3 |
| A-470 | CF3 | CO | C | C | H | COCH3 | H | 5 | 3.66 | 377.8 | 377.3 |
| A-471 | CF3 | CO | C | C | CONHCH3 | CH3 | H | 5 | 2.84 | 371.3 | 370.4 |
| A-472 | CF2CHF2 | CO | C | C | CONHCH3 | CH3 | H | 5 | 3.90 | 403.3 | 402.4 |
| A-473 | CF2CF3 | CO | C | C | CONHCH3 | CH3 | H | 5 | 3.21 | 421.3 | 420.4 |
| A-474 | CH(CH3)CH2CH3 | CO | C | C | CONHCH3 | CH3 | H | 5 | 3.11 | 359.4 | 358.5 |
| A-475 | cyclopropyl | CO | C | C | CONHCH3 | CH3 | H | 5 | 2.68 | 343.3 | 342.4 |
| A-476 | CF3 | CO | C | C | NO2 | CH3 | H | 5 | 3.66 | 359.2 | 358.3 |
| A-477 | CF2CF3 | CO | C | C | NO2 | CH3 | H | 5 | 3.96 | 409.2 | 408.3 |
| A-478 | CH(CH3)CH2CH3 | CO | C | C | NO2 | CH3 | H | 5 | 3.92 | 347.3 | 346.4 |
| A-479 | CH3CH3 | CO | C | C | CONHCH3 | CH3 | H | 5 | 2.91 | 345.3 | 344.5 |
| A-480 | CH3CH3 | CO | C | C | CONHCH3 | CH3 | H | 5 | 2.88 | 345.3 | 344.5 |
| A-481 | CH3CH3 | CO | C | C | CH3 | CH3 | H | 5 | 2.64 | 331.3 | 330.4 |
| A-482 | CH2CH2CH3 | CO | C | N | NO2 | CH3 | H | 5 | 3.72 | 333.3 | 332.4 |
| A-483 | CH(CH3)2 | CO | C | N | NO2 | CH3 | H | 5 | 3.70 | 333.3 | 332.4 |
| A-484 | CH3CH3 | CO | C | N | NO2 | CH3 | H | 5 | 3.47 | 319.3 | 318.4 |
| A-485 | CF3 | CO | C | N | — | CH3CH3 | H | 5 | 3.51 | 329.2 | 328.3 |
| A-486 | CF2CHF2 | CO | C | N | — | CH3CH3 | H | 5 | 3.53 | 361.3 | 360.4 |
| A-487 | CF2CF3 | CO | C | N | — | CH3CH3 | H | 5 | 3.86 | 379.3 | 378.3 |
| A-488 | CF(CF3)2 | CO | C | N | — | CH3CH3 | H | 5 | 4.12 | 429.2 | 428.4 |
| A-489 | CH(CH3)CH2CH3 | CO | C | N | — | CH3CH3 | H | 5 | 3.81 | 317.3 | 316.4 |
| A-490 | cyclopropyl | CO | C | N | — | CH3CH3 | H | 5 | 3.30 | 301.3 | 300.4 |
| A-491 | CF3 | CO | C | N | — | CH(CH3)2 | H | 5 | 3.85 | 343.3 | 342.4 |
| A-492 | CF2CHF2 | CO | C | N | — | CH(CH3)2 | H | 5 | 3.85 | 375.3 | 374.4 |
| A-493 | CF2CF3 | CO | C | N | — | CH(CH3)2 | H | 5 | 4.16 | 393.3 | 392.4 |
| A-494 | CF(CF3)2 | CO | C | N | — | CH(CH3)2 | H | 5 | 4.40 | 443.3 | 442.4 |
| A-495 | CH(CH3)CH2CH3 | CO | C | N | — | CH(CH3)2 | H | 5 | 4.15 | 331.4 | 330.5 |
| A-496 | cyclopropyl | CO | C | N | — | CH(CH3)2 | H | 5 | 3.65 | 315.3 | 314.4 |
| A-497 | CH2CH2CH3 | CO | C | N | — | CH(CH3)2 | H | 5 | 3.59 | 303.3 | 302.4 |
| A-498 | CH(CH3)2 | CO | C | N | — | CH(CH3)2 | H | 5 | 3.56 | 303.3 | 302.4 |
| A-499 | CH3CH3 | CO | C | N | — | CH3CH3 | H | 5 | 3.29 | 289.3 | 288.4 |
| A-500 | CH(CH3)2 | CO | C | N | — | CH(CH3)2 | H | 5 | 3.94 | 317.3 | 316.4 |
| A-501 | CH(CH3)2 | CO | C | N | — | CH(CH3)2 | H | 5 | 3.91 | 317.3 | 316.4 |
| A-502 | CH2CH3 | CO | C | N | — | CH(CH3)2 | H | 5 | 3.66 | 303.3 | 302.4 |

TABLE A-continued

| | | | | | | | | | |
|---|---|---|---|---|---|---|---|---|---|
| A-503 | CH(CH₃)₂ | CO | C | C | Cl | H | Cl | 5 | 4.03 | 327.8 | 328.2 |
| A-504 | CH₂CH₂CH₃ | CO | C | C | Cl | H | Cl | 5 | 4.05 | 327.8 | 328.2 |
| A-505 | CH₂CH₃ | CO | C | C | Cl | H | Cl | 5 | 3.77 | 313.8 | 314.2 |
| A-506 | CH₂CH₂CH₃ | CO | N | C | — | CH₃ | Y3—S—C≡C—Y4, (CH₂)₄ | 6 | 4.72 | 384.7 | 384.5 |
| A-507 | CH(CH₃)₂ | CO | N | C | — | CH₃ | Y3—S—C≡C—Y4, (CH₂)₄ | 6 | 4.70 | 384.7 | 384.5 |
| A-508 | CH₂CH₃ | CO | N | C | — | CH₃ | Y3—S—C≡C—Y4, (CH₂)₄ | 6 | 4.49 | 370.7 | 370.5 |
| A-509 | CF₂CH₃ | CO | C | C | CH₃ | CH₃ | H | 4 | 3.34 | 310.2 | 309.4 |
| A-510 | CHF₂ | CO | C | C | CH₃ | CH₃ | H | 4 | 3.14 | 296.2 | 295.3 |
| A-511 | CH₂OCH₃ | CO | C | C | CH₃ | CH₃ | H | 4 | 2.89 | 290.2 | 289.4 |
| A-512 | CH₂CH₂CH₃ | CO | C | C | CH₃ | CH₃ | H | 4 | 3.25 | 298.2 | 297.4 |
| A-513 | CF₂CH₃ | CO | C | C | H | CH₃ | H | 4 | 3.32 | 310.1 | 309.4 |
| A-514 | CHF₂ | CO | C | C | H | CH₃ | H | 4 | 3.04 | 296.2 | 295.3 |
| A-515 | CH₂CH₂CCH | CO | C | C | H | CH₃ | H | 4 | 3.22 | 298.2 | 297.4 |
| A-516 | CH(CH₃)CH₂CH₂CH₃ | CO | C | C | H | COCH₃ | H | 4 | 3.82 | 330.3 | 329.4 |
| A-517 | CH(CH₃)CH₂CH₂CH₃ | CO | C | C | H | CH(CH₃)₂ | H | 4 | 4.16 | 330.3 | 329.5 |
| A-518 | CF₂CH₃ | CO | C | C | H | CH(CH₃)₂ | H | 4 | 3.50 | 324.3 | 323.4 |
| A-519 | CHF₂ | CO | C | C | H | CH(CH₃)₂ | H | 4 | 3.30 | 310.2 | 309.4 |
| A-520 | CH₂OCH₃ | CO | C | C | H | CH(CH₃)₂ | H | 4 | 3.04 | 304.3 | 303.4 |
| A-521 | CH(CH₃)CH₂CH₃ | CO | C | C | H | OCH₃ | H | 4 | 3.92 | 317.9 | 317.4 |
| A-522 | CH(CH₃)CH₂CH₂CH₃ | CO | C | C | H | OCH₃ | H | 4 | 4.19 | 331.9 | 331.5 |
| A-523 | CF₂CH₃ | CO | C | C | H | OCH₃ | H | 4 | 3.11 | 296.2 | 295.3 |
| A-524 | CHF₂ | CO | C | C | H | CH₃ | H | 4 | 2.88 | 282.2 | 281.3 |
| A-525 | CH₂OCH₃ | CO | C | C | H | CH₃ | H | 4 | 2.64 | 276.2 | 275.3 |
| A-526 | CH₂OCH₃ | CO | C | C | H | CH₃ | H | 4 | 3.03 | 284.2 | 283.4 |
| A-527 | cyclopropyl | CO | C | C | H | CH₃ | H | 4 | 3.44 | 302.2 | 301.4 |
| A-528 | CH(CH₃)CH₂CH₂CH₃ | CO | C | C | H | OCH₂CH₃ | H | 4 | 4.14 | 332.4 | 331.5 |
| A-529 | CH₂OCH₃ | CO | C | C | H | OCH₂CH₃ | H | 4 | 3.05 | 306.2 | 305.4 |
| A-530 | cyclopropyl | CO | C | C | H | OCH₂CH₃ | H | 4 | 3.36 | 288.2 | 287.4 |
| A-531 | CH(CH₃)CH₂CH₂CH₃ | CO | C | C | H | OCH₃ | H | 4 | 4.05 | 318.3 | 317.4 |
| A-532 | CF₂CH₃ | CO | C | C | H | OCH₃ | H | 4 | 3.41 | 312.2 | 311.3 |
| A-533 | CHF₂ | CO | C | C | H | OCH₃ | H | 4 | 3.23 | 298.2 | 297.3 |
| A-534 | CH₂OCH₃ | CO | C | C | H | OCH₃ | H | 4 | 2.95 | 292.2 | 291.3 |
| A-535 | CH₂CH₂CCH | CO | C | C | H | OCH₃ | H | 4 | 3.33 | 300.2 | 299.4 |
| A-536 | CF₂CF₃ | CO | C | N | — | CH₃ | CH₃ | 4 | 3.55 | 365.2 | 364.3 |
| A-537 | CF₂CF₃ | CO | C | N | — | OCH₃ | H | 4 | 3.55 | 367.2 | 366.3 |
| A-538 | CF₃ | CO | C | N | — | CH₃ | CH₃ | 4 | 4.02 | 331.2 | 330.3 |
| A-539 | CF₃ | CO | C | N | — | OCH₂CH₃ | CH₃ | 4 | 4.25 | 345.2 | 344.3 |
| A-540 | CF₃ | CO | C | N | — | CH₃ | OCH₃ | 4 | 3.55 | 331.2 | 330.3 |
| A-541 | CF₃ | CO | C | N | — | OCH₃ | OCH₂CH₃ | 4 | 3.82 | 345.2 | 344.3 |
| A-542 | CF₂CHF₂ | CO | C | N | — | OCH₂CH₃ | CH₃ | 4 | 4.03 | 363.2 | 362.3 |
| A-543 | CF₂CHF₂ | CO | C | N | — | CH₃ | OCH₃ | 4 | 4.25 | 377.2 | 376.4 |
| A-544 | CF₂CHF₂ | CO | C | N | — | CH₃ | OCH₃ | 4 | 3.59 | 363.2 | 362.3 |
| A-545 | CF₂CHF₂ | CO | C | N | — | CH₃ | OCH₂CH₃ | 4 | 3.84 | 377.2 | 376.4 |

TABLE A-continued

| No. | | | | | | | | | | |
|---|---|---|---|---|---|---|---|---|---|---|
| A-546 | CF₂CF₃ | CO | N | C | — | OCH₃ | CH₃ | 4 | 4.32 | 381.2 | 380.3 |
| A-547 | CF₂CF₃ | CO | N | C | — | OCH₂CH₃ | CH₃ | 4 | 4.52 | 395.2 | 394.3 |
| A-548 | CF₂CF₃ | CO | N | C | — | CH₃ | OCH₃ | 4 | 3.90 | 381.2 | 380.3 |
| A-549 | CF₂CF₃ | CO | N | C | — | CH₃ | OCH₂CH₃ | 4 | 4.14 | 395.2 | 394.3 |
| A-550 | CH(CH₃)₂ | CO | N | C | — | OCH₃ | OCH₂CH₃ | 4 | 3.71 | 341.2 | 340.4 |
| A-551 | CH(CH₃)₂ | CO | N | C | — | OCH₃ | CH₃ | 4 | 4.11 | 305.2 | 304.4 |
| A-552 | CH(CH₃)₂ | CO | N | C | — | OCH₂CH₃ | CH₃ | 4 | 4.35 | 319.3 | 318.4 |
| A-553 | CH(CH₃)₂ | CO | N | C | — | CH₃ | OCH₃ | 4 | 3.89 | 319.3 | 318.4 |
| A-554 | CH(CH₃)CH₂CH₃ | CO | N | C | — | OCH₃ | CH₃ | 4 | 4.34 | 319.3 | 318.4 |
| A-555 | CH(CH₃)CH₂CH₃ | CO | N | C | — | OCH₂CH₃ | CH₃ | 4 | 4.56 | 333.3 | 332.4 |
| A-556 | CH(CH₃)CH₂CH₃ | CO | N | C | — | CH₃ | OCH₃ | 4 | 3.86 | 319.3 | 318.4 |
| A-557 | CH(CH₃)CH₂CH₃ | CO | N | C | — | CH₃ | OCH₂CH₃ | 4 | 4.13 | 333.3 | 332.4 |
| A-558 | cyclopropyl | CO | N | C | — | OCH₂CH₃ | CH₃ | 4 | 3.86 | 303.2 | 302.4 |
| A-559 | cyclopropyl | CO | N | C | — | OCH₂CH₃ | OCH₃ | 4 | 4.10 | 317.2 | 316.4 |
| A-560 | cyclopropyl | CO | N | C | — | CH₃ | OCH₃ | 4 | 3.35 | 303.2 | 302.4 |
| A-561 | cyclopropyl | CO | N | C | — | CH₃ | OCH₂CH₃ | 4 | 3.64 | 317.2 | 316.4 |
| A-562 | CF₂CH₃ | CO | N | C | — | OCH₂CH₃ | CH₃ | 4 | 4.18 | 340.8 | 340.4 |
| A-563 | CF₂CH₃ | CO | N | C | — | CH₃ | OCH₃ | 4 | 3.42 | 326.8 | 326.3 |
| A-564 | CH(CH₃)₂ | CO | N | C | — | CH₃ | OCH₃ | 4 | 3.59 | 305.2 | 304.4 |
| A-565 | CF₂CF₃ | CO | N | C | — | H | OCH₃ | 4 | 3.68 | 387.2 | 386.3 |
| A-566 | CF₃ | CO | N | C | — | H | Y3—CH—CH—CH—CH—Y4 | 4 | 3.34 | 337.2 | 336.3 |
| A-567 | CF₂CF₃ | CO | N | C | — | H | Y3—CH—CH—CH—CH—Y4 | 4 | 3.74 | 393.2 | 392.4 |
| A-568 | CF₂CHF₂ | CO | N | C | — | H | Y3—S—CH—CH—Y4 | 4 | 3.44 | 362.2 | 361.3 |
| A-569 | CF₃ | CO | N | C | OCH₃ | CH₃ | H | 4 | 3.41 | 330.2 | 329.3 |
| A-570 | cyclopropyl | CO | C | C | OCH₃ | CH₃ | H | 4 | 3.25 | 302.2 | 301.4 |
| A-571 | CF₂CF₃ | CO | C | C | OCH₃ | CH₃ | H | 4 | 3.74 | 380.2 | 379.3 |
| A-572 | CH₂CH₃ | CO | C | C | OCH₃ | CH₃ | H | 4 | 2.70 | 288.8 | 288.3 |
| A-573 | CH(CH₃)₂ | CO | C | C | H | CONH₂ | H | 4 | 2.94 | 302.8 | 302.4 |
| A-574 | CH(CH₃)₂ | CO | C | C | H | CONH₂ | H | 4 | 2.97 | 302.8 | 302.4 |
| A-575 | CH₂CH₂CH₃ | CO | C | C | H | CONH₂ | H | 4 | 2.97 | 316.8 | 316.4 |
| A-576 | CH(CH₃)CH₂CH₃ | CO | C | C | H | CONH₂ | H | 4 | 3.18 | 316.8 | 316.4 |
| A-577 | cyclopropyl | CO | C | C | H | CONH₂ | H | 4 | 2.73 | 300.8 | 300.4 |
| A-578 | CF₂CHF₂ | CO | N | C | H | CONH₂ | H | 4 | 2.89 | 328.8 | 328.3 |
| A-579 | CF₂CF₃ | CO | N | C | H | CONH₂ | H | 4 | 2.97 | 360.7 | 360.3 |
| A-580 | CF₂CH₃ | CO | N | C | H | OCH₃ | CH₃ | 4 | 3.28 | 378.7 | 378.3 |
| A-581 | CF₃ | CO | N | C | H | CH₃ | H | 4 | 2.81 | 324.8 | 324.3 |
| A-582 | CF₂CHF₂ | CO | C | C | — | H | H | 4 | 3.24 | 349.2 | 348.3 |
| A-583 | CF₂CF₃ | CO | C | C | — | H | Y3—CH—CH—CH—CH—Y4 | 4 | 3.25 | 347.3 | 346.3 |
| A-584 | CF₂CF₃ | CO | N | C | — | CH₃ | CH₃ | 4 | 3.39 | 369.2 | 368.3 |
| A-585 | CF₂CHF₂ | CO | N | C | — | H | Y3—S—CH—CH—Y4 | 4 | 3.40 | 343.2 | 342.3 |
| A-586 | CF₃ | CO | N | C | — | H | Y3—S—CH—CH—Y4 | 4 | 3.45 | 375.1 | 374.4 |
| A-587 | CF₂CF₃ | CO | C | C | — | OCH₂CH₃ | CH₃ | 5 | 4.21 | 394.2 | 393.4 |
| A-588 | CF₂CH₃ | CO | C | C | — | OCH₂CH₃ | CH₃ | 5 | 3.92 | 376.2 | 375.4 |
| A-589 | CF₃ | CO | C | C | — | OCH₂CH₃ | CH₃ | 5 | 3.91 | 344.2 | 343.3 |
| A-590 | CHF₂ | CO | C | C | — | OCH₂CH₃ | CH₃ | 5 | 3.60 | 326.2 | 325.4 |
| A-591 | CF₂CF₃ | CO | C | C | — | OCH₂CH₃ | CH₃ | 5 | 3.79 | 340.2 | 339.4 |
| A-592 | CF₂CHF₂ | CO | C | C | — | OCH(CH₃)₂ | CH₃ | 5 | 4.46 | 408.2 | 407.4 |
| A-593 | CF₃ | CO | C | C | — | OCH(CH₃)₂ | CH₃ | 5 | 4.19 | 390.2 | 389.4 |
| A-594 | CHF₂ | CO | C | C | — | OCH(CH₃)₂ | CH₃ | 5 | 4.19 | 358.2 | 357.4 |
| A-595 | CF₂CH₃ | CO | C | C | — | OCH(CH₃)₂ | H | 5 | 3.91 | 340.2 | 339.4 |
| A-596 | CF₂CF₃ | CO | C | C | — | OCH(CH₃)₂ | H | 5 | 4.08 | 354.3 | 353.4 |
| A-597 | CF₂CHF₂ | CO | C | C | — | OCH(CH₃)₂ | H | 5 | 3.91 | 394.2 | 393.4 |
| A-598 | CHF₂ | CO | C | C | — | OCH(CH₃)₂ | H | 5 | 3.78 | 326.2 | 325.4 |

TABLE A-continued

| | | | | | | | | | | | | |
|---|---|---|---|---|---|---|---|---|---|---|---|---|
| A-599 | CF₂CH₃ | CO | C | C | C | H | OCH(CH₃)₂ | H | 5 | 3.78 | 340.2 | 339.4 |
| A-600 | CF₃ | CO | C | C | C | H | OCH(CH₃)₂ | H | 5 | 3.90 | 344.2 | 343.3 |
| A-601 | CHF₂ | CO | C | C | C | H | COCH₃ | H | 5 | 2.96 | 310.1 | 309.3 |
| A-602 | CF₂CH₃ | CO | C | C | C | H | OCH₃ | CH₃ | 5 | 3.17 | 324.2 | 323.3 |
| A-603 | CHF₂ | CO | C | C | C | H | OCH₃ | CH₃ | 5 | 3.32 | 312.2 | 311.3 |
| A-604 | CF₂CH₃ | CO | C | C | C | H | OCH₃ | H | 5 | 3.51 | 326.2 | 325.4 |
| A-605 | CF₃ | CO | C | C | C | H | OCH₃ | H | 5 | 3.64 | 330.2 | 329.3 |
| A-606 | CF₂CHF₂ | CO | C | C | C | H | OCH₂CH₃ | H | 5 | 3.67 | 362.2 | 361.3 |
| A-607 | CF₂CF₃ | CO | C | C | C | H | OCH₂CH₃ | H | 5 | 3.98 | 380.2 | 379.3 |
| A-608 | CHF₂ | CO | C | C | C | H | OCH₂CH₃ | H | 5 | 3.33 | 312.2 | 311.3 |
| A-609 | CF₂CH₃ | CO | C | C | C | H | OCH₂CH₃ | H | 5 | 3.53 | 326.2 | 325.4 |
| A-610 | CH(CH₃)₂ | CO | C | C | C | H | OCH₂CH₃ | H | 5 | 3.69 | 304.2 | 303.4 |
| A-611 | CH(CH₃)CH₂CH₃ | CO | C | C | C | H | OCH₂CH₃ | H | 5 | 3.93 | 318.3 | 317.4 |
| A-612 | CF₂CF₃ | CO | C | C | C | H | O(CH₂)₂CH₃ | H | 5 | 4.20 | 394.2 | 393.4 |
| A-613 | CF₂CHF₂ | CO | C | C | C | H | O(CH₂)₂CH₃ | H | 5 | 3.92 | 376.2 | 375.4 |
| A-614 | CF₃ | CO | C | C | C | H | O(CH₂)₂CH₃ | H | 5 | 3.91 | 344.2 | 343.3 |
| A-615 | CHF₂ | CO | C | C | C | H | O(CH₂)₂CH₃ | H | 5 | 3.62 | 326.2 | 325.4 |
| A-616 | CF₃ | CO | C | C | C | H | CONHCH₃ | H | 5 | 3.09 | 343.2 | 342.3 |
| A-617 | CF₂CF₃ | CO | C | C | C | H | CONHCH₃ | H | 5 | 3.46 | 393.1 | 392.3 |
| A-618 | CF₂CHF₂ | CO | C | C | C | H | CONHCH₃ | H | 5 | 3.17 | 375.2 | 374.3 |
| A-619 | CHF₂ | CO | C | C | C | H | CONHCH₃ | H | 5 | 2.81 | 325.2 | 324.3 |
| A-620 | Cl | CO | C | C | C | — | OCH₂CH₃ | H | 5 | 3.36 | 296.1 | 295.8 |
| A-621 | CHF₂ | CO | C | C | N | — | CH(CH₃)₂ | CH₃ | 5 | 1.43 | 325.1 | 324.4 |
| A-622 | CF₂CH₃ | CO | C | C | N | — | CH(CH₃)₂ | CH₃ | 5 | 1.50 | 339.1 | 338.4 |
| A-623 | CF₂Cl | CO | C | C | N | — | CH(CH₃)₂ | CH₃ | 5 | 1.56 | 359.0 | 358.8 |
| A-624 | CF₂CH₃ | CO | C | C | N | — | CH₂CH₃ | CH₃ | 5 | 1.43 | 325.1 | 324.4 |
| A-625 | CF₂Cl | CO | C | C | C | H | CH₂CH₃ | CH₃ | 5 | 1.50 | 345.1 | 344.8 |
| A-626 | N(CH₃)₂ | CO | C | C | C | H | OCH₂CH₃ | H | 5 | 3.07 | 305.2 | 304.4 |
| A-627 | CF₃ | CO | C | C | C | H | CN | CH₃ | 5 | 3.42 | 324.7 | 324.3 |
| A-628 | CHF₂ | CO | C | C | C | H | CN | CH₃ | 5 | 3.11 | 306.8 | 306.3 |
| A-629 | CF₂CH₃ | CO | C | C | C | H | CN | CH₃ | 5 | 3.32 | 320.8 | 320.3 |
| A-630 | CF₂CHF₂ | CO | C | C | C | H | CN | CH₃ | 5 | 3.47 | 356.7 | 356.3 |
| A-631 | CF₂CF₃ | CO | C | C | C | H | CN | CH₃ | 5 | 3.77 | 374.7 | 374.3 |
| A-632 | CH(CH₃)CH₂CH₃ | CO | C | C | C | H | CN | CH₃ | 11 | 3.14 | 299.2 | 298.4 |
| A-633 | cyclopropyl | CO | C | C | C | H | CN | CH₃ | 5 | 3.72 | 313.2 | 312.4 |
| A-634 | CH₂Cl | CO | C | C | C | H | CN | CH₃ | 5 | 3.24 | 297.2 | 296.4 |
| A-635 | CH₂N(CH₃)₂ | CO | C | C | C | H | CN | H | 5 | 3.15 | 305.1 | 304.8 |
| A-636 | CF₃ | CO | C | C | N | CN | OCHF₂ | CH₃ | 5 | 3.19 | 314.2 | 313.4 |
| A-637 | CF₂CH₃ | CO | C | C | C | — | OCHF₂ | CH₃ | 5 | 3.87 | 352.1 | 351.3 |
| A-638 | CF₂CHF₂ | CO | C | C | N | CN | OCHF₂ | H | 5 | 3.88 | 384.1 | 383.3 |
| A-639 | CF₂CF₃ | CO | C | C | C | — | H | Y3—CH=CH—CH=CH—Y4 | 5 | 4.13 | 402.1 | 401.3 |
| A-640 | CF₃ | CO | C | C | C | — | phenyl | H | 5 | 3.74 | 361.1 | 360.3 |
| A-641 | CF₃ | CO | C | C | N | H | CN | CH₃ | 5 | 4.06 | 363.1 | 362.4 |
| A-642 | Cl | CO | C | C | C | — | H | Y3—CH=CH—CH=CH—Y4 | 5 | 3.13 | 291.1 | 290.8 |
| A-643 | CH(CH₃)₂ | CO | C | C | N | CN | phenyl | H | 5 | 3.72 | 335.2 | 334.4 |
| A-644 | CH(CH₃)CH₂CH₃ | CO | C | C | N | — | H | CH₃ | 5 | 4.04 | 337.3 | 336.4 |
| A-645 | CH(CH₃)₂ | CO | C | C | N | — | OCH(CH₃)₂ | H | 5 | 3.89 | 326.2 | 325.4 |
| A-646 | CH(CH₃)₂ | CO | C | C | N | — | H | Y3—O—CH=CH—CH=Y4 | 5 | 3.31 | 301.2 | 300.4 |
| A-647 | CF₃ | CO | C | C | C | H | OCH₃ | Y3—O—CH=CH—CH=Y4 | 5 | 3.26 | 327.1 | 326.3 |
| A-648 | CF₂Cl | CO | C | C | C | H | OCH₂CH₃ | CH₃ | 5 | 3.78 | 346.1 | 345.8 |
| A-649 | CF₂Cl | CO | C | C | C | H | H | H | 5 | 3.78 | 346.1 | 345.8 |
| A-650 | CF₃ | CO | C | C | C | CF₃ | OCH₃ | H | 5 | 3.70 | 354.1 | 353.3 |
| A-651 | CH(CH₃)₂ | CO | C | C | C | CF₃ | H | H | 5 | 3.77 | 328.2 | 327.3 |

TABLE A-continued

| No | R¹ | Y¹ | Y² | Y³ | Y⁴ | R¹² | R¹³ | R¹⁴ | R¹⁵ | | | | Synt. Methods |
|---|---|---|---|---|---|---|---|---|---|---|---|---|---|
| A-652 | CF₃ | CO | N | C | C | C | — | N(CH₃)₂ | CH₃ | 5 | 4.22 | 358.2 | 357.4 |
| A-653 | CF₃ | CO | N | C | C | C | — | SCH₃ | NH₂ | 5 | 3.40 | 348.1 | 347.4 |
| A-654 | CHF₂ | CO | C | C | C | C | H | N(CH₃)₂ | H | 5 | 3.12 | 311.2 | 310.3 |
| A-655 | CF₃ | CO | C | N | C | C | H | N(CH₃)₂ | H | 5 | 3.43 | 329.2 | 328.3 |
| A-656 | CF₂CHF₂ | CO | C | C | C | C | H | N(CH₃)₂ | H | 5 | 3.35 | 361.2 | 360.4 |
| A-657 | CF₂CF₃ | CO | C | C | C | C | H | N(CH₃)₂ | H | 5 | 3.78 | 379.2 | 378.3 |
| A-658 | CF₃ | CO | C | N | C | C | H | H | Y3—O—CH₂—CH₂—O—Y4 | 5 | 3.16 | 344.1 | 343.3 |
| A-659 | CHF₂ | CO | C | N | C | C | H | H | Y3—O—CH₂—CH₂—O—Y4 | 5 | 2.84 | 326.1 | 325.3 |
| A-660 | CF₃ | CO | C | C | C | C | — | N-pyrrolidinyl | CH₃ | 5 | 3.95 | 370.2 | 369.4 |
| A-661 | CF₃ | CO | C | C | C | C | H | H | Y3—CH=C(OCF₃)—CH=CH—Y4 | 5 | 4.11 | 420.1 | 419.3 |
| A-662 | CF₃ | CO | C | C | C | C | H | H | Y3—CH=CH—CH=CH—Y4 | 5 | 3.22 | 337.1 | 336.3 |
| A-663 | SCH₃ | CO | C | C | C | C | H | OCH₃ | CH₃ | 11 | 1.96 | 308.1 | 307.4 |
| A-664 | SF₅ | CO | C | C | C | C | H | OCH₃ | CH₃ | 5 | 3.82 | 388.1 | 387.4 |
| A-665 | SF₅ | CO | C | C | C | C | H | OCH₃ | H | 5 | 3.62 | 374.0 | 373.3 |
| A-666 | SO₂CH₃ | CO | C | C | C | C | H | OCH₃ | H | 5 | 2.73 | 326.1 | 325.4 |
| A-667 | CH₂CH₃ | SO₂ | C | C | C | C | H | H | Y3—CH=CH—CH=CH—Y4 | 8 | 1.43 | 332.1 | 331.4 |
| A-668 | CH₂CH₂CH₃ | SO₂ | C | C | C | C | H | H | Y3—CH=CH—CH=CH—Y4 | 8 | 1.51 | 346.1 | 345.5 |
| A-669 | CH₂CH₂CH₃ | SO₂ | C | C | C | C | H | CH₃ | Y3—CH=CH—CH=CH—Y4 | 5 | 4.05 | 359.9 | 359.5 |
| A-670 | CH₂CH₃ | SO₂ | C | C | C | C | H | CH₃ | Y3—CH=CH—CH=CH—Y4 | 8 | 1.51 | 346.1 | 345.5 |
| A-671 | CH(CH₃)₂ | SO₂ | C | C | C | C | H | CH₃ | Y3—CH=CH—CH=CH—Y4 | 8 | 1.58 | 360.1 | 359.5 |
| A-672 | CH(CH₃)₂ | SO₂ | C | C | C | C | H | H | Y3—CH=CH—CH=CH—Y4 | 8 | 1.52 | 346.1 | 345.5 |
| A-673 | CH(CH₃)₂C₂H₅ | CS | C | C | C | C | H | H | Y3—CH=C(CF₃)—CH=CH—Y4 | 9 | 1.54 | 408.1 | 407.5 |

(X = CO)

| No | R¹ | Y¹ | Y² | Y³ | Y⁴ | R¹² | R¹³ | R¹⁴ | R¹⁵ | Synt. Methods |
|---|---|---|---|---|---|---|---|---|---|---|
| A-674 | CH₂CH₃ | C | C | C | C | H | OCH₂CH₃ | CH₃ | H | 12F-G; 1C; 16C |
| A-675 | CH₂CH₂CH₃ | C | C | C | C | H | OCH₂CH₃ | CH₃ | H | 12F-G; 1C; 16C |
| A-676 | CH(CH₃)₂ | C | C | C | C | H | OCH₂CH₃ | CH₃ | H | 12F-G; 1C; 16C |
| A-677 | CH(CH₃)CH₂CH₃ | C | C | C | C | H | OCH₂CH₃ | CH₃ | H | 12F-G; 1C; 16C |
| A-678 | cyclopropyl | C | C | C | C | H | OCH₂CH₃ | CH₃ | H | 12F-G; 1C; 16C |
| A-679 | 2-methylcyclopropyl | C | C | C | C | H | OCH₂CH₃ | CH₃ | H | 12F-G; 1C; 16C |
| A-680 | CFHCH₃ | C | C | C | C | H | OCH₂CH₃ | CH₃ | H | 12F-G; 9A, C, D; 16C |
| A-681 | N(CH₃)₂ | C | C | C | C | H | OCH₂CH₃ | CH₃ | H | 12F-G; 16C |
| A-682 | CH₂N(CH₃)₂ | C | C | C | C | H | OCH₂CH₃ | CH₃ | H | 12F-G; 16C |
| A-683 | CH₂NHCH₃ | C | C | C | C | H | OCH₂CH₃ | CH₃ | H | 12F-G; 16C |
| A-684 | CH₂CH₃ | C | C | C | C | H | OCH₂CH₂CH₃ | CH₃ | H | 12F-G; 1C; 16C |
| A-685 | CH₂CH₂CH₃ | C | C | C | C | H | OCH₂CH₂CH₃ | CH₃ | H | 12F-G; 1C; 16C |
| A-686 | CH(CH₃)₂ | C | C | C | C | H | OCH₂CH₂CH₃ | CH₃ | H | 12F-G; 1C; 16C |
| A-687 | CH(CH₃)CH₂CH₃ | C | C | C | C | H | OCH₂CH₂CH₃ | CH₃ | H | 12F-G; 1C; 16C |
| A-688 | CF₃ | C | C | C | C | H | OCH₂CH₂CH₃ | CH₃ | H | 12F-G; 20A-D; 16C |
| A-689 | CF₂CHF₂ | C | C | C | C | H | OCH₂CH₂CH₃ | CH₃ | H | 12F-G; 20A-D; 16C |
| A-690 | CF₂CF₃ | C | C | C | C | H | OCH₂CH₂CH₃ | CH₃ | H | 12F-G; 20A-D; 16C |
| A-691 | CF₂CH₃ | C | C | C | C | H | OCH₂CH₂CH₃ | CH₃ | H | 12F-G; 20A-D; 16C |
| A-692 | CF₂H | C | C | C | C | H | OCH₂CH₂CH₃ | CH₃ | H | 12F-G; 20A-D; 16C |
| A-693 | cyclopropyl | C | C | C | C | H | OCH₂CH₂CH₃ | CH₃ | H | 12F-G; 1C; 16C |
| A-694 | 2-methylcyclopropyl | C | C | C | C | H | OCH₂CH₂CH₃ | CH₃ | H | 12F-G; 1C; 16C |
| A-695 | CFHCH₃ | C | C | C | C | H | OCH₂CH₂CH₃ | CH₃ | H | 12F-G; 9A, C, D; 16C |
| A-696 | N(CH₃)₂ | C | C | C | C | H | OCH₂CH₂CH₃ | CH₃ | H | 12F-G; 16C |
| A-697 | CH₂N(CH₃)₂ | C | C | C | C | H | OCH₂CH₂CH₃ | CH₃ | H | 12F-G; 16C |
| A-698 | CH₂NHCH₃ | C | C | C | C | H | OCH₂CH₂CH₃ | CH₃ | H | 12F-G; 16C |
| A-699 | CH₂CH₃ | C | C | C | C | H | OCH(CH₃)₂ | CH₃ | H | 12F-G; 1C; 16C |

TABLE A-continued

| | | | | | | | |
|---|---|---|---|---|---|---|---|
| A-700 | CH₂CH₂CH₃ | C | C | H | OCH(CH₃)₂ | CH₃ | 12F-G; 1C; 16C |
| A-701 | CH(CH₃)₂ | C | C | H | OCH(CH₃)₂ | CH₃ | 12F-G; 1C; 16C |
| A-702 | CH(CH₃)CH₂CH₃ | C | C | H | OCH(CH₃)₂ | CH₃ | 12F-G; 1C; 16C |
| A-703 | cyclopropyl | C | C | H | OCH(CH₃)₂ | CH₃ | 12F-G; 1C; 16C |
| A-704 | 2-methylcyclopropyl | C | C | H | OCH(CH₃)₂ | CH₃ | 12F-G; 1C; 16C |
| A-705 | CFHCH₃ | C | C | H | OCH(CH₃)₂ | CH₃ | 12F-G; 9A, C, D; 16C |
| A-706 | CH₂CH₃ | C | C | H | OCH(CH₃)₂ | H | 12F-G; 1C; 16C |
| A-707 | N(CH₃)₂ | C | C | H | OCH(CH₃)₂ | CH₃ | 12F-G; 1C; 16C |
| A-708 | CH₂N(CH₃)₂ | C | C | H | OCH(CH₃)₂ | H | 12F-G; 1C; 16C |
| A-709 | CH₂NHCH₃ | C | C | H | OCH(CH₃)₂ | H | 12F-G; 1C; 16C |
| A-710 | CH₂CH₂CH₃ | C | C | H | OCH(CH₃)₂ | H | 12F-G; 1C; 16C |
| A-711 | CH(CH₃)CH₂CH₃ | C | C | H | OCH(CH₃)₂ | H | 12F-G; 1C; 16C |
| A-712 | cyclopropyl | C | C | H | OCH(CH₃)₂ | H | 12F-G; 1C; 16C |
| A-713 | 2-methylcyclopropyl | C | C | H | OCH(CH₃)₂ | H | 12F-G; 1C; 16C |
| A-714 | CFHCH₃ | C | C | H | OCH(CH₃)₂ | H | 12F-G; 9A, C, D; 16C |
| A-715 | N(CH₃)₂ | C | C | H | OCH(CH₃)₂ | H | 12F-G; 1C; 16C |
| A-716 | CH₂N(CH₃)₂ | C | C | H | OCH(CH₃)₂ | H | 12F-G; 1C; 16C |
| A-717 | CH₂NHCH₃ | C | C | H | OCH(CH₃)₂ | H | 12F-G; 1C; 16C |
| A-718 | CH₂CH₃ | C | C | H | OCH₂CH₂CH₃ | H | 12F-G; 1C; 16C |
| A-719 | CH₂CH₂CH₃ | C | C | H | OCH₂CH₂CH₃ | H | 12F-G; 1C; 16C |
| A-720 | CH(CH₃)₂ | C | C | H | OCH₂CH₂CH₃ | H | 12F-G; 1C; 16C |
| A-721 | CH(CH₃)CH₂CH₃ | C | C | H | OCH₂CH₂CH₃ | H | 12F-G; 1C; 16C |
| A-722 | cyclopropyl | C | C | H | OCH₂CH₂CH₃ | H | 12F-G; 20A-D; 16C |
| A-723 | 2-methylcyclopropyl | C | C | H | OCH₂CH₂CH₃ | H | 12F-G; 1C; 16C |
| A-724 | CFHCH₃ | C | C | H | OCH₂CH₂CH₃ | H | 12F-G; 9A, C, D; 16C |
| A-725 | N(CH₃)₂ | C | C | H | OCH₂CH₂CH₃ | H | 12F-G; 16C |
| A-726 | CH₂N(CH₃)₂ | C | C | H | OCH₂CH₂CH₃ | H | 12F-G; 1C; 16C |
| A-727 | CH₂NHCH₃ | C | C | H | OCH₂CH₂CH₃ | H | 12F-G; 16C |
| A-728 | CH₂CH₃ | C | C | H | OCH₂CH₂CH₃ | H | 12F-G; 1C; 16C |
| A-729 | CH₂CH₃ | C | C | H | OCH₃ | CH₂CH₃ | 12F-G; 1C; 16C |
| A-730 | CH₂CH₂CH₃ | C | C | H | OCH₃ | CH₂CH₃ | 12F-G; 1C; 16C |
| A-731 | CH(CH₃)₂ | C | C | H | OCH₃ | CH₂CH₃ | 12F-G; 1C; 16C |
| A-732 | CH(CH₃)CH₂CH₃ | C | C | H | OCH₃ | CH₂CH₃ | 12F-G; 1C; 16C |
| A-733 | CF₃ | C | C | H | OCH₃ | CH₂CH₃ | 12F-G; 1C; 16C |
| A-734 | CF₂CHF₂ | C | C | H | OCH₃ | CH₂CH₃ | 12F-G; 20A-D; 16C |
| A-735 | CF₂CF₃ | C | C | H | OCH₃ | CH₂CH₃ | 12F-G; 20A-D; 16C |
| A-736 | CF₂CH₃ | C | C | H | OCH₃ | CH₂CH₃ | 12F-G; 20A-D; 16C |
| A-737 | CF₂H | C | C | H | OCH₃ | CH₂CH₃ | 12F-G; 20A-D; 16C |
| A-738 | cyclopropyl | C | C | H | OCH₃ | CH₂CH₃ | 12F-G; 20A-D; 16C |
| A-739 | 2-methylcyclopropyl | C | C | H | OCH₃ | CH₂CH₃ | 12F-G; 1C; 16C |
| A-740 | CFHCH₃ | C | C | H | OCH₃ | CH₂CH₃ | 12F-G; 9A, C, D; 16C |
| A-741 | N(CH₃)₂ | C | C | H | OCH₃ | CH₂CH₃ | 12F-G; 16C |
| A-742 | CH₂N(CH₃)₂ | C | C | H | OCH₃ | CH₂CH₃ | 12F-G; 1C; 16C |
| A-743 | CH₂NHCH₃ | C | C | H | OCH₃ | CH₂CH₃ | 12F-G; 16C |
| A-744 | CH₂CH₃ | C | C | H | OCH₂CH₃ | CH₂CH₃ | 12F-G; 1C; 16C |
| A-745 | CH₂CH₂CH₃ | C | C | H | OCH₂CH₃ | CH₂CH₃ | 12F-G; 1C; 16C |
| A-746 | CH(CH₃)₂ | C | C | H | OCH₂CH₃ | CH₂CH₃ | 12F-G; 1C; 16C |
| A-747 | CH(CH₃)CH₂CH₃ | C | C | H | OCH₂CH₃ | CH₂CH₃ | 12F-G; 1C; 16C |
| A-748 | CF₃ | C | C | H | OCH₂CH₃ | CH₂CH₃ | 12F-G; 1C; 16C |
| A-749 | CF₂CHF₂ | C | C | H | OCH₂CH₃ | CH₂CH₃ | 12F-G; 20A-D; 16C |
| A-750 | CF₂CF₃ | C | C | H | OCH₂CH₃ | CH₂CH₃ | 12F-G; 20A-D; 16C |
| A-751 | CF₂CH₃ | C | C | H | OCH₂CH₃ | CH₂CH₃ | 12F-G; 20A-D; 16C |
| A-752 | CF₂H | C | C | H | OCH₂CH₃ | CH₂CH₃ | 12F-G; 20A-D; 16C |

| ID | | | | | | | |
|---|---|---|---|---|---|---|---|
| A-753 | cyclopropyl | C | C | H | OCH$_2$CH$_3$ | CH$_2$CH$_3$ | 12F-G; 1C; 16C |
| A-754 | 2-methylcyclopropyl | C | C | H | OCH$_2$CH$_3$ | CH$_2$CH$_3$ | 12F-G; 1C; 16C |
| A-755 | CFHCH$_3$ | C | C | H | OCH$_2$CH$_3$ | CH$_2$CH$_3$ | 12F-G; 9A, C, D; 16C |
| A-756 | N(CH$_3$)$_2$ | C | C | H | OCH$_2$CH$_3$ | CH$_2$CH$_3$ | 12F-G; 16C |
| A-757 | CH$_2$N(CH$_3$)$_2$ | C | C | H | OCH$_2$CH$_3$ | CH$_2$CH$_3$ | 12F-G; 16C |
| A-758 | CH$_2$NHCH$_3$ | C | C | H | OCH$_2$CH$_3$ | CH$_2$CH$_3$ | 12F-G; 16C |
| A-759 | CH$_2$CH$_3$ | C | C | H | OCH$_3$ | CH(CH$_3$)$_2$ | 12F-G; 1C; 16C |
| A-760 | CH$_2$CH$_2$CH$_3$ | C | C | H | OCH$_3$ | CH(CH$_3$)$_2$ | 12F-G; 1C; 16C |
| A-761 | CH(CH$_3$)$_2$ | C | C | H | OCH$_3$ | CH(CH$_3$)$_2$ | 12F-G; 1C; 16C |
| A-762 | CH(CH$_3$)$_2$CH$_2$CH$_3$ | C | C | H | OCH$_3$ | CH(CH$_3$)$_2$ | 12F-G; 1C; 16C |
| A-763 | CF$_3$ | C | C | H | OCH$_3$ | CH(CH$_3$)$_2$ | 12F-G; 20A-D; 16C |
| A-764 | CF$_2$CHF$_2$ | C | C | H | OCH$_3$ | CH(CH$_3$)$_2$ | 12F-G; 20A-D; 16C |
| A-765 | CF$_2$CF$_3$ | C | C | H | OCH$_3$ | CH(CH$_3$)$_2$ | 12F-G; 20A-D; 16C |
| A-766 | CF$_2$CH$_3$ | C | C | H | OCH$_3$ | CH(CH$_3$)$_2$ | 12F-G; 20A-D; 16C |
| A-767 | CF$_2$H | C | C | H | OCH$_3$ | CH(CH$_3$)$_2$ | 12F-G; 20A-D; 16C |
| A-768 | cyclopropyl | C | C | H | OCH$_3$ | CH(CH$_3$)$_2$ | 12F-G; 1C; 16C |
| A-769 | 2-methylcyclopropyl | C | C | H | OCH$_3$ | CH(CH$_3$)$_2$ | 12F-G; 1C; 16C |
| A-770 | CFHCH$_3$ | C | C | H | OCH$_3$ | CH(CH$_3$)$_2$ | 12F-G; 9A, C, D; 16C |
| A-771 | N(CH$_3$)$_2$ | C | C | H | OCH$_3$ | CH(CH$_3$)$_2$ | 12F-G; 16C |
| A-772 | CH$_2$N(CH$_3$)$_2$ | C | C | H | OCH$_3$ | CH(CH$_3$)$_2$ | 12F-G; 16C |
| A-773 | CH$_2$NHCH$_3$ | C | C | H | OCH$_3$ | CH(CH$_3$)$_2$ | 12F-G; 16C |
| A-774 | CH$_2$CH$_3$ | C | C | H | OCH$_2$CH$_3$ | CH(CH$_3$)$_2$ | 12F-G; 1C; 16C |
| A-775 | N(CH$_3$)$_2$ | C | C | H | OCH$_3$ | CH$_3$ | 12F-G; 1C; 16C |
| A-776 | CH$_2$N(CH$_3$)$_2$ | C | C | H | OCH$_3$ | CH$_3$ | 12F-G; 1C; 16C |
| A-777 | CH$_2$NHCH$_3$ | C | C | H | OCH$_3$ | CH$_3$ | 12F-G; 1C; 16C |
| A-778 | N(CH$_3$)$_2$ | C | C | H | OCH$_3$ | H | 12F-G; 1C; 16C |
| A-779 | CH$_2$N(CH$_3$)$_2$ | C | C | H | OCH$_3$ | H | 12F-G; 1C; 16C |
| A-780 | CH$_2$NHCH$_3$ | C | C | H | OCH$_3$ | H | 12F-G; 1C; 16C |
| A-781 | N(CH$_3$)$_2$ | C | C | H | CH$_3$ | H | 13B; 16C |
| A-782 | CH$_2$N(CH$_3$)$_2$ | C | C | H | CH$_3$ | H | 13B; 16C |
| A-783 | CH$_2$NHCH$_3$ | C | C | H | CH$_3$ | H | 13B; 16C |
| A-784 | CH$_2$CH$_2$CH$_3$ | C | C | H | OCH$_2$CH$_3$ | CH(CH$_3$)$_2$ | 12F-G; 1C; 16C |
| A-785 | CH(CH$_3$)$_2$ | C | C | H | OCH$_2$CH$_3$ | CH(CH$_3$)$_2$ | 12F-G; 1C; 16C |
| A-786 | CH(CH$_3$)CH$_2$CH$_3$ | C | C | H | OCH$_2$CH$_3$ | CH(CH$_3$)$_2$ | 12F-G; 1C; 16C |
| A-787 | CF$_3$ | C | C | H | OCH$_2$CH$_3$ | CH(CH$_3$)$_2$ | 12F-G; 20A-D; 16C |
| A-788 | CF$_2$CHF$_2$ | C | C | H | OCH$_2$CH$_3$ | CH(CH$_3$)$_2$ | 12F-G; 20A-D; 16C |
| A-789 | CF$_2$CF$_3$ | C | C | H | OCH$_2$CH$_3$ | CH(CH$_3$)$_2$ | 12F-G; 20A-D; 16C |
| A-790 | CF$_2$CH$_3$ | C | C | H | OCH$_2$CH$_3$ | CH(CH$_3$)$_2$ | 12F-G; 20A-D; 16C |
| A-791 | CF$_2$H | C | C | H | OCH$_2$CH$_3$ | CH(CH$_3$)$_2$ | 12F-G; 20A-D; 16C |
| A-792 | cyclopropyl | C | C | H | OCH$_2$CH$_3$ | CH(CH$_3$)$_2$ | 12F-G; 1C; 16C |
| A-793 | 2-methylcyclopropyl | C | C | H | OCH$_2$CH$_3$ | CH(CH$_3$)$_2$ | 12F-G; 1C; 16C |
| A-794 | CFHCH$_3$ | C | C | H | OCH$_2$CH$_3$ | CH(CH$_3$)$_2$ | 12F-G; 9A, C, D; 16C |
| A-795 | N(CH$_3$)$_2$ | C | C | H | OCH$_2$CH$_3$ | CH(CH$_3$)$_2$ | 12F-G; 16C |
| A-796 | CH$_2$N(CH$_3$)$_2$ | C | C | H | OCH$_2$CH$_3$ | CH(CH$_3$)$_2$ | 12F-G; 16C |
| A-797 | CH$_2$NHCH$_3$ | C | C | H | OCH$_2$CH$_3$ | CH(CH$_3$)$_2$ | 12F-G; 16C |
| A-798 | N(CH$_3$)$_2$ | C | C | H | CH(CH$_3$)$_2$ | H | 13B; 16C |
| A-799 | CH$_2$N(CH$_3$)$_2$ | C | C | H | CH(CH$_3$)$_2$ | H | 13B; 16C |
| A-800 | CH$_2$NHCH$_3$ | C | C | H | CH(CH$_3$)$_2$ | H | 13B; 16C |
| A-801 | CH$_2$CH$_3$ | C | C | H | CH$_2$CH$_3$ | H | 13B; 1C; 16C |
| A-802 | CH$_2$CH$_2$CH$_3$ | C | C | H | CH$_2$CH$_3$ | H | 13B; 1C; 16C |
| A-803 | CH(CH$_3$)$_2$ | C | C | H | CH$_2$CH$_3$ | H | 13B; 1C; 16C |
| A-804 | CH(CH$_3$)CH$_2$CH$_3$ | C | C | H | CH$_2$CH$_3$ | H | 13B; 1C; 16C |
| A-805 | CF$_3$ | C | C | H | CH$_2$CH$_3$ | H | 13B; 20A-D; 16C |

TABLE A-continued

| ID | | | | | | | |
|---|---|---|---|---|---|---|---|
| A-806 | $CF_2CHF_2$ | C | C | H | $CH_2CH_3$ | H | 13B; 20A-D; 16C |
| A-807 | $CF_2CF_3$ | C | C | H | $CH_2CH_3$ | H | 13B; 20A-D; 16C |
| A-808 | $CF_2CH_3$ | C | C | H | $CH_2CH_3$ | H | 13B; 20A-D; 16C |
| A-809 | $CF_2H$ | C | C | H | $CH_2CH_3$ | H | 13B; 20A-D; 16C |
| A-810 | cyclopropyl | C | C | H | $CH_2CH_3$ | H | 13B; 1C; 16C |
| A-811 | 2-methylcyclopropyl | C | C | H | $CH_2CH_3$ | H | 13B; 1C; 16C |
| A-812 | $N(CH_3)_2$ | C | C | H | $CH_2CH_3$ | H | 13B; 9A, C, D; 16C |
| A-813 | $CH_2N(CH_3)_2$ | C | C | H | $CH_2CH_3$ | H | 13B; 16C |
| A-814 | $CH_2NHCH_3$ | C | C | H | $CH_2CH_3$ | H | 13B; 16C |
| A-815 | $N(CH_3)_2$ | C | C | H | $CH_3$ | H | 13B; 16C |
| A-816 | $CH_2N(CH_3)_2$ | C | C | H | $CH_3$ | H | 13B; 16C |
| A-817 | $CH_2NHCH_3$ | C | C | H | $CH_3$ | H | 13B; 16C |
| A-818 | $N(CH_3)_2$ | C | C | $CH_3$ | $CH_3$ | H | 13B; 16C |
| A-819 | $CH_2N(CH_3)_2$ | C | C | $CH_3$ | $CH_3$ | H | 13B; 16C |
| A-820 | $CH_2NHCH_3$ | C | C | $CH_3$ | $CH_3$ | H | 13B; 16C |
| A-821 | $CH_2NHCH_3$ | C | C | H | $CH_3$ | H | 13B; 16C |
| A-822 | $CH_2CH_3$ | C | C | H | $CH_2CH_2CH_3$ | H | 13B; 1C; 16C |
| A-823 | $CH_2CH_2CH_3$ | C | C | H | $CH_2CH_2CH_3$ | H | 13B; 1C; 16C |
| A-824 | $CH(CH_3)_2$ | C | C | H | $CH_2CH_2CH_3$ | H | 13B; 1C; 16C |
| A-825 | $CH(CH_3)CH_2CH_3$ | C | C | H | $CH_2CH_2CH_3$ | H | 13B; 1C; 16C |
| A-826 | $CF_3$ | C | C | H | $CH_2CH_2CH_3$ | H | 13B; 20A-D; 16C |
| A-827 | $CF_2CHF_2$ | C | C | H | $CH_2CH_2CH_3$ | H | 13B; 20A-D; 16C |
| A-828 | $CF_2CF_3$ | C | C | H | $CH_2CH_2CH_3$ | H | 13B; 20A-D; 16C |
| A-829 | $CF_2CH_3$ | C | C | H | $CH_2CH_2CH_3$ | H | 13B; 20A-D; 16C |
| A-830 | $CF_2H$ | C | C | H | $CH_2CH_2CH_3$ | H | 13B; 20A-D; 16C |
| A-831 | cyclopropyl | C | C | H | $CH_2CH_2CH_3$ | H | 13B; 1C; 16C |
| A-832 | 2-methylcyclopropyl | C | C | H | $CH_2CH_2CH_3$ | H | 13B; 1C; 16C |
| A-833 | $CHFCH_3$ | C | C | H | $CH_2CH_2CH_3$ | H | 13B; 9A, C, D; 16C |
| A-834 | $N(CH_3)_2$ | C | C | H | $CH_2CH_2CH_3$ | H | 13B; 16C |
| A-835 | $CH_2N(CH_3)_2$ | C | C | H | $CH_2CH_2CH_3$ | H | 13B; 16C |
| A-836 | $CH_2NHCH_3$ | C | C | H | $CH_2CH_2CH_3$ | H | 13B; 16C |
| A-837 | $CH_2CH_3$ | C | C | H | $COCH_2CH_3$ | H | 12G; 1C; 16C |
| A-838 | $CH_2CH_2CH_3$ | C | C | H | $COCH_2CH_3$ | H | 12G; 1C; 16C |
| A-839 | $CH(CH_3)_2$ | C | C | H | $COCH_2CH_3$ | H | 12G; 1C; 16C |
| A-840 | $CH(CH_3)CH_2CH_3$ | C | C | H | $COCH_2CH_3$ | H | 12G; 1C; 16C |
| A-841 | $CF_3$ | C | C | H | $COCH_2CH_3$ | H | 12G; 20A-D; 16C |
| A-842 | $CF_2CHF_2$ | C | C | H | $COCH_2CH_3$ | H | 12G; 20A-D; 16C |
| A-843 | $CF_2CF_3$ | C | C | H | $COCH_2CH_3$ | H | 12G; 20A-D; 16C |
| A-844 | $CF_2CH_3$ | C | C | H | $COCH_2CH_3$ | H | 12G; 20A-D; 16C |
| A-845 | $CF_2H$ | C | C | H | $COCH_2CH_3$ | H | 12G; 20A-D; 16C |
| A-846 | cyclopropyl | C | C | H | $COCH_2CH_3$ | H | 12G; 1C; 16C |
| A-847 | 2-methylcyclopropyl | C | C | H | $COCH_2CH_3$ | H | 12G; 1C; 16C |
| A-848 | $N(CH_3)_2$ | C | C | H | $COCH_2CH_3$ | H | 12G; 9A, C, D; 16C |
| A-849 | $CH_2N(CH_3)_2$ | C | C | H | $COCH_2CH_3$ | H | 12G; 16C |
| A-850 | $CH_2NHCH_3$ | C | C | H | $COCH_2CH_3$ | H | 12G; 16C |
| A-851 | $CH_2CH_3$ | C | C | H | $COCH_3$ | $CH_3$ | 12G; 16C |
| A-852 | $CH_2CH_2CH_3$ | C | C | H | $COCH_3$ | $CH_3$ | 12G; 1C; 16C |
| A-853 | $CH(CH_3)_2$ | C | C | H | $COCH_3$ | $CH_3$ | 12G; 1C; 16C |
| A-854 | $CH(CH_3)CH_2CH_3$ | C | C | H | $COCH_3$ | $CH_3$ | 12G; 1C; 16C |
| A-855 | $CF_3$ | C | C | H | $COCH_3$ | $CH_3$ | 12G; 20A-D; 16C |
| A-856 | $CF_2CHF_2$ | C | C | H | $COCH_3$ | $CH_3$ | 12G; 20A-D; 16C |
| A-857 | $CF_2CF_3$ | C | C | H | $COCH_3$ | $CH_3$ | 12G; 20A-D; 16C |
| A-858 | $CF_2CF_3$ | C | C | H | $COCH_3$ | $CH_3$ | 12G; 20A-D; 16C |

TABLE A-continued

| ID | R1 | X | Y | R2 | R3 | R4 | refs |
|---|---|---|---|---|---|---|---|
| A-859 | CF$_2$CH$_3$ | C | C | H | COCH$_3$ | CH$_3$ | 12G; 20A-D; 16C |
| A-860 | CF$_2$H | C | C | H | COCH$_3$ | CH$_3$ | 12G; 20A-D; 16C |
| A-861 | cyclopropyl | C | C | H | COCH$_3$ | CH$_3$ | 12G; 1C; 16C |
| A-862 | 2-methylcyclopropyl | C | C | H | COCH$_3$ | CH$_3$ | 12G; 1C; 16C |
| A-863 | CFHCH$_3$ | C | C | H | COCH$_3$ | CH$_3$ | 12G; 9A, C, D; 16C |
| A-864 | N(CH$_3$)$_2$ | C | C | H | COCH$_3$ | CH$_3$ | 12G; 16C |
| A-865 | CH$_2$N(CH$_3$)$_2$ | C | C | H | COCH$_3$ | CH$_3$ | 12G; 16C |
| A-866 | CH$_2$NHCH$_3$ | C | C | H | COCH$_3$ | CH$_3$ | 12G; 16C |
| A-867 | CH$_2$CH$_3$ | C | C | CH$_3$ | OCH$_3$ | CH$_3$ | 12F-G; 1C; 16C |
| A-868 | CH$_2$CH$_2$CH$_3$ | C | C | CH$_3$ | OCH$_3$ | CH$_3$ | 12F-G; 1C; 16C |
| A-869 | CH(CH$_3$)$_2$ | C | C | CH$_3$ | OCH$_3$ | CH$_3$ | 12F-G; 1C; 16C |
| A-870 | CH(CH$_3$)CH$_2$CH$_3$ | C | C | CH$_3$ | OCH$_3$ | CH$_3$ | 12F-G; 1C; 16C |
| A-871 | CF$_3$ | C | C | CH$_3$ | OCH$_3$ | CH$_3$ | 12F-G; 20A-D; 16C |
| A-872 | CF$_2$CHF$_2$ | C | C | CH$_3$ | OCH$_3$ | CH$_3$ | 12F-G; 20A-D; 16C |
| A-873 | CF$_2$CF$_3$ | C | C | CH$_3$ | OCH$_3$ | CH$_3$ | 12F-G; 20A-D; 16C |
| A-874 | CF$_2$CH$_3$ | C | C | CH$_3$ | OCH$_3$ | CH$_3$ | 12F-G; 20A-D; 16C |
| A-875 | CF$_2$H | C | C | CH$_3$ | OCH$_3$ | CH$_3$ | 12F-G; 20A-D; 16C |
| A-876 | cyclopropyl | C | C | CH$_3$ | OCH$_3$ | CH$_3$ | 12F-G; 1C; 16C |
| A-877 | 2-methylcyclopropyl | C | C | CH$_3$ | OCH$_3$ | CH$_3$ | 12F-G; 1C; 16C |
| A-878 | CFHCH$_3$ | C | C | H | OCH$_3$ | CH$_3$ | 12F-G; 9A, C, D; 16C |
| A-879 | N(CH$_3$)$_2$ | C | C | CH$_3$ | OCH$_3$ | CH$_3$ | 12F-G; 16C |
| A-880 | CH$_2$N(CH$_3$)$_2$ | C | C | CH$_3$ | OCH$_3$ | CH$_3$ | 12F-G; 16C |
| A-881 | CH$_2$NHCH$_3$ | C | C | CH$_3$ | OCH$_3$ | CH$_3$ | 12F-G; 16C |
| A-882 | CH$_2$CH$_3$ | C | C | H | OCH$_3$ | CH$_3$ | 12F-G; 1C; 16C |
| A-883 | CH$_2$CH$_2$CH$_3$ | C | C | H | OCH$_3$ | CH$_3$ | 12F-G; 1C; 16C |
| A-884 | CH(CH$_3$)$_2$ | C | C | H | OCH$_3$ | CH$_3$ | 12F-G; 1C; 16C |
| A-885 | CH(CH$_3$)CH$_2$CH$_3$ | C | C | H | OCH$_3$ | CH$_3$ | 12F-G; 1C; 16C |
| A-886 | CF$_3$ | C | C | H | OCH$_3$ | CH$_3$ | 12F-G; 20A-D; 16C |
| A-887 | CF$_2$CHF$_2$ | C | C | H | OCH$_3$ | CH$_3$ | 12F-G; 20A-D; 16C |
| A-888 | CF$_2$CF$_3$ | C | C | H | OCH$_3$ | CH$_3$ | 12F-G; 20A-D; 16C |
| A-889 | CF$_2$CH$_3$ | C | C | H | OCH$_3$ | CH$_3$ | 12F-G; 20A-D; 16C |
| A-890 | CF$_2$H | C | C | H | OCH$_3$ | CH$_3$ | 12F-G; 20A-D; 16C |
| A-891 | cyclopropyl | C | C | H | OCH$_3$ | CH$_3$ | 12F-G; 1C; 16C |
| A-892 | 2-methylcyclopropyl | C | C | H | OCH$_3$ | CH$_3$ | 12F-G; 1C; 16C |
| A-893 | CFHCH$_3$ | C | C | H | OCH$_3$ | CH$_3$ | 12F-G; 9A, C, D; 16C |
| A-894 | N(CH$_3$)$_2$ | C | C | H | OCH$_3$ | CH$_3$ | 12F-G; 16C |
| A-895 | CH$_2$N(CH$_3$)$_2$ | C | C | H | OCH$_3$ | CH$_3$ | 12F-G; 16C |
| A-896 | CH$_2$NHCH$_3$ | C | C | H | OCH$_3$ | CH$_3$ | 12F-G; 16C |
| A-897 | CH$_2$CH$_3$ | N | C | H | — | H | 1C; 3A-B, 16C |
| A-898 | CH$_2$CH$_2$CH$_3$ | N | C | H | — | H | 1C; 3A-B, 16C |
| A-899 | CH(CH$_3$)$_2$ | N | C | H | — | H | 1C; 3A-B, 16C |
| A-900 | CH(CH$_3$)CH$_2$CH$_3$ | N | C | H | — | H | 1C; 3A-B, 16C |
| A-901 | CF$_3$ | N | C | H | — | H | 20A-D; 3A-B, 16C |
| A-902 | CF$_2$CHF$_2$ | N | C | H | — | H | 20A-D; 3A-B, 16C |
| A-903 | CF$_2$CF$_3$ | N | C | H | — | H | 20A-D; 3A-B, 16C |
| A-904 | CF$_2$CH$_3$ | N | C | H | — | H | 20A-D; 3A-B, 16C |
| A-905 | CF$_2$H | N | C | H | — | H | 20A-D; 3A-B, 16C |
| A-906 | cyclopropyl | N | C | H | — | H | 1C; 3A-B, 16C |
| A-907 | 2-methylcyclopropyl | N | C | H | — | H | 1C; 3A-B, 16C |
| A-908 | CFHCH$_3$ | N | C | H | — | H | 9A, C, D; 16C |
| A-909 | N(CH$_3$)$_2$ | N | C | H | — | H | 3A-B, 16C |
| A-910 | CH$_2$N(CH$_3$)$_2$ | N | C | H | — | H | 3A-B, 16C |
| A-911 | CH$_2$NHCH$_3$ | N | C | H | — | H | 3A-B, 16C |

TABLE A-continued

| | | | | | | |
|---|---|---|---|---|---|---|
| A-912 | CH₂CH₃ | C | N | H | — | Y3—CH=CH—CH=CH—Y4 | 1C; 3A-B, 16C |
| A-913 | CH₂CH₂CH₃ | C | N | H | — | Y3—CH=CH—CH=CH—Y4 | 1C; 3A-B, 16C |
| A-914 | CH(CH₃)₂ | C | N | H | — | Y3—CH=CH—CH=CH—Y4 | 1C; 3A-B, 16C |
| A-915 | CH(CH₃)CH₂CH₃ | C | N | H | — | Y3—CH=CH—CH=CH—Y4 | 1C; 3A-B, 16C |
| A-916 | CF₂CHF₂ | C | N | H | — | Y3—CH=CH—CH=CH—Y4 | 1C; 3A-B, 16C |
| A-917 | CF₂CF₃ | C | N | H | — | Y3—CH=CH—CH=CH—Y4 | 20A-D; 3A-B, 16C |
| A-918 | CF₂CH₃ | C | N | H | — | Y3—CH=CH—CH=CH—Y4 | 20A-D; 3A-B, 16C |
| A-919 | CF₃H | C | N | H | — | Y3—CH=CH—CH=CH—Y4 | 20A-D; 3A-B, 16C |
| A-920 | cyclopropyl | C | N | H | — | Y3—CH=CH—CH=CH—Y4 | 1C; 3A-B, 16C |
| A-921 | 2-methylcyclopropyl | C | N | H | — | Y3—CH=CH—CH=CH—Y4 | 1C; 3A-B, 16C |
| A-922 | CFHCH₃ | C | N | H | — | Y3—CH=CH—CH=CH—Y4 | 9A, C, D; 16C |
| A-923 | N(CH₃)₂ | C | N | H | — | Y3—CH=CH—CH=CH—Y4 | 3A-B, 16C |
| A-924 | CH₂N(CH₃)₃ | C | N | H | — | Y3—CH=CH—CH=CH—Y4 | 3A-B, 16C |
| A-925 | CH₂NHCH₃ | C | N | H | — | Y3—CH=CH—CH=CH—Y4 | 3A-B, 16C |
| A-926 | CH₂CH₃ | C | C | H | SCH₃ | Y3—CH=CH—CH=CH—Y4 | 1C; 3A-B, 16C |
| A-927 | CH₂CH₂CH₃ | C | C | H | SCH₃ | Y3—CH=CH—CH=CH—Y4 | 1C; 3A-B, 16C |
| A-928 | CH(CH₃)₂ | C | C | H | SCH₃ | Y3—CH=CH—CH=CH—Y4 | 1C; 3A-B, 16C |
| A-929 | CH(CH₃)CH₂CH₃ | C | C | H | SCH₃ | Y3—CH=CH—CH=CH—Y4 | 1C; 3A-B, 16C |
| A-930 | CF₃ | C | C | H | SCH₃ | Y3—CH=CH—CH=CH—Y4 | 20A-D; 3A-B, 16C |
| A-931 | CF₂CHF₂ | C | C | H | SCH₃ | Y3—CH=CH—CH=CH—Y4 | 20A-D; 3A-B, 16C |
| A-932 | CF₂CF₃ | C | C | H | SCH₃ | Y3—CH=CH—CH=CH—Y4 | 20A-D; 3A-B, 16C |
| A-933 | CF₂CH₃ | C | C | H | SCH₃ | Y3—CH=CH—CH=CH—Y4 | 20A-D; 3A-B, 16C |
| A-934 | CF₂H | C | C | H | SCH₃ | Y3—CH=CH—CH=CH—Y4 | 1C; 3A-B, 16C |
| A-935 | cyclopropyl | C | C | H | SCH₃ | Y3—CH=CH—CH=CH—Y4 | 1C; 3A-B, 16C |
| A-936 | 2-methylcyclopropyl | C | C | H | SCH₃ | Y3—CH=CH—CH=CH—Y4 | 12F-G; 9A, C, D; 16C |
| A-937 | CFHCH₃ | C | C | H | SCH₃ | Y3—CH=CH—CH=CH—Y4 | 3A-B, 16C |
| A-938 | N(CH₃)₂ | C | C | H | SCH₃ | Y3—CH=CH—CH=CH—Y4 | 3A-B, 16C |
| A-939 | CH₂N(CH₃)₂ | C | C | H | SCH₃ | Y3—CH=CH—CH=CH—Y4 | 3A-B, 16C |
| A-940 | CH₂NHCH₃ | C | C | H | SCH₃ | Y3—CH=CH—CH=CH—Y4 | 3A-B, 16C |
| A-941 | CH₂CH₃ | C | C | H | NHCOCH₃ | Y3—CH=CH—CH=CH—Y4 | 1C; 3A-B, 16C |
| A-942 | CH₂CH₂CH₃ | C | C | H | NHCOCH₃ | Y3—CH=CH—CH=CH—Y4 | 20A-D; 3A-B, 16C |
| A-943 | CH(CH₃)₂ | C | C | H | NHCOCH₃ | Y3—CH=CH—CH=CH—Y4 | 20A-D; 3A-B, 16C |
| A-944 | CH(CH₃)CH₂CH₃ | C | C | H | NHCOCH₃ | Y3—CH=CH—CH=CH—Y4 | 20A-D; 3A-B, 16C |
| A-945 | CF₃ | C | C | H | NHCOCH₃ | Y3—CH=CH—CH=CH—Y4 | 20A-D; 3A-B, 16C |
| A-946 | CF₂CHF₂ | C | C | H | NHCOCH₃ | Y3—CH=CH—CH=CH—Y4 | 20A-D; 3A-B, 16C |
| A-947 | CF₂CF₃ | C | C | H | NHCOCH₃ | Y3—CH=CH—CH=CH—Y4 | 20A-D; 3A-B, 16C |
| A-948 | CF₂CH₃ | C | C | H | NHCOCH₃ | Y3—CH=CH—CH=CH—Y4 | 20A-D; 3A-B, 16C |
| A-949 | CF₂H | C | C | H | NHCOCH₃ | Y3—CH=CH—CH=CH—Y4 | 1C; 3A-B, 16C |
| A-950 | cyclopropyl | C | C | H | NHCOCH₃ | Y3—CH=CH—CH=CH—Y4 | 1C; 3A-B, 16C |
| A-951 | 2-methylcyclopropyl | C | C | H | NHCOCH₃ | Y3—CH=CH—CH=CH—Y4 | 3A-B; 9A, C, D; 16C |
| A-952 | CFHCH₃ | C | C | H | NHCOCH₃ | Y3—CH=CH—CH=CH—Y4 | 3A-B, 16C |
| A-953 | N(CH₃)₂ | C | C | H | NHCOCH₃ | Y3—CH=CH—CH=CH—Y4 | 3A-B, 16C |
| A-954 | CH₂N(CH₃)₂ | C | C | H | NHCOCH₃ | Y3—CH=CH—CH=CH—Y4 | 3A-B, 16C |
| A-955 | CH₂NHCH₃ | C | C | H | NHCOCH₃ | Y3—CH=CH—CH=CH—Y4 | 3A-B, 16C |
| A-956 | CH₂CH₃ | C | C | H | H | Y3—O—CH₂—CH₂—O—Y4 | 1C; 12-G, 16C |
| A-957 | CH₂CH₂CH₃ | C | C | H | H | Y3—O—CH₂—CH₂—O—Y4 | 1C; 12-G, 16C |
| A-958 | CH(CH₃)₂ | C | C | H | H | Y3—O—CH₂—CH₂—O—Y4 | 1C; 12-G, 16C |
| A-959 | CH(CH₃)CH₂CH₃ | C | C | H | H | Y3—O—CH₂—CH₂—O—Y4 | 1C; 12-G, 16C |
| A-960 | CF₃ | C | C | H | H | Y3—O—CH₂—CH₂—O—Y4 | 20A-D; 12-G, 16C |
| A-961 | CF₂CHF₂ | C | C | H | H | Y3—O—CH₂—CH₂—O—Y4 | 20A-D; 12-G, 16C |
| A-962 | CF₂CF₃ | C | C | H | H | Y3—O—CH₂—CH₂—O—Y4 | 20A-D; 12-G, 16C |
| A-963 | CF₂CH₃ | C | C | H | H | Y3—O—CH₂—CH₂—O—Y4 | 20A-D; 12-G, 16C |
| A-964 | CF₂H | C | C | H | H | Y3—O—CH₂—CH₂—O—Y4 | 20A-D; 12-G, 16C |

TABLE A-continued

| | | | | | | |
|---|---|---|---|---|---|---|
| A-965 | cyclopropyl | C | H | H | Y3—O—CH₂—CH₂—O—Y4 | 1C; 12-G, 16C |
| A-966 | 2-methylcyclopropyl | C | H | H | Y3—O—CH₂—CH₂—O—Y4 | 1C; 12-G, 16C |
| A-967 | CFHCH₃ | C | H | H | Y3—O—CH₂—CH₂—O—Y4 | 12F-G; 9A, C, D; 16C |
| A-968 | N(CH₃)₂ | C | H | H | Y3—O—CH₂—CH₂—O—Y4 | 12-G, 16C |
| A-969 | CH₂N(CH₃)₂ | C | H | H | Y3—O—CH₂—CH₂—O—Y4 | 12-G, 16C |
| A-970 | CH₂NHCH₃ | C | H | H | Y3—O—CH₂—CH₂—O—Y4 | 12-G, 16C |
| A-971 | CH₂CH₃ | C | H | H | Y3—O—CH₂—CH₂—CH₂—Y4 | 1C; 12-G, 16C |
| A-972 | CH₂CH₂CH₃ | C | H | H | Y3—O—CH₂—CH₂—CH₂—Y4 | 1C; 12-G, 16C |
| A-973 | CH(CH₃)₂ | C | H | H | Y3—O—CH₂—CH₂—CH₂—Y4 | 1C; 12-G, 16C |
| A-974 | CH(CH₃)CH₂CH₃ | C | H | H | Y3—O—CH₂—CH₂—CH₂—Y4 | 1C; 12-G, 16C |
| A-975 | CF₃ | C | H | H | Y3—O—CH₂—CH₂—CH₂—Y4 | 20A-D; 12-G, 16C |
| A-976 | CF₂CHF₂ | C | H | H | Y3—O—CH₂—CH₂—CH₂—Y4 | 20A-D; 12-G, 16C |
| A-977 | CF₂CF₃ | C | H | H | Y3—O—CH₂—CH₂—CH₂—Y4 | 20A-D; 12-G, 16C |
| A-978 | CF₂CH₃ | C | H | H | Y3—O—CH₂—CH₂—CH₂—Y4 | 20A-D; 12-G, 16C |
| A-979 | CF₂H | C | H | H | Y3—O—CH₂—CH₂—CH₂—Y4 | 1C; 12-G, 16C |
| A-980 | cyclopropyl | C | H | H | Y3—O—CH₂—CH₂—CH₂—Y4 | 1C; 12-G, 16C |
| A-981 | 2-methylcyclopropyl | C | H | H | Y3—O—CH₂—CH₂—CH₂—Y4 | 1C; 12-G, 16C |
| A-982 | CFHCH₃ | C | H | H | Y3—O—CH₂—CH₂—CH₂—Y4 | 12F-G; 9A, C, D; 16C |
| A-983 | N(CH₃)₂ | C | H | H | Y3—O—CH₂—CH₂—CH₂—Y4 | 12-G, 16C |
| A-984 | CH₂N(CH₃)₂ | C | H | H | Y3—O—CH₂—CH₂—CH₂—Y4 | 12-G, 16C |
| A-985 | CH₂NHCH₃ | C | H | H | Y3—O—CH₂—CH₂—CH₂—Y4 | 12-G, 16C |
| A-986 | CH₂CH₃ | C | H | H | Y3—O—CH₂—CH₂—Y4 | 1C; 12-G, 16C |
| A-987 | CH₂CH₂CH₃ | C | H | H | Y3—O—CH₂—CH₂—Y4 | 1C; 12-G, 16C |
| A-988 | CH(CH₃)₂ | C | H | H | Y3—O—CH₂—CH₂—Y4 | 1C; 12-G, 16C |
| A-989 | CH(CH₃)CH₂CH₃ | C | H | H | Y3—O—CH₂—CH₂—Y4 | 1C; 12-G, 16C |
| A-990 | CF₃ | C | H | H | Y3—O—CH₂—CH₂—Y4 | 20A-D; 12-G, 16C |
| A-991 | CF₂CHF₂ | C | H | H | Y3—O—CH₂—CH₂—Y4 | 20A-D; 12-G, 16C |
| A-992 | CF₂CF₃ | C | H | H | Y3—O—CH₂—CH₂—Y4 | 20A-D; 12-G, 16C |
| A-993 | CF₂CH₃ | C | H | H | Y3—O—CH₂—CH₂—Y4 | 20A-D; 12-G, 16C |
| A-994 | CF₂H | C | H | H | Y3—O—CH₂—CH₂—Y4 | 1C; 12-G, 16C |
| A-995 | cyclopropyl | C | H | H | Y3—O—CH₂—CH₂—Y4 | 1C; 12-G, 16C |
| A-996 | 2-methylcyclopropyl | C | H | H | Y3—O—CH₂—CH₂—Y4 | 12G; 9A, C, D; 16C |
| A-997 | CFHCH₃ | C | H | H | Y3—O—CH₂—CH₂—Y4 | 12-G, 16C |
| A-998 | N(CH₃)₂ | C | H | H | Y3—O—CH₂—CH₂—Y4 | 12-G, 16C |
| A-999 | CH₂N(CH₃)₂ | C | H | H | Y3—O—CH₂—CH₂—Y4 | 12-G, 16C |
| A-1000 | CH₂NHCH₃ | C | H | CONHCH₃ | H | 1C; 3A-B, 16C |
| A-1001 | CH₂CH₃ | C | H | CONHCH₃ | H | 1C; 3A-B, 16C |
| A-1002 | CH₂CH₂CH₃ | C | H | CONHCH₃ | H | 1C; 3A-B, 16C |
| A-1003 | CH(CH₃)₂ | C | H | CONHCH₃ | H | 1C; 3A-B, 16C |
| A-1004 | CH(CH₃)CH₂CH₃ | C | H | CONHCH₃ | H | 1C; 3A-B, 16C |
| A-1005 | CF₃ | C | H | CONHCH₃ | H | 20A-D; 3A-B, 16C |
| A-1006 | CF₂CHF₂ | C | H | CONHCH₃ | H | 20A-D; 3A-B, 16C |
| A-1007 | CF₂CF₃ | C | H | CONHCH₃ | H | 20A-D; 3A-B, 16C |
| A-1008 | CF₂CH₃ | C | H | CONHCH₃ | H | 20A-D; 3A-B, 16C |
| A-1009 | CF₂H | C | H | CONHCH₃ | H | 1C; 3A-B, 16C |
| A-1010 | cyclopropyl | C | H | CONHCH₃ | H | 1C; 3A-B, 16C |
| A-1011 | 2-methylcyclopropyl | C | H | CONHCH₃ | H | 1C; 3A-B, 16C |
| A-1012 | CFHCH₃ | C | H | CONHCH₃ | H | 3A-B; 9A, C, D; 16C |
| A-1013 | N(CH₃)₂ | C | H | CONHCH₃ | H | 3A-B, 16C |
| A-1014 | CH₂N(CH₃)₂ | C | H | CONHCH₃ | H | 3A-B, 16C |
| A-1015 | CH₂NHCH₃ | C | H | CONHCH₃ | H | 3A-B, 16C |
| A-1016 | CH₂CH₃ | C | H | CON(CH₃)₂ | H | 1C; 3A-B, 16C |
| A-1017 | CH₂CH₂CH₃ | C | H | CON(CH₃)₂ | H | 1C; 3A-B, 16C |

TABLE A-continued

| | | | | | |
|---|---|---|---|---|---|
| A-1018 | CH(CH$_3$)$_2$ | C | H | CON(CH$_3$)$_2$ | H | 1C; 3A-B, 16C |
| A-1019 | CH(CH$_3$)CH$_2$CH$_3$ | C | H | CON(CH$_3$)$_2$ | H | 1C; 3A-B, 16C |
| A-1020 | CF$_3$ | C | H | CON(CH$_3$)$_2$ | H | 20A-D; 3A-B, 16C |
| A-1021 | CF$_2$CHF$_2$ | C | H | CON(CH$_3$)$_2$ | H | 20A-D; 3A-B, 16C |
| A-1022 | CF$_2$CF$_3$ | C | H | CON(CH$_3$)$_2$ | H | 20A-D; 3A-B, 16C |
| A-1023 | CF$_2$CH$_3$ | C | H | CON(CH$_3$)$_2$ | H | 20A-D; 3A-B, 16C |
| A-1024 | CF$_2$H | C | H | CON(CH$_3$)$_2$ | H | 1C; 3A-B, 16C |
| A-1025 | cyclopropyl | C | H | CON(CH$_3$)$_2$ | H | 1C; 3A-B, 16C |
| A-1026 | 2-methylcyclopropyl | C | H | CON(CH$_3$)$_2$ | H | 12F-G; 9A, C, D; 16C |
| A-1027 | CFHCH$_3$ | C | H | CON(CH$_3$)$_2$ | H | 3A-B, 16C |
| A-1028 | N(CH$_3$)$_2$ | C | H | CON(CH$_3$)$_2$ | H | 3A-B, 16C |
| A-1029 | CH$_2$N(CH$_3$)$_2$ | C | H | CON(CH$_3$)$_2$ | H | 3A-B, 16C |
| A-1030 | CH$_2$NHCH$_3$ | C | H | CON(CH$_3$)$_2$ | H | 3A-B, 16C |
| A-1031 | CF$_2$Cl | C | H | OCH$_2$CH$_2$CH$_3$ | CH$_3$ | 12F-G; 20A-D; 16C |
| A-1032 | CF$_2$Cl | C | H | OCH$_2$CH$_2$CH$_3$ | H | 12F-G; 20A-D; 16C |
| A-1033 | CF$_2$Cl | C | H | OCH$_3$ | CH$_2$CH$_3$ | 12F-G; 20A-D; 16C |
| A-1034 | CF$_2$Cl | C | H | OCH$_3$ | CH$_2$CH$_3$ | 12F-G; 20A-D; 16C |
| A-1035 | CF$_2$Cl | C | H | OCH$_3$ | CH(CH$_3$)$_2$ | 12F-G; 20A-D; 16C |
| A-1036 | CF$_2$Cl | C | H | OCH$_2$CH$_3$ | CH(CH$_3$)$_2$ | 12F-G; 20A-D; 16C |
| A-1037 | CF$_2$Cl | C | H | CH$_2$CH$_3$ | H | 13B; 20A-D; 16C |
| A-1038 | CF$_2$Cl | C | H | CH$_2$CH$_2$CH$_3$ | H | 13B; 20A-D; 16C |
| A-1039 | CF$_2$Cl | C | H | COCH$_2$CH$_3$ | H | 12G; 20A-D; 16C |
| A-1040 | CF$_2$Cl | C | H | OCH$_3$ | CH$_3$ | 12F-G; 20A-D; 16C |
| A-1041 | CF$_2$Cl | C | CH$_3$ | OCH$_3$ | CH$_3$ | 12F-G; 20A-D; 16C |
| A-1042 | CF$_2$Cl | C | H | OCH$_3$ | CH$_3$ | 12F-G; 20A-D; 16C |
| A-1043 | CF$_2$Cl | C | H | SCH$_3$ | H | 20A-D; 3A-B, 16C |
| A-1044 | CH$_2$CH$_3$ | C | CH$_3$ | OCH$_3$ | H | 12F-G; 1C; 16C |
| A-1045 | CH$_2$CH$_2$CH$_3$ | C | CH$_3$ | OCH$_3$ | H | 12F-G; 1C; 16C |
| A-1046 | CH(CH$_3$)$_2$ | C | CH$_3$ | OCH$_3$ | H | 12F-G; 1C; 16C |
| A-1047 | CH(CH$_3$)CH$_2$CH$_3$ | C | CH$_3$ | OCH$_3$ | H | 12F-G; 1C; 16C |
| A-1048 | CF$_3$ | C | CH$_3$ | OCH$_3$ | H | 12F-G; 20A-D; 16C |
| A-1049 | CF$_2$CHF$_2$ | C | CH$_3$ | OCH$_3$ | H | 12F-G; 20A-D; 16C |
| A-1050 | CF$_2$CF$_3$ | C | CH$_3$ | OCH$_3$ | H | 12F-G; 20A-D; 16C |
| A-1051 | CF$_2$CH$_3$ | C | CH$_3$ | OCH$_3$ | H | 12F-G; 20A-D; 16C |
| A-1052 | CF$_2$H | C | CH$_3$ | OCH$_3$ | H | 12F-G; 1C; 16C |
| A-1053 | cyclopropyl | C | CH$_3$ | OCH$_3$ | H | 12F-G; 1C; 16C |
| A-1054 | 2-methylcyclopropyl | C | CH$_3$ | OCH$_3$ | H | 12F-G; 1C; 16C |
| A-1055 | CF$_2$Cl | C | CH$_3$ | OCH$_2$CH$_3$ | H | 12F-G; 20A-D; 16C |
| A-1056 | CH$_2$CH$_3$ | C | CH$_3$ | OCH$_2$CH$_3$ | H | 12F-G; 1C; 16C |
| A-1057 | CH$_2$CH$_2$CH$_3$ | C | CH$_3$ | OCH$_2$CH$_3$ | H | 12F-G; 1C; 16C |
| A-1058 | CH(CH$_3$)$_2$ | C | CH$_3$ | OCH$_2$CH$_3$ | H | 12F-G; 1C; 16C |
| A-1059 | CH(CH$_3$)CH$_2$CH$_3$ | C | CH$_3$ | OCH$_2$CH$_3$ | H | 12F-G; 1C; 16C |
| A-1060 | CF$_3$ | C | CH$_3$ | OCH$_2$CH$_3$ | H | 12F-G; 20A-D; 16C |
| A-1061 | CF$_2$CHF$_2$ | C | CH$_3$ | OCH$_2$CH$_3$ | H | 12F-G; 20A-D; 16C |
| A-1062 | CF$_2$CF$_3$ | C | CH$_3$ | OCH$_2$CH$_3$ | H | 12F-G; 20A-D; 16C |
| A-1063 | CF$_2$CH$_3$ | C | CH$_3$ | OCH$_2$CH$_3$ | H | 12F-G; 20A-D; 16C |
| A-1064 | CF$_2$H | C | CH$_3$ | OCH$_2$CH$_3$ | H | 12F-G; 1C; 16C |
| A-1065 | cyclopropyl | C | CH$_3$ | OCH$_2$CH$_3$ | H | 12F-G; 1C; 16C |
| A-1066 | 2-methylcyclopropyl | C | CH$_3$ | OCH$_2$CH$_3$ | H | 12F-G; 1C; 16C |
| A-1067 | CF$_2$Cl | C | CH$_3$ | OCH$_3$ | CH$_3$ | 12F-G; 1C; 16C |
| A-1068 | CH$_2$CH$_3$ | C | CH$_3$ | OCH$_3$ | CH$_3$ | 12F-G; 1C; 16C |
| A-1069 | CH$_2$CH$_2$CH$_3$ | C | H | OCH$_3$ | CH$_3$ | 12F-G; 1C; 16C |
| A-1070 | CH(CH$_3$)$_2$ | C | H | OCH$_3$ | CH$_3$ | 12F-G; 1C; 16C |

| | | | | | | |
|---|---|---|---|---|---|---|
| A-1071 | CH(CH₃)CH₂CH₃ | C | H | OCH₃ | H | CH₃ | 12F-G; 1C; 16C |
| A-1072 | CF₃ | C | H | OCH₃ | H | CH₃ | 12F-G; 20A-D; 16C |
| A-1073 | CF₂CHF₂ | C | H | OCH₃ | H | CH₃ | 12F-G; 20A-D; 16C |
| A-1074 | CF₂CF₃ | C | H | OCH₃ | H | CH₃ | 12F-G; 20A-D; 16C |
| A-1075 | CF₂CH₃ | C | H | OCH₃ | H | CH₃ | 12F-G; 20A-D; 16C |
| A-1076 | CF₂H | C | H | OCH₃ | H | CH₃ | 12F-G; 20A-D; 16C |
| A-1077 | cyclopropyl | C | H | OCH₃ | H | CH₃ | 12F-G; 1C; 16C |
| A-1078 | 2-methylcyclopropyl | C | H | OCH₃ | H | CH₃ | 12F-G; 1C; 16C |
| A-1079 | CF₂Cl | C | H | OCH₃ | H | CH₃ | 12F-G; 20A-D; 16C |
| A-1080 | CH₂CH₃ | C | H | OCH₂CH₃ | H | CH₃ | 12F-G; 1C; 16C |
| A-1081 | CH₂CH₂CH₃ | C | H | OCH₂CH₃ | H | CH₃ | 12F-G; 1C; 16C |
| A-1082 | CH(CH₃)₂ | C | H | OCH₂CH₃ | H | CH₃ | 12F-G; 1C; 16C |
| A-1083 | CH(CH₃)CH₂CH₃ | C | H | OCH₂CH₃ | H | CH₃ | 12F-G; 1C; 16C |
| A-1084 | CF₃ | C | H | OCH₂CH₃ | H | CH₃ | 12F-G; 20A-D; 16C |
| A-1085 | CF₂CHF₂ | C | H | OCH₂CH₃ | H | CH₃ | 12F-G; 20A-D; 16C |
| A-1086 | CF₂CF₃ | C | H | OCH₂CH₃ | H | CH₃ | 12F-G; 20A-D; 16C |
| A-1087 | CF₂CH₃ | C | H | OCH₂CH₃ | H | CH₃ | 12F-G; 20A-D; 16C |
| A-1088 | CF₂H | C | H | OCH₂CH₃ | H | CH₃ | 12F-G; 1C; 16C |
| A-1089 | cyclopropyl | C | H | OCH₂CH₃ | H | CH₃ | 12F-G; 1C; 16C |
| A-1090 | 2-methylcyclopropyl | C | H | OCH₂CH₃ | H | CH₃ | 12F-G; 1C; 16C |
| A-1091 | CF₂Cl | C | H | OCH₂CH₃ | H | CH₃ | 12F-G; 20A-D; 16C |
| A-1092 | CH₂CH₃ | C | H | OCH₂-cyclopropyl | H | H | 12F-G; 1C; 16C |
| A-1093 | CH₂CH₂CH₃ | C | H | OCH₂-cyclopropyl | H | H | 12F-G; 1C; 16C |
| A-1094 | CH(CH₃)₂ | C | H | OCH₂-cyclopropyl | H | H | 12F-G; 1C; 16C |
| A-1095 | CH(CH₃)CH₂CH₃ | C | H | OCH₂-cyclopropyl | H | H | 12F-G; 1C; 16C |
| A-1096 | CF₃ | C | H | OCH₂-cyclopropyl | H | H | 12F-G; 20A-D; 16C |
| A-1097 | CF₂CHF₂ | C | H | OCH₂-cyclopropyl | H | H | 12F-G; 20A-D; 16C |
| A-1098 | CF₂CF₃ | C | H | OCH₂-cyclopropyl | H | H | 12F-G; 20A-D; 16C |
| A-1099 | CF₂CH₃ | C | H | OCH₂-cyclopropyl | H | H | 12F-G; 20A-D; 16C |
| A-1100 | CF₂H | C | H | OCH₂-cyclopropyl | H | H | 12F-G; 1C; 16C |
| A-1101 | cyclopropyl | C | H | OCH₂-cyclopropyl | H | H | 12F-G; 1C; 16C |
| A-1102 | 2-methylcyclopropyl | C | H | OCH₂-cyclopropyl | H | H | 12F-G; 1C; 16C |
| A-1103 | CF₂Cl | C | H | OCH₂-cyclopropyl | H | H | 12F-G; 20A-D; 16C |
| A-1104 | CH₂CH₃ | C | H | SCH₂CH₃ | H | H | 1C; 3A-B, 16C |
| A-1105 | CH₂CH₂CH₃ | C | H | SCH₂CH₃ | H | H | 1C; 3A-B, 16C |
| A-1106 | CH(CH₃)₂ | C | H | SCH₂CH₃ | H | H | 1C; 3A-B, 16C |
| A-1107 | CH(CH₃)CH₂CH₃ | C | H | SCH₂CH₃ | H | H | 1C; 3A-B, 16C |
| A-1108 | CF₃ | C | H | SCH₂CH₃ | H | H | 20A-D; 3A-B, 16C |
| A-1109 | CF₂CHF₂ | C | H | SCH₂CH₃ | H | H | 20A-D; 3A-B, 16C |
| A-1110 | CF₂CF₃ | C | H | SCH₂CH₃ | H | H | 20A-D; 3A-B, 16C |
| A-1111 | CF₂CH₃ | C | H | SCH₂CH₃ | H | H | 20A-D; 3A-B, 16C |
| A-1112 | CF₂H | C | H | SCH₂CH₃ | H | H | 1C; 3A-B, 16C |
| A-1113 | cyclopropyl | C | H | SCH₂CH₃ | H | H | 1C; 3A-B, 16C |
| A-1114 | 2-methylcyclopropyl | C | H | SCH₂CH₃ | H | H | 1C; 3A-B, 16C |
| A-1115 | CF₂Cl | C | H | SCH₂CH₃ | H | H | 12F-G; 9A, C, D; 16C |
| A-1116 | N(CH₃)₂ | C | H | SCH₂CH₃ | H | H | 3A-B, 16C |
| A-1117 | CH₂N(CH₃)₂ | C | H | SCH₂CH₃ | H | H | 3A-B, 16C |
| A-1118 | CH₂NHCH₃ | C | H | SCH₂CH₃ | H | H | 3A-B, 16C |
| A-1119 | CF₂Cl | C | H | SCH₂CH₃ | H | H | 20A-D; 3A-B, 16C |
| A-1120 | CH₂CH₃ | C | H | SCH₃ | CH₃ | H | 1C; 3A-B, 16C |
| A-1121 | CH₂CH₂CH₃ | C | H | SCH₃ | CH₃ | H | 1C; 3A-B, 16C |
| A-1122 | CH(CH₃)₂ | C | H | SCH₃ | CH₃ | H | 1C; 3A-B, 16C |
| A-1123 | CH(CH₃)CH₂CH₃ | C | H | SCH₃ | CH₃ | H | 1C; 3A-B, 16C |

TABLE A-continued

| | | | | | |
|---|---|---|---|---|---|
| A-1124 | CF₃ | C | H | SCH₃ | CH₃ | 20A-D; 3A-B, 16C |
| A-1125 | CF₂CHF₂ | C | H | SCH₃ | CH₃ | 20A-D; 3A-B, 16C |
| A-1126 | CF₂CF₃ | C | H | SCH₃ | CH₃ | 20A-D; 3A-B, 16C |
| A-1127 | CF₂CH₃ | C | H | SCH₃ | CH₃ | 20A-D; 3A-B, 16C |
| A-1128 | CF₂H | C | H | SCH₃ | CH₃ | 20A-D; 3A-B, 16C |
| A-1129 | cyclopropyl | C | H | SCH₃ | CH₃ | 1C; 3A-B, 16C |
| A-1130 | 2-methylcyclopropyl | C | H | SCH₃ | CH₃ | 1C; 3A-B, 16C |
| A-1131 | CFHCH₃ | C | H | SCH₃ | CH₃ | 12F-G; 9A, C, D; 16C |
| A-1132 | N(CH₃)₂ | C | H | SCH₃ | CH₃ | 3A-B, 16C |
| A-1133 | CH₂N(CH₃)₂ | C | H | SCH₃ | CH₃ | 3A-B, 16C |
| A-1134 | CH₂NHCH₃ | C | H | SCH₃ | CH₃ | 3A-B, 16C |
| A-1135 | CF₂Cl | C | H | SCH₃ | CH₃ | 20A-D; 3A-B, 16C |
| A-1136 | SF₅ | C | H | OCH₂CH₂CH₃ | H | 12F-G; 20A-D; 16C |
| A-1137 | SF₅ | C | H | OCH₂CH₂CH₃ | H | 12F-G; 20A-D; 16C |
| A-1138 | SF₅ | C | H | OCH₃ | CH₂CH₃ | 12F-G; 20A-D; 16C |
| A-1139 | SF₅ | C | H | OCH₂CH₃ | CH₂CH₃ | 12F-G; 20A-D; 16C |
| A-1140 | SF₅ | C | H | OCH₃ | CH(CH₃)₂ | 12F-G; 20A-D; 16C |
| A-1141 | SF₅ | C | H | OCH₂CH₃ | CH(CH₃)₂ | 12F-G; 20A-D; 16C |
| A-1142 | SF₅ | C | H | CH₂CH₃ | H | 13B; 20A-D; 16C |
| A-1143 | SF₅ | C | H | CH₂CH₂CH₃ | H | 13B; 20A-D; 16C |
| A-1144 | SF₅ | C | H | COCH₂CH₃ | CH₃ | 12G; 20A-D; 16C |
| A-1145 | SF₅ | C | CH₃ | OCH₃ | CH₃ | 12G; 20A-D; 16C |
| A-1146 | SF₅ | C | H | OCH₃ | H | 12F-G; 20A-D; 16C |
| A-1147 | SF₅ | C | H | SCH₃ | CH₃ | 12F-G; 20A-D; 16C |
| A-1148 | SF₅ | C | H | NHCOCH₃ | CH₃ | 20A-D; 3A-B, 16C |
| A-1149 | SF₅ | C | CH₃ | OCH₂CH₃ | H | 12F-G; 20A-D; 16C |
| A-1150 | SF₅ | C | H | OCH₂CH₃ | CH₃ | 12F-G; 20A-D; 16C |
| A-1151 | SF₅ | C | H | OCH₃ | CH₃ | 12F-G; 20A-D; 16C |
| A-1152 | SF₅ | C | CH₃ | OCH₃ | CH₃ | 12F-G; 20A-D; 16C |
| A-1153 | SF₅ | C | CH₃ | OCH₂-cyclopropyl | H | 12F-G; 20A-D; 16C |
| A-1154 | SF₅ | C | H | SCH₂CH₃ | CH₃ | 20A-D; 3A-B, 16C |
| A-1155 | CH₃ | C | H | SCH₃ | CH₃ | 20A-D; 3A-B, 16C |
| A-1156 | CH₃ | C | CH₃ | OCH₃ | CH₃ | 12G; 1C; 16C |
| A-1157 | CH₃ | C | CH₃ | CH₃ | H | 16B; 1C; 16C |
| A-1158 | CH₂CHF₂ | C | CH₃ | CH₃ | H | 16B; 1C; 16C |
| A-1159 | CH₂CHF₂ | C | H | CH₃ | H | 16B; 1C; 16C |
| A-1160 | CH₂CH₂CH₃ | C | H | CH₃ | H | 16B; 12A-E; 16C |
| A-1161 | CF₃ | C | H | CF₃ | H | 12G; 1C; 16C |
| A-1162 | CF₃ | C | H | COCH₃ | H | 12G; 12A-E; 16C |

Further examples of specific compounds of the present invention include each of the compounds of table A above wherein X=SO₂ instead of CO and each of the compounds of table A wherein X=CS instead of CO if not already contained in table A.

Further examples of specific compounds of the present invention include each compound in table A above and each analogue wherein X=SO₂ or wherein X=CS in form of its pyridine N-oxide, such as the pyridine N-oxides shown in the table below:

| No | Structure | HPLC | Rt | m/z | MW |
|---|---|---|---|---|---|
| Aa-1 | 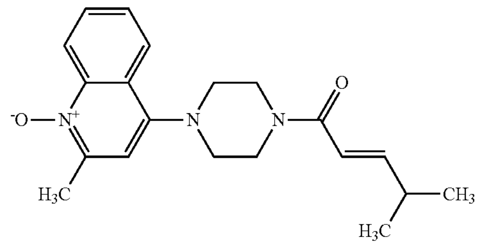 | 5 | 3.110 | 339.8 | 339.4 |
| Aa-2 | 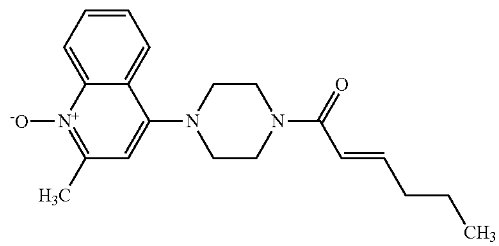 | 5 | 3.133 | 339.9 | 339.4 |
| Aa-3 | 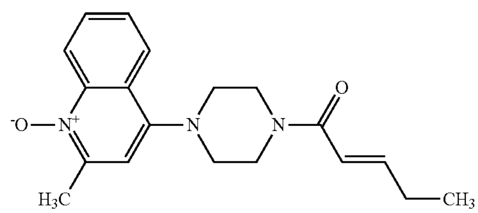 | 5 | 2.874 | 325.8 | 325.4 |

Table B below provides for each of the synthesized compounds of the formula (B) the structure, the calculated molecular weight (MW) (gram/mol), the observed MS signal (m/z), the HPLC retention time (Rt) in minutes, and the number of the HPLC-method as described in paragraph C above ("Analytics: HPLC-Methods") used for analysis. In Table B—in case of a ring formation between $Y^3$ and $Y^4$ by the substituents $R^{14}$ and $R^{15}$—in the columns for $R^{14}$ and $R^{15}$ the symbols Y3 and Y4 indicate the ring atoms $Y^3$ and $Y^4$ in formula (B) to which the respective substituents are bound.

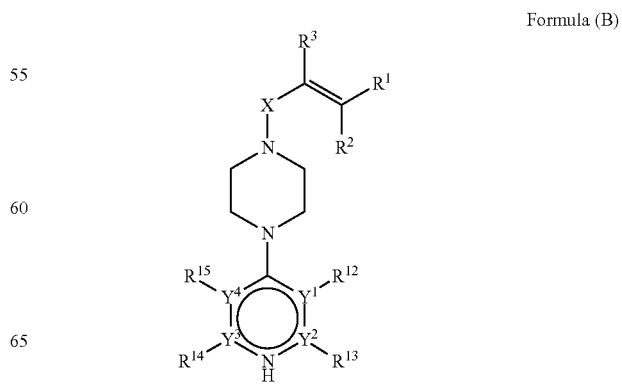

Formula (B)

TABLE B

| No | $R^1$ | $R^2$ | $R^3$ | X | $Y^1$ | $Y^2$ | $Y^3$ | $Y^4$ | $R^{12}$ | $R^{13}$ | $R^{14}$ | $R^{15}$ | HPLC | Rt | m/z | MW |
|---|---|---|---|---|---|---|---|---|---|---|---|---|---|---|---|---|
| B-1 | $CH_3$ | $NH_2$ | H | CO | C | C | C | C | H | $CH_3$ | Y3—CH=CH—CH=CH—Y4 | | 8 | 1.24 | 312.1 | 310.4 |
| B-2 | H | $CF_2CF_3$ | H | CO | C | C | C | C | H | $CH_3$ | Y3—CH=CH—CH=CH—Y4 | | 8 | 1.79 | 400.1 | 399.4 |
| B-3 | H | $CF_2CF_3$ | H | CO | C | C | C | C | H | H | Y3—CH=CH—CH=CH—Y4 | | 8 | 1.73 | 386.1 | 385.3 |
| B-4 | H | $CF_2CHF_2$ | H | CO | C | C | C | C | H | $CH_3$ | Y3—CH=CH—CH=CH—Y4 | | 8 | 1.44 | 382.1 | 381.4 |
| B-5 | H | $CF_2Cl$ | H | CO | C | C | C | C | H | H | Y3—CH=CH—CH=CH—Y4 | | 8 | 1.40 | 352.1 | 351.8 |
| B-6 | $CH_3$ | $CH_3$ | H | CO | C | C | C | C | H | H | Y3—CH=CCl—CH=CH—Y4 | | 2 | 2.56 | 329.9 | 329.8 |
| B-7 | H | Cl | H | CO | C | C | C | C | H | H | Y3—CH=CH—CH=CH—Y4 | | 8 | 1.27 | 302.0 | 301.8 |
| B-8 | H | Cl | H | CO | C | C | C | C | H | $CH_3$ | Y3—CH=CH—CH=CH—Y4 | | 5 | 3.17 | 315.8 | 315.8 |
| B-9 | $CH_3$ | H | $CH_3$ | CO | C | C | C | C | H | H | Y3—CH=CCl—CH=CH—Y4 | | 2 | 2.37 | 330.0 | 329.8 |
| B-10 | $CH_3$ | H | $CH_3$ | CO | C | C | C | C | H | $CH_3$ | Y3—CH=CH—CH=CH—Y4 | | 2 | 2.27 | 310.0 | 309.4 |
| B-11 | $CH(CH_3)_2$ | H | $CH_3$ | CO | C | C | C | C | H | H | Y3—CH=CH—CH=CH—Y4 | | 3 | 4.39 | 324.2 | 323.4 |
| B-12 | $CH(CH_3)_2$ | H | $CH_3$ | CO | C | C | C | C | H | $CH_3$ | Y3—CH=CH—CH=CH—Y4 | | 3 | 4.51 | 338.2 | 337.5 |
| B-13 | Phenyl | H | $CH_3$ | CO | C | C | C | C | H | H | Y3—CH=CCl—CH=CH—Y4 | | 2 | 3.04 | 391.9 | 391.9 |
| B-14 | H | $CH_2Cl$ | H | CO | C | C | C | C | H | H | Y3—CH=CH—CH=CH—Y4 | | 5 | 3.37 | 315.7 | 315.8 |
| B-15 | $CF_3$ | $CH_3$ | H | CO | C | C | C | C | H | $OCH_3$ | H | H | 4 | 3.63 | 330.2 | 329.3 |
| B-16 | $CF_3$ | H | $CH_3$ | CO | C | C | C | C | H | $CH_3$ | $CH_3$ | H | 4 | 3.43 | 328.2 | 327.3 |
| B-17 | $CF_3$ | H | $CH_3$ | CO | C | C | C | C | H | $OCH_3$ | H | H | 4 | 3.62 | 330.2 | 329.3 |
| B-18 | H | Cl | H | CO | C | C | C | C | H | $OCH_2CH_3$ | H | H | 5 | 3.14 | 296.2 | 295.7 |
| B-19 | H | $N(CH_3)_2$ | H | CO | C | C | C | C | H | $OCH_2CH_3$ | H | H | 5 | 3.07 | 305.2 | 304.4 |

Table C below provides for each of the synthesized compounds of the formula (C) the structure, the calculated molecular weight (MW) (gram/mol), the observed MS signal (m/z), the HPLC retention time (Rt) in minutes, and the number of the HPLC-method as described in paragraph C above ("Analytics: HPLC-Methods") used for analysis. From compound C-98 until to the end of the table the methods by which the compounds are synthesized are identified by referring to the synthesis steps described in the synthesis examples of paragraph B above ("Synthesis Examples").

In Table C—in case of a ring formation between $Y^3$ and $Y^4$ by the substituents $R^{14}$ and $R^{15}$—in the columns for $R^{14}$ and $R^{15}$ the symbols Y3 and Y4 indicate the ring atoms $Y^3$ and $Y^4$ in formula (C) to which the respective substituents are bound. If a compound contains a chiral center, the absolute configuration of the synthesized compound is indicated in the column R/S.

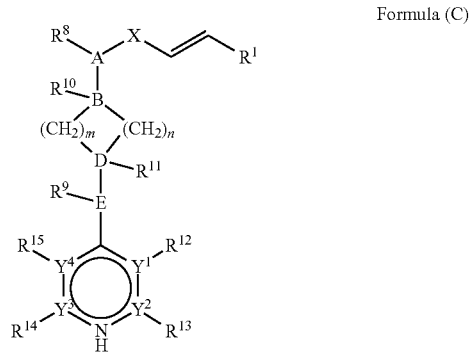

Formula (C)

TABLE C (X = CO)

| No | $R^1$ | A | $R^8$ | B | $R^{10}$ | D | $R^{11}$ | E | $R^9$ | m | n | R/S | $Y^1$ | $Y^2$ | $Y^3$ | $Y^4$ | $R^{12}$ |
|---|---|---|---|---|---|---|---|---|---|---|---|---|---|---|---|---|---|
| C-1 | $CH(CH_3)_2$ | — | — | N | — | N | — | — | — | 3 | 2 | — | C | C | C | C | H |
| C-2 | $CH(CH_3)_2$ | — | — | N | — | N | — | — | — | 3 | 2 | — | C | C | C | C | H |
| C-3 | $CH(CH_3)_2$ | N | H | C | H | N | — | — | — | 3 | 1 | S | C | C | C | C | H |
| C-4 | $CH_2CH_2CH_3$ | — | — | N | — | N | — | — | — | 3 | 2 | — | C | C | C | C | H |
| C-5 | $CH_2CH_2CH_3$ | — | — | N | — | N | — | — | — | 3 | 2 | — | C | C | C | C | H |
| C-6 | $CH_2CH_2CH_3$ | N | H | C | H | N | — | — | — | 3 | 1 | R | C | C | C | C | H |
| C-7 | $CH_2CH_2CH_3$ | N | H | C | H | N | — | — | — | 3 | 1 | S | C | C | C | C | H |
| C-8 | $CH_2CH_3$ | — | — | N | — | N | — | — | — | 3 | 2 | — | C | C | C | C | H |
| C-9 | $CH_2CH_3$ | N | H | C | H | N | — | — | — | 3 | 1 | R | C | C | C | C | H |
| C-10 | $CH_2CH_3$ | — | — | N | — | N | — | — | — | 3 | 2 | — | C | C | C | C | H |
| C-11 | $CH_2CH_3$ | N | H | C | H | N | — | — | — | 3 | 1 | R | C | C | C | C | H |
| C-12 | $CH_2CH_3$ | N | H | C | H | N | — | — | — | 3 | 1 | S | C | C | C | C | H |
| C-13 | $CH(CH_3)_2$ | N | H | C | H | N | — | — | — | 3 | 1 | R | C | C | C | C | H |
| C-14 | $CH(CH_3)_2$ | N | H | C | H | N | — | — | — | 3 | 1 | S | C | C | C | C | H |
| C-15 | $CH(CH_3)_2$ | N | H | C | H | N | — | — | — | 2 | 2 | — | C | C | C | C | H |
| C-16 | $CH(CH_3)_2$ | N | H | C | H | N | — | — | — | 3 | 1 | R | C | C | C | C | H |
| C-17 | $CH(CH_3)_2$ | N | H | C | H | N | — | — | — | 2 | 2 | — | C | C | C | C | H |
| C-18 | $CH_2CH_2CH_3$ | N | H | C | H | N | — | — | — | 3 | 1 | R | C | C | C | C | H |
| C-19 | $CH_2CH_2CH_3$ | N | H | C | H | N | — | — | — | 3 | 1 | S | C | C | C | C | H |
| C-20 | $CH_2CH_2CH_3$ | N | H | C | H | N | — | — | — | 2 | 2 | — | C | C | C | C | H |
| C-21 | $CH_2CH_2CH_3$ | N | H | C | H | N | — | — | — | 2 | 2 | — | C | C | C | C | H |
| C-22 | $CH_2CH_3$ | N | H | C | H | N | — | — | — | 3 | 1 | S | C | C | C | C | H |
| C-23 | $CH_2CH_3$ | N | H | C | H | N | — | — | — | 2 | 2 | — | C | C | C | C | H |
| C-24 | $CH_2CH_3$ | N | H | C | H | N | — | — | — | 2 | 2 | — | C | C | C | C | H |
| C-25 | $CH_2CH_2CH_3$ | N | H | C | H | N | — | — | — | 1 | 2 | R | C | C | C | C | H |
| C-26 | $CH_2CH_2CH_3$ | N | H | C | H | N | — | — | — | 1 | 2 | R | C | C | C | C | H |
| C-27 | $CH_2CH_2CH_3$ | N | H | C | H | N | — | — | — | 1 | 1 | — | C | C | C | C | H |
| C-28 | $CH_2CH_2CH_3$ | N | H | C | H | N | — | — | — | 1 | 1 | — | C | C | C | C | H |

TABLE C-continued

| No | | | | | | | | | | | | | | | | | |
|---|---|---|---|---|---|---|---|---|---|---|---|---|---|---|---|---|---|
| C-29 | CH(CH₃)₂ | N | H | C | H | N | — | — | — | 1 | 1 | — | C | C | C | C | H |
| C-30 | CH(CH₃)₂ | N | H | C | H | N | — | — | — | 1 | 1 | — | C | C | C | C | H |
| C-31 | CH₂CH₃ | N | H | C | H | N | — | — | — | 1 | 1 | — | C | C | C | C | H |
| C-32 | CH(CH₃)₂ | — | — | N | — | C | H | — | — | 2 | 2 | — | C | C | C | C | H |
| C-33 | CH₂CH₂CH₃ | — | — | N | — | C | H | — | — | 2 | 2 | — | C | C | C | C | H |
| C-34 | CH₂CH₃ | — | — | N | — | C | H | — | — | 2 | 2 | — | C | C | C | C | H |
| C-35 | CH(CH₃)₂ | — | — | N | — | C | H | — | — | 2 | 2 | — | N | C | C | C | — |
| C-36 | CH₂CH₂CH₃ | — | — | N | — | C | H | — | — | 2 | 2 | — | N | C | C | C | — |
| C-37 | CH₂CH₂CH₃ | — | — | N | — | C | H | — | — | 2 | 2 | — | N | C | C | C | — |
| C-38 | CH₂CH₃ | — | — | N | — | C | H | — | — | 2 | 2 | — | N | C | C | C | — |
| C-39 | CH₂CH₃ | — | — | N | — | C | H | — | — | 2 | 2 | — | N | C | C | C | — |
| C-40 | CH(CH₃)₂ | — | — | N | — | C | H | — | — | 2 | 2 | — | C | C | C | C | H |
| C-41 | CH₂CH₂CH₃ | — | — | N | — | C | H | — | — | 2 | 2 | — | C | C | C | C | H |
| C-42 | CH₂CH₃ | — | — | N | — | C | H | — | — | 2 | 2 | — | C | C | C | C | H |
| C-43 | CH₂CH₃ | — | — | C | H | N | — | — | — | 2 | 2 | — | C | C | C | C | H |
| C-44 | CH₂CH₂CH₃ | — | — | C | H | N | — | — | — | 2 | 2 | — | C | C | C | C | H |
| C-45 | CH(CH₃)₂ | — | — | C | H | N | — | — | — | 2 | 2 | — | C | C | C | C | H |
| C-46 | CH(CH₃)₂ | — | — | N | — | N | — | — | — | 3 | 2 | — | C | C | C | C | H |
| C-47 | CH₂CH₃ | — | — | N | — | N | — | — | — | 3 | 2 | — | C | C | C | C | H |
| C-48 | CH₂CH₂CH₃ | — | — | N | — | N | — | — | — | 3 | 2 | — | C | C | C | C | H |
| C-49 | CF₃ | — | — | N | — | N | — | — | — | 3 | 2 | — | C | C | C | C | H |
| C-50 | CH(CH₃)₂ | — | — | N | — | C | H | N | CH₃ | 2 | 2 | — | C | C | C | C | H |
| C-51 | CH(CH₃)₂ | — | — | N | — | C | H | N | CH₃ | 2 | 2 | — | C | C | C | C | H |
| C-52 | CH₂CH₂CH₃ | — | — | N | — | C | H | N | CH₃ | 2 | 2 | — | C | C | C | C | H |
| C-53 | CH₂CH₂CH₃ | — | — | N | — | C | H | N | CH₃ | 2 | 2 | — | C | C | C | C | H |
| C-54 | CH₂CH₃ | — | — | N | — | C | H | N | CH₃ | 2 | 2 | — | C | C | C | C | H |
| C-55 | CH₂CH₃ | — | — | N | — | C | H | N | CH₃ | 2 | 2 | — | C | C | C | C | H |
| C-56 | CH(CH₃)₂ | — | — | N | — | C | H | N | H | 2 | 2 | — | N | C | C | C | — |
| C-57 | CH₂CH₂CH₃ | — | — | N | — | C | H | N | H | 2 | 2 | — | N | C | C | C | — |
| C-58 | CH₂CH₃ | — | — | N | — | C | H | N | H | 2 | 2 | — | N | C | C | C | — |
| C-59 | CH(CH₃)₂ | — | — | N | — | C | H | N | H | 2 | 2 | — | C | C | C | C | H |
| C-60 | CH(CH₃)₂ | — | — | N | — | C | H | N | H | 1 | 2 | S | C | C | C | C | H |
| C-61 | CH(CH₃)₂ | — | — | N | — | C | H | N | H | 1 | 2 | R | C | C | C | C | H |
| C-62 | CH(CH₃)₂ | — | — | N | — | C | H | N | H | 1 | 3 | R | C | C | C | C | H |
| C-63 | CH(CH₃)₂ | — | — | N | — | C | H | N | H | 1 | 3 | R | C | C | C | C | H |
| C-64 | CH(CH₃)₂ | — | — | N | — | C | H | N | H | 1 | 3 | S | C | C | C | C | H |
| C-65 | CH₂CH₂CH₃ | — | — | N | — | C | H | N | H | 1 | 2 | S | C | C | C | C | H |
| C-66 | CH₂CH₂CH₃ | — | — | N | — | C | H | N | H | 1 | 3 | R | C | C | C | C | H |
| C-67 | CH₂CH₂CH₃ | — | — | N | — | C | H | N | H | 2 | 2 | — | C | C | C | C | H |
| C-68 | CH₂CH₂CH₃ | — | — | N | — | C | H | N | H | 1 | 3 | R | C | C | C | C | H |
| C-69 | CH₂CH₂CH₃ | — | — | N | — | C | H | N | H | 1 | 3 | S | C | C | C | C | H |
| C-70 | CH₂CH₃ | — | — | N | — | C | H | N | H | 1 | 2 | S | C | C | C | C | H |
| C-71 | CH₂CH₃ | — | — | N | — | C | H | N | H | 1 | 3 | S | C | C | C | C | H |
| C-72 | CH₂CH₃ | — | — | N | — | C | H | N | H | 2 | 2 | — | C | C | C | C | H |
| C-73 | CH(CH₃)₂ | — | — | N | — | C | H | N | H | 1 | 2 | R | C | C | C | C | H |
| C-74 | CH(CH₃)₂ | — | — | N | — | C | H | N | H | 1 | 3 | S | C | C | C | C | H |
| C-75 | CH(CH₃)₂ | — | — | N | — | C | H | N | H | 2 | 2 | — | C | C | C | C | H |
| C-76 | CH(CH₃)₂ | — | — | N | — | C | H | N | H | 1 | 2 | S | C | C | C | C | H |
| C-77 | CH₂CH₂CH₃ | — | — | N | — | C | H | N | H | 1 | 2 | R | C | C | C | C | H |
| C-78 | CH₂CH₂CH₃ | — | — | N | — | C | H | N | H | 1 | 3 | S | C | C | C | C | H |
| C-79 | CH₂CH₂CH₃ | — | — | N | — | C | H | N | H | 2 | 2 | — | C | C | C | C | H |
| C-80 | CH₂CH₂CH₃ | — | — | N | — | C | H | N | H | 1 | 2 | S | C | C | C | C | H |
| C-81 | CH₂CH₂CH₃ | — | — | N | — | C | H | N | H | 1 | 2 | R | C | C | C | C | H |
| C-82 | CH₂CH₃ | — | — | N | — | C | H | N | H | 1 | 2 | R | C | C | C | C | H |
| C-83 | CH₂CH₃ | — | — | N | — | C | H | N | H | 1 | 3 | R | C | C | C | C | H |
| C-84 | CH₂CH₃ | — | — | N | — | C | H | N | H | 1 | 3 | S | C | C | C | C | H |
| C-85 | CH₂CH₃ | — | — | N | — | C | H | N | H | 2 | 2 | — | C | C | C | C | H |
| C-86 | CH₂CH₃ | — | — | N | — | C | H | N | H | 1 | 2 | S | C | C | C | C | H |
| C-87 | CH₂CH₃ | — | — | N | — | C | H | N | H | 1 | 2 | R | C | C | C | C | H |
| C-88 | CH₂CH₃ | — | — | N | — | C | H | N | H | 1 | 3 | R | C | C | C | C | H |
| C-89 | CH₂CH₃ | — | — | N | — | N | — | N | H | 2 | 2 | — | C | C | C | C | H |
| C-90 | CH₂CH₂CH₃ | — | — | N | — | C | H | N | H | 1 | 1 | — | C | C | C | C | H |
| C-91 | CH₂CH₂CH₃ | — | — | N | — | C | H | N | H | 1 | 1 | — | C | C | C | C | H |
| C-92 | CH(CH₃)₂ | — | — | N | — | C | H | N | H | 1 | 1 | — | C | C | C | C | H |
| C-93 | CH(CH₃)₂ | — | — | N | — | C | H | N | H | 1 | 1 | — | C | C | C | C | H |
| C-94 | CH(CH₃)₂ | — | — | N | — | N | — | N | H | 2 | 2 | — | C | C | C | C | H |
| C-95 | CH₂CH₂CH₃ | — | — | N | — | N | — | N | H | 2 | 2 | — | C | C | C | C | H |
| C-96 | CH₂CH₃ | — | — | N | — | C | H | N | H | 1 | 1 | — | C | C | C | C | H |
| C-97 | CH₂CH₃ | — | — | N | — | C | H | N | H | 1 | 1 | — | C | C | C | C | H |

(X = CO)

| No | R¹³ | R¹⁴ | R¹⁵ | HPLC | Rt | m/z | MW |
|---|---|---|---|---|---|---|---|
| C-1 | H | Y3—CH=CH—CH=CH—Y4 | | 10 | 3.32 | 324.0 | 323.4 |
| C-2 | CH₃ | Y3—CH=CH—CH=CH—Y4 | | 3 | 4.28 | 338.0 | 337.5 |
| C-3 | CH₃ | Y3—CH=CH—CH=CH—Y4 | | 3 | 4.32 | 338.0 | 337.5 |
| C-4 | H | Y3—CH=CH—CH=CH—Y4 | | 3 | 4.17 | 324.0 | 323.4 |
| C-5 | CH₃ | Y3—CH=CH—CH=CH—Y4 | | 3 | 4.31 | 338.0 | 337.5 |
| C-6 | CH₃ | Y3—CH=CH—CH=CH—Y4 | | 3 | 4.34 | 338.0 | 337.5 |

TABLE C-continued

| | | | | | | |
|---|---|---|---|---|---|---|
| C-7 | CH₃ | Y3—CH=CH—CH=CH—Y4 | 3 | 4.34 | 338.0 | 337.5 |
| C-8 | H | Y3—CH=CH—CH=CH—Y4 | 3 | 3.88 | 310.0 | 309.4 |
| C-9 | H | Y3—CH=CH—CH=CH—Y4 | 3 | 3.94 | 310.0 | 309.4 |
| C-10 | CH₃ | Y3—CH=CH—CH=CH—Y4 | 3 | 4.01 | 324.0 | 323.4 |
| C-11 | CH₃ | Y3—CH=CH—CH=CH—Y4 | 3 | 4.06 | 324.0 | 323.4 |
| C-12 | CH₃ | Y3—CH=CH—CH=CH—Y4 | 3 | 4.06 | 324.0 | 323.4 |
| C-13 | H | Y3—CH=CH—CH=CH—Y4 | 4 | 3.76 | 323.8 | 323.4 |
| C-14 | H | Y3—CH=CH—CH=CH—Y4 | 4 | 3.76 | 323.8 | 323.4 |
| C-15 | H | Y3—CH=CH—CH=CH—Y4 | 4 | 3.69 | 323.8 | 323.4 |
| C-16 | CH₃ | Y3—CH=CH—CH=CH—Y4 | 4 | 3.86 | 337.8 | 337.5 |
| C-17 | CH₃ | Y3—CH=CH—CH=CH—Y4 | 4 | 3.78 | 337.8 | 337.5 |
| C-18 | H | Y3—CH=CH—CH=CH—Y4 | 4 | 3.78 | 323.8 | 323.4 |
| C-19 | H | Y3—CH=CH—CH=CH—Y4 | 4 | 3.78 | 323.8 | 323.4 |
| C-20 | H | Y3—CH=CH—CH=CH—Y4 | 4 | 3.71 | 323.8 | 323.4 |
| C-21 | CH₃ | Y3—CH=CH—CH=CH—Y4 | 4 | 3.80 | 337.8 | 337.5 |
| C-22 | H | Y3—CH=CH—CH=CH—Y4 | 4 | 3.55 | 309.8 | 309.4 |
| C-23 | H | Y3—CH=CH—CH=CH—Y4 | 4 | 3.55 | 309.8 | 309.4 |
| C-24 | CH₃ | Y3—CH=CH—CH=CH—Y4 | 4 | 3.57 | 323.8 | 323.4 |
| C-25 | H | Y3—CH=CH—CH=CH—Y4 | 4 | 3.60 | 309.9 | 309.4 |
| C-26 | CH₃ | Y3—CH=CH—CH=CH—Y4 | 4 | 3.79 | 323.8 | 323.4 |
| C-27 | CH₃ | Y3—CH=CH—CH=CH—Y4 | 4 | 3.72 | 309.7 | 309.4 |
| C-28 | H | Y3—CH=CH—CH=CH—Y4 | 4 | 3.54 | 295.7 | 295.4 |
| C-29 | CH₃ | Y3—CH=CH—CH=CH—Y4 | 4 | 3.69 | 309.7 | 309.4 |
| C-30 | H | Y3—CH=CH—CH=CH—Y4 | 4 | 3.52 | 295.7 | 295.4 |
| C-31 | CH₃ | Y3—CH=CH—CH=CH—Y4 | 5 | 3.29 | 295.9 | 295.4 |
| C-32 | H | H  H | 5 | 3.28 | 258.9 | 258.4 |
| C-33 | H | H  H | 5 | 3.31 | 258.9 | 258.4 |
| C-34 | H | H  H | 5 | 3.02 | 244.9 | 244.3 |
| C-35 | H | Y3—CH=CH—CH=CH—Y4 | 5 | 3.78 | 323.9 | 323.4 |
| C-36 | H | Y3—CH=CH—CH=CH—Y4 | 5 | 3.58 | 309.9 | 309.4 |
| C-37 | H | Y3—CH=CH—CH=CH—Y4 | 5 | 3.81 | 323.9 | 323.4 |
| C-38 | H | Y3—CH=CH—CH=CH—Y4 | 5 | 3.30 | 295.6 | 295.4 |
| C-39 | H | Y3—CH=CH—CH=CH—Y4 | 5 | 3.52 | 309.9 | 309.4 |
| C-40 | H | Y3—CH=CH—CH=CH—Y4 | 5 | 3.72 | 308.9 | 308.4 |
| C-41 | H | Y3—CH=CH—CH=CH—Y4 | 5 | 3.73 | 308.9 | 308.4 |
| C-42 | H | Y3—CH=CH—CH=CH—Y4 | 5 | 3.48 | 294.9 | 294.4 |
| C-43 | CH₃ | Y3—CH=CH—CH=CH—Y4 | 9 | 1.25 | 309.2 | 308.4 |
| C-44 | CH₃ | Y3—CH=CH—CH=CH—Y4 | 9 | 1.38 | 323.2 | 322.4 |
| C-45 | CH₃ | Y3—CH=CH—CH=CH—Y4 | 9 | 1.36 | 323.2 | 322.4 |
| C-46 | CH₃ | H  H | 5 | 3.52 | 288.0 | 287.4 |
| C-47 | CH₃ | H  H | 5 | 3.17 | 274.0 | 273.4 |
| C-48 | CH₃ | H  H | 5 | 3.45 | 288.0 | 287.4 |
| C-49 | CH₃ | H  H | 5 | 3.29 | 313.9 | 313.3 |
| C-50 | H | Y3—CH=CH—CH=CH—Y4 | 4 | 3.89 | 338.0 | 337.5 |
| C-51 | CH₃ | Y3—CH=CH—CH=CH—Y4 | 4 | 3.98 | 352.0 | 351.5 |
| C-52 | H | Y3—CH=CH—CH=CH—Y4 | 4 | 3.92 | 338.0 | 337.5 |
| C-53 | CH₃ | Y3—CH=CH—CH=CH—Y4 | 4 | 4.02 | 352.0 | 351.5 |
| C-54 | H | Y3—CH=CH—CH=CH—Y4 | 4 | 3.67 | 324.0 | 323.4 |
| C-55 | CH₃ | Y3—CH=CH—CH=CH—Y4 | 4 | 3.77 | 338.0 | 337.5 |
| C-56 | H | Y3—S—C(CH₃)=C(CH₃)—Y4 | 3 | 3.87 | 330.9 | 330.5 |
| C-57 | H | Y3—S—C(CH₃)=C(CH₃)—Y4 | 3 | 3.90 | 330.9 | 330.5 |
| C-58 | H | Y3—S—C(CH₃)=C(CH₃)—Y4 | 3 | 3.58 | 316.9 | 316.4 |
| C-59 | H | Y3—CH=CH—CH=CH—Y4 | 3 | 4.00 | 323.9 | 323.4 |
| C-60 | CH₃ | Y3—CH=CH—CH=CH—Y4 | 4 | 3.58 | 323.8 | 323.4 |
| C-61 | H | Y3—CH=CH—CH=CH—Y4 | 4 | 3.46 | 309.9 | 309.4 |
| C-62 | CH₃ | Y3—CH=CH—CH=CH—Y4 | 4 | 3.72 | 337.9 | 337.5 |
| C-63 | H | Y3—CH=CH—CH=CH—Y4 | 4 | 3.60 | 324.0 | 323.4 |
| C-64 | H | Y3—CH=CH—CH=CH—Y4 | 4 | 3.77 | 323.9 | 323.4 |
| C-65 | CH₃ | Y3—CH=CH—CH=CH—Y4 | 4 | 3.59 | 323.9 | 323.4 |
| C-66 | CH₃ | Y3—CH=CH—CH=CH—Y4 | 4 | 3.77 | 337.9 | 337.5 |
| C-67 | H | Y3—CH=CH—CH=CH—Y4 | 4 | 3.63 | 323.9 | 323.4 |
| C-68 | H | Y3—CH=CH—CH=CH—Y4 | 4 | 3.63 | 323.9 | 323.4 |
| C-69 | H | Y3—CH=CH—CH=CH—Y4 | 4 | 3.78 | 323.9 | 323.4 |
| C-70 | CH₃ | Y3—CH=CH—CH=CH—Y4 | 4 | 3.35 | 309.9 | 309.4 |
| C-71 | H | Y3—CH=CH—CH=CH—Y4 | 4 | 3.55 | 309.9 | 309.4 |
| C-72 | H | Y3—CH=CH—CH=CH—Y4 | 4 | 3.39 | 309.9 | 309.4 |
| C-73 | CH₃ | Y3—CH=CH—CH=CH—Y4 | 4 | 3.59 | 324.0 | 323.4 |
| C-74 | CH₃ | Y3—CH=CH—CH=CH—Y4 | 4 | 3.74 | 337.9 | 337.5 |
| C-75 | CH₃ | Y3—CH=CH—CH=CH—Y4 | 4 | 3.78 | 338.0 | 337.5 |
| C-76 | H | Y3—CH=CH—CH=CH—Y4 | 4 | 3.46 | 309.9 | 309.4 |
| C-77 | CH₃ | Y3—CH=CH—CH=CH—Y4 | 4 | 3.61 | 323.9 | 323.4 |
| C-78 | CH₃ | Y3—CH=CH—CH=CH—Y4 | 4 | 3.80 | 337.9 | 337.5 |
| C-79 | CH₃ | Y3—CH=CH—CH=CH—Y4 | 4 | 3.82 | 337.9 | 337.5 |
| C-80 | H | Y3—CH=CH—CH=CH—Y4 | 4 | 3.49 | 309.9 | 309.4 |
| C-81 | H | Y3—CH=CH—CH=CH—Y4 | 4 | 3.49 | 309.9 | 309.4 |
| C-82 | CH₃ | Y3—CH=CH—CH=CH—Y4 | 4 | 3.37 | 309.9 | 309.4 |
| C-83 | CH₃ | Y3—CH=CH—CH=CH—Y4 | 4 | 3.55 | 323.9 | 323.4 |
| C-84 | CH₃ | Y3—CH=CH—CH=CH—Y4 | 4 | 3.54 | 323.9 | 323.4 |
| C-85 | CH₃ | Y3—CH=CH—CH=CH—Y4 | 4 | 3.55 | 323.9 | 323.4 |
| C-86 | H | Y3—CH=CH—CH=CH—Y4 | 4 | 3.25 | 295.6 | 295.4 |

TABLE C-continued

| | | | | | | | |
|---|---|---|---|---|---|---|---|
| C-87 | H | Y3—CH=CH—CH=CH—Y4 | 4 | 3.25 | 295.9 | 295.4 | |
| C-88 | H | Y3—CH=CH—CH=CH—Y4 | 4 | 3.41 | 309.9 | 309.4 | |
| C-89 | H | Y3—CH=CH—CH=CH—Y4 | 4 | 3.40 | 310.9 | 310.4 | |
| C-90 | H | Y3—CH=CH—CH=CH—Y4 | 4 | 3.41 | 295.9 | 295.4 | |
| C-91 | CH$_3$ | Y3—CH=CH—CH=CH—Y4 | 4 | 3.51 | 309.9 | 309.4 | |
| C-92 | H | Y3—CH=CH—CH=CH—Y4 | 4 | 3.38 | 295.8 | 295.4 | |
| C-93 | CH$_3$ | Y3—CH=CH—CH=CH—Y4 | 4 | 3.49 | 309.9 | 309.4 | |
| C-94 | H | Y3—CH=CH—CH=CH—Y4 | 4 | 3.62 | 324.9 | 324.4 | |
| C-95 | H | Y3—CH=CH—CH=CH—Y4 | 4 | 3.64 | 324.9 | 324.4 | |
| C-96 | H | Y3—CH=CH—CH=CH—Y4 | 4 | 3.17 | 281.7 | 281.4 | |
| C-97 | CH$_3$ | Y3—CH=CH—CH=CH—Y4 | 5 | 3.11 | 295.9 | 295.4 | |

(X = CO; Y$^1$, Y$^2$, Y$^3$, Y$^4$ = C)

| No | R$^1$ | A | R$^8$ | B | R$^{10}$ | D | R$^{11}$ | E | R$^9$ | m | n | R/S | R$^{12}$ | R$^{13}$ | R$^{14}$ | R$^{15}$ | Synth. Methods |
|---|---|---|---|---|---|---|---|---|---|---|---|---|---|---|---|---|---|
| C-98 | CF$_3$ | — | — | N | — | C | H | N | H | 1 | 2 | RS | H | OCH$_3$ | H | H | 20A-D; 6A-B; 20H |
| C-99 | CHF$_2$ | — | — | N | — | C | H | N | H | 1 | 2 | RS | H | OCH$_3$ | H | H | 20A-D; 6A-B; 20H |
| C-100 | CF$_2$CHF$_2$ | — | — | N | — | C | H | N | H | 1 | 2 | RS | H | OCH$_3$ | H | H | 20A-D; 6A-B; 20H |
| C-101 | CF$_2$CF$_3$ | — | — | N | — | C | H | N | H | 1 | 2 | RS | H | OCH$_3$ | H | H | 20A-D; 6A-B; 20H |
| C-102 | CF$_2$CH$_3$ | — | — | N | — | C | H | N | H | 1 | 2 | RS | H | OCH$_3$ | H | H | 20A-D; 6A-B; 20H |
| C-103 | cyclopropyl | — | — | N | — | C | H | N | H | 1 | 2 | RS | H | OCH$_3$ | H | H | 1C; 6A-B; 20H |
| C-104 | 2-methylcyclopropyl | — | — | N | — | C | H | N | H | 1 | 2 | RS | H | OCH$_3$ | H | H | 1C; 6A-B; 20H |
| C-105 | CH$_2$CH$_3$ | — | — | N | — | C | H | N | H | 1 | 2 | RS | H | OCH$_3$ | H | H | 1C; 6A-B; 20H |
| C-106 | (CH$_2$)$_2$CH$_3$ | — | — | N | — | C | H | N | H | 1 | 2 | RS | H | OCH$_3$ | H | H | 1C; 6A-B; 20H |
| C-107 | CH(CH$_3$)$_2$ | — | — | N | — | C | H | N | H | 1 | 2 | RS | H | OCH$_3$ | H | H | 1C; 6A-B; 20H |
| C-108 | CH(CH$_3$)CH$_2$CH$_3$ | — | — | N | — | C | H | N | H | 1 | 2 | RS | H | OCH$_3$ | H | H | 1C; 6A-B; 20H |
| C-109 | CF$_2$Cl | — | — | N | — | C | H | N | H | 1 | 2 | RS | H | OCH$_3$ | H | H | 20A-D; 6A-B; 20H |
| C-110 | SF$_5$ | — | — | N | — | C | H | N | H | 1 | 2 | RS | H | OCH$_3$ | H | H | 20A-D; 6A-B; 20H |
| C-111 | CF$_3$ | — | — | N | — | C | H | N | H | 1 | 2 | RS | H | OCH$_2$CH$_3$ | H | H | 20A-D; 6A-B; 20H |
| C-112 | CHF$_2$ | — | — | N | — | C | H | N | H | 1 | 2 | RS | H | OCH$_2$CH$_3$ | H | H | 20A-D; 6A-B; 20H |
| C-113 | CF$_2$CHF$_2$ | — | — | N | — | C | H | N | H | 1 | 2 | RS | H | OCH$_2$CH$_3$ | H | H | 20A-D; 6A-B; 20H |
| C-114 | CF$_2$CF$_3$ | — | — | N | — | C | H | N | H | 1 | 2 | RS | H | OCH$_2$CH$_3$ | H | H | 20A-D; 6A-B; 20H |
| C-115 | CF$_2$CH$_3$ | — | — | N | — | C | H | N | H | 1 | 2 | RS | H | OCH$_2$CH$_3$ | H | H | 20A-D; 6A-B; 20H |
| C-116 | cyclopropyl | — | — | N | — | C | H | N | H | 1 | 2 | RS | H | OCH$_2$CH$_3$ | H | H | 1C; 6A-B; 20H |
| C-117 | 2-methylcyclopropyl | — | — | N | — | C | H | N | H | 1 | 2 | RS | H | OCH$_2$CH$_3$ | H | H | 1C; 6A-B; 20H |
| C-118 | CH$_2$CH$_3$ | — | — | N | — | C | H | N | H | 1 | 2 | RS | H | OCH$_2$CH$_3$ | H | H | 1C; 6A-B; 20H |
| C-119 | (CH$_2$)$_2$CH$_3$ | — | — | N | — | C | H | N | H | 1 | 2 | RS | H | OCH$_2$CH$_3$ | H | H | 1C; 6A-B; 20H |
| C-120 | CH(CH$_3$)$_2$ | — | — | N | — | C | H | N | H | 1 | 2 | RS | H | OCH$_2$CH$_3$ | H | H | 1C; 6A-B; 20H |
| C-121 | CH(CH$_3$)CH$_2$CH$_3$ | — | — | N | — | C | H | N | H | 1 | 2 | RS | H | OCH$_2$CH$_3$ | H | H | 1C; 6A-B; 20H |
| C-122 | CF$_2$Cl | — | — | N | — | C | H | N | H | 1 | 2 | RS | H | OCH$_2$CH$_3$ | H | H | 20A-D; 6A-B; 20H |
| C-123 | SF$_5$ | — | — | N | — | C | H | N | H | 1 | 2 | RS | H | OCH$_2$CH$_3$ | H | H | 20A-D; 6A-B; 20H |
| C-124 | CF$_3$ | — | — | N | — | C | H | N | H | 1 | 2 | RS | H | OCH$_3$ | CH$_3$ | H | 20A-D; 6A-B; 20H |
| C-125 | CHF$_2$ | — | — | N | — | C | H | N | H | 1 | 2 | RS | H | OCH$_3$ | CH$_3$ | H | 20A-D; 6A-B; 20H |
| C-126 | CF$_2$CHF$_2$ | — | — | N | — | C | H | N | H | 1 | 2 | RS | H | OCH$_3$ | CH$_3$ | H | 20A-D; 6A-B; 20H |
| C-127 | CF$_2$CF$_3$ | — | — | N | — | C | H | N | H | 1 | 2 | RS | H | OCH$_3$ | CH$_3$ | H | 20A-D; 6A-B; 20H |
| C-128 | CF$_2$CH$_3$ | — | — | N | — | C | H | N | H | 1 | 2 | RS | H | OCH$_3$ | CH$_3$ | H | 20A-D; 6A-B; 20H |
| C-129 | cyclopropyl | — | — | N | — | C | H | N | H | 1 | 2 | RS | H | OCH$_3$ | CH$_3$ | H | 1C; 6A-B; 20H |
| C-130 | 2-methylcyclopropyl | — | — | N | — | C | H | N | H | 1 | 2 | RS | H | OCH$_3$ | CH$_3$ | H | 1C; 6A-B; 20H |
| C-131 | CH$_2$CH$_3$ | — | — | N | — | C | H | N | H | 1 | 2 | RS | H | OCH$_3$ | CH$_3$ | H | 1C; 6A-B; 20H |
| C-132 | (CH$_2$)$_2$CH$_3$ | — | — | N | — | C | H | N | H | 1 | 2 | RS | H | OCH$_3$ | CH$_3$ | H | 1C; 6A-B; 20H |
| C-133 | CH(CH$_3$)$_2$ | — | — | N | — | C | H | N | H | 1 | 2 | RS | H | OCH$_3$ | CH$_3$ | H | 1C; 6A-B; 20H |
| C-134 | CH(CH$_3$)CH$_2$CH$_3$ | — | — | N | — | C | H | N | H | 1 | 2 | RS | H | OCH$_3$ | CH$_3$ | H | 1C; 6A-B; 20H |
| C-135 | CF$_2$Cl | — | — | N | — | C | H | N | H | 1 | 2 | RS | H | OCH$_3$ | CH$_3$ | H | 20A-D; 6A-B; 20H |
| C-136 | SF$_5$ | — | — | N | — | C | H | N | H | 1 | 2 | RS | H | OCH$_3$ | CH$_3$ | H | 20A-D; 6A-B; 20H |
| C-137 | CF$_3$ | — | — | N | — | C | H | N | H | 1 | 1 | RS | H | OCH$_3$ | H | H | 20A-D; 6A-B; 20H |
| C-138 | CHF$_2$ | — | — | N | — | C | H | N | H | 1 | 1 | RS | H | OCH$_3$ | H | H | 20A-D; 6A-B; 20H |
| C-139 | CF$_2$CHF$_2$ | — | — | N | — | C | H | N | H | 1 | 1 | RS | H | OCH$_3$ | H | H | 20A-D; 6A-B; 20H |
| C-140 | CF$_2$CF$_3$ | — | — | N | — | C | H | N | H | 1 | 1 | RS | H | OCH$_3$ | H | H | 20A-D; 6A-B; 20H |
| C-141 | CF$_2$CH$_3$ | — | — | N | — | C | H | N | H | 1 | 1 | RS | H | OCH$_3$ | H | H | 20A-D; 6A-B; 20H |
| C-142 | cyclopropyl | — | — | N | — | C | H | N | H | 1 | 1 | RS | H | OCH$_3$ | H | H | 1C; 6A-B; 20H |
| C-143 | 2-methylcyclopropyl | — | — | N | — | C | H | N | H | 1 | 1 | RS | H | OCH$_3$ | H | H | 1C; 6A-B; 20H |
| C-144 | CH$_2$CH$_3$ | — | — | N | — | C | H | N | H | 1 | 1 | RS | H | OCH$_3$ | H | H | 1C; 6A-B; 20H |
| C-145 | (CH$_2$)$_2$CH$_3$ | — | — | N | — | C | H | N | H | 1 | 1 | RS | H | OCH$_3$ | H | H | 1C; 6A-B; 20H |
| C-146 | CH(CH$_3$)$_2$ | — | — | N | — | C | H | N | H | 1 | 1 | RS | H | OCH$_3$ | H | H | 1C; 6A-B; 20H |
| C-147 | CH(CH$_3$)CH$_2$CH$_3$ | — | — | N | — | C | H | N | H | 1 | 1 | RS | H | OCH$_3$ | H | H | 1C; 6A-B; 20H |
| C-148 | CF$_2$Cl | — | — | N | — | C | H | N | H | 1 | 1 | RS | H | OCH$_3$ | H | H | 20A-D; 6A-B; 20H |
| C-149 | SF$_5$ | — | — | N | — | C | H | N | H | 1 | 1 | RS | H | OCH$_3$ | H | H | 20A-D; 6A-B; 20H |
| C-150 | CF$_3$ | — | — | N | — | C | H | N | H | 1 | 1 | RS | H | OCH$_2$CH$_3$ | H | H | 20A-D; 6A-B; 20H |
| C-151 | CHF$_2$ | — | — | N | — | C | H | N | H | 1 | 1 | RS | H | OCH$_2$CH$_3$ | H | H | 20A-D; 6A-B; 20H |
| C-152 | CF$_2$CHF$_2$ | — | — | N | — | C | H | N | H | 1 | 1 | RS | H | OCH$_2$CH$_3$ | H | H | 20A-D; 6A-B; 20H |
| C-153 | CF$_2$CF$_3$ | — | — | N | — | C | H | N | H | 1 | 1 | RS | H | OCH$_2$CH$_3$ | H | H | 20A-D; 6A-B; 20H |
| C-154 | CF$_2$CH$_3$ | — | — | N | — | C | H | N | H | 1 | 1 | RS | H | OCH$_2$CH$_3$ | H | H | 20A-D; 6A-B; 20H |
| C-155 | cyclopropyl | — | — | N | — | C | H | N | H | 1 | 1 | RS | H | OCH$_2$CH$_3$ | H | H | 1C; 6A-B; 20H |
| C-156 | 2-methylcyclopropyl | — | — | N | — | C | H | N | H | 1 | 1 | RS | H | OCH$_2$CH$_3$ | H | H | 1C; 6A-B; 20H |
| C-157 | CH$_2$CH$_3$ | — | — | N | — | C | H | N | H | 1 | 1 | RS | H | OCH$_2$CH$_3$ | H | H | 1C; 6A-B; 20H |
| C-158 | (CH$_2$)$_2$CH$_3$ | — | — | N | — | C | H | N | H | 1 | 1 | RS | H | OCH$_2$CH$_3$ | H | H | 1C; 6A-B; 20H |
| C-159 | CH(CH$_3$)$_2$ | — | — | N | — | C | H | N | H | 1 | 1 | RS | H | OCH$_2$CH$_3$ | H | H | 1C; 6A-B; 20H |
| C-160 | CH(CH$_3$)CH$_2$CH$_3$ | — | — | N | — | C | H | N | H | 1 | 1 | RS | H | OCH$_2$CH$_3$ | H | H | 1C; 6A-B; 20H |
| C-161 | CF$_2$Cl | — | — | N | — | C | H | N | H | 1 | 1 | RS | H | OCH$_2$CH$_3$ | H | H | 20A-D; 6A-B; 20H |

TABLE C-continued

| | | | | | | | | | | | | | | | | | |
|---|---|---|---|---|---|---|---|---|---|---|---|---|---|---|---|---|---|
| C-162 | SF$_5$ | — | — | N | — | C | H | N | H | 1 | 1 | RS | H | OCH$_2$CH$_3$ | H | H | 20A-D; 6A-B; 20H |
| C-163 | CF$_3$ | — | — | N | — | C | H | N | H | 1 | 1 | RS | H | OCH$_3$ | CH$_3$ | H | 20A-D; 6A-B; 20H |
| C-164 | CHF$_2$ | — | — | N | — | C | H | N | H | 1 | 1 | RS | H | OCH$_3$ | CH$_3$ | H | 20A-D; 6A-B; 20H |
| C-165 | CF$_2$CHF$_2$ | — | — | N | — | C | H | N | H | 1 | 1 | RS | H | OCH$_3$ | CH$_3$ | H | 20A-D; 6A-B; 20H |
| C-166 | CF$_2$CF$_3$ | — | — | N | — | C | H | N | H | 1 | 1 | RS | H | OCH$_3$ | CH$_3$ | H | 20A-D; 6A-B; 20H |
| C-167 | CF$_2$CH$_3$ | — | — | N | — | C | H | N | H | 1 | 1 | RS | H | OCH$_3$ | CH$_3$ | H | 20A-D; 6A-B; 20H |
| C-168 | cyclopropyl | — | — | N | — | C | H | N | H | 1 | 1 | RS | H | OCH$_3$ | CH$_3$ | H | 1C; 6A-B; 20H |
| C-169 | 2-methylcyclopropyl | — | — | N | — | C | H | N | H | 1 | 1 | RS | H | OCH$_3$ | CH$_3$ | H | 1C; 6A-B; 20H |
| C-170 | CH$_2$CH$_3$ | — | — | N | — | C | H | N | H | 1 | 1 | RS | H | OCH$_3$ | CH$_3$ | H | 1C; 6A-B; 20H |
| C-171 | (CH$_2$)$_2$CH$_3$ | — | — | N | — | C | H | N | H | 1 | 1 | RS | H | OCH$_3$ | CH$_3$ | H | 1C; 6A-B; 20H |
| C-172 | CH(CH$_3$)$_2$ | — | — | N | — | C | H | N | H | 1 | 1 | RS | H | OCH$_3$ | CH$_3$ | H | 1C; 6A-B; 20H |
| C-173 | CH(CH$_3$)CH$_2$CH$_3$ | — | — | N | — | C | H | N | H | 1 | 1 | RS | H | OCH$_3$ | CH$_3$ | H | 1C; 6A-B; 20H |
| C-174 | CF$_2$Cl | — | — | N | — | C | H | N | H | 1 | 1 | RS | H | OCH$_3$ | CH$_3$ | H | 20A-D; 6A-B; 20H |
| C-175 | SF$_5$ | — | — | N | — | C | H | N | H | 1 | 1 | RS | H | OCH$_3$ | CH$_3$ | H | 20A-D; 6A-B; 20H |
| C-176 | CF$_3$ | — | — | N | — | C | H | N | H | 1 | 3 | RS | H | OCH$_3$ | H | H | 20A-D; 6A-B; 20H |
| C-177 | CHF$_2$ | — | — | N | — | C | H | N | H | 1 | 3 | RS | H | OCH$_3$ | H | H | 20A-D; 6A-B; 20H |
| C-178 | CF$_2$CHF$_2$ | — | — | N | — | C | H | N | H | 1 | 3 | RS | H | OCH$_3$ | H | H | 20A-D; 6A-B; 20H |
| C-179 | CF$_2$CF$_3$ | — | — | N | — | C | H | N | H | 1 | 3 | RS | H | OCH$_3$ | H | H | 20A-D; 6A-B; 20H |
| C-180 | CF$_2$CH$_3$ | — | — | N | — | C | H | N | H | 1 | 3 | RS | H | OCH$_3$ | H | H | 20A-D; 6A-B; 20H |
| C-181 | cyclopropyl | — | — | N | — | C | H | N | H | 1 | 3 | RS | H | OCH$_3$ | H | H | 1C; 6A-B; 20H |
| C-182 | 2-methylcyclopropyl | — | — | N | — | C | H | N | H | 1 | 3 | RS | H | OCH$_3$ | H | H | 1C; 6A-B; 20H |
| C-183 | CH$_2$CH$_3$ | — | — | N | — | C | H | N | H | 1 | 3 | RS | H | OCH$_3$ | H | H | 1C; 6A-B; 20H |
| C-184 | (CH$_2$)$_2$CH$_3$ | — | — | N | — | C | H | N | H | 1 | 3 | RS | H | OCH$_3$ | H | H | 1C; 6A-B; 20H |
| C-185 | CH(CH$_3$)$_2$ | — | — | N | — | C | H | N | H | 1 | 3 | RS | H | OCH$_3$ | H | H | 1C; 6A-B; 20H |
| C-186 | CH(CH$_3$)CH$_2$CH$_3$ | — | — | N | — | C | H | N | H | 1 | 3 | RS | H | OCH$_3$ | H | H | 1C; 6A-B; 20H |
| C-187 | CF$_2$Cl | — | — | N | — | C | H | N | H | 1 | 3 | RS | H | OCH$_3$ | H | H | 20A-D; 6A-B; 20H |
| C-188 | SF$_5$ | — | — | N | — | C | H | N | H | 1 | 3 | RS | H | OCH$_3$ | H | H | 20A-D; 6A-B; 20H |
| C-189 | CF$_3$ | — | — | N | — | C | H | N | H | 1 | 3 | RS | H | OCH$_2$CH$_3$ | H | H | 20A-D; 6A-B; 20H |
| C-190 | CHF$_2$ | — | — | N | — | C | H | N | H | 1 | 3 | RS | H | OCH$_2$CH$_3$ | H | H | 20A-D; 6A-B; 20H |
| C-191 | CF$_2$CHF$_2$ | — | — | N | — | C | H | N | H | 1 | 3 | RS | H | OCH$_2$CH$_3$ | H | H | 20A-D; 6A-B; 20H |
| C-192 | CF$_2$CF$_3$ | — | — | N | — | C | H | N | H | 1 | 3 | RS | H | OCH$_2$CH$_3$ | H | H | 20A-D; 6A-B; 20H |
| C-193 | CF$_2$CH$_3$ | — | — | N | — | C | H | N | H | 1 | 3 | RS | H | OCH$_2$CH$_3$ | H | H | 20A-D; 6A-B; 20H |
| C-194 | cyclopropyl | — | — | N | — | C | H | N | H | 1 | 3 | RS | H | OCH$_2$CH$_3$ | H | H | 1C; 6A-B; 20H |
| C-195 | 2-methylcyclopropyl | — | — | N | — | C | H | N | H | 1 | 3 | RS | H | OCH$_2$CH$_3$ | H | H | 1C; 6A-B; 20H |
| C-196 | CH$_2$CH$_3$ | — | — | N | — | C | H | N | H | 1 | 3 | RS | H | OCH$_2$CH$_3$ | H | H | 1C; 6A-B; 20H |
| C-197 | (CH$_2$)$_2$CH$_3$ | — | — | N | — | C | H | N | H | 1 | 3 | RS | H | OCH$_2$CH$_3$ | H | H | 1C; 6A-B; 20H |
| C-198 | CH(CH$_3$)$_2$ | — | — | N | — | C | H | N | H | 1 | 3 | RS | H | OCH$_2$CH$_3$ | H | H | 1C; 6A-B; 20H |
| C-199 | CH(CH$_3$)CH$_2$CH$_3$ | — | — | N | — | C | H | N | H | 1 | 3 | RS | H | OCH$_2$CH$_3$ | H | H | 1C; 6A-B; 20H |
| C-200 | CF$_2$Cl | — | — | N | — | C | H | N | H | 1 | 3 | RS | H | OCH$_2$CH$_3$ | H | H | 20A-D; 6A-B; 20H |
| C-201 | SF$_5$ | — | — | N | — | C | H | N | H | 1 | 3 | RS | H | OCH$_2$CH$_3$ | H | H | 20A-D; 6A-B; 20H |
| C-202 | CF$_3$ | — | — | N | — | C | H | N | H | 1 | 3 | RS | H | OCH$_3$ | CH$_3$ | H | 20A-D; 6A-B; 20H |
| C-203 | CHF$_2$ | — | — | N | — | C | H | N | H | 1 | 3 | RS | H | OCH$_3$ | CH$_3$ | H | 20A-D; 6A-B; 20H |
| C-204 | CF$_2$CHF$_2$ | — | — | N | — | C | H | N | H | 1 | 3 | RS | H | OCH$_3$ | CH$_3$ | H | 20A-D; 6A-B; 20H |
| C-205 | CF$_2$CF$_3$ | — | — | N | — | C | H | N | H | 1 | 3 | RS | H | OCH$_3$ | CH$_3$ | H | 20A-D; 6A-B; 20H |
| C-206 | CF$_2$CH$_3$ | — | — | N | — | C | H | N | H | 1 | 3 | RS | H | OCH$_3$ | CH$_3$ | H | 20A-D; 6A-B; 20H |
| C-207 | cyclopropyl | — | — | N | — | C | H | N | H | 1 | 3 | RS | H | OCH$_3$ | CH$_3$ | H | 1C; 6A-B; 20H |
| C-208 | 2-methylcyclopropyl | — | — | N | — | C | H | N | H | 1 | 3 | RS | H | OCH$_3$ | CH$_3$ | H | 1C; 6A-B; 20H |
| C-209 | CH$_2$CH$_3$ | — | — | N | — | C | H | N | H | 1 | 3 | RS | H | OCH$_3$ | CH$_3$ | H | 1C; 6A-B; 20H |
| C-210 | (CH$_2$)$_2$CH$_3$ | — | — | N | — | C | H | N | H | 1 | 3 | RS | H | OCH$_3$ | CH$_3$ | H | 1C; 6A-B; 20H |
| C-211 | CH(CH$_3$)$_2$ | — | — | N | — | C | H | N | H | 1 | 3 | RS | H | OCH$_3$ | CH$_3$ | H | 1C; 6A-B; 20H |
| C-212 | CH(CH$_3$)CH$_2$CH$_3$ | — | — | N | — | C | H | N | H | 1 | 3 | RS | H | OCH$_3$ | CH$_3$ | H | 1C; 6A-B; 20H |
| C-213 | CF$_2$Cl | — | — | N | — | C | H | N | H | 1 | 3 | RS | H | OCH$_3$ | CH$_3$ | H | 20A-D; 6A-B; 20H |
| C-214 | SF$_5$ | — | — | N | — | C | H | N | H | 1 | 3 | RS | H | OCH$_3$ | CH$_3$ | H | 20A-D; 6A-B; 20H |
| C-215 | CF$_3$ | N | H | C | H | N | — | — | — | 1 | 2 | RS | H | OCH$_3$ | H | H | 20A-D; 1A; 14A; 20H |
| C-216 | CHF$_2$ | N | H | C | H | N | — | — | — | 1 | 2 | RS | H | OCH$_3$ | H | H | 20A-D; 1A; 14A; 20H |
| C-217 | CF$_2$CHF$_2$ | N | H | C | H | N | — | — | — | 1 | 2 | RS | H | OCH$_3$ | H | H | 20A-D; 1A; 14A; 20H |
| C-218 | CF$_2$CF$_3$ | N | H | C | H | N | — | — | — | 1 | 2 | RS | H | OCH$_3$ | H | H | 20A-D; 1A; 14A; 20H |
| C-219 | CF$_2$CH$_3$ | N | H | C | H | N | — | — | — | 1 | 2 | RS | H | OCH$_3$ | H | H | 20A-D; 1A; 14A; 20H |
| C-220 | cyclopropyl | N | H | C | H | N | — | — | — | 1 | 2 | RS | H | OCH$_3$ | H | H | 1C; 1A; 14A; 20H |
| C-221 | 2-methylcyclopropyl | N | H | C | H | N | — | — | — | 1 | 2 | RS | H | OCH$_3$ | H | H | 1C; 1A; 14A; 20H |
| C-222 | CH$_2$CH$_3$ | N | H | C | H | N | — | — | — | 1 | 2 | RS | H | OCH$_3$ | H | H | 1C; 1A; 14A; 20H |
| C-223 | (CH$_2$)$_2$CH$_3$ | N | H | C | H | N | — | — | — | 1 | 2 | RS | H | OCH$_3$ | H | H | 1C; 1A; 14A; 20H |
| C-224 | CH(CH$_3$)$_2$ | N | H | C | H | N | — | — | — | 1 | 2 | RS | H | OCH$_3$ | H | H | 1C; 1A; 14A; 20H |
| C-225 | CH(CH$_3$)CH$_2$CH$_3$ | N | H | C | H | N | — | — | — | 1 | 2 | RS | H | OCH$_3$ | H | H | 1C; 1A; 14A; 20H |
| C-226 | CF$_2$Cl | N | H | C | H | N | — | — | — | 1 | 2 | RS | H | OCH$_3$ | H | H | 20A-D; 1A; 14A; 20H |
| C-227 | SF$_5$ | N | H | C | H | N | — | — | — | 1 | 2 | RS | H | OCH$_3$ | H | H | 20A-D; 1A; 14A; 20H |
| C-228 | CF$_3$ | N | H | C | H | N | — | — | — | 1 | 2 | RS | H | OCH$_2$CH$_3$ | H | H | 20A-D; 1A; 14A; 20H |
| C-229 | CHF$_2$ | N | H | C | H | N | — | — | — | 1 | 2 | RS | H | OCH$_2$CH$_3$ | H | H | 20A-D; 1A; 14A; 20H |
| C-230 | CF$_2$CHF$_2$ | N | H | C | H | N | — | — | — | 1 | 2 | RS | H | OCH$_2$CH$_3$ | H | H | 20A-D; 1A; 14A; 20H |
| C-231 | CF$_2$CF$_3$ | N | H | C | H | N | — | — | — | 1 | 2 | RS | H | OCH$_2$CH$_3$ | H | H | 20A-D; 1A; 14A; 20H |
| C-232 | CF$_2$CH$_3$ | N | H | C | H | N | — | — | — | 1 | 2 | RS | H | OCH$_2$CH$_3$ | H | H | 20A-D; 1A; 14A; 20H |
| C-233 | cyclopropyl | N | H | C | H | N | — | — | — | 1 | 2 | RS | H | OCH$_2$CH$_3$ | H | H | 1C; 1A; 14A; 20H |
| C-234 | 2-methylcyclopropyl | N | H | C | H | N | — | — | — | 1 | 2 | RS | H | OCH$_2$CH$_3$ | H | H | 1C; 1A; 14A; 20H |
| C-235 | CH$_2$CH$_3$ | N | H | C | H | N | — | — | — | 1 | 2 | RS | H | OCH$_2$CH$_3$ | H | H | 1C; 1A; 14A; 20H |
| C-236 | (CH$_2$)$_2$CH$_3$ | N | H | C | H | N | — | — | — | 1 | 2 | RS | H | OCH$_2$CH$_3$ | H | H | 1C; 1A; 14A; 20H |
| C-237 | CH(CH$_3$)$_2$ | N | H | C | H | N | — | — | — | 1 | 2 | RS | H | OCH$_2$CH$_3$ | H | H | 1C; 1A; 14A; 20H |
| C-238 | CH(CH$_3$)CH$_2$CH$_3$ | N | H | C | H | N | — | — | — | 1 | 2 | RS | H | OCH$_2$CH$_3$ | H | H | 1C; 1A; 14A; 20H |
| C-239 | CF$_2$Cl | N | H | C | H | N | — | — | — | 1 | 2 | RS | H | OCH$_2$CH$_3$ | H | H | 20A-D; 1A; 14A; 20H |
| C-240 | SF$_5$ | N | H | C | H | N | — | — | — | 1 | 2 | RS | H | OCH$_2$CH$_3$ | H | H | 20A-D; 1A; 14A; 20H |
| C-241 | CF$_3$ | N | H | C | H | N | — | — | — | 1 | 2 | RS | H | OCH$_3$ | CH$_3$ | H | 20A-D; 1A; 14A; 20H |

TABLE C-continued

| | | | | | | | | | | | | | | | | | |
|---|---|---|---|---|---|---|---|---|---|---|---|---|---|---|---|---|---|
| C-242 | CHF$_2$ | N | H | C | H | N | — | — | — | 1 | 2 | RS | H | OCH$_3$ | CH$_3$ | H | 20A-D; 1A; 14A; 20H |
| C-243 | CF$_2$CHF$_2$ | N | H | C | H | N | — | — | — | 1 | 2 | RS | H | OCH$_3$ | CH$_3$ | H | 20A-D; 1A; 14A; 20H |
| C-244 | CF$_2$CF$_3$ | N | H | C | H | N | — | — | — | 1 | 2 | RS | H | OCH$_3$ | CH$_3$ | H | 20A-D; 1A; 14A; 20H |
| C-245 | CF$_2$CH$_3$ | N | H | C | H | N | — | — | — | 1 | 2 | RS | H | OCH$_3$ | CH$_3$ | H | 20A-D; 1A; 14A; 20H |
| C-246 | cyclopropyl | N | H | C | H | N | — | — | — | 1 | 2 | RS | H | OCH$_3$ | CH$_3$ | H | 1C; 1A; 14A; 20H |
| C-247 | 2-methylcyclopropyl | N | H | C | H | N | — | — | — | 1 | 2 | RS | H | OCH$_3$ | CH$_3$ | H | 1C; 1A; 14A; 20H |
| C-248 | CH$_2$CH$_3$ | N | H | C | H | N | — | — | — | 1 | 2 | RS | H | OCH$_3$ | CH$_3$ | H | 1C; 1A; 14A; 20H |
| C-249 | (CH$_2$)$_2$CH$_3$ | N | H | C | H | N | — | — | — | 1 | 2 | RS | H | OCH$_3$ | CH$_3$ | H | 1C; 1A; 14A; 20H |
| C-250 | CH(CH$_3$)$_2$ | N | H | C | H | N | — | — | — | 1 | 2 | RS | H | OCH$_3$ | CH$_3$ | H | 1C; 1A; 14A; 20H |
| C-251 | CH(CH$_3$)CH$_2$CH$_3$ | N | H | C | H | N | — | — | — | 1 | 2 | RS | H | OCH$_3$ | CH$_3$ | H | 1C; 1A; 14A; 20H |
| C-252 | CF$_2$Cl | N | H | C | H | N | — | — | — | 1 | 2 | RS | H | OCH$_3$ | CH$_3$ | H | 20A-D; 1A; 14A; 20H |
| C-253 | SF$_5$ | N | H | C | H | N | — | — | — | 1 | 2 | RS | H | OCH$_3$ | CH$_3$ | H | 20A-D; 1A; 14A; 20H |
| C-254 | CF$_3$ | N | H | C | H | N | — | — | — | 1 | 1 | RS | H | OCH$_3$ | H | H | 20A-D; 1A; 14A; 20H |
| C-255 | CHF$_2$ | N | H | C | H | N | — | — | — | 1 | 1 | RS | H | OCH$_3$ | H | H | 20A-D; 1A; 14A; 20H |
| C-256 | CF$_2$CHF$_2$ | N | H | C | H | N | — | — | — | 1 | 1 | RS | H | OCH$_3$ | H | H | 20A-D; 1A; 14A; 20H |
| C-257 | CF$_2$CF$_3$ | N | H | C | H | N | — | — | — | 1 | 1 | RS | H | OCH$_3$ | H | H | 20A-D; 1A; 14A; 20H |
| C-258 | CF$_2$CH$_3$ | N | H | C | H | N | — | — | — | 1 | 1 | RS | H | OCH$_3$ | H | H | 20A-D; 1A; 14A; 20H |
| C-259 | cyclopropyl | N | H | C | H | N | — | — | — | 1 | 1 | RS | H | OCH$_3$ | H | H | 1C; 1A; 14A; 20H |
| C-260 | 2-methylcyclopropyl | N | H | C | H | N | — | — | — | 1 | 1 | RS | H | OCH$_3$ | H | H | 1C; 1A; 14A; 20H |
| C-261 | CH$_2$CH$_3$ | N | H | C | H | N | — | — | — | 1 | 1 | RS | H | OCH$_3$ | H | H | 1C; 1A; 14A; 20H |
| C-262 | (CH$_2$)$_2$CH$_3$ | N | H | C | H | N | — | — | — | 1 | 1 | RS | H | OCH$_3$ | H | H | 1C; 1A; 14A; 20H |
| C-263 | CH(CH$_3$)$_2$ | N | H | C | H | N | — | — | — | 1 | 1 | RS | H | OCH$_3$ | H | H | 1C; 1A; 14A; 20H |
| C-264 | CH(CH$_3$)CH$_2$CH$_3$ | N | H | C | H | N | — | — | — | 1 | 1 | RS | H | OCH$_3$ | H | H | 1C; 1A; 14A; 20H |
| C-265 | CF$_2$Cl | N | H | C | H | N | — | — | — | 1 | 1 | RS | H | OCH$_3$ | H | H | 20A-D; 1A; 14A; 20H |
| C-266 | SF$_5$ | N | H | C | H | N | — | — | — | 1 | 1 | RS | H | OCH$_3$ | H | H | 20A-D; 1A; 14A; 20H |
| C-267 | CF$_3$ | N | H | C | H | N | — | — | — | 1 | 1 | RS | H | OCH$_2$CH$_3$ | H | H | 20A-D; 1A; 14A; 20H |
| C-268 | CHF$_2$ | N | H | C | H | N | — | — | — | 1 | 1 | RS | H | OCH$_2$CH$_3$ | H | H | 20A-D; 1A; 14A; 20H |
| C-269 | CF$_2$CHF$_2$ | N | H | C | H | N | — | — | — | 1 | 1 | RS | H | OCH$_2$CH$_3$ | H | H | 20A-D; 1A; 14A; 20H |
| C-270 | CF$_2$CF$_3$ | N | H | C | H | N | — | — | — | 1 | 1 | RS | H | OCH$_2$CH$_3$ | H | H | 20A-D; 1A; 14A; 20H |
| C-271 | CF$_2$CH$_3$ | N | H | C | H | N | — | — | — | 1 | 1 | RS | H | OCH$_2$CH$_3$ | H | H | 20A-D; 1A; 14A; 20H |
| C-272 | cyclopropyl | N | H | C | H | N | — | — | — | 1 | 1 | RS | H | OCH$_2$CH$_3$ | H | H | 1C; 1A; 14A; 20H |
| C-273 | 2-methylcyclopropyl | N | H | C | H | N | — | — | — | 1 | 1 | RS | H | OCH$_2$CH$_3$ | H | H | 1C; 1A; 14A; 20H |
| C-274 | CH$_2$CH$_3$ | N | H | C | H | N | — | — | — | 1 | 1 | RS | H | OCH$_2$CH$_3$ | H | H | 1C; 1A; 14A; 20H |
| C-275 | (CH$_2$)$_2$CH$_3$ | N | H | C | H | N | — | — | — | 1 | 1 | RS | H | OCH$_2$CH$_3$ | H | H | 1C; 1A; 14A; 20H |
| C-276 | CH(CH$_3$)$_2$ | N | H | C | H | N | — | — | — | 1 | 1 | RS | H | OCH$_2$CH$_3$ | H | H | 1C; 1A; 14A; 20H |
| C-277 | CH(CH$_3$)CH$_2$CH$_3$ | N | H | C | H | N | — | — | — | 1 | 1 | RS | H | OCH$_2$CH$_3$ | H | H | 1C; 1A; 14A; 20H |
| C-278 | CF$_2$Cl | N | H | C | H | N | — | — | — | 1 | 1 | RS | H | OCH$_2$CH$_3$ | H | H | 20A-D; 1A; 14A; 20H |
| C-279 | SF$_5$ | N | H | C | H | N | — | — | — | 1 | 1 | RS | H | OCH$_2$CH$_3$ | H | H | 20A-D; 1A; 14A; 20H |
| C-280 | CF$_3$ | N | H | C | H | N | — | — | — | 1 | 1 | RS | H | OCH$_3$ | CH$_3$ | H | 20A-D; 1A; 14A; 20H |
| C-281 | CHF$_2$ | N | H | C | H | N | — | — | — | 1 | 1 | RS | H | OCH$_3$ | CH$_3$ | H | 20A-D; 1A; 14A; 20H |
| C-282 | CF$_2$CHF$_2$ | N | H | C | H | N | — | — | — | 1 | 1 | RS | H | OCH$_3$ | CH$_3$ | H | 20A-D; 1A; 14A; 20H |
| C-283 | CF$_2$CF$_3$ | N | H | C | H | N | — | — | — | 1 | 1 | RS | H | OCH$_3$ | CH$_3$ | H | 20A-D; 1A; 14A; 20H |
| C-284 | CF$_2$CH$_3$ | N | H | C | H | N | — | — | — | 1 | 1 | RS | H | OCH$_3$ | CH$_3$ | H | 20A-D; 1A; 14A; 20H |
| C-285 | cyclopropyl | N | H | C | H | N | — | — | — | 1 | 1 | RS | H | OCH$_3$ | CH$_3$ | H | 1C; 1A; 14A; 20H |
| C-286 | 2-methylcyclopropyl | N | H | C | H | N | — | — | — | 1 | 1 | RS | H | OCH$_3$ | CH$_3$ | H | 1C; 1A; 14A; 20H |
| C-287 | CH$_2$CH$_3$ | N | H | C | H | N | — | — | — | 1 | 1 | RS | H | OCH$_3$ | CH$_3$ | H | 1C; 1A; 14A; 20H |
| C-288 | (CH$_2$)$_2$CH$_3$ | N | H | C | H | N | — | — | — | 1 | 1 | RS | H | OCH$_3$ | CH$_3$ | H | 1C; 1A; 14A; 20H |
| C-289 | CH(CH$_3$)$_2$ | N | H | C | H | N | — | — | — | 1 | 1 | RS | H | OCH$_3$ | CH$_3$ | H | 1C; 1A; 14A; 20H |
| C-290 | CH(CH$_3$)CH$_2$CH$_3$ | N | H | C | H | N | — | — | — | 1 | 1 | RS | H | OCH$_3$ | CH$_3$ | H | 1C; 1A; 14A; 20H |
| C-291 | CF$_2$Cl | N | H | C | H | N | — | — | — | 1 | 1 | RS | H | OCH$_3$ | CH$_3$ | H | 20A-D; 1A; 14A; 20H |
| C-292 | SF$_5$ | N | H | C | H | N | — | — | — | 1 | 1 | RS | H | OCH$_3$ | CH$_3$ | H | 20A-D; 1A; 14A; 20H |
| C-293 | CF$_3$ | N | H | C | H | N | — | — | — | 1 | 3 | RS | H | OCH$_3$ | H | H | 20A-D; 1A; 14A; 20H |
| C-294 | CHF$_2$ | N | H | C | H | N | — | — | — | 1 | 3 | RS | H | OCH$_3$ | H | H | 20A-D; 1A; 14A; 20H |
| C-295 | CF$_2$CHF$_2$ | N | H | C | H | N | — | — | — | 1 | 3 | RS | H | OCH$_3$ | H | H | 20A-D; 1A; 14A; 20H |
| C-296 | CF$_2$CF$_3$ | N | H | C | H | N | — | — | — | 1 | 3 | RS | H | OCH$_3$ | H | H | 20A-D; 1A; 14A; 20H |
| C-297 | CF$_2$CH$_3$ | N | H | C | H | N | — | — | — | 1 | 3 | RS | H | OCH$_3$ | H | H | 20A-D; 1A; 14A; 20H |
| C-298 | cyclopropyl | N | H | C | H | N | — | — | — | 1 | 3 | RS | H | OCH$_3$ | H | H | 1C; 1A; 14A; 20H |
| C-299 | 2-methylcyclopropyl | N | H | C | H | N | — | — | — | 1 | 3 | RS | H | OCH$_3$ | H | H | 1C; 1A; 14A; 20H |
| C-300 | CH$_2$CH$_3$ | N | H | C | H | N | — | — | — | 1 | 3 | RS | H | OCH$_3$ | H | H | 1C; 1A; 14A; 20H |
| C-301 | (CH$_2$)$_2$CH$_3$ | N | H | C | H | N | — | — | — | 1 | 3 | RS | H | OCH$_3$ | H | H | 1C; 1A; 14A; 20H |
| C-302 | CH(CH$_3$)$_2$ | N | H | C | H | N | — | — | — | 1 | 3 | RS | H | OCH$_3$ | H | H | 1C; 1A; 14A; 20H |
| C-303 | CH(CH$_3$)CH$_2$CH$_3$ | N | H | C | H | N | — | — | — | 1 | 3 | RS | H | OCH$_3$ | H | H | 1C; 1A; 14A; 20H |
| C-304 | CF$_2$Cl | N | H | C | H | N | — | — | — | 1 | 3 | RS | H | OCH$_3$ | H | H | 20A-D; 1A; 14A; 20H |
| C-305 | SF$_5$ | N | H | C | H | N | — | — | — | 1 | 3 | RS | H | OCH$_3$ | H | H | 20A-D; 1A; 14A; 20H |
| C-306 | CF$_3$ | N | H | C | H | N | — | — | — | 1 | 3 | RS | H | OCH$_2$CH$_3$ | H | H | 20A-D; 1A; 14A; 20H |
| C-307 | CHF$_2$ | N | H | C | H | N | — | — | — | 1 | 3 | RS | H | OCH$_2$CH$_3$ | H | H | 20A-D; 1A; 14A; 20H |
| C-308 | CF$_2$CHF$_2$ | N | H | C | H | N | — | — | — | 1 | 3 | RS | H | OCH$_2$CH$_3$ | H | H | 20A-D; 1A; 14A; 20H |
| C-309 | CF$_2$CF$_3$ | N | H | C | H | N | — | — | — | 1 | 3 | RS | H | OCH$_2$CH$_3$ | H | H | 20A-D; 1A; 14A; 20H |
| C-310 | CF$_2$CH$_3$ | N | H | C | H | N | — | — | — | 1 | 3 | RS | H | OCH$_2$CH$_3$ | H | H | 20A-D; 1A; 14A; 20H |
| C-311 | cyclopropyl | N | H | C | H | N | — | — | — | 1 | 3 | RS | H | OCH$_2$CH$_3$ | H | H | 1C; 1A; 14A; 20H |
| C-312 | 2-methylcyclopropyl | N | H | C | H | N | — | — | — | 1 | 3 | RS | H | OCH$_2$CH$_3$ | H | H | 1C; 1A; 14A; 20H |
| C-313 | CH$_2$CH$_3$ | N | H | C | H | N | — | — | — | 1 | 3 | RS | H | OCH$_2$CH$_3$ | H | H | 1C; 1A; 14A; 20H |
| C-314 | (CH$_2$)$_2$CH$_3$ | N | H | C | H | N | — | — | — | 1 | 3 | RS | H | OCH$_2$CH$_3$ | H | H | 1C; 1A; 14A; 20H |
| C-315 | CH(CH$_3$)$_2$ | N | H | C | H | N | — | — | — | 1 | 3 | RS | H | OCH$_2$CH$_3$ | H | H | 1C; 1A; 14A; 20H |
| C-316 | CH(CH$_3$)CH$_2$CH$_3$ | N | H | C | H | N | — | — | — | 1 | 3 | RS | H | OCH$_2$CH$_3$ | H | H | 1C; 1A; 14A; 20H |
| C-317 | CF$_2$Cl | N | H | C | H | N | — | — | — | 1 | 3 | RS | H | OCH$_2$CH$_3$ | H | H | 20A-D; 1A; 14A; 20H |
| C-318 | SF$_5$ | N | H | C | H | N | — | — | — | 1 | 3 | RS | H | OCH$_2$CH$_3$ | H | H | 20A-D; 1A; 14A; 20H |
| C-319 | CF$_3$ | N | H | C | H | N | — | — | — | 1 | 3 | RS | H | OCH$_3$ | CH$_3$ | H | 20A-D; 1A; 14A; 20H |
| C-320 | CHF$_2$ | N | H | C | H | N | — | — | — | 1 | 3 | RS | H | OCH$_3$ | CH$_3$ | H | 20A-D; 1A; 14A; 20H |
| C-321 | CF$_2$CHF$_2$ | N | H | C | H | N | — | — | — | 1 | 3 | RS | H | OCH$_3$ | CH$_3$ | H | 20A-D; 1A; 14A; 20H |

TABLE C-continued

| | | | | | | | | | | | | | | | | | |
|---|---|---|---|---|---|---|---|---|---|---|---|---|---|---|---|---|---|
| C-322 | $CF_2CF_3$ | N | H | C | H | N | — | — | — | 1 | 3 | RS | H | $OCH_3$ | $CH_3$ | H | 20A-D; 1A; 14A; 20H |
| C-323 | $CF_2CH_3$ | N | H | C | H | N | — | — | — | 1 | 3 | RS | H | $OCH_3$ | $CH_3$ | H | 20A-D; 1A; 14A; 20H |
| C-324 | cyclopropyl | N | H | C | H | N | — | — | — | 1 | 3 | RS | H | $OCH_3$ | $CH_3$ | H | 1C; 1A; 14A; 20H |
| C-325 | 2-methylcyclopropyl | N | H | C | H | N | — | — | — | 1 | 3 | RS | H | $OCH_3$ | $CH_3$ | H | 1C; 1A; 14A; 20H |
| C-326 | $CH_2CH_3$ | N | H | C | H | N | — | — | — | 1 | 3 | RS | H | $OCH_3$ | $CH_3$ | H | 1C; 1A; 14A; 20H |
| C-327 | $(CH_2)_2CH_3$ | N | H | C | H | N | — | — | — | 1 | 3 | RS | H | $OCH_3$ | $CH_3$ | H | 1C; 1A; 14A; 20H |
| C-328 | $CH(CH_3)_2$ | N | H | C | H | N | — | — | — | 1 | 3 | RS | H | $OCH_3$ | $CH_3$ | H | 1C; 1A; 14A; 20H |
| C-329 | $CH(CH_3)CH_2CH_3$ | N | H | C | H | N | — | — | — | 1 | 3 | RS | H | $OCH_3$ | $CH_3$ | H | 1C; 1A; 14A; 20H |
| C-330 | $CF_3$ | N | H | C | H | N | — | — | — | 1 | 3 | RS | H | $OCH_3$ | $CH_3$ | H | 20A-D; 1A; 14A; 20H |
| C-331 | $CHF_2$ | N | H | C | H | N | — | — | — | 1 | 3 | RS | H | $OCH_3$ | $CH_3$ | H | 20A-D; 1A; 14A; 20H |

Further examples of specific compounds of the present invention include each of the compounds of table C above wherein $X=SO_2$ instead of CO and each of the compounds of table C wherein X=CS instead of CO.

Further examples of specific compounds of the present invention include each compound in table C above and each each analogue wherein $X=SO_2$ or wherein X=CS, in form of its pyridine N-oxide.

Table D below provides for each of the synthesized compounds of the formula (D) the structure, the calculated molecular weight (MW) (gram/mol), the observed MS signal (m/z), the HPLC retention time (Rt) in minutes, and the number of the HPLC-method as described in paragraph C above ("Analytics: HPLC-Methods") used for analysis. From compound D-61 until to the end of the table the methods by which the compounds are synthesized are identified by referring to the synthesis steps described in the synthesis examples of paragraph B above ("Synthesis Examples"). In Table D—in case of a ring formation between $Y^3$ and $Y^4$ by the substituents $R^{14}$ and $R^{15}$—in the columns for $R^{14}$ and $R^{15}$ the symbols Y3 and Y4 indicate the ring atoms $Y^3$ and $Y^4$ in formula (D) to which the respective substituents are bound. If a compound contains a chiral center, the absolute configuration of the enantiomer is given (R/S). If the piperazine contains one chiral center, "R" and "S" denote the absolute configuration of that chiral center, the value "RS" means that the racemate is present. If two chiral centers are present in the piperazine, one specific enantiomer is denoted or a mixture of specific enantiomers is denoted. If $R^1$ contains a chiral center, both isomers with regard to this chiral center are present.

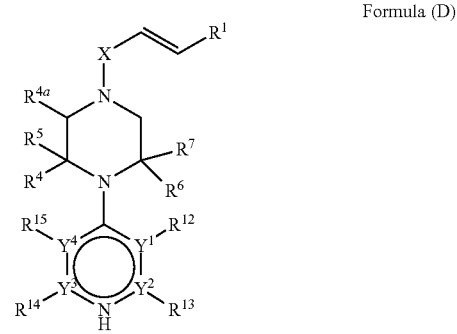

Formula (D)

TABLE D

| | | | | | | | | | |
|---|---|---|---|---|---|---|---|---|---|
| \multicolumn{10}{c}{$(X = CO, Y^1, Y^2, Y^3, Y^4 = C)$} |
| No | $R^1$ | $R^4$ | $R^5$ | $R^{4a}$ | $R^6$ | $R^7$ | R/S | $R^{12}$ | $R^{13}$ |
| D-1 | $CF_2CF_3$ | H | H | H | $CH_3$ | H | S | H | $CH_3$ |
| D-2 | $CF_2CHF_2$ | H | H | H | $CH_3$ | H | S | H | $CH_3$ |
| D-3 | $CF_3$ | H | H | H | $CH_3$ | H | S | H | $CH_3$ |
| D-4 | $CH(CH_3)(CH_2CH_3)$ | H | H | H | $CH_3$ | H | S | H | $CH_3$ |
| D-5 | $CH(CH_3)_2$ | H | H | H | $CH_3$ | H | S | H | $CH_3$ |
| D-6 | $CH_2CH_2CH_3$ | H | H | H | $CH_3$ | H | S | H | $CH_3$ |
| D-7 | $CH_2CH_3$ | H | H | H | $CH_3$ | H | S | H | $CH_3$ |
| D-8 | cyclopropyl | H | H | H | $CH_3$ | H | S | H | $CH_3$ |
| D-9 | $n\text{-}CF_2CF_2CF_3$ | H | H | H | $CH_3$ | H | S | H | $CH_3$ |
| D-10 | $CF_2CF_3$ | H | H | H | $CH_3$ | H | S | H | $CH_3$ |
| D-11 | $CF_2CHF_2$ | H | H | H | $CH_3$ | H | S | H | $CH_3$ |
| D-12 | $CF_3$ | H | H | H | $CH_3$ | H | S | H | $CH_3$ |
| D-13 | $CH(CH_3)(CH_2CH_3)$ | H | H | H | $CH_3$ | H | S | H | $CH_3$ |
| D-14 | $CH(CH_3)_2$ | H | H | H | $CH_3$ | H | S | H | $CH_3$ |
| D-15 | $CH_2CH_2CH_3$ | H | H | H | $CH_3$ | H | S | H | $CH_3$ |
| D-16 | $CH_2CH_3$ | H | H | H | $CH_3$ | H | S | H | $CH_3$ |
| D-17 | cyclopropyl | H | H | H | $CH_3$ | H | S | H | $CH_3$ |
| D-18 | $n\text{-}CF_2CF_2CF_3$ | H | H | H | $CH_3$ | H | S | H | $CH_3$ |
| D-19 | $CF_2CF_3$ | H | H | H | $CH_3$ | H | S | H | H |
| D-20 | $CF_2CHF_2$ | H | H | H | $CH_3$ | H | S | H | H |
| D-21 | $CF_3$ | H | H | H | $CH_3$ | H | S | H | H |
| D-22 | $CH(CH_3)(CH_2CH_3)$ | H | H | H | $CH_3$ | H | S | H | H |
| D-23 | $CH(CH_3)_2$ | H | H | H | $CH_3$ | H | S | H | H |
| D-24 | $CH_2CH_2CH_3$ | H | H | H | $CH_3$ | H | S | H | H |
| D-25 | $CH_2CH_3$ | H | H | H | $CH_3$ | H | S | H | H |
| D-26 | cyclopropyl | H | H | H | $CH_3$ | H | S | H | H |
| D-27 | $n\text{-}CF_2CF_2CF_3$ | H | H | H | $CH_3$ | H | S | H | H |
| D-28 | $CH(CH_3)_2$ | H | H | $CH_2$ | | H | SS | H | $CH_3$ |
| D-29 | $CH_2CH_2CH_3$ | H | H | $CH_2$ | | H | SS | H | $CH_3$ |
| D-30 | $CH_2CH_3$ | H | H | $CH_2$ | | H | SS | H | $CH_3$ |

TABLE D-continued

| No | | | | | | | | | |
|---|---|---|---|---|---|---|---|---|---|
| D-31 | CH(CH₃)₂ | H | H | CH₃ | CH₃ | H | RS, SR | H | CH₃ |
| D-32 | CH₂CH₂CH₃ | H | H | CH₃ | CH₃ | H | RS, SR | H | CH₃ |
| D-33 | CH₂CH₃ | H | H | CH₃ | CH₃ | H | RS, SR | H | CH₃ |
| D-34 | CH(CH₃)₂ | H | H | H | CH₃ | H | R | H | CH₃ |
| D-35 | CH(CH₃)₂ | H | H | H | CH₃ | H | S | H | CH₃ |
| D-36 | CH₂CH₂CH₃ | H | H | H | CH₃ | H | R | H | CH₃ |
| D-37 | CH₂CH₂CH₃ | H | H | H | CH₃ | H | S | H | CH₃ |
| D-38 | CH₂CH₃ | H | H | H | CH₃ | H | R | H | CH₃ |
| D-39 | CH₂CH₃ | H | H | H | CH₃ | H | S | H | CH₃ |
| D-40 | CH(CH₃)₂ | H | H | CH₂ | | | SS | H | H |
| D-41 | CH₂CH₂CH₃ | H | H | CH₂ | | | SS | H | H |
| D-42 | CH₂CH₃ | H | H | CH₂ | | | SS | H | H |
| D-43 | CH(CH₃)₂ | H | H | CH₃ | CH₃ | H | RS, SR | H | H |
| D-44 | CH₂CH₂CH₃ | H | H | CH₃ | CH₃ | H | RS, SR | H | H |
| D-45 | CH₂CH₃ | H | H | CH₃ | CH₃ | H | RS, SR | H | H |
| D-46 | CH(CH₃)₂ | H | H | H | CH₃ | H | S | H | H |
| D-47 | CH(CH₃)₂ | H | H | H | CH₃ | H | R | H | H |
| D-48 | CH₂CH₂CH₃ | H | H | H | CH₃ | H | S | H | H |
| D-49 | CH₂CH₂CH₃ | H | H | H | CH₃ | H | R | H | H |
| D-50 | CH₂H₃ | H | H | H | CH₃ | H | S | H | H |
| D-51 | CH₂CH₃ | H | H | H | CH₃ | H | R | H | H |
| D-52 | CF₃ | H | H | H | Oxo | | — | H | H |
| D-53 | CH(CH₃)₂ | H | H | H | Oxo | | — | H | H |
| D-54 | CH₂CH₂CH₃ | H | H | H | Oxo | | — | H | H |
| D-55 | CH₂CH₃ | H | H | H | Oxo | | — | H | H |
| D-56 | CF₃ | H | H | H | CH₂CO₂CH₃ | H | RS | H | OCH₂CH₃ |
| D-57 | CF₃ | H | H | H | CH₂CO₂CH₃ | H | RS | H | CH₃ |
| D-58 | CF₂CF₃ | H | H | H | CH₂CO₂CH₃ | H | RS | H | OCH₂CH₃ |
| D-59 | CF₂CHF₂ | H | H | H | CH₂CO₂CH₃ | H | RS | H | OCH₂CH₃ |
| D-60 | CHF₂ | H | H | H | CH₂CO₂CH₃ | H | RS | H | OCH₂CH₃ |

(X = CO, Y¹, Y², Y³, Y⁴ = C)

| No | R¹⁴ | R¹⁵ | HPLC | Rt | m/z | MW |
|---|---|---|---|---|---|---|
| D-1 | CH₃ | H | 5 | 4.01 | 378.3 | 377.4 |
| D-2 | CH₃ | H | 5 | 3.64 | 360.3 | 359.4 |
| D-3 | CH₃ | H | 5 | 3.61 | 328.3 | 327.3 |
| D-4 | CH₃ | H | 5 | 4.01 | 316.3 | 315.5 |
| D-5 | CH₃ | H | 5 | 3.70 | 302.3 | 301.4 |
| D-6 | CH₃ | H | 5 | 3.75 | 302.3 | 301.4 |
| D-7 | CH₃ | H | 5 | 3.39 | 288.3 | 287.4 |
| D-8 | CH₃ | H | 5 | 3.42 | 300.3 | 299.4 |
| D-9 | CH₃ | H | 5 | 4.34 | 428.3 | 427.4 |
| D-10 | H | H | 5 | 3.73 | 364.2 | 363.3 |
| D-11 | H | H | 5 | 3.39 | 346.2 | 345.3 |
| D-12 | H | H | 5 | 3.36 | 314.2 | 313.3 |
| D-13 | H | H | 5 | 3.68 | 302.3 | 301.4 |
| D-14 | H | H | 5 | 3.42 | 288.3 | 287.4 |
| D-15 | H | H | 5 | 3.46 | 288.3 | 287.4 |
| D-16 | H | H | 5 | 3.16 | 274.2 | 273.4 |
| D-17 | H | H | 5 | 3.17 | 286.2 | 285.4 |
| D-18 | H | H | 5 | 4.00 | 414.2 | 413.3 |
| D-19 | Y3—CH=C(OCH₃)—CH=CH—Y4 | | 5 | 4.09 | 430.2 | 429.4 |
| D-20 | Y3—CH=C(OCH₃)—CH=CH—Y4 | | 5 | 3.79 | 412.3 | 411.4 |
| D-21 | Y3—CH=C(OCH₃)—CH=CH—Y4 | | 5 | 3.79 | 380.3 | 379.4 |
| D-22 | Y3—CH=C(OCH₃)—CH=CH—Y4 | | 5 | 4.07 | 368.3 | 367.5 |
| D-23 | Y3—CH=C(OCH₃)—CH=CH—Y4 | | 5 | 3.85 | 354.3 | 353.5 |
| D-24 | Y3—CH=C(OCH₃)—CH=CH—Y4 | | 5 | 3.87 | 354.3 | 353.5 |
| D-25 | Y3—CH=C(OCH₃)—CH=CH—Y4 | | 5 | 3.61 | 340.3 | 339.4 |
| D-26 | Y3—CH=C(OCH₃)—CH=CH—Y4 | | 5 | 3.61 | 352.3 | 351.4 |
| D-27 | Y3—CH=C(OCH₃)—CH=CH—Y4 | | 5 | 4.31 | 480.3 | 479.4 |
| D-28 | Y3—CH=CH—CH=CH—Y4 | | 5 | 3.98 | 336.0 | 335.4 |
| D-29 | Y3—CH=CH—CH=CH—Y4 | | 3 | 4.01 | 336.0 | 335.4 |
| D-30 | Y3—CH=CH—CH=CH—Y4 | | 3 | 3.71 | 322.0 | 321.4 |
| D-31 | Y3—CH=CH—CH=CH—Y4 | | 4 | 4.07 | 352.0 | 351.5 |
| D-32 | Y3—CH=CH—CH=CH—Y4 | | 4 | 4.09 | 352.0 | 351.5 |
| D-33 | Y3—CH=CH—CH=CH—Y4 | | 4 | 3.85 | 337.9 | 337.5 |
| D-34 | Y3—CH=CH—CH=CH—Y4 | | 4 | 3.74 | 338.0 | 337.5 |
| D-35 | Y3—CH=CH—CH=CH—Y4 | | 4 | 3.97 | 338.0 | 337.5 |
| D-36 | Y3—CH=CH—CH=CH—Y4 | | 4 | 3.80 | 338.0 | 337.5 |
| D-37 | Y3—CH=CH—CH=CH—Y4 | | 4 | 4.00 | 337.9 | 337.5 |
| D-38 | Y3—CH=CH—CH=CH—Y4 | | 4 | 3.55 | 323.9 | 323.4 |
| D-39 | Y3—CH=CH—CH=CH—Y4 | | 4 | 3.75 | 323.9 | 323.4 |
| D-40 | Y3—CH=CH—CH=CH—Y4 | | 4 | 3.49 | 321.8 | 321.4 |
| D-41 | Y3—CH=CH—CH=CH—Y4 | | 4 | 3.88 | 322.0 | 321.4 |
| D-42 | Y3—CH=CH—CH=CH—Y4 | | 4 | 3.59 | 308.0 | 307.4 |
| D-43 | Y3—CH=CH—CH=CH—Y4 | | 4 | 3.97 | 338.0 | 337.5 |
| D-44 | Y3—CH=CH—CH=CH—Y4 | | 4 | 3.99 | 338.0 | 337.5 |
| D-45 | Y3—CH=CH—CH=CH—Y4 | | 4 | 3.75 | 323.9 | 323.4 |

TABLE D-continued

| | | | | | | | | | | | |
|---|---|---|---|---|---|---|---|---|---|---|---|
| D-46 | | | | Y3—CH=CH—CH=CH—Y4 | | | | 4 | 3.87 | 324.0 | 323.4 |
| D-47 | | | | Y3—CH=CH—CH=CH—Y4 | | | | 4 | 3.87 | 324.0 | 323.4 |
| D-48 | | | | Y3—CH=CH—CH=CH—Y4 | | | | 4 | 3.90 | 323.9 | 323.4 |
| D-49 | | | | Y3—CH=CH—CH=CH—Y4 | | | | 4 | 3.90 | 323.9 | 323.4 |
| D-50 | | | | Y3—CH=CH—CH=CH—Y4 | | | | 4 | 3.65 | 309.9 | 309.4 |
| D-51 | | | | Y3—CH=CH—CH=CH—Y4 | | | | 4 | 3.65 | 309.9 | 309.4 |
| D-52 | | | | Y3—CH=CH—CH=CH—Y4 | | | | 9 | 1.16 | 350.1 | 349.3 |
| D-53 | | | | Y3—CH=CH—CH=CH—Y4 | | | | 8 | 1.56 | 324.1 | 323.3 |
| D-54 | | | | Y3—CH=CH—CH=CH—Y4 | | | | 8 | 1.56 | 324.1 | 323.3 |
| D-55 | | | | Y3—CH=CH—CH=CH—Y4 | | | | 8 | 1.46 | 310.1 | 309.4 |
| D-56 | | | | H | | H | | 5 | 3.73 | 401.7 | 401.4 |
| D-57 | | | | Y3—CH=CH—CH=CH—Y4 | | | | 5 | 3.70 | 421.7 | 421.4 |
| D-58 | | | | H | | H | | 5 | 4.04 | 451.7 | 451.4 |
| D-59 | | | | H | | H | | 5 | 3.76 | 433.7 | 433.4 |
| D-60 | | | | H | | H | | 5 | 3.46 | 383.7 | 383.4 |

$(X = CO, Y^1, Y^2, Y^3, Y^4 = C)$

| No | $R^1$ | $R^4$ | $R^5$ | $R^{4a}$ | $R^6$ | $R^7$ | R/S | $R^{12}$ | $R^{13}$ | $R^{14}$ | $R^{15}$ | No |
|---|---|---|---|---|---|---|---|---|---|---|---|---|
| D-61 | CH(CH$_3$)$_2$ | H | H | H | C(O)OCH$_3$ | H | RS | H | CH$_3$ | H | H | 6A, B; 6C |
| D-62 | CH$_3$ | H | H | H | C(O)OCH$_3$ | H | RS | H | CH$_3$ | H | H | 6A, B; 6C |
| D-63 | CF$_3$ | H | H | H | C(O)OCH$_3$ | H | RS | H | CH$_3$ | H | H | 6A, B; 6C |
| D-64 | CH(CH$_3$)$_2$ | H | H | H | C(O)OCH$_3$ | H | RS | H | CH$_3$ | Y3—CH=CH—CH=CH—Y4 | | 6A, B; 6C |
| D-65 | CH$_3$ | H | H | H | C(O)OCH$_3$ | H | RS | H | CH$_3$ | Y3—CH=CH—CH=CH—Y4 | | 6A, B; 6C |
| D-66 | CF$_3$ | H | H | H | C(O)OCH$_3$ | H | RS | H | CH$_3$ | Y3—CH=CH—CH=CH—Y4 | | 6A, B; 6C |
| D-67 | CH(CH$_3$)$_2$ | H | H | H | CH$_2$C(O)OCH$_3$ | H | RS | H | CH$_3$ | H | H | 6A, B; 6C |
| D-68 | CH$_3$ | H | H | H | CH$_2$C(O)OCH$_3$ | H | RS | H | CH$_3$ | H | H | 6A, B; 6C |
| D-69 | CF$_3$ | H | H | H | CH$_2$C(O)OCH$_3$ | H | RS | H | CH$_3$ | H | H | 6A, B; 6C |
| D-70 | CH(CH$_3$)$_2$ | H | H | H | CH$_2$C(O)OCH$_3$ | H | RS | H | CH$_3$ | Y3—CH=CH—CH=CH—Y4 | | 6A, B; 6C |
| D-71 | CH$_3$ | H | H | H | CH$_2$C(O)OCH$_3$ | H | RS | H | CH$_3$ | Y3—CH=CH—CH=CH—Y4 | | 6A, B; 6C |
| D-72 | CF$_3$ | H | H | H | CH$_2$C(O)OCH$_3$ | H | RS | H | CH$_3$ | Y3—CH=CH—CH=CH—Y4 | | 6A, B; 6C |
| D-73 | CH(CH$_3$)$_2$ | H | H | H | COOH | H | RS | H | CH$_3$ | H | H | 6A, B; 6C |
| D-74 | CH$_3$ | H | H | H | COOH | H | RS | H | CH$_3$ | H | H | 6A, B; 6C |
| D-75 | CF$_3$ | H | H | H | COOH | H | RS | H | CH$_3$ | H | H | 6A, B; 6C |
| D-76 | CH(CH$_3$)$_2$ | H | H | H | COOH | H | RS | H | CH$_3$ | Y3—CH=CH—CH=CH—Y4 | | 6A, B; 6C |
| D-77 | CF$_3$ | H | H | H | COOH | H | RS | H | CH$_3$ | Y3—CH=CH—CH=CH—Y4 | | 6A, B; 6C |
| D-78 | CH$_3$ | H | H | H | COOH | H | RS | H | CH$_3$ | Y3—CH=CH—CH=CH—Y4 | | 6A, B; 6C |
| D-79 | CH(CH$_3$)$_2$ | H | H | H | CONH$_2$ | H | RS | H | CH$_3$ | H | H | 6A, B; 6C |
| D-80 | CH$_3$ | H | H | H | CONH$_2$ | H | RS | H | CH$_3$ | H | H | 6A, B; 6C |
| D-81 | CF$_3$ | H | H | H | CONH$_2$ | H | RS | H | CH$_3$ | H | H | 6A, B; 6C |
| D-82 | CH(CH$_3$)$_2$ | H | H | H | CONH$_2$ | H | RS | H | CH$_3$ | Y3—CH=CH—CH=CH—Y4 | | 6A, B; 6C |
| D-83 | CF$_3$ | H | H | H | CONH$_2$ | H | RS | H | CH$_3$ | Y3—CH=CH—CH=CH—Y4 | | 6A, B; 6C |
| D-84 | CH$_3$ | H | H | H | CONH$_2$ | H | RS | H | CH$_3$ | Y3—CH=CH—CH=CH—Y4 | | 6A, B; 6C |
| D-85 | CH(CH$_3$)$_2$ | H | H | H | CONHCH$_3$ | H | RS | H | CH$_3$ | H | H | 6A, B; 6C |
| D-86 | CH$_3$ | H | H | H | CONHCH$_3$ | H | RS | H | CH$_3$ | H | H | 6A, B; 6C |
| D-87 | CF$_3$ | H | H | H | CONHCH$_3$ | H | RS | H | CH$_3$ | H | H | 6A, B; 6C |
| D-88 | CH(CH$_3$)$_2$ | H | H | H | CONHCH$_3$ | H | RS | H | CH$_3$ | Y3—CH=CH—CH=CH—Y4 | | 6A, B; 6C |
| D-89 | CF$_3$ | H | H | H | CONHCH$_3$ | H | RS | H | CH$_3$ | Y3—CH=CH—CH=CH—Y4 | | 6A, B; 6C |
| D-90 | CH$_3$ | H | H | H | CONHCH$_3$ | H | RS | H | CH$_3$ | Y3—CH=CH—CH=CH—Y4 | | 6A, B; 6C |
| D-91 | CH(CH$_3$)$_2$ | H | H | H | CH$_2$OH | H | RS | H | CH$_3$ | H | H | 6A, B; 6C |
| D-92 | CH$_3$ | H | H | H | CH$_2$OH | H | RS | H | CH$_3$ | H | H | 6A, B; 6C |
| D-93 | CF$_3$ | H | H | H | CH$_2$OH | H | RS | H | CH$_3$ | H | H | 6A, B; 6C |
| D-94 | CH(CH$_3$)$_2$ | H | H | H | CH$_2$OH | H | RS | H | CH$_3$ | Y3—CH=CH—CH=CH—Y4 | | 6A, B; 6C |
| D-95 | CF$_3$ | H | H | H | CH$_2$OH | H | RS | H | CH$_3$ | Y3—CH=CH—CH=CH—Y4 | | 6A, B; 6C |

Further examples of specific compounds of the present invention include each of the compounds of table D above wherein X=SO$_2$ instead of CO and each of the compounds of table D wherein X=CS instead of CO.

Further examples of specific compounds of the present invention include each compound in table D above and each analogue wherein X=SO$_2$ or wherein X=CS, in form of its pyridine N-oxide.

E. Biological Examples: Activity Against *Ascaridia galli* and *Oesophagostomum dentatum*

Anthelmintic effects of compounds of this invention were tested in vitro using gut-welling larval stages of two parasitic nematode species: *Ascaridia galli* (intestinal roundworm of chicken), larval stage 3 ("L3"); and *Oesophagostumum dentatum* (nodular worm of swine), larval stages 3 and 4 (respectively "L3" and "L4"). When conducting these experiments, DMSO-solutions of various concentrations of compounds of this invention were prepared and incubated in 96-well microtiter plates. The parasites were then distributed at 20 larvae per well. The anthelmintic effects were classified by microscopic examination. The microscopic examination included assessing mortality, damage, motility, progression of development, and neutral red uptake by the larvae in comparison to a DMSO-control. The anthelmintic effects were defined by the minimum effective concentration ("MEC"), which is the concentration by which at least one of the larvae shows mortality, damage, change in motility, change in progression of development, or no neutral red uptake. The following compounds showed activity against one or both of the nematodes with an MEC of 50 µM or less: A-1-A-4, A-6-A-10, A-12-A-17, A-19-A-24, A-26, A-31, A-33, A-36-A-47, A-49-A-59, A-61-A-86, A-88-A-93, A-95-A-109, A-111, A-113, A-116, A-118-A-121, A-123, A-126-A-128, A-130, A-133, A-135, A-136, A-138, A-140, A-142, A-143, A-145, A-146, A-148-A-160, A-162-A-165, A-169, A-172, A-173, A-175, A-178, A-179, A-181-A-196, A-198-A-206, A-208-A-220, A-222-A-293, A-297-A-311, A-313-A-315, A-318-A-326, A-328, A-333-A-341, A-343-A-351, A-353, A-354, A-359, A-361, A-363, A-365, A-367, A-368, A-370-A-404, A-405-A-406, A-408-A-427, A-429, A-431, A-433-A-452, A-454-A-456, A-458-A-473, A-475-A-479, A-483, A-485-A-502, A-506, A-507, A-509-A551, A-553, A-554, A-556-A-558, A-560, A-562-A-575, A-577-A-625, A-627-A-634, A-637-A-643, A-645-A-665, A-667-A-672, B-2-B-5, B-7, B-8, B-11-B-18, C-1-C-14, C-18-C-25, C-27-C-37, C-39-C-43, C-45, C-49-C-72, C-76-C-83, C-86-C-88, C-90, C-92, D1-D-17, D-19-D-28, D-31-D-33, D-35, D-37, D-39-D-60, Aa-1-Aa-3.

F Formulation Examples

Formulation A: 5% Suspension:
4.5 g of compound A (a compound according to this invention, but which may be any compound in line with the invention) was dissolved in DMSO, the resulting solution was mixed with a 0.1% solution of methyl cellulose in isotonic NaCl to give a homogeneous suspension of compound A (5% by weight).

Formulation B: 0.5% Suspension:
18.6 mg of compound B (a compound according to this invention, but which may be any compound in line with the invention) was dissolved in DMSO, the resulting solution was mixed with a 0.1% solution of methyl cellulose in isotonic NaCl to give a homogeneous suspension of compound B (0.5% by weight).

Formulation C: 5% Solution:
0.25 g of Compound C (a compound according to this invention, but which may be any compound in line with the invention) was dissolved in 1-methyl-2-pyrrolidinone (3.25 ml). 1,2-Propanediol (0.75 ml) and water was added until a total volume of 5.0 ml was reached to give a homogeneous solution with a content by weight of 5% compound C.

The formulations can be used i.a. for parenteral and oral administration to animals, e.g. sheep or cattle.

DEFINITIONS

The term "alkyl" (alone or in combination with (an)other term(s)) means straight-chain or branched-chain saturated hydrocarbyl substituent (i.e., a substituent containing only carbon and hydrogen) which unless otherwise specified typically contains from 1 to 6 carbon atoms, and even more typically from 1 to about 4 carbon atoms. Examples of such substituents include methyl, ethyl, n-propyl, isopropyl, n-butyl, iso-butyl, sec-butyl, tert-butyl, pentyl, iso-pentyl, hexyl, and octyl. For instance the term "$C_1$-$C_6$-alkyl" includes but is not limited to methyl, ethyl, n-propyl, isopropyl, n-butyl, iso-butyl, sec-butyl, tert-butyl, n-pentyl, iso-pentyl, neo-pentyl, n-hexyl, iso-hexyl.

The term "alkenyl" (alone or in combination with (an)other term(s)) means a straight- or branched-chain hydrocarbyl substituent containing one or more double bonds and unless otherwise specified typically contains from 2 to 6 carbon atoms, even more typically from 2 to 4 carbon atoms. Examples of such substituents include ethenyl (vinyl); 2-propenyl; 3-propenyl; 1,4-pentadienyl; 1,4-butadienyl; 1-butenyl; 2-butenyl; 3-butenyl; and 2-hexenyl.

The term "alkynyl" (alone or in combination with (an)other term(s)) means a straight- or branched-chain hydrocarbyl substituent containing one or more triple bonds and unless otherwise specified typically from 2 to 6 atoms, even more typically from 2 to 4 carbon atoms. Examples of such substituents include ethynyl, 2-propynyl, 3-propynyl, 1-butynyl, 2-butynyl, 3-butynyl, and 2-hexynyl.

The term "cycloalkyl" (alone or in combination with (an) other term(s)) means a cyclic saturated hydrocarbyl substituent (i.e., a substituent containing only carbon and hydrogen) which unless otherwise specified typically contains from 3 to 8 carbon atoms. The cycle or ring in the "cycloalkyl" substituent may be formed by all carbon atoms of the substituent, or may be formed by some, but not all of the carbon atoms of the substituent. In the latter case, the substituent may be connected at a carbon atom that is part of a cycle or that is not part of a cycle. Examples of such substituents include cyclopropyl, cyclobutyl, cyclopentyl, cyclohexyl, cycloheptyl, 2-methylcyclopropyl, cyclopropylmethyl, cyclohexylmethyl.

The term "halogen" (alone or in combination with (an) other term(s)) means a fluorine radical ("fluoro", which may be depicted as F), chlorine radical ("chloro", which may be depicted as Cl), bromine radical ("bromo", which may be depicted as Br), or iodine radical ("iodo", which may be depicted as I). Typically, fluoro or chloro is preferred.

When a chemical formula is used to describe a monovalent substituent, the dash on the left side of the formula indicates the portion of the substituent that has the free valence. To illustrate, benzene substituted with —C(O)—OH has the following structure:

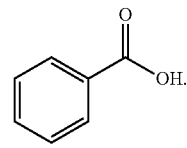

When a chemical formula is used to describe a di-valent (or "linking") component between two other components of a depicted chemical structure (the right and left components), the leftmost dash of the linking component indicates the portion of the linking component that is bound to the left component in the depicted structure. The rightmost dash, on the other hand, indicates the portion of the linking component that is bound to the right component in the depicted structure.

The term "pharmaceutically acceptable" is used adjectivally to mean that the modified noun is appropriate for use in a pharmaceutical product. When it is used, for example, to describe a salt, solvate, N-oxide, active compound or excipient, it characterizes the salt, solvate, N-oxide, active compound or excipient as being compatible with the other ingredients of the composition, and not deleterious to the intended recipient animal, e.g. to the extent that the benefit(s) outweigh(s) the deleterious effect(s).

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

The invention claimed is:
1. A compound of the formula (I) and pharmaceutically acceptable, N-oxides, salts and prodrugs thereof,

Formula (I)

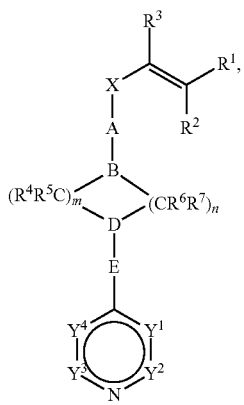

wherein
- R$^1$ is halogen, amino, C$_1$-C$_6$-alkylamino, di-(C$_1$-C$_6$-alkyl) amino, C$_1$-C$_6$-alkylamino-C$_1$-C$_6$-alkyl, di-(C$_1$-C$_6$-alkyl)amino-C$_1$-C$_6$-alkyl, C$_1$-C$_6$-alkyl, hydroxy-C$_1$-C$_6$-alkyl, C$_1$-C$_6$-alkyloxy, C$_1$-C$_6$-alkylthio, C$_2$-C$_6$-alkenyl, C$_2$-C$_6$-alkynyl, C$_1$-C$_6$-alkyloxy C$_1$-C$_6$-alkyl, C$_1$-C$_6$-alkylthio C$_1$-C$_6$-alkyl, C$_1$-C$_6$-alkyl carbonyl, C$_1$-C$_6$-alkyloxy carbonyl, C$_2$-C$_6$-alkenyl carbonyl, SF$_5$, C$_1$-C$_6$-alkyl sulfonyl wherein each of the carbon-containing radicals optionally is substituted by one or more halogen atoms,
- R$^2$ is hydrogen, halogen, amino, C$_1$-C$_6$-alkylamino, di-(C$_1$-C$_6$-alkyl)amino, C$_1$-C$_6$-alkylamino-C$_1$-C$_6$-alkyl, di-(C$_1$-C$_6$-alkyl)amino-C$_1$-C$_6$-alkyl, C$_1$-C$_6$-alkyl, hydroxy-C$_1$-C$_6$-alkyl, C$_1$-C$_6$-alkyloxy, C$_1$-C$_6$-alkylthio, C$_2$-C$_6$-alkenyl, C$_2$-C$_6$-alkynyl, C$_1$-C$_6$-alkyloxy C$_1$-C$_6$-alkyl, C$_1$-C$_6$-alkylthio C$_1$-C$_6$-alkyl, C$_1$-C$_6$-alkyl carbonyl, C$_1$-C$_6$-alkyloxy carbonyl, C$_2$-C$_6$-alkenyl carbonyl, wherein each of the carbon-containing radicals optionally is substituted by one or more halogen atoms,
- R$^3$ is hydrogen, C$_1$-C$_6$-alkyl or cycloalkyl,
- R$^4$ is hydrogen, C$_1$-C$_6$-alkyl or cycloalkyl,
- R$^5$ is hydrogen, C$_1$-C$_6$-alkyl or cycloalkyl,
- R$^6$ is hydrogen, C$_1$-C$_6$-alkyl, cycloalkyl, hydroxy, C$_1$-C$_6$-alkyloxy, phenyl C$_1$-C$_6$-alkyloxy, hydroxy C$_1$-C$_6$-alkyl, C$_1$-C$_6$-alkyloxy C$_1$-C$_6$-alkyl, phenyl C$_1$-C$_6$-alkyloxy C$_1$-C$_6$-alkyl, thiol C$_1$-C$_6$-alkyl, C$_1$-C$_6$-alkylthio C$_1$-C$_6$-alkyl, phenyl C$_1$-C$_6$-alkylthio C$_1$-C$_6$-alkyl, hydroxycarbonyl, hydroxycarbonyl C$_1$-C$_6$-alkyl, C$_1$-C$_6$-alkyloxycarbonyl, C$_1$-C$_6$-alkyloxycarbonyl C$_1$-C$_6$-alkyl, aminocarbonyl, aminocarbonyl C$_1$-C$_6$-alkyl, C$_1$-C$_6$-alkylaminocarbonyl, C$_1$-C$_6$-alkylaminocarbonyl (C$_1$-C$_6$-alkyl), di(C$_1$-C$_6$-alkyl)aminocarbonyl, di(C$_1$-C$_6$-alkyl)aminocarbonyl (C$_1$-C$_6$-alkyl), C$_1$-C$_6$-alkylamino C$_1$-C$_6$-alkyl, di(C$_1$-C$_6$-alkyl)amino C$_1$-C$_6$-alkyl, phenyl, phenyl C$_1$-C$_6$-alkyl, wherein each phenyl group is optionally substituted by hydroxy, C$_1$-C$_6$-alkyloxy or cycloalkyloxy,
- R$^7$ is hydrogen, C$_1$-C$_6$-alkyl or cycloalkyl,
- or R$^6$ and R$^7$ together represent an oxo-group or a thioxo-group or R$^6$ or R$^7$ is joined together with R$^4$ or R$^5$ to form a C$_1$-C$_3$-alkylene group which is optionally substituted by one or more radicals selected from the group of C$_1$-C$_6$-alkyl, and cycloalkyl,
- m is 2,
- n is 2,
- X is a carbonyl, thiocarbonyl or sulfonyl group,
- A is a bond or NR$^8$, wherein R$^8$ is hydrogen or C$_1$-C$_6$-alkyl,
- E is a bond or NR$^9$, wherein R$^9$ is hydrogen or C$_1$-C$_6$-alkyl,
- B is N,
- D is N,
- Y$^1$ is CR$^{12}$ or N, wherein C is substituted by R$^{12}$ which is hydrogen, halogen, C$_1$-C$_6$-alkyl, C$_1$-C$_6$-alkenyl, Cycloalkyl, C$_1$-C$_6$-haloalkyl, C$_1$-C$_6$-alkoxy, Cycloalkyloxy, C$_1$-C$_6$-haloalkoxy, nitrilo, nitro, amino, C$_1$-C$_6$-alkylamino, Cycloalkylamino, (C$_1$-C$_6$-alkyl)-(Cycloalkyl)amino, di(C$_1$-C$_6$-alkyl)amino, N-pyrrolidinyl, N-piperidinyl, N-morpholinyl, C$_1$-C$_6$-alkylthio, Cycloalkylthio, C$_1$-C$_6$-haloalkylthio, C$_1$-C$_6$-alkyl carbonyl, C$_1$-C$_6$-haloalkyl carbonyl, C$_1$-C$_6$-alkylcarbonylamino, aminocarbonyl, C$_1$-C$_6$-alkylaminocarbonyl, di(C$_1$-C$_6$-alkyl)aminocarbonyl, C$_1$-C$_6$-alkoxycarbonyl, phenyl, dioxolane, dioxane, or dioxepane, each said ring being unsubstituted or substituted by C$_1$-C$_6$-alkyl,
- Y$^2$ is CR$^{13}$ or N, wherein C is substituted by R$^{13}$ which is hydrogen, halogen, C$_1$-C$_6$-alkyl, C$_1$-C$_6$-alkenyl, Cycloalkyl, Cycloalkyloxy, C$_1$-C$_6$-haloalkyl, C$_1$-C$_6$-alkoxy, C$_1$-C$_6$-haloalkoxy, nitrilo, nitro, amino, C$_1$-C$_6$-alkylamino, Cycloalkylamino, (C$_1$-C$_6$-alkyl)-(Cycloalkyl)amino, di(C$_1$-C$_6$-alkyl)amino, N-pyrrolidinyl, N-piperidinyl, N-morpholinyl, thiol, hydroxy, C$_1$-C$_6$-alkylthio, Cycloalkylthio, C$_1$-C$_6$-haloalkylthio, C$_1$-C$_6$-alkyl carbonyl, C$_1$-C$_6$-haloalkyl carbonyl, aminocarbonyl, C$_1$-C$_6$-alkylaminocarbonyl, di(C$_1$-C$_6$-alkyl)aminocarbonyl, C$_1$-C$_6$-alkylcarbonylamino, C$_1$-C$_6$-alkoxycarbonyl, dioxolane, dioxane, or dioxepane, each said ring being unsubstituted or substituted by C$_1$-C$_6$-alkyl,
- Y$^3$ is CR$^{14}$ or N, wherein C is substituted by R$^{14}$ which is hydrogen, halogen, C$_1$-C$_6$-alkyl, C$_1$-C$_6$-alkenyl, Cycloalkyl, Cycloalkyloxy, C$_1$-C$_6$-haloalkyl, C$_1$-C$_6$-alkoxy, C$_1$-C$_6$-haloalkoxy, nitrilo, nitro, amino, C$_1$-C$_6$-alkylamino, Cycloalkylamino, (C$_1$-C$_6$-alkyl)-(Cycloalkyl)amino, di(C$_1$-C$_6$-alkyl)amino, N-pyrrolidinyl, N-piperidinyl, N-morpholinyl, thiol, hydroxy, C$_1$-C$_6$-alkylthio, Cycloalkylthio, C$_1$-C$_6$-haloalkylthio, C$_1$-C$_6$-alkyl carbonyl, C$_1$-C$_6$-haloalkyl carbonyl, C$_1$-C$_6$-alkylcarbonylamino, aminocarbonyl, C$_1$-C$_6$-alkylaminocarbonyl, di(C$_1$-C$_6$-alkyl)aminocarbonyl, C$_1$-C$_6$-alkoxycarbonyl, dioxolane, dioxane, or dioxepane, each said ring being unsubstituted or substituted by C$_1$-C$_6$-alkyl,
- Y$^4$ is CR$^{15}$ or N, wherein C is substituted by R$^{15}$ which is hydrogen, halogen, C$_1$-C$_6$-alkyl, C$_1$-C$_6$-alkenyl, Cycloalkyl, Cycloalkyloxy, C$_1$-C$_6$-haloalkyl, C$_1$-C$_6$-alkoxy, C$_1$-C$_6$-haloalkoxy, nitrilo, nitro, amino, C$_1$-C$_6$-alkylamino, Cycloalkylamino, (C$_1$-C$_6$-alkyl)-(Cycloalkyl)amino, di(C$_1$-C$_6$-alkyl)amino, N-pyrrolidinyl, N-piperidinyl, N-morpholinyl, C$_1$-C$_6$-alkylthio, Cycloalkylthio, C$_1$-C$_6$-haloalkylthio, C$_1$-C$_6$-alkyl carbonyl, C$_1$-C$_6$-haloalkyl carbonyl, C$_1$-C$_6$-alkylcarbonylamino, aminocarbonyl, C$_1$-C$_6$-alkylaminocarbonyl, di(C$_1$-C$_6$-alkyl)aminocarbonyl, C$_1$-C$_6$-alkoxycarbonyl, phenyl, dioxolane, dioxane, or dioxepane, each said ring being unsubstituted or substituted by C$_1$-C$_6$-alkyl,
- or Y$^1$ and Y$^2$ and/or Y$^3$ and Y$^4$ are joined together to form a ring system, and wherein R$^1$ and R$^2$ are both different from a perfluorinated methyl group if the group of the formula (A)

Formula (A)

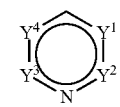

represents a thienopyrimidine group substituted by C$_1$-C$_6$-alkyl.

2. A compound according to claim 1, wherein
$R^1$ is halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_1$-$C_6$-alkyloxy carbonyl, $C_2$-$C_6$-alkenyl carbonyl, $SF_5$, $C_1$-$C_6$-alkyl sulfonyl, wherein each of the carbon-containing radicals optionally is substituted by one or more halogen atoms, $R^2$ is hydrogen, halogen, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl, hydroxy-$C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals is optionally substituted by one or more halogen atoms, $R^3$ is hydrogen, $(CR^4R^5)_m$ is a $C_1$-$C_3$-alkylene group, which is optionally substituted by one or more $C_1$-$C_6$-alkyl radicals, $(CR^6R^7)_n$ is a $C_1$-$C_3$-alkylene group, which is optionally substituted by one or more $C_1$-$C_6$-alkyl radicals, A is a bond or $NR^8$, wherein $R^8$ is H or $C_1$-$C_6$-alkyl, E is a bond or $NR^9$, wherein $R^9$ is H or $C_1$-$C_6$-alkyl, B is N, D is N, $Y^1$ is $CR^{12}$ or N, wherein C is substituted by $R^{12}$ which is hydrogen, halogen, $C_1$-$C_6$-alkyl, $C_1$-$C_6$-alkenyl, Cycloalkyl, $C_1$-$C_6$-haloalkyl, $C_1$-$C_6$-alkoxy, Cycloalkyloxy, $C_1$-$C_6$-haloalkoxy, nitrilo, nitro, amino, $C_1$-$C_6$-alkylamino, di($C_1$-$C_6$-alkyl)amino, Cycloalkylamino, ($C_1$-$C_6$-alkyl)-(Cycloalkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane, dioxane, or dioxepane, each said ring being unsubstituted or substituted by $C_1$-$C_6$-alkyl, $Y^2$ is $CR^{13}$ or N, wherein C is substituted $R^{13}$ which is hydrogen, halogen, $C_1$-$C_6$-alkyl, $C_1$-$C_6$-alkenyl, Cycloalkyl, $C_1$-$C_6$-haloalkyl, $C_1$-$C_6$-alkoxy, Cycloalkyloxy, $C_1$-$C_6$-haloalkoxy, nitrilo, nitro, amino, $C_1$-$C_6$-alkylamino, di($C_1$-$C_6$-alkyl)amino, Cycloalkylamino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane, dioxane, or dioxepane, each said ring being unsubstituted or substituted by $C_1$-$C_6$-alkyl, $Y^3$ is $CR^{14}$ or N, wherein C is substituted by $R^{14}$ which is hydrogen, halogen, $C_1$-$C_6$-alkyl, $C_1$-$C_6$-alkenyl, Cycloalkyl, $C_1$-$C_6$-haloalkyl, $C_1$-$C_6$-alkoxy, Cycloalkyloxy, $C_1$-$C_6$-haloalkoxy, nitrilo, nitro, amino, $C_1$-$C_6$-alkylamino, di($C_1$-$C_6$-alkyl)amino, Cycloalkylamino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane, dioxane, or dioxepane, each said ring being unsubstituted or substituted by $C_1$-$C_6$-alkyl, $Y^4$ is $CR^{15}$ or N, wherein C is substituted by $R^{15}$ which is hydrogen, halogen, $C_1$-$C_6$-alkyl, $C_1$-$C_6$-alkenyl, Cycloalkyl, $C_1$-$C_6$-haloalkyl, $C_1$-$C_6$-alkoxy, Cycloalkyloxy, $C_1$-$C_6$-haloalkoxy, nitrilo, nitro, amino, $C_1$-$C_6$-alkylamino, di($C_1$-$C_6$-alkyl)amino, Cycloalkylamino, ($C_1$-$C_6$-alkyl)-(Cycloalkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane, dioxane, or dioxepane, each said ring being unsubstituted or substituted by $C_1$-$C_6$-alkyl, or $Y^1$ and $Y^2$ and/or $Y^3$ and $Y^4$ are joined together to form a ring system.

3. A compound of the formula (II) according to claim 1, wherein

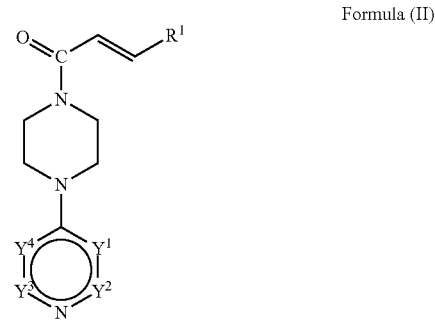

Formula (II)

$R^1$ is $C_1$-$C_6$-alkyl, $C_1$-$C_6$-alkyloxy $C_1$-$C_6$-alkyl, $C_1$-$C_6$-alkylamino-$C_1$-$C_6$-alkyl, di-($C_1$-$C_6$-alkyl)amino-$C_1$-$C_6$-alkyl, or $C_1$-$C_6$-alkylthio $C_1$-$C_6$-alkyl, wherein each of the radicals is unsubstituted or substituted by one or more halogen atoms, $Y^1$ is $CR^{12}$ or N, wherein C is substituted by $R^{12}$ which is hydrogen, halogen, $C_1$-$C_6$-alkyl, $C_1$-$C_6$-haloalkyl, $C_1$-$C_6$-alkoxy, Cycloalkyl, Cycloalkyloxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, phenyl, $Y^2$ is $CR^{13}$ or N, wherein C is substituted by $R^{13}$ which is hydrogen, halogen, $C_1$-$C_6$-alkyl, $C_1$-$C_6$-haloalkyl, $C_1$-$C_6$-alkoxy, Cycloalkyl, Cycloalkyloxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane dioxane, or dioxepane, each said ring being unsubstituted or substituted by $C_1$-$C_6$-alkyl, $Y^3$ is $CR^{14}$ or N, wherein $R^{14}$ which is hydrogen, halogen, $C_1$-$C_6$-alkyl, $C_1$-$C_6$-haloalkyl, $C_1$-$C_6$-alkoxy, Cycloalkyl, Cycloalkyloxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane, dioxane, or dioxepane, each said ring being unsubstituted or substituted by $C_1$-$C_6$-alkyl, $Y^4$ is $CR^{15}$ or N, wherein $R^{15}$ is hydrogen, halogen, $C_1$-$C_6$-alkyl, $C_1$-$C_6$-haloalkyl, $C_1$-$C_6$-alkoxy, Cycloalkyl, Cycloalkyloxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, phenyl, or $Y^1$ and $Y^2$ and/or $Y^3$ and $Y^4$ are joined together to form a 5- or 6-membered ring system.

4. A compound according to claim 3, wherein
$R^1$ is $C_1$-$C_6$-alkyl, $C_1$-$C_6$-alkyloxy $C_1$-$C_6$-alkyl, or $C_1$-$C_6$-alkylthio $C_1$-$C_6$-alkyl, wherein each of the radicals unsubstituted or substituted by one or more halogen atoms,
$Y^1$ is C or N, wherein C is substituted by $R^{12}$ which is hydrogen, $C_1$-$C_6$-alkyl, or $C_1$-$C_6$-alkoxy,
$Y^2$ is C, wherein C is substituted by $R^{13}$ which is hydrogen, $C_1$-$C_6$-alkyl, $C_1$-$C_6$-alkoxy, $C_1$-$C_6$-alkyl carbonyl,
$Y^3$ is C, wherein C is substituted by $R^{14}$ which is hydrogen, $C_1$-$C_6$-alkyl, $C_1$-$C_6$-alkoxy, $C_1$-$C_6$-alkyl carbonyl,
$Y^4$ is C, wherein C is substituted by $R^{15}$ which is hydrogen, $C_1$-$C_6$-alkyl, $C_1$-$C_6$-alkoxy,
or $Y^1$ and $Y^2$ or $Y^3$ and $Y^4$ are joined together to form a 5- or 6-membered ring system.

5. A compound according to claim 1, wherein the group of the formula (A)

Formula (A)

represents a pyridine, pyrimidine, quinoline, quinazoline, thienopyrimidine, thienopyridine, triazolopyrimidine, pyridopyridine, pyrrolopyridine, pyrazolopyrimidine, pyrazolopyridine, furopyridine, 2,3-dihydrofuropyridine, 2,3-dihydro-1,4-dioxinopyridine, furopyrimidine, pyridazine or cinnoline group, wherein each group is optionally substituted by one or more radicals, selected from the group of $C_1$-$C_6$-alkyl, $C_1$-$C_6$-haloalkyl, $C_1$-$C_6$-alkenyl, Cycloalkyl, Cycloalkyloxy, $C_1$-$C_6$-alkoxy, $C_1$-$C_6$-haloalkoxy, halogen, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane, dioxane, or dioxepane, wherein each ring is unsubstituted or substituted by $C_1$-$C_6$-alkyl.

6. A compound according to claim 1, wherein
$R^2$ is hydrogen,
$R^3$ is hydrogen,
$R^4$ is hydrogen,
$R^5$ is hydrogen,
$R^6$ is hydrogen or $C_1$-$C_6$-alkyl,
$R^7$ is hydrogen,
X is a carbonyl group,
m is 2
n is 2,
the group of formula (A) represents a pyridine, pyrimidine or quinoline group, preferably a pyridine or pyrimidine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, Cycloalkyl, Cycloalkyloxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane, dioxane, or dioxepane, wherein each ring is unsubstituted or substituted by $C_1$-$C_6$-alkyl.

7. A pharmaceutical composition, wherein the composition comprises:

a) one or more compounds as defined in claim 1; and
b) one or more pharmaceutically acceptable excipients and/or one or more pharmaceutically acceptable active ingredients which differ in structure from component a).

8. A compound of formula (1-III)

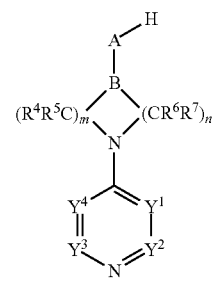

1-III in which $Y^1$, $Y^2$, $Y^3$ and $Y^4$ are C and wherein
a) $R^{12}$ and $R^{15}$ are hydrogen, $R^{13}$ is $C_1$-$C_6$-alkoxy or $C_1$-$C_6$-haloalkoxy, $R^{14}$ is $C_1$-$C_6$-alkyl or $C_1$-$C_6$-haloalkyl, B is N, A is N or a bond, n is 2, m is 2, and $R^6$, $R^7$, $R^8$ and $R^9$ are defined as in claim 1,
b) $R^{12}$ and $R^{15}$ are hydrogen, $R^{13}$ is $C_1$-$C_6$-alkylcarbonyl or $C_1$-$C_6$-haloalkylcarbonyl, $R^{14}$ is $C_1$-$C_6$-alkyl or $C_1$-$C_6$-haloalkyl, B is N, A is N or a bond, n is 2, m is 2, and $R^6$, $R^7$, $R^8$ and $R^9$ are defined as in claim 1, or
c) $R^{12}$ is $C_1$-$C_6$-alkyl or $C_1$-$C_6$-haloalkyl, $R^{13}$ is $C_1$-$C_6$-alkoxy or $C_1$-$C_6$-haloalkoxy, $R^{14}$ is defined as in claim 1, $R^{15}$ is hydrogen, B is N, A is N or a bond, n is 2, m is 2, and $R^6$, $R^7$, $R^8$ and $R^9$ are defined as in claim 1.

9. A kit, wherein the kit comprises:
a) one or more compounds as defined in claim 1, and
b) one or more other components selected from the group consisting of an excipient, an active ingredient, an apparatus for combining the compound of component a) with an excipient and/or active ingredient, an apparatus for administering the compound of component a) to an animal, and a diagnostic tool.

10. A method of treating a parasitic infection, wherein the method comprises administering to an animal the pharmaceutical composition as defined in claim 7.

11. A method of claim 10, wherein the animal is a non-human animal.

12. A compound of the formula (I a) and pharmaceutically acceptable, N-oxides and salts thereof,

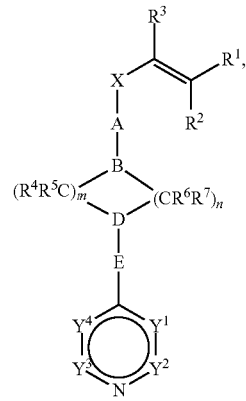

Formula (I a)

wherein
$R^1$ is hydrogen, halogen, amino, $C_1$-$C_6$-alkylamino, cycloalkylamino, di-($C_1$-$C_6$-alkyl)amino, di-(cycloalkyl)amino, $C_1$-$C_6$-alkylamino-$C_1$-$C_6$-alkyl, $C_1$-$C_6$-alkylamino-cycloalkyl, cycloalkylamino-$C_1$-$C_6$-alkyl, cycloalkylamino-cycloalkyl, di-($C_1$-$C_6$-alkyl)amino-$C_1$-$C_6$-alkyl, di-(cycloalkyl)amino-$C_1$-$C_6$-alkyl, di-($C_1$-$C_6$-alkyl)amino-cycloalkyl, di-(cycloalkyl)amino-cycloalkyl, $C_1$-$C_6$-alkyl, cycloalkyl, hydroxy-$C_1$-$C_6$-alkyl, hydroxy-cycloalkyl, $C_1$-$C_6$-alkyloxy, cycloalkyloxy, $C_1$-$C_6$-alkylthio, cycloalkylthio, $C_2$-$C_6$-alkenyl, $C_2$-$C_6$-alkynyl, $C_1$-$C_6$-alkyloxy $C_1$-$C_6$-alkyl, cycloalkyloxy $C_1$-$C_6$-alkyl, $C_1$-$C_6$-alkyloxy cycloalkyl, cycloalkyloxy cycloalkyl, $C_1$-$C_6$-alkylthio $C_1$-$C_6$-alkyl, $C_1$-$C_6$-alkylthio cycloalkyl, cycloalkylthio $C_1$-$C_6$-alkyl, cycloalkylthio cycloalkyl, $C_1$-$C_6$-alkyl carbonyl, cycloalkyl carbonyl, $C_1$-$C_6$-alkyloxy carbonyl, cycloalkyloxy carbonyl, $C_2$-$C_6$-alkenyl carbonyl, phenyl, furanyl, or thiophenyl, wherein each of the carbon-containing radicals optionally is substituted by one or more halogen atoms, or $R^1$ is phenyl, furanyl, imidazolyl or thiophenyl, wherein each of the rings is optionally substituted by one or more radicals from the group of halogen, cycloalkyl and $C_1$-$C_6$-alkyl, $R^2$ is hydrogen, halogen, amino, $C_1$-$C_6$-alkylamino, cycloalkylamino, di-($C_1$-$C^6$-alkyl)amino, di-(cycloalkyl)amino, $C_1$-$C_6$-alkylamino-$C_1$-$C_6$-alkyl, $C_1$-$C_6$-alkylamino-cycloalkyl, cycloalkylamino-$C_1$-$C_6$-alkyl, cycloalkylamino-cycloalkyl, di-($C_1$-$C_6$-alkyl)amino-$C_1$-$C_6$-alkyl, di-(cycloalkyl)amino-$C_1$-$C_6$-alkyl, di-($C_1$-$C_6$-alkyl)amino-cycloalkyl, di-(cycloalkyl)amino-cycloalkyl, $C_1$-$C_6$-alkyl, cycloalkyl, hydroxy-$C_1$-$C_6$-alkyl, hydroxy-cycloalkyl, $C_1$-$C_6$-alkyloxy, cycloalkyloxy, $C_1$-$C_6$-alkylthio, cycloalkylthio, $C_2$-$C_6$-alkenyl, $C_2$-$C_6$-alkynyl, $C_1$-$C_6$-alkyloxy $C_1$-$C_6$-alkyl, cycloalkyloxy $C_1$-$C_6$-alkyl, $C_1$-$C_6$-alkyloxy cycloalkyl, cycloalkyloxy cycloalkyl, $C_1$-$C_6$-alkylthio $C_1$-$C_6$-alkyl, $C_1$-$C_6$-alkylthio cycloalkyl, cycloalkylthio $C_1$-$C_6$-alkyl, cycloalkylthio cycloalkyl, $C_1$-$C_6$-alkyl carbonyl, cycloalkyl carbonyl, $C_1$-$C_6$-alkyloxy carbonyl, cycloalkyloxy carbonyl, $C_2$-$C_6$-alkenyl carbonyl, phenyl, furanyl, or thiophenyl, wherein each of the carbon-containing radicals optionally is substituted by one or more halogen atoms, or $R^2$ is phenyl, furanyl, imidazolyl or thiophenyl, wherein each of the rings is optionally substituted by one or more radicals/from the group of halogen, cycloalkyl and $C_1$-$C_6$-alkyl, $R^3$ is hydrogen, cycloalkyl or $C_1$-$C_6$-alkyl,
$R^4$ is hydrogen, cycloalkyl or $C_1$-$C_6$-alkyl,
$R^5$ is hydrogen, cycloalkyl or $C_1$-$C_6$-alkyl,
$R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy, cycloalkyloxy or $C_1$-$C_6$-alkyloxy, $R^7$ is hydrogen, cycloalkyl or $C_1$-$C_6$-alkyl,
or $R^6$ and $R^7$ together represent an oxo-group or a thioxo-group or $R^6$ or $R^7$ is joined together with $R^4$ or $R^5$ to form a $C_1$-$C_3$-alkylene group which is optionally substituted by one or more radicals selected from the group of cycloalkyl, and $C_1$-$C_6$-alkyl, m is 2,
n is 2,
X is a carbonyl or sulfonyl group,
A is a bond or $NR^8$, wherein $R^8$ is hydrogen or $C_1$-$C_6$-alkyl,
E is a bond or $NR^9$, wherein $R^9$ is hydrogen or $C_1$-$C_6$-alkyl,
B is N,
D is N,
$Y^1$ is $CR^{12}$ or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, phenyl, dioxolane, dioxane or dioxepane, each said ring being unsubstituted or substituted by $C_1$-$C_6$-alkyl or cycloalkyl, $Y^2$ is $CR^{13}$ or N, wherein $R^{13}$ is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, dioxane, or dioxepane, each said ring being unsubstituted or substituted by $C_1$-$C_6$-alkyl or cycloalkyl, $Y^3$ is $CR^{14}$ or N, wherein $R^{14}$ is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, dioxolane, dioxane, or dioxepane, each said ring being unsubstituted or substituted by $C_1$-$C_6$-alkyl or cycloalkyl, $Y^4$ is $CR^{15}$ or N, wherein $R^{15}$ hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, phenyl, dioxolane, dioxane, or dioxepane, each said ring being unsubstituted or substituted by $C_1$-$C_6$-alkyl or cycloalkyl, or $Y^1$ and $Y^2$ and/or $Y^3$ and $Y^4$ are joined together to form a ring system for treating a helminth infection.

13. An anthelmintic composition, wherein the composition comprises:
a) one or more compounds as defined in claim 12; and
b) one or more pharmaceutically acceptable excipients and optionally one or more pharmaceutically acceptable active ingredients which differ from the said one or more compounds as defined in claim 12.

14. The method of claim 11, wherein the parasitic infection is helminth infection.

15. The method of claim 14, wherein the helminth infection is selected from the group consisting of a nematode infection, a cestode infection and a trematode infection.

16. The compound of claim 3, wherein
$R^1$ is $CF_2CF_3$,
$Y^1$ is $CR^{12}$, wherein $R^{12}$ is hydrogen,
$Y^2$ is $CR^{13}$, wherein $R^{13}$ is $OCH_3$,
$Y^3$ is $CR^{14}$, wherein $R^{14}$ is $CH_3$, and
$Y^4$ is $CR^{15}$, wherein $R^{15}$ is hydrogen.

* * * * *